United States Patent
Albrecht et al.

(10) Patent No.: US 10,155,764 B2
(45) Date of Patent: Dec. 18, 2018

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Alexandre Cote, Cambridge, MA (US); Terry Crawford, South San Francisco, CA (US); Martin Duplessis, Cambridge, MA (US); Andrew Charles Good, Cambridge, MA (US); Yves LeBlanc, Cambridge, MA (US); Steven Magnuson, South San Francisco, CA (US); Christopher G. Nasveschuk, Cambridge, MA (US); Richard Pastor, South San Francisco, CA (US); Anthony F. Romero, South San Francisco, CA (US); Alexander M. Taylor, Cambridge, MA (US)

(73) Assignees: GENENTECH, INC, South San Francisco, CA (US); CONSTELLATION PHARMACEUTICALS, INC., Cambridge, MA (US)

(*) Notice: Subject to any disclaimer, the term of this patent is extended or adjusted under 35 U.S.C. 154(b) by 0 days.

(21) Appl. No.: 15/449,692

(22) Filed: Mar. 3, 2017

(65) Prior Publication Data
US 2017/0275289 A1   Sep. 28, 2017

Related U.S. Application Data

(63) Continuation of application No. PCT/US2015/048354, filed on Sep. 3, 2015.
(Continued)

(51) Int. Cl.
| | |
|---|---|
| *C07D 487/04* | (2006.01) |
| *C07D 403/12* | (2006.01) |
| *C07D 401/12* | (2006.01) |
| *C07D 237/32* | (2006.01) |
| *C07D 471/04* | (2006.01) |
| *A61K 31/502* | (2006.01) |
| *A61K 31/5025* | (2006.01) |

(Continued)

(52) U.S. Cl.
CPC ......... *C07D 487/04* (2013.01); *A61K 31/502* (2013.01); *A61K 31/5025* (2013.01); *A61K 31/5377* (2013.01); *A61K 31/55* (2013.01); *C07D 237/32* (2013.01); *C07D 237/34* (2013.01); *C07D 401/12* (2013.01); *C07D 403/12* (2013.01); *C07D 405/12* (2013.01); *C07D 471/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,591,743 A | 1/1997 | Patoiseau et al. | |
| 7,803,795 B2* | 9/2010 | Mevellec | C07D 401/04 514/217.05 |

(Continued)

FOREIGN PATENT DOCUMENTS

| | | |
|---|---|---|
| WO | 2006003147 A1 | 1/2006 |
| WO | 2011150183 A1 | 12/2011 |

(Continued)

OTHER PUBLICATIONS

Elagawany et al., Design, synthesis, and molecular modeling of pyridazinone and phthalazinone derivatives as protein kinases inhibitors Bioorganic & Medicinal Chemistry Letters (2013), 23(7), 2007-2013.*

(Continued)

*Primary Examiner* — Paul V Ward
(74) *Attorney, Agent, or Firm* — Viksnins Harris Padys Malen LLP

(57) ABSTRACT

The present invention relates to methods for treating PCAF and GCN5 mediated disorders using a compound of formula (I) or a pharmaceutically acceptable salt thereof:

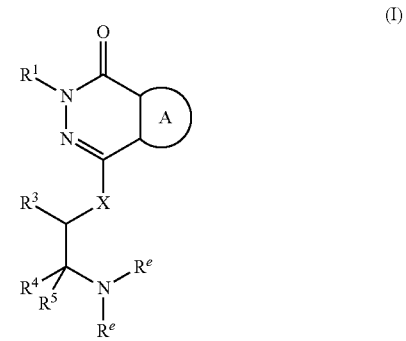

wherein ring A, $R^1$, $R^3$, $R^4$, $R^5$, and each $R^e$ have any of the values defined in the specification. Also included are novel compounds of Formula (I) and salts thereof, as well as pharmaceutical compositions comprising a compound of formula (I) or a pharmaceutically acceptable salt thereof.

23 Claims, No Drawings

Related U.S. Application Data

(60) Provisional application No. 62/046,756, filed on Sep. 5, 2014.

(51) Int. Cl.
*A61K 31/5377* (2006.01)
*A61K 31/55* (2006.01)
*C07D 237/34* (2006.01)
*C07D 405/12* (2006.01)

(56) References Cited

U.S. PATENT DOCUMENTS

2014/0275069 A1  9/2014  Jantos et al.
2017/0334883 A1  11/2017  Albrecht et al.

FOREIGN PATENT DOCUMENTS

WO   2014068388 A1   5/2014
WO   2014144721 A2   9/2014
WO   2016112298 A1   7/2016

OTHER PUBLICATIONS

Cingolani et al, Farmaco, Edizione Scientifica (1965), 20(4), 259-69.*
Sladowska et al., Farmaco (1998), 53(7), 475-479.*
Kormendy et al., Acta Chimica Academiae Scientiarum Hungaricae (1976), 88(2), 129-36.*
Garnier, et al., "BET bromodomain inhibitors: a patent review", Expert Opinion on Therapeutic Patents vol. 24 (2), 185-199 (2014).
Jeanmougin, "The bromodomain revisited", Trends Biochem Sci 22(5), 151-153 (1997).
Malinka, et al., "New derivatives of pyrrolo[3,4-d]pyridazinone and their anticancer effects", IL Farmaco 59, 457-462 (2004).
Manzo, et al., "Histone acetyltransferase inhibitors and preclinical studies", Expert Opin Ther Patents 19(6), 761-774 (2009).
Muller, et al., "Bromodomains as therapeutic targets", Expert Rev Mol Med 13 (29), 1-21 (2011).
Patent Cooperation Treaty, International Searching Authority, Search Report and Written Opinion for PCT/US2015/048354, 12 pages, dated Dec. 14, 2015.
Pring, et al., "Synthesis and Mechanism of Formation of 2,3-Dialkyl-1,2,3,4-tetrahydrophthalazine-1,4-diones by Utilizing an O—N Rearrangement of 1-Alkoxy-3-alkyl-3,4-dihydrophthalazin-4-ones", Acta Chemica Scandinavica 27, 1891-1899 (1973).
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila* homeotic genes structurally related to the yeast transcriptional activator SNF2/SWI2", Cell 68, 561-572 (1992).
Pccompound-selected items 1-200 of 518, creation date Jul. 21, 2009 to Oct. 23, 2012.
Pccompound-selected items 14, creation date Jul. 21, 2009 to Oct. 23, 2012.
Pccompound-selected items 201-400 of 518, creation date Jul. 21, 2009 to Oct. 23, 2012.
Pccompound-selected items 401_518 of 518, creation date Jul. 21, 2009 to Oct. 23, 2012.
Cecil Textbook of Medicine, edited by Bennet, J.C. and Plum, F., 20th edition, vol. 1, 1004-1010 (1996).
Dermer, "Another Anniversary for the War on Cancer", Bio/Technology 12, 320 (1994).
Freshney, et al., "Culture of Animal Cells, A Manual of Basic Technique", Alan R. Liss, Inc., New York, 7 pages (1983).
Golub, et al., "Molecular Classification of Cancer: Class Discovery and Clas Prediction by Gene Expression Monitoring", Science 286, 531-537 (1999).
U.S. Appl. No. 15/449,706, 2017-0334883.
Venkatesh, et al., "Role of the Development Scientist in Compound Lead Selection and Optimization", Journal of Pharmaceutical Sciences 89 (2), 145-154 (2000).

\* cited by examiner

THERAPEUTIC COMPOUNDS AND USES THEREOF

CROSS-REFERENCE TO RELATED APPLICATION

This application is a continuation of International Application serial no. PCT/US2015/048354, filed Sep. 3, 2015, which claims the benefit of priority of U.S. application Ser. No. 62/046,756, filed Sep. 5, 2014, which applications are herein incorporated by reference.

TECHNICAL FIELD OF THE INVENTION

The present invention relates to compounds useful as inhibitors of P300/CBP-associated factor (PCAF) as well as its closely related homolog GCN5, and methods of treating cancer using such inhibitors.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., Genes Dev., 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., Trends Biochem. Sci., 1997, 22, 5, 151-153; and Tamkun J. W., et al., Cell, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., Trends Pharm. Sci., 33(3):146-153 (2012) and Muller et al., Expert Rev., 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Hence, the selective inhibition of bromodomains across a specific family, such as the selective inhibition of a bromodomain of PCAF, creates varied opportunities as novel therapeutic agents in human dysfunction.

There is a need for treatments for cancer, immunological disorders, and other PCAF bromodomain related diseases. There is also a need for treatments for GCN5 mediated disorders

SUMMARY OF THE INVENTION

One aspect includes a compound of formula (I):

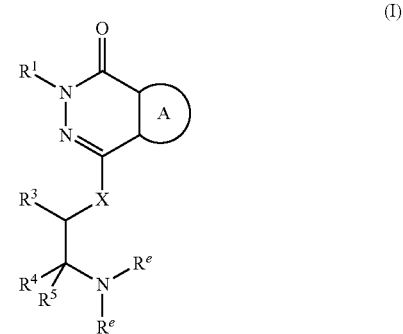

or a salt thereof, wherein:

$R^1$ is selected from the group consisting of H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, and $C_{1-6}$alkoxy;

X is O, $N(R^a)$, or S;

each $R^a$ is independently selected from the group consisting of hydrogen, $C_{1-6}$alkyl, $C_{2-6}$alkenyl, $C_{2-6}$alkynyl, $C_{1-6}$alkoxy, and carbocyclyl, wherein each $C_{1-6}$alkyl, $C_{2-6}$alkenyl, $C_{2-6}$alkynyl, $C_{1-6}$alkoxy, and carbocyclyl is optionally substituted with one or more groups independently selected from the group consisting of oxo, halo, amino, hydroxy, $C_{1-6}$alkoxy, and $C_1$-$C_6$ alkyl that is optionally substituted with one or more groups independently selected from the group consisting of oxo and halo;

$R^3$ and $R^4$ are each independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups $R^b$; or $R^3$ and $R^4$ taken together with the atoms to which they are attached form a carbocyclyl or heterocyclyl, which carbocyclyl and heterocyclyl is optionally substituted with one or more groups $R^b$;

$R^5$ is hydrogen or $C_{1-6}$alkyl, or $R^4$ and $R^5$ taken together with the atoms to which they are attached form a carbocyclyl or heterocyclyl, which carbocyclyl and heterocyclyl is optionally substituted with one or more groups independently selected from the group consisting of $C_{1-6}$alkyl, $C_2$% alkenyl, $C_{2-6}$alkynyl, $C_{1-6}$alkoxy, $C_{3-6}$carbocyclyl, oxo, halo, hydroxy, and —$NO_2$, wherein any $C_{1-6}$alkyl, $C_{2-6}$alkenyl, $C_{2-6}$alkynyl, $C_{1-6}$alkoxy, and $C_{3-6}$carbocyclyl, is optionally substituted with one or more groups independently selected from the group consisting of halo, hydroxy, and $C_{1-6}$alkoxy;

each $R^b$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^c)_2$, —CN, —C(O)—N$(R^c)_2$, —S(O)—N$(R^c)_2$, —S(O)$_2$—N$(R^c)_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —C(O)—N$(R^c)_2$, —N$(R^c)$—C(O)—$R^c$, —N$(R^c)$—S(O)—$R^c$, and —N$(R^c)$—S(O)$_2$—$R^c$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^c)_2$, —CN, —C(O)—N$(R^c)_2$, —S(O)—N$(R^c)_2$, —S(O)$_2$—N$(R^c)_2$, —O—$R^c$, —S—$R^c$, —O—C(O)—$R^c$, —C(O)—$R^c$, —C(O)—O—$R^c$, —S(O)—$R^c$, —S(O)$_2$—$R^c$, —C(O)—N$(R^c)_2$, —N$(R^c)$—C(O)—$R^c$, —N$(R^c)$—S(O)—$R^c$, and —N$(R^c)$—S(O)$_2$—$R^c$;

each $R^c$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

ring A is a 5- or 6-membered heterocyclyl or a 5- or 6-membered carbocyclyl, which 5- or 6-membered heterocyclyl and 5- or 6-membered carbocyclyl is optionally substituted with one or more groups independently selected from the group consisting of $C_{1-6}$alkyl, $C_{2-6}$alkenyl, $C_{2-6}$alkynyl, carbocyclyl, heterocyclyl, halo, —$NO_2$, —$N(R^d)_2$, —CN, —C(O)—N$(R^d)_2$, —S(O)—N$(R^d)_2$, —S(O)$_2$—N$(R^d)_2$, —O—$R^d$, —S—$R^d$, —O—C(O)—$R^d$, —C(O)—$R^d$, —C(O)—O—$R^d$, —S(O)—$R^d$, —S(O)$_2$—$R^d$, —C(O)—N$(R^d)_2$, —N$(R^d)$—C(O)—$R^d$, —N$(R^c)$—S(O)—$R^d$, —O—C(O)—N$(R^d)_2$, —N$(R^d)$—C(O)—O—$R^d$, —N$(R^d)$—C(O)—N$(R^d)_2$, and —N$(R^d)$—S(O)$_2$—$R^d$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^d)_2$, —CN, —C(O)—N$(R^d)_2$, —S(O)—N$(R^d)_2$, —S(O)$_2$—N$(R^d)_2$, —O—$R^d$, —S—$R^d$, —O—C(O)—$R^d$, —C(O)—$R^d$, —C(O)—O—$R^d$, —S(O)—$R^d$, —S(O)$_2$—$R^d$, —C(O)—N$(R^d)_2$, —N$(R^d)$—C(O)—$R^d$, —N$(R^d)$—S(O)—$R^d$, —O—C(O)—N$(R^d)_2$, —N$(R^d)$—C(O)—O—$R^d$, —N$(R^d)$—C(O)—N$(R^d)_2$, and —N$(R^d)$—S(O)$_2$—$R^d$;

each $R^d$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups $R^f$; or two $R^d$ are taken together with the nitrogen to which they are attached to form a heterocyclyl that is optionally substituted with one or more groups $R^f$;

each $R^e$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo;

or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo; or one $R^e$ taken together with $R^3$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from the group consisting of oxo, halo, amino, hydroxy, $C_{1-6}$alkoxy and carbocyclyl;

or one $R^e$ taken together with $R^4$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl;

each $R^f$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^g)_2$, —CN, —C(O)—N$(R^g)_2$, —S(O)—N$(R^g)_2$, —S(O)$_2$—N$(R^g)_2$, —O—$R^g$, —S—$R^g$, —O—C(O)—$R^g$, —C(O)—$R^g$, —C(O)—O$R^g$, —S(O)—$R^g$, —S(O)$_2$—$R^g$, —N$(R^g)$—C(O)—$R^g$, —N$(R^g)$—S(O)—$R^g$, —N$(R^g)$—C(O)—N$(R^g)_2$, and —N$(R^g)$—S(O)$_2$—$R^g$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^g)_2$, —CN, —C(O)—N$(R^g)_2$, —S(O)—N$(R^g)_2$, —S(O)$_2$—N$(R^g)_2$, —O—$R^g$, —S—$R^g$, —O—C(O)—$R^g$, —C(O)—$R^g$, —C(O)—O—$R^g$, —S(O)—$R^g$, —S(O)$_2$—$R^g$, —N$(R^g)$—C(O)—$R^g$, —N$(R^g)$—S(O)—$R^g$, —N$(R^g)$—C(O)—N$(R^g)_2$, and —N$(R^g)$—S(O)$_2$—$R^g$; and each $R^g$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^g$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo.

Another aspect includes a composition comprising a compound of formula (I) or a pharmaceutically acceptable salt thereof, and a pharmaceutically acceptable adjuvant, carrier, or vehicle.

Another aspect includes a method for treating a PCAF mediated disorder or a GCN5 mediated disorder in an animal (e.g., a mammal such as a human) comprising administering to the animal a compound of formula (I), or a pharmaceutically acceptable salt thereof.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a PCAF mediated disorder.

Another aspect includes the use of a compound of formula (I) or a pharmaceutically acceptable salt thereof to prepare a medicament for treating a PCAF mediated disorder in an animal (e.g., a mammal such as a human).

Another aspect includes compounds for the study of PCAF.

Another aspect includes novel compounds of formula (I) and salts thereof.

Another aspect includes a method of a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human) comprising administering to the animal an effective amount of a compound of formula (I) or a pharmaceutically acceptable salt thereof.

Another aspect includes a compound of formula (I) or a pharmaceutically acceptable salt thereof as described in claim 1 for a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human).

Another aspect includes the use of a compound of formula (I) or a pharmaceutically acceptable salt thereof to prepare a medicament for a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human).

Another aspect includes a method of treating cancer in an individual (e.g., a patient) comprising administering to the individual (a) a compound of formula (I) or a pharmaceutically acceptable salt thereof and (b) a cytotoxic agent.

Another aspect includes a compound of formula (I) or a pharmaceutically acceptable salt thereof for the prophylactic or therapeutic treatment of cancer in combination with a cytotoxic agent.

Another aspect includes the use of a compound of formula (I) or a pharmaceutically acceptable salt thereof to prepare a medicament for treating cancer in combination with a cytotoxic agent.

Another aspect includes a method for treating a GCN5 mediated disorder in an animal (e.g., a mammal such as a human) comprising administering to the animal a compound of formula (I), or a pharmaceutically acceptable salt thereof.

Another aspect includes a compound of formula (I) or a pharmaceutically acceptable salt thereof for the prophylactic or therapeutic treatment of a GCN5 mediated disorder.

Another aspect includes the use of a compound of formula (I) or a pharmaceutically acceptable salt thereof to prepare a medicament for treating a GCN5 mediated disorder in an animal (e.g., a mammal such as a human).

Another aspect includes compounds for the study of GCN5.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "unsaturated", as used herein, means that a moiety has one or more units of unsaturation.

The term "carbocyclyl" used alone or as part of a larger moiety, refers to a saturated, partially unsaturated, or aromatic (e.g., aryl) ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, phthalimidyl, naphthimidyl, phenantriidinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, pyrid-2-yl N-oxide, and pyrazolo[4,3-c]pyridinyl. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono-, bi- or tri-cyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6, 7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "inhibitor" refers to a compound that binds to and inhibits PCAF with measurable affinity and activity. In certain embodiments, an inhibitor has an $IC_{50}$ or binding constant of less about 20 μM, less than about 1 μM, less than about 500 nM, less than about 100 nM, or less than about 10 nM.

The terms "measurable affinity" and "measurably inhibit," as used herein, refer to a measurable reduction in activity (e.g., reduction in recognition of lysine acetyl recognition of chromatin) of the bromodomain PCAF between: (i) a sample comprising a compound of formula I or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein).

"PCAF bromodomain inhibitor" or refers to a compound that binds to the PCAF bromodomain and inhibits and/or reduces a biological activity of PCAF. In some embodiments, PCAF bromodomain inhibitor binds to PCAF primarily (e.g., solely) through contacts and/or interactions with the PCAF bromodomain. In some embodiments, PCAF bromodomain inhibitor substantially or completely inhibits the biological activity of PCAF. In some embodiments, the biological activity is binding of the bromodomain of PCAF to chromatin (e.g., histones associated with DNA) and/or another acetylated protein.

The terms "PCAF" and "P300/CBP-Associated Factor", "K(lysine)acetyltransferase 2B", "KAT2B", "Histone Acetylase PCAF", "Histone Acetyltransferase PCAF", "Lysine Acetyltransferase 2B", "P/CAF", "EC 2.3.1.48", "CAF", "CREBBP-Associated Factor", and "Histone Acetyltransferase KAT2B" as used herein, may be used interchangeably, and refer to any native PCAF from any vertebrate source, including mammals such as primates (e.g. humans) and rodents (e.g. mice and rats), unless otherwise indicated. The term encompasses "full-length" unprocessed PCAF as well as any form of PCAF that results from processing in the cell. The term also encompasses naturally occurring variants of PCAF, e.g. splice variants or allelic variants.

The term GCN5 includes GCN5L2, PCAF-b, KAT2A, STAF97, and the like.

As used herein, "a" or "an" means one or more, unless clearly indicated otherwise.

As used herein, "another" means at least a second or more.

Exemplary Values

In one embodiment the compound of formula (I) has a formula selected from formulae I(a-j):

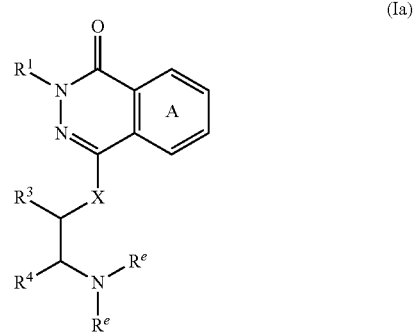

(Ia)

-continued (Ib)
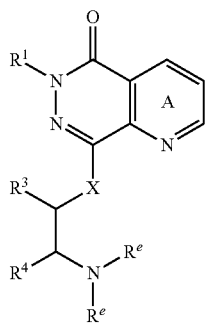

(Ic)
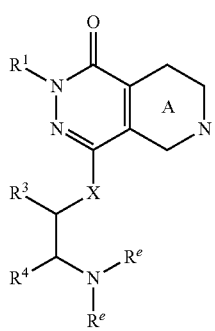

(Id)
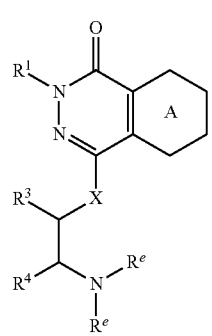

(Ie)
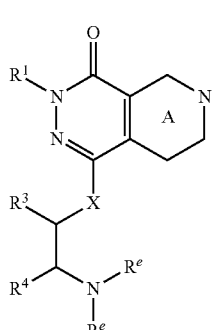

(If)
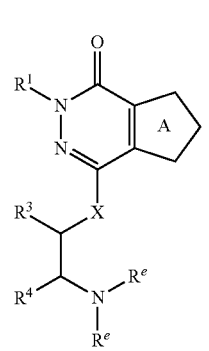

-continued (Ig)
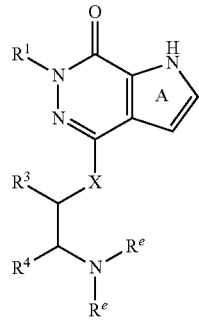

(Ih)
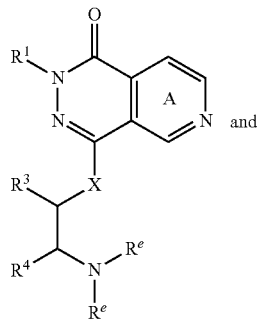
and (Ij)
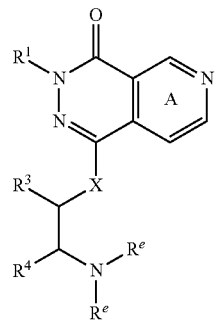

wherein ring A is optionally substituted with one or more groups independently selected from the group consisting of $C_{1-6}$alkyl, $C_{2-4}$alkenyl, $C_{2-6}$alkynyl, carbocyclyl, heterocyclyl, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, and —N(R$^d$)—S(O)$_2$—R$^d$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, —N(R$^d$)—S(O)$_2$—R$^d$; and salts thereof.

In another embodiment ring A is optionally substituted with one or more groups independently selected from the group consisting of $C_{1-6}$alkyl, phenyl, halo, and —O—R$^d$, wherein any $C_{1-6}$alkyl and phenyl is optionally substituted with one or more groups independently selected from halo.

In another embodiment ring A is optionally substituted with one or more groups independently selected from the group consisting of methoxy, 4-chlorophenyl, fluoro, and methyl.

In another embodiment $R^1$ is $C_{1-6}$alkyl, optionally substituted with one or more groups independently selected from the group consisting of oxo, halo, amino, hydroxy, and $C_{1-6}$alkoxy.

In another embodiment $R^1$ is methyl or ethyl.

In another embodiment X is O or S.

In another embodiment X is N(H).

In another embodiment $R^3$ is hydrogen or $C_{1-6}$alkyl.

In another embodiment $R^3$ is hydrogen, methyl, or ethyl.

In another embodiment $R^4$ is hydrogen, $C_{1-6}$alkyl, carbocyclyl, or heterocyclyl, wherein each $C_{1-6}$alkyl, carbocyclyl, and heterocyclyl is optionally substituted with one or more groups $R^b$.

In another embodiment $R^4$ is selected from the group consisting of H, phenyl, methyl, ethyl, cyclohexyl, 4-fluorophenyl, 4-methoxyphenyl, 4-chlorophenyl, 1-methyltriazol-4-yl, 1-phenylpyrazol-4-yl, 1-methylpyrazol-4-yl, pyrid-3-yl, 4-(phenylsulfonyl)phenyl, 4-hydroxyphenyl, 4-(methoxycarbonyl)phenyl, 2-chlorophenyl, 2-fluorophenyl, 4-carboxyphenyl,

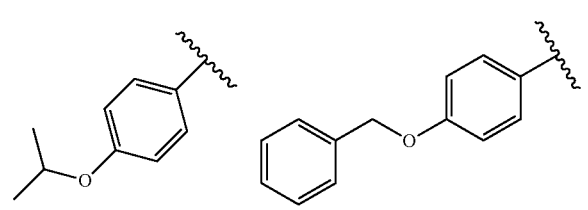

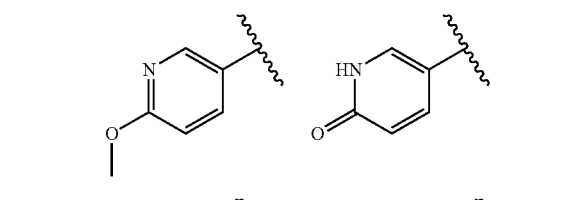

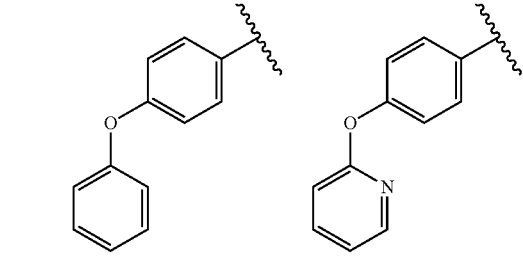

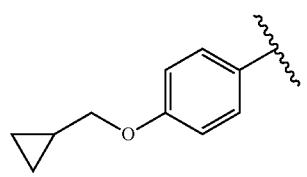

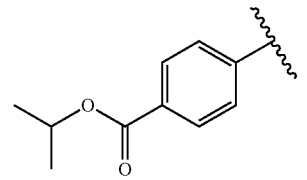

-continued

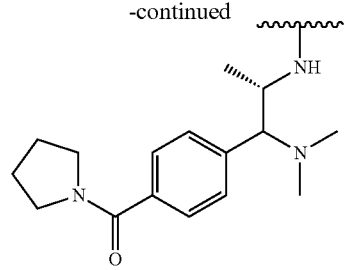

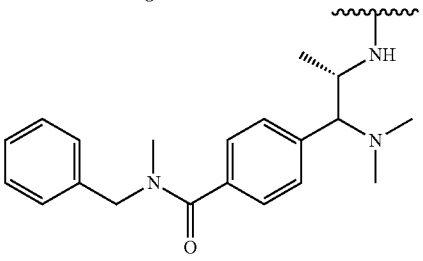

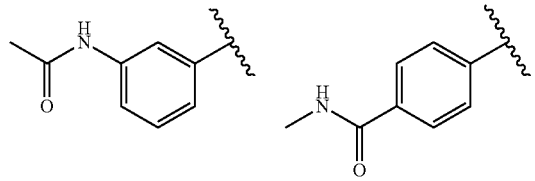

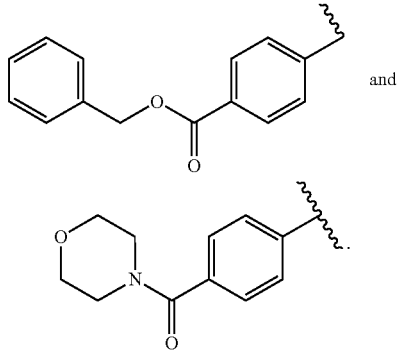

and

In another embodiment $R^3$ and $R^4$ taken together with the atoms to which they are attached form a carbocyclyl or heterocyclyl, which carbocyclyl and heterocyclyl is optionally substituted with one or more groups $R^b$.

In another embodiment $R^3$ and $R^4$ taken together with the atoms to which they are attached form a carbocyclyl or heterocyclyl selected from the group consisting of: cyclohexane, cyclopentane, piperidine, and indane, which carbocyclyl and heterocyclyl is optionally substituted with one or more groups $R^b$.

In another embodiment one $R^e$ taken together with $R^3$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl.

In another embodiment one $R^e$ taken together with $R^3$ and the atoms to which they are attached form an azetidine ring, which ring is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl.

In another embodiment one $R^e$ taken together with $R^4$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl.

In another embodiment one $R^e$ taken together with $R^4$ and the atoms to which they are attached form a heterocyclyl that is selected from the group consisting of pyrrolidine, piperidine, and azepane, which heterocyclyl is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl.

In another embodiment the group:

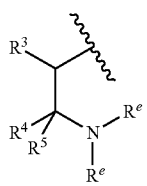

is selected from the group consisting of:

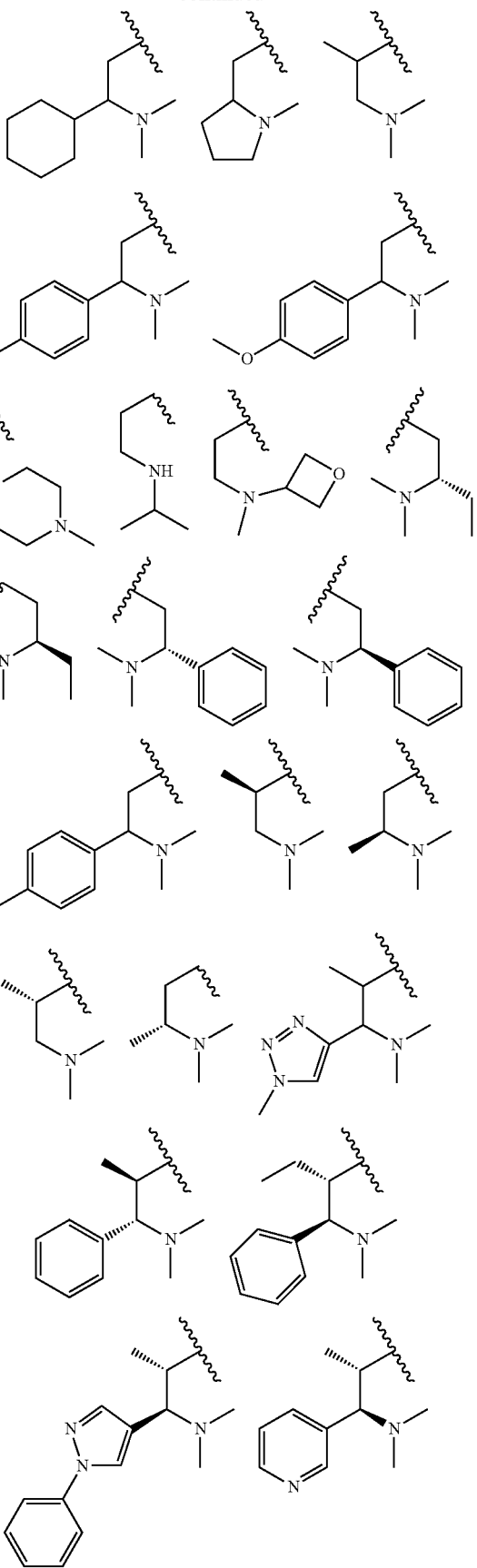

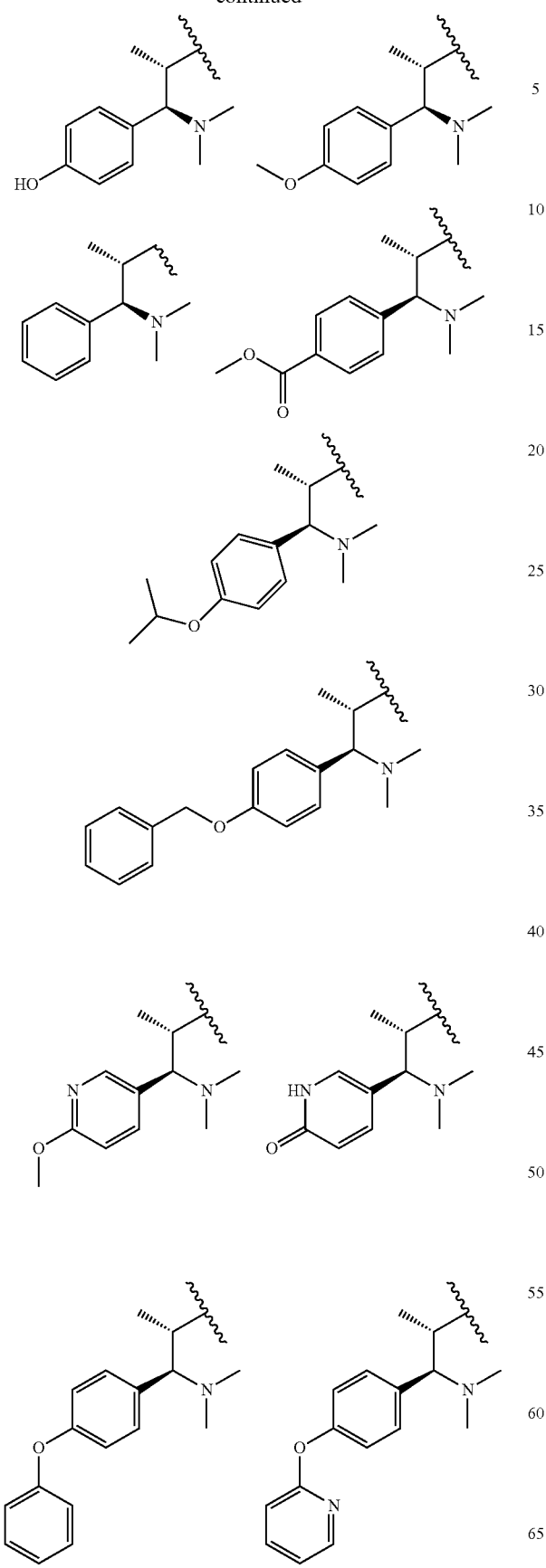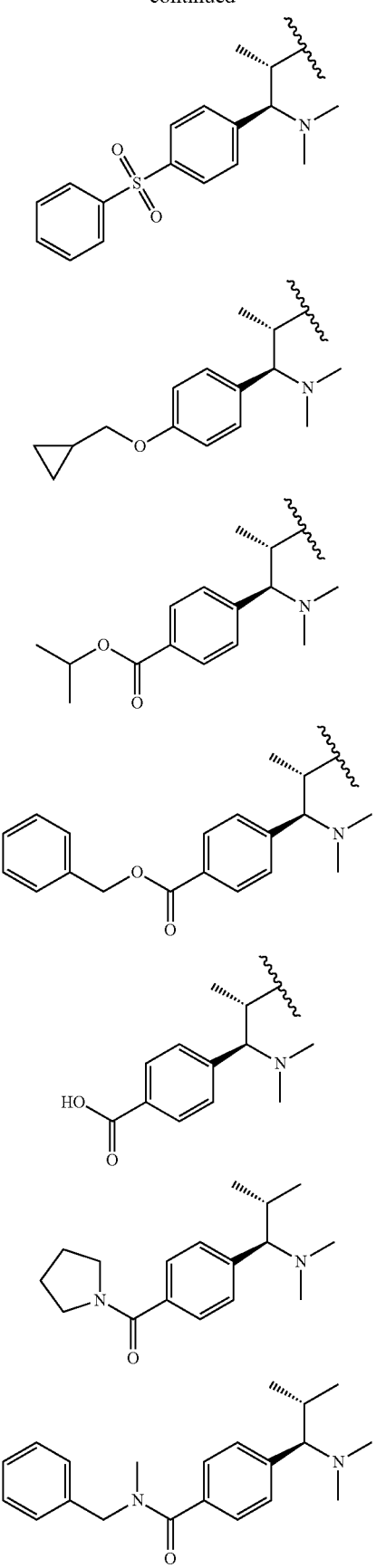

-continued
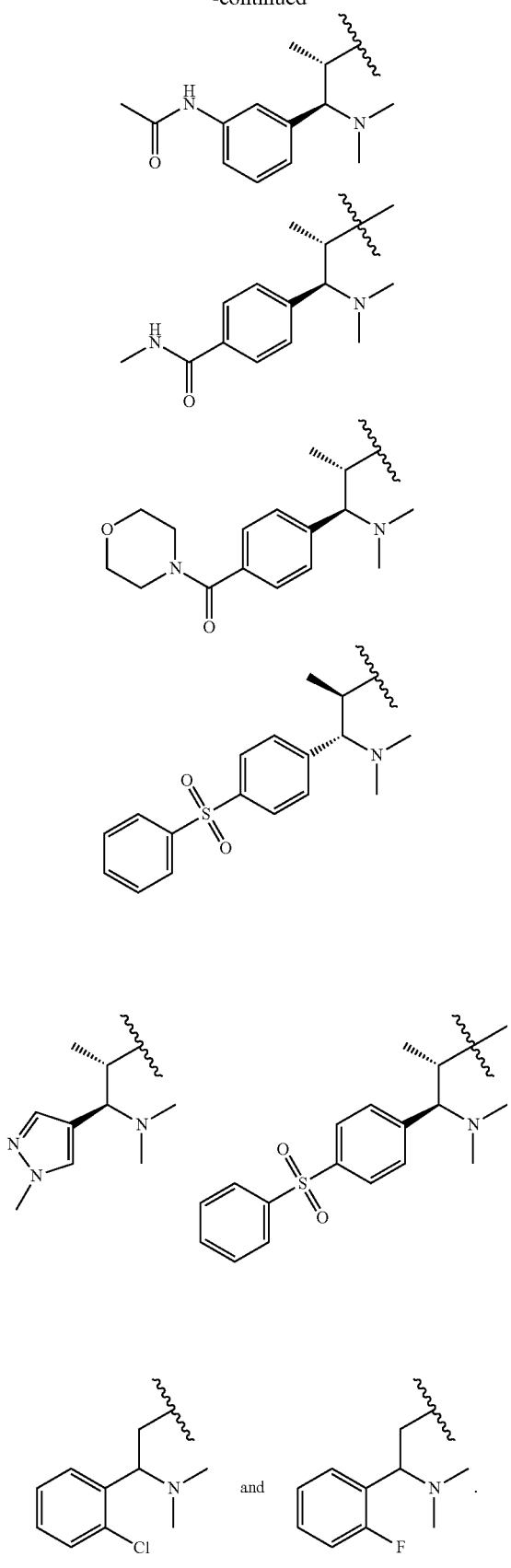
In another embodiment the group:
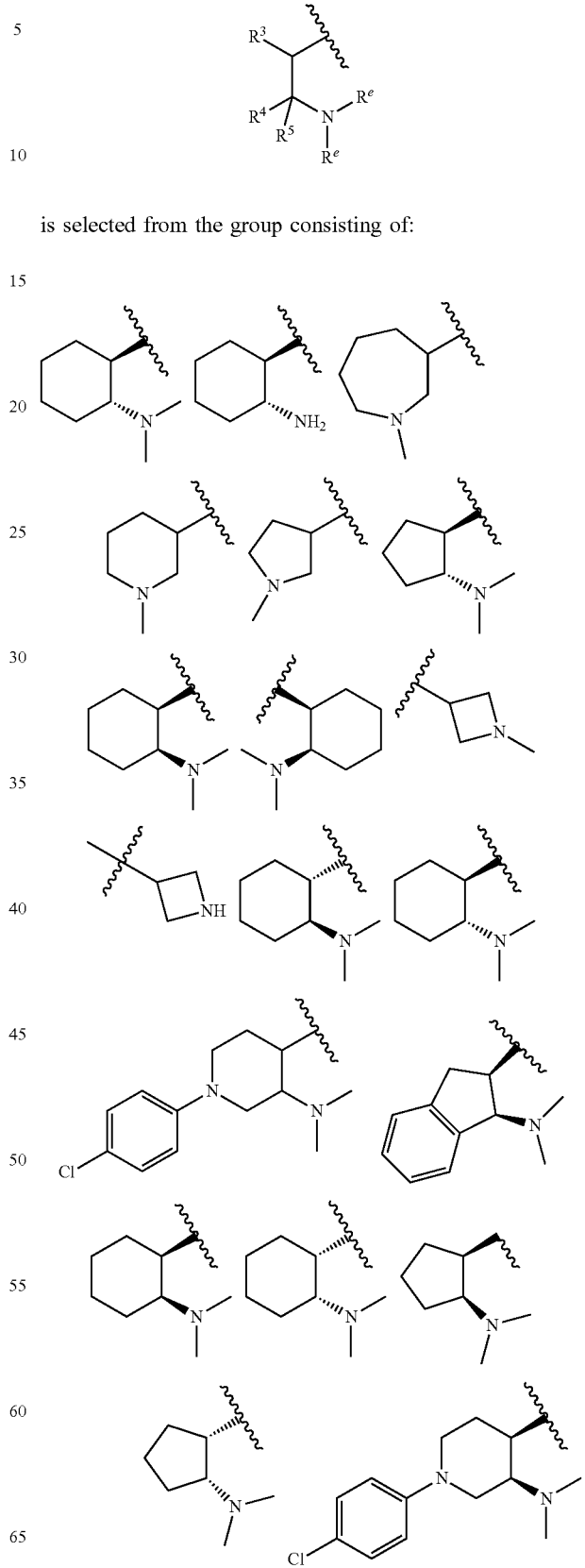
is selected from the group consisting of:

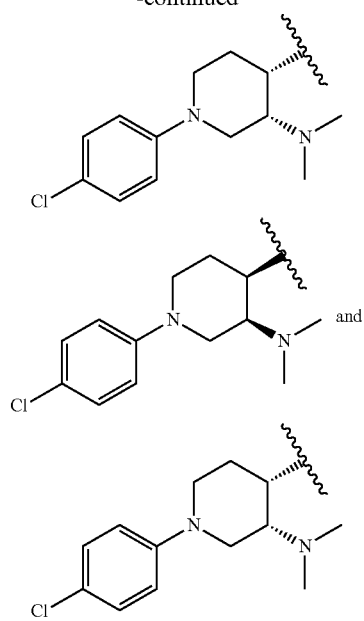
In another embodiment the group:
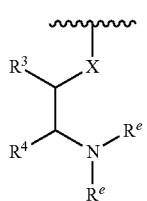
is selected from the group consisting of:
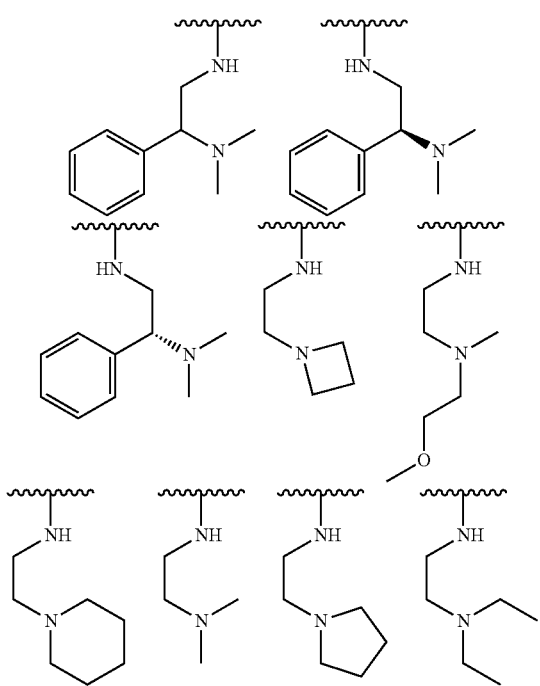
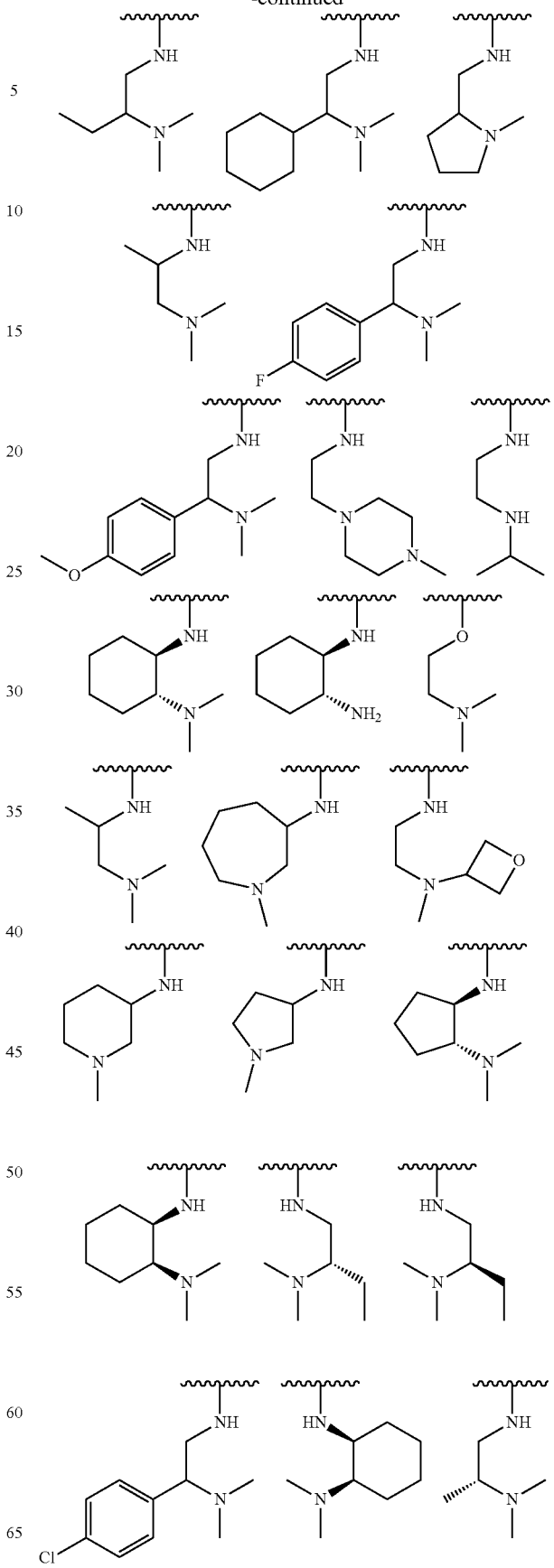

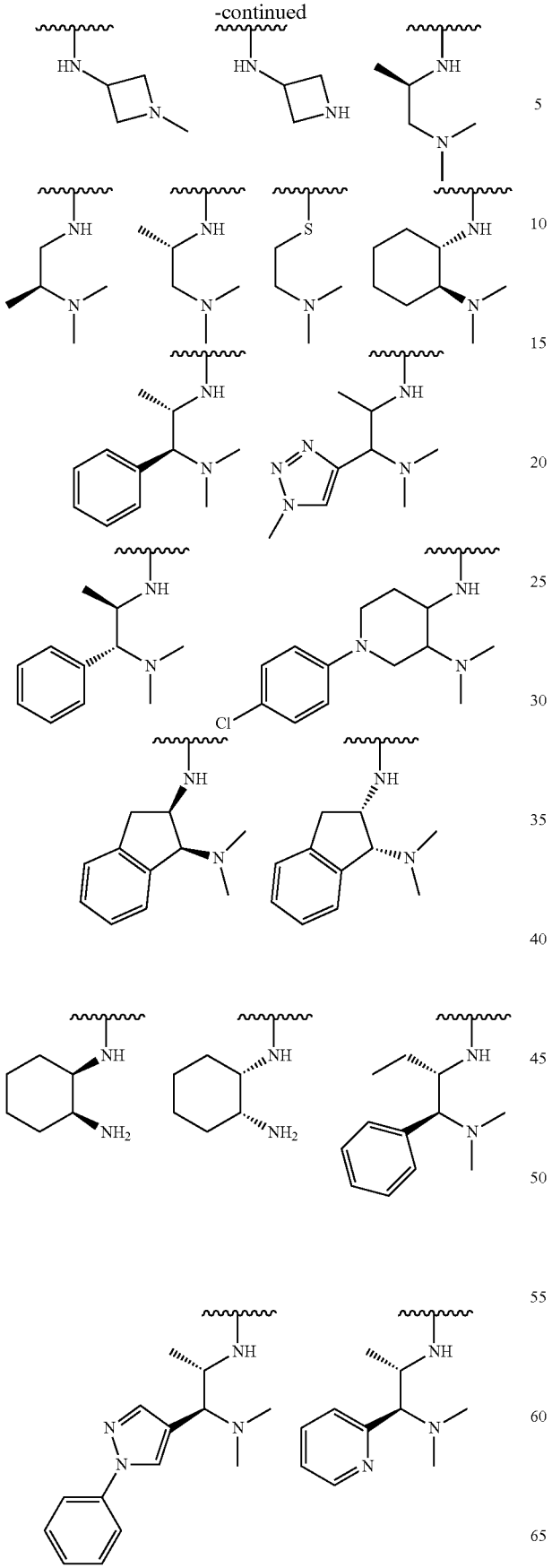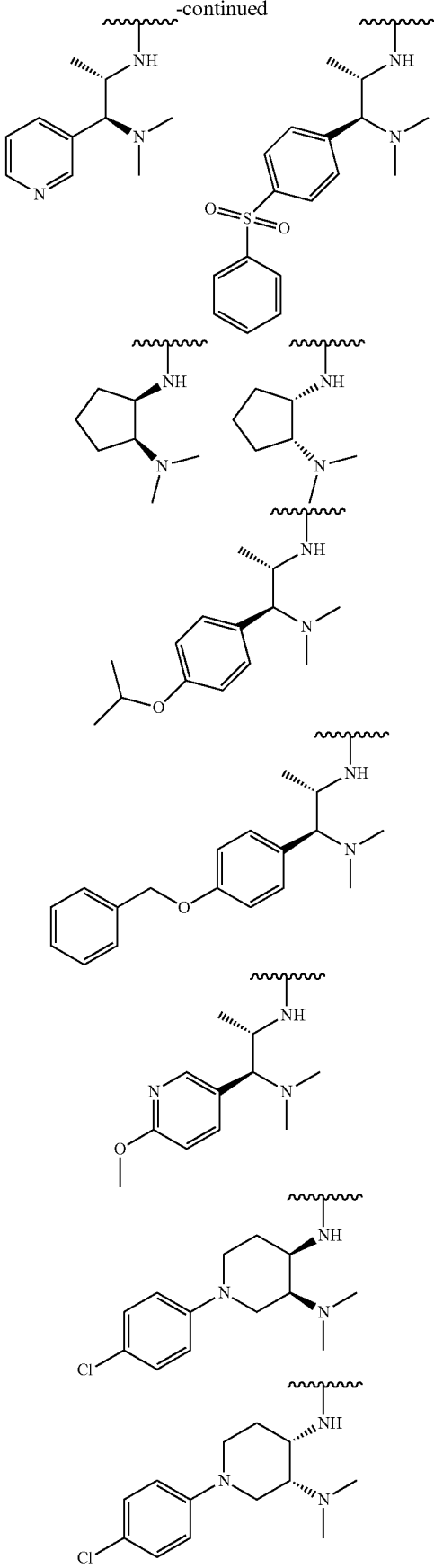

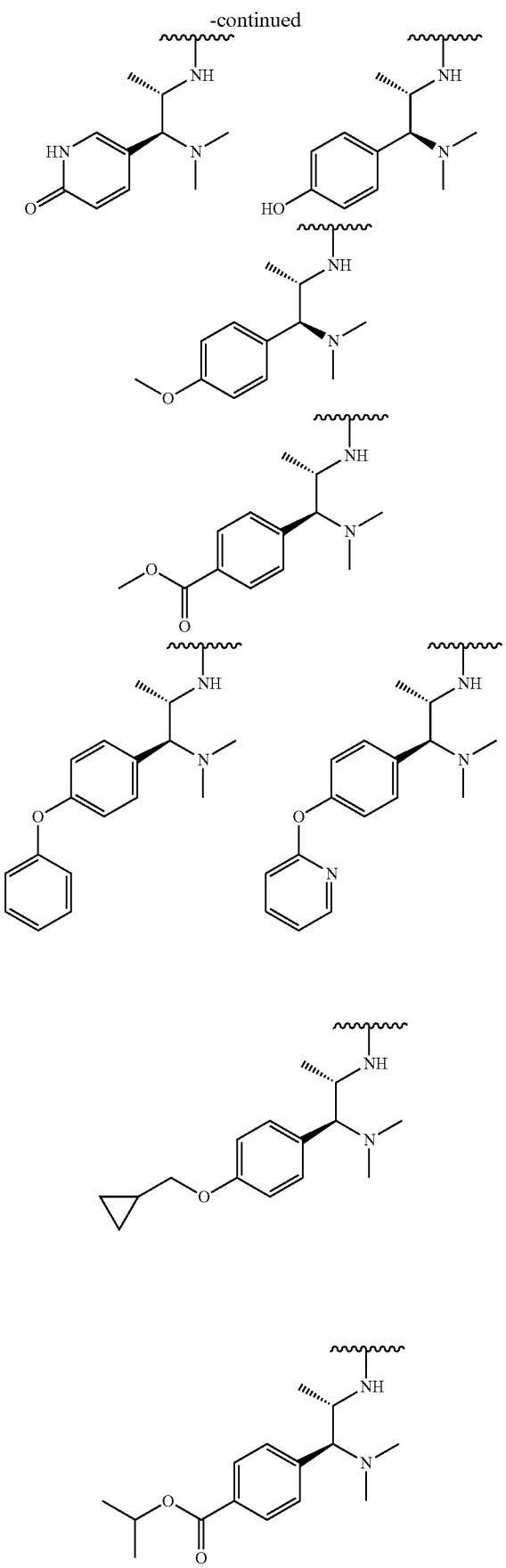
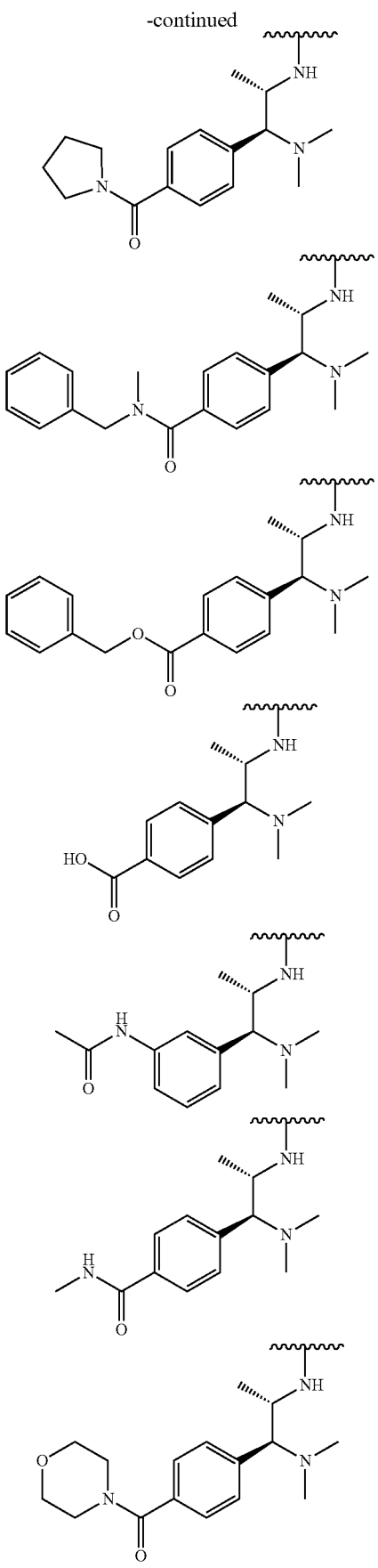

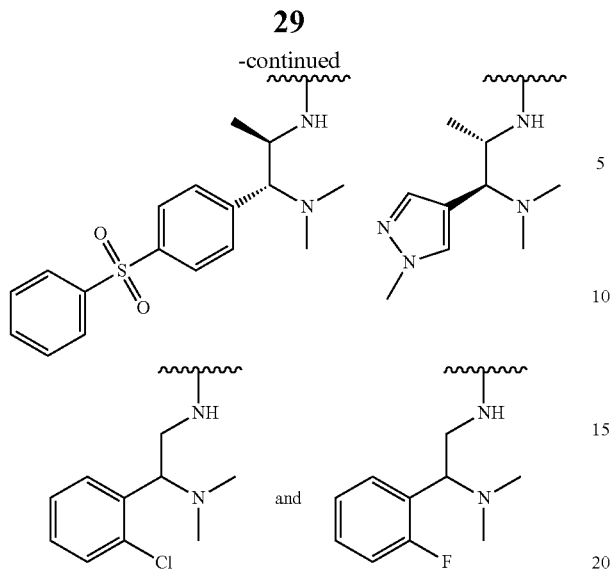
In another embodiment the compound is selected from the group consisting of:
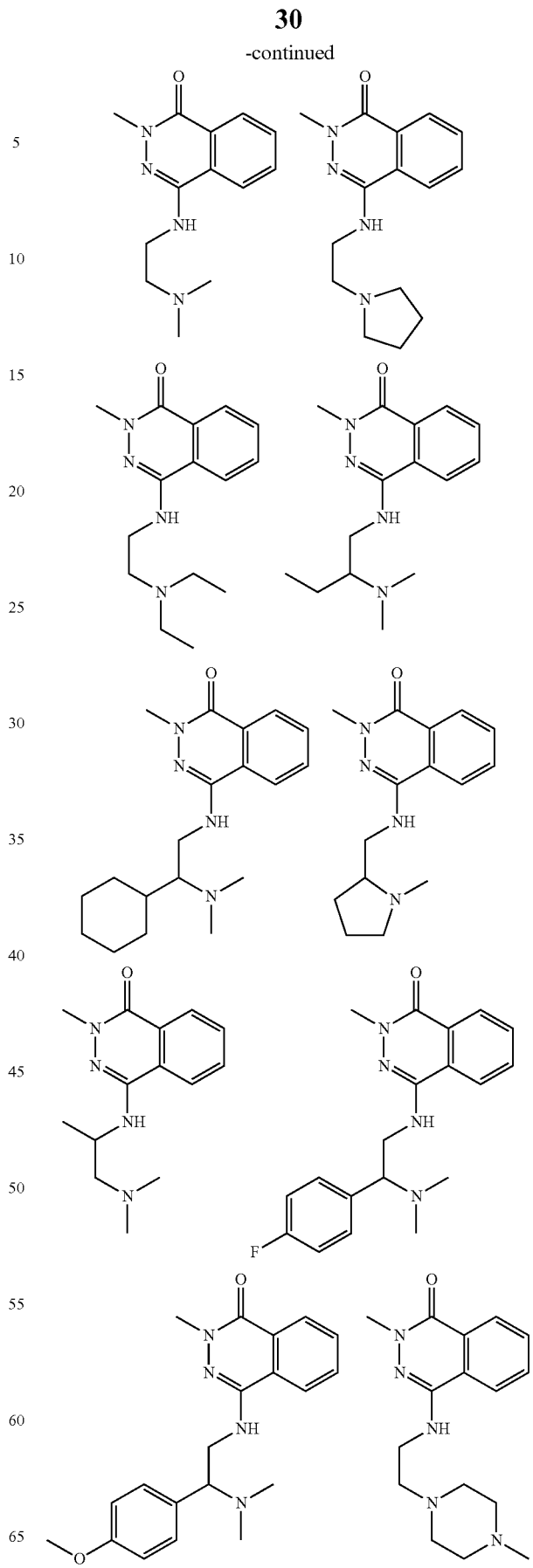

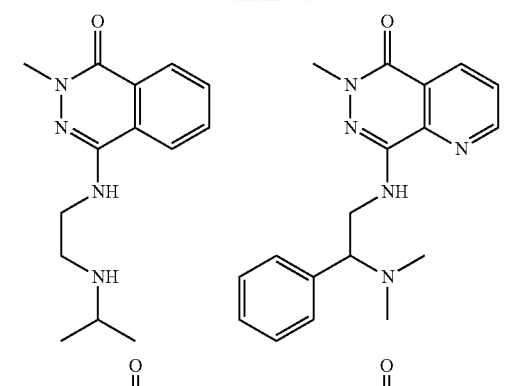
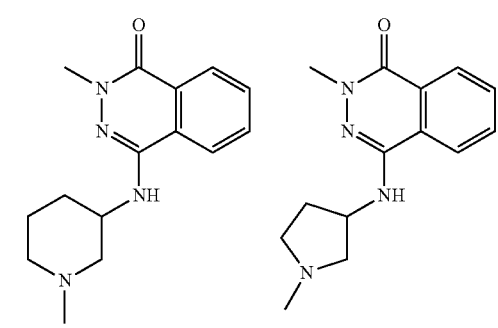
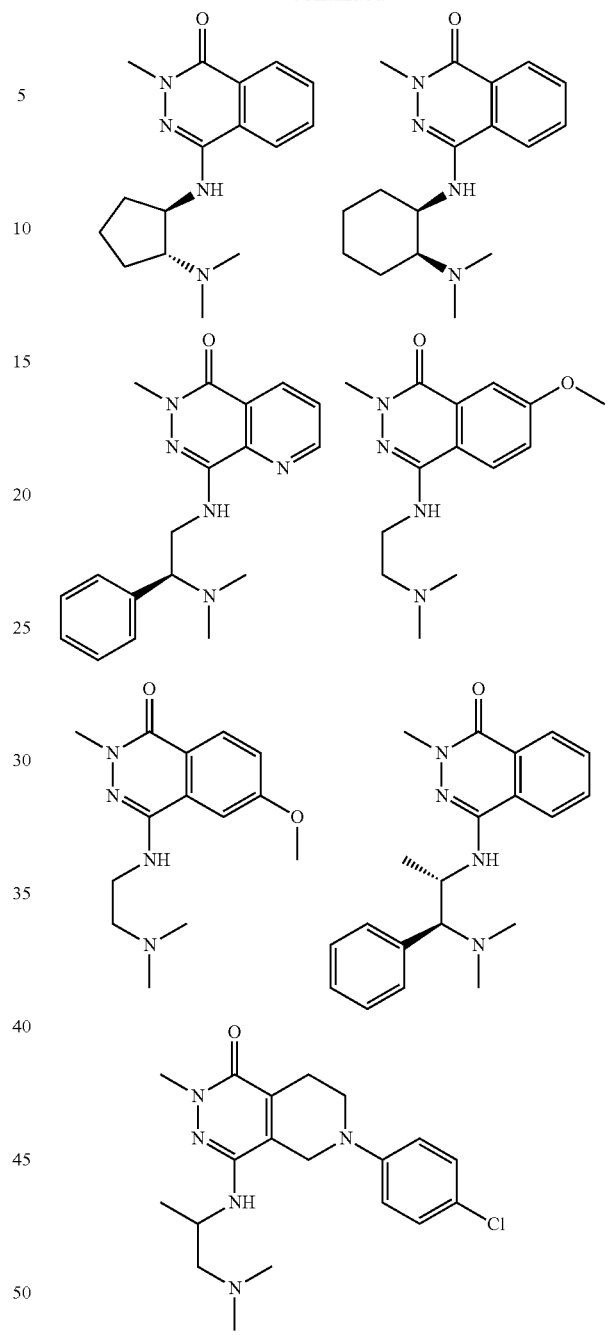
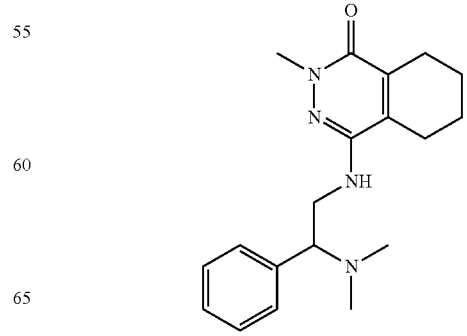

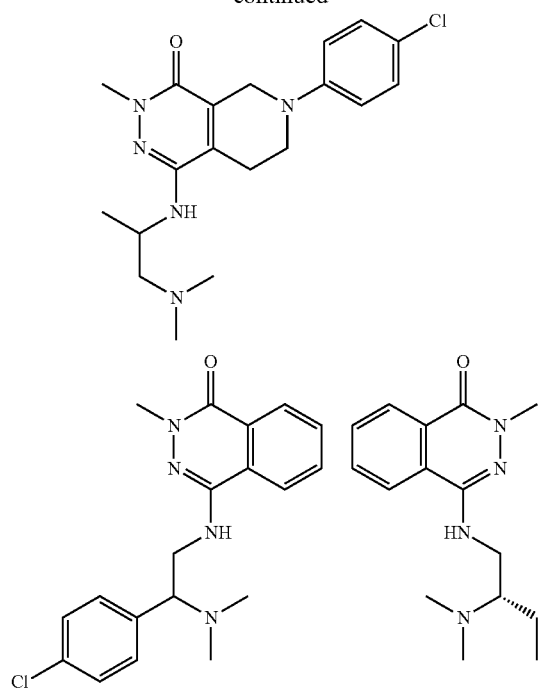
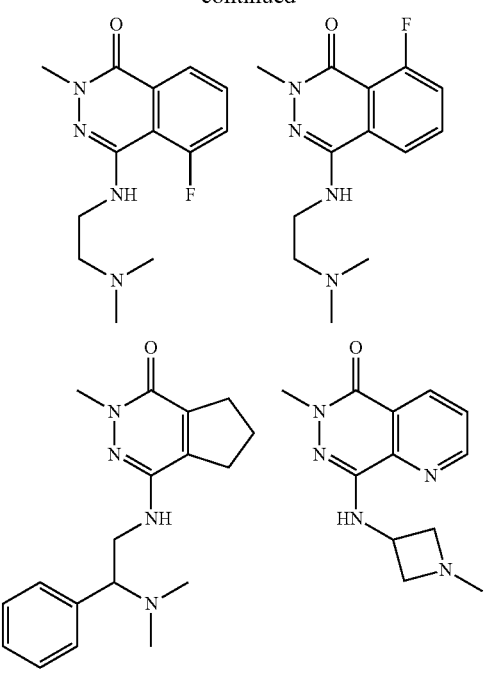
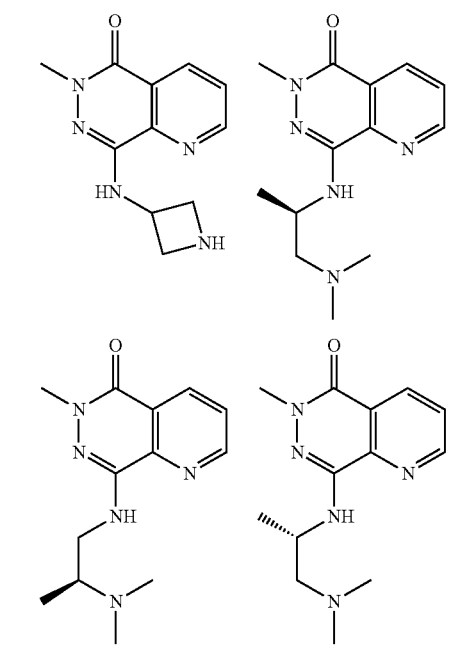
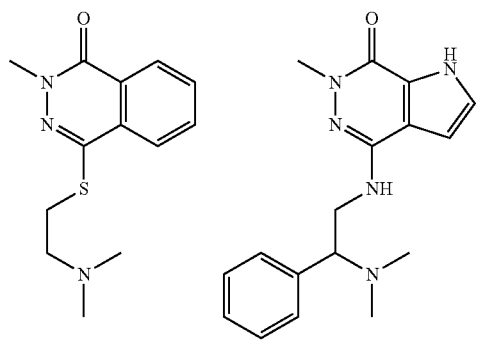

35
-continued
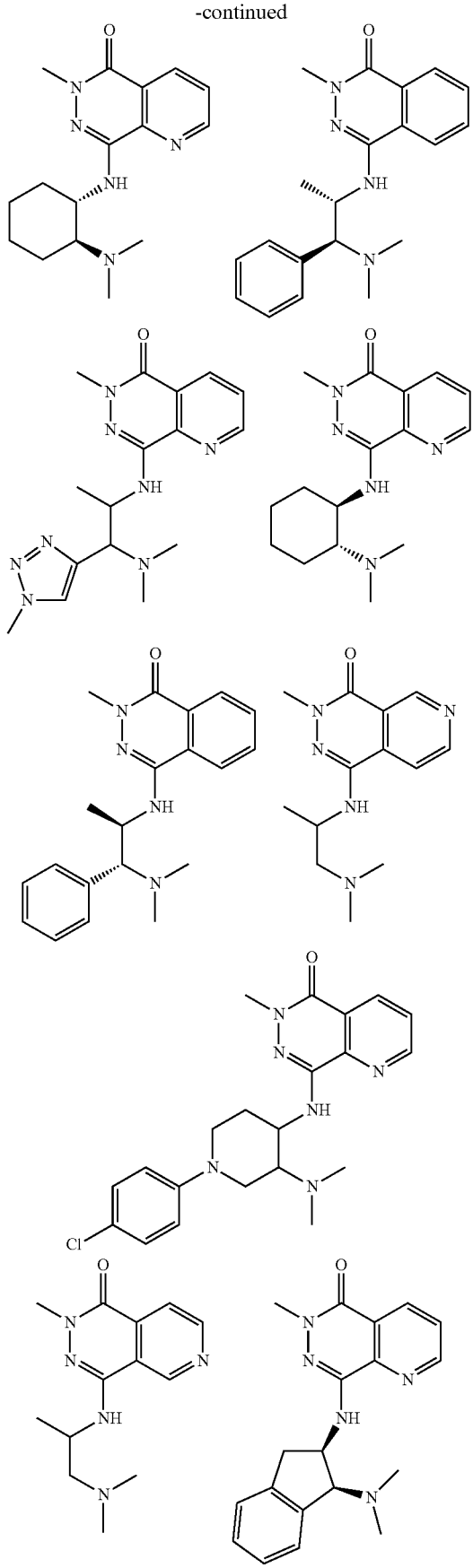
36
-continued
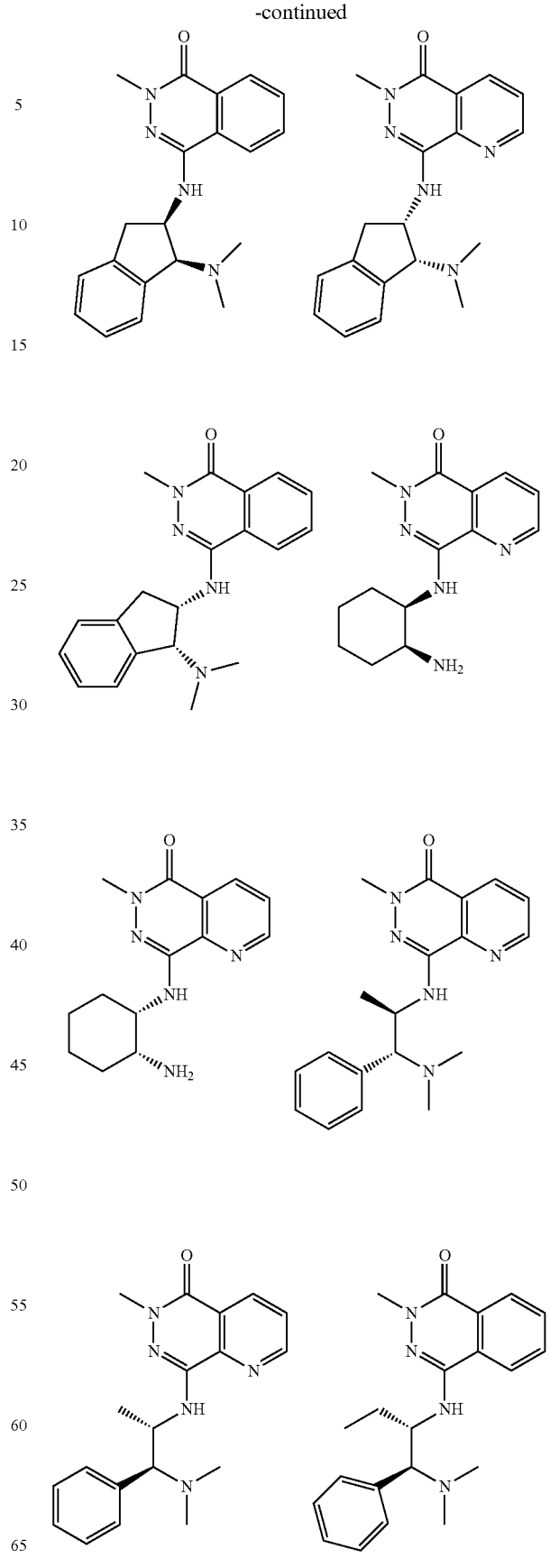

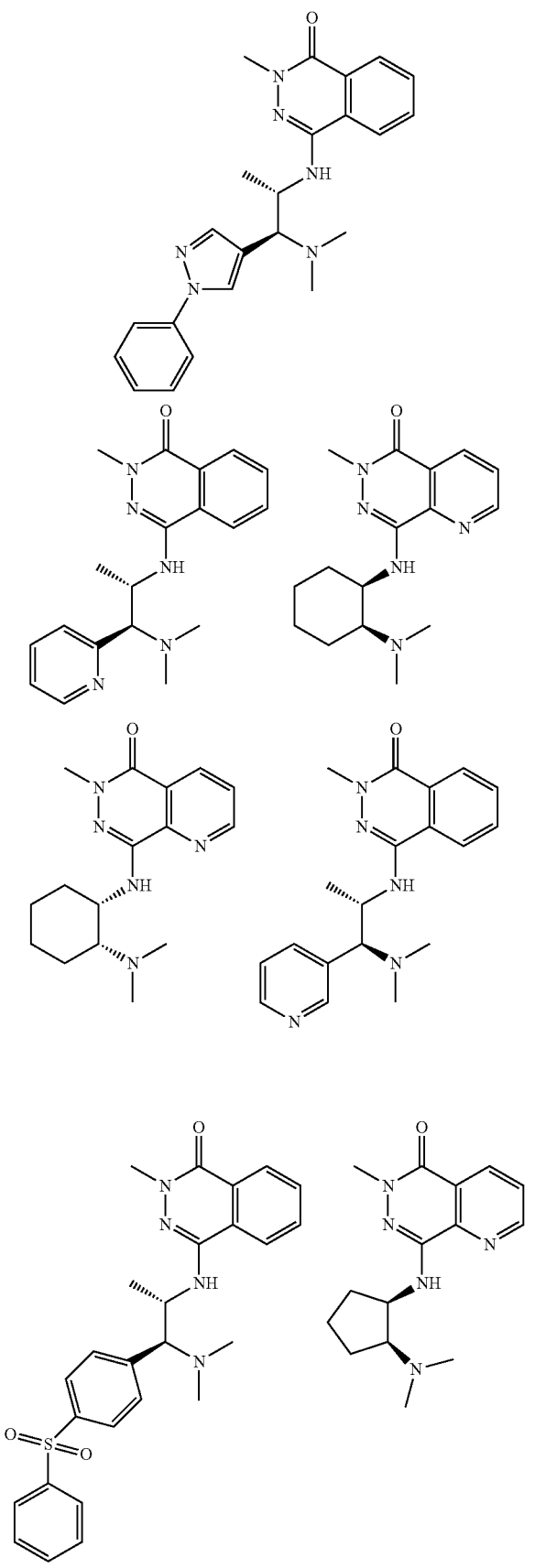
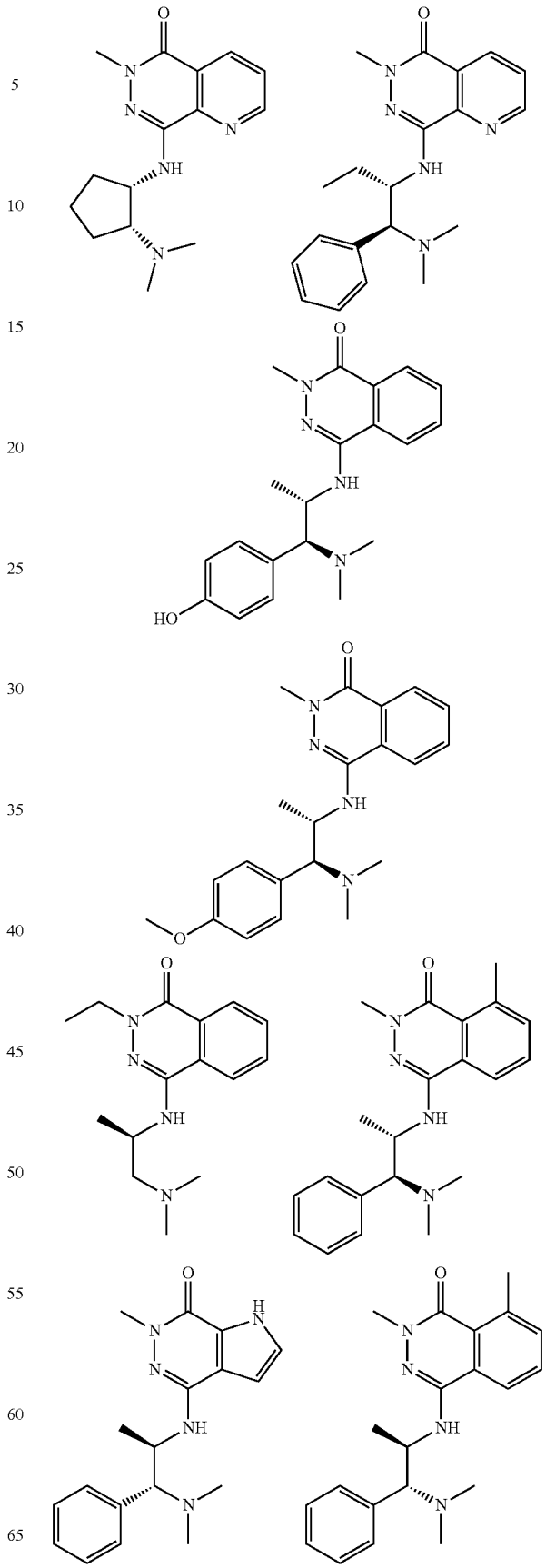

39
-continued
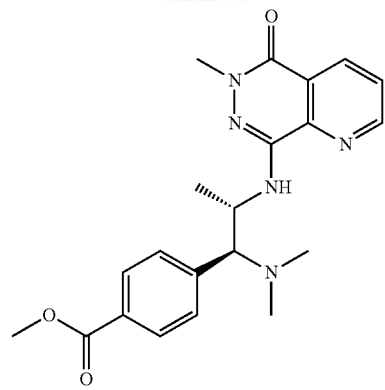
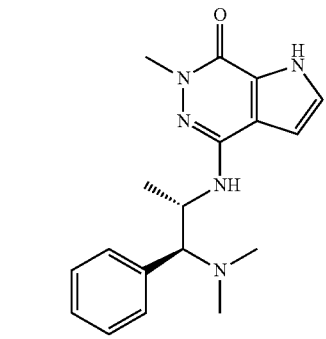
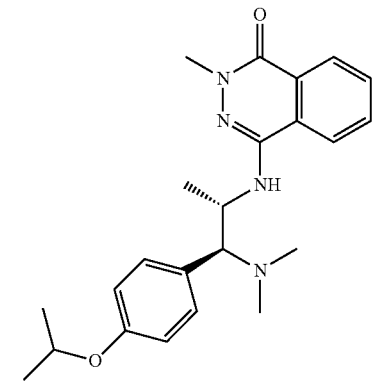
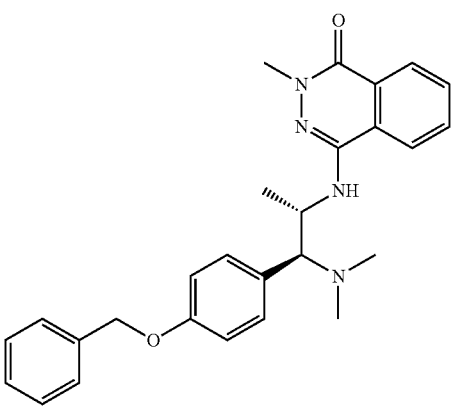
40
-continued
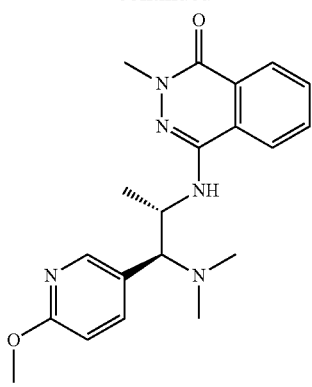
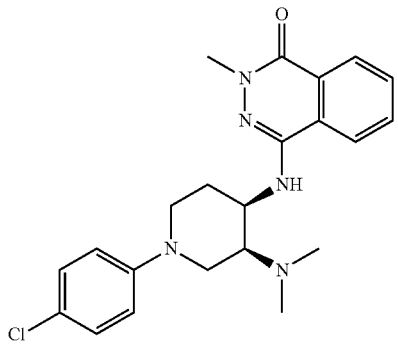
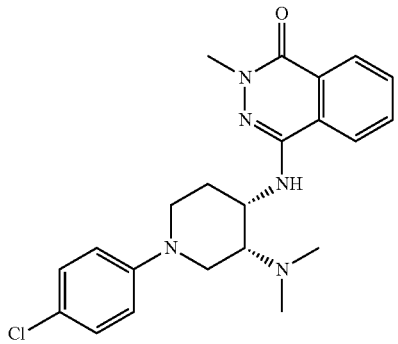
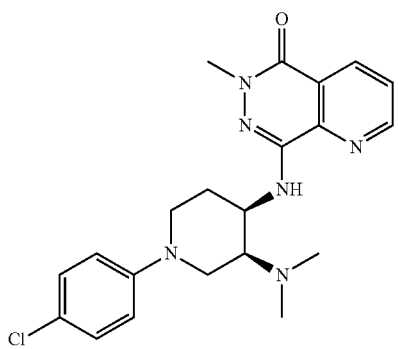

41
-continued
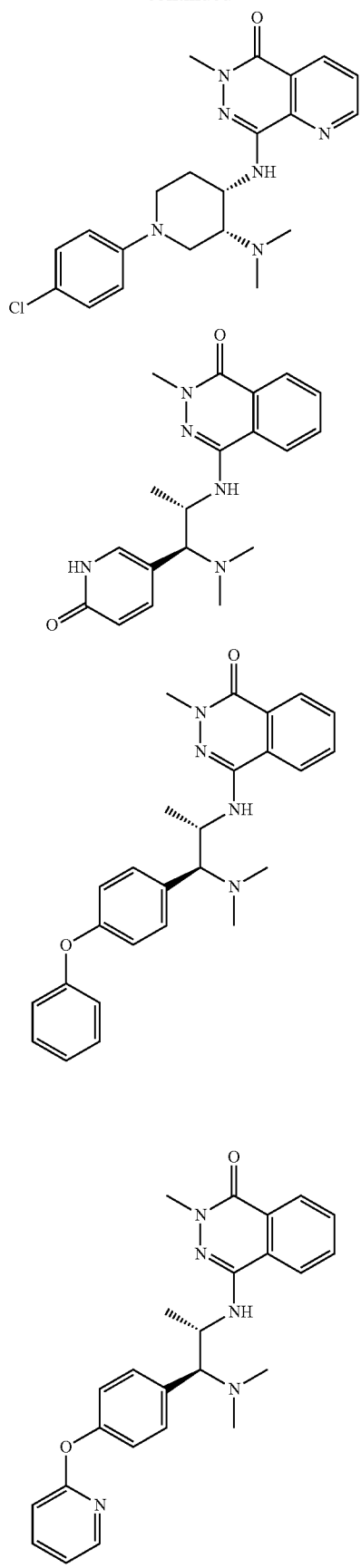
42
-continued
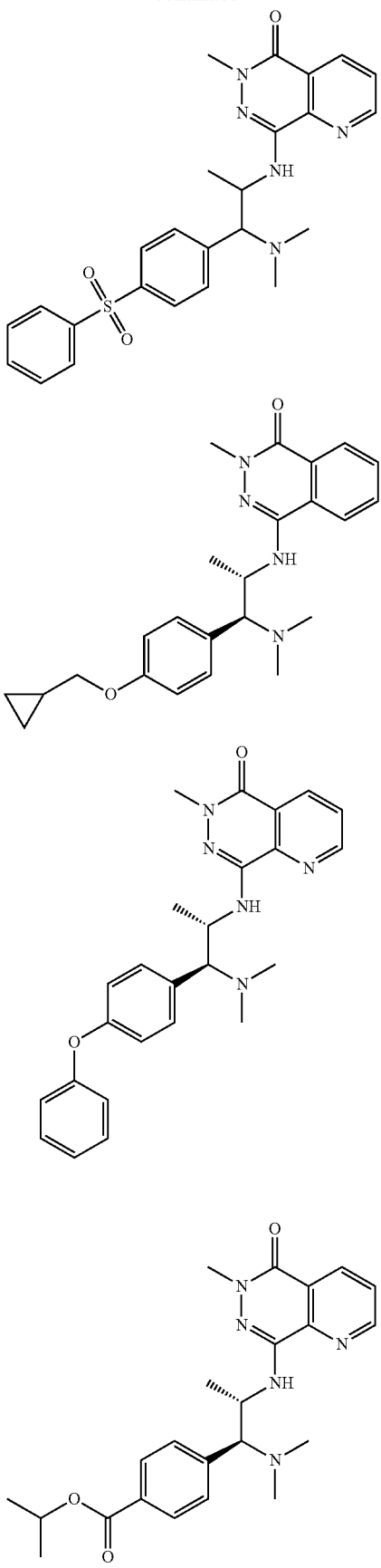

43
-continued
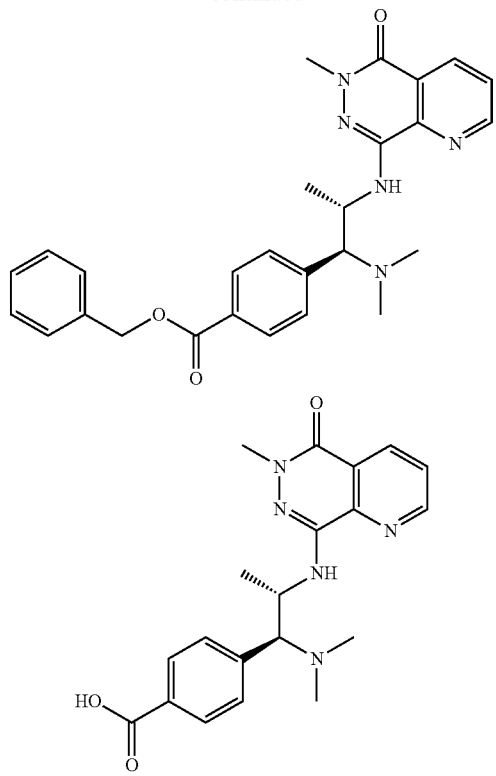
44
-continued
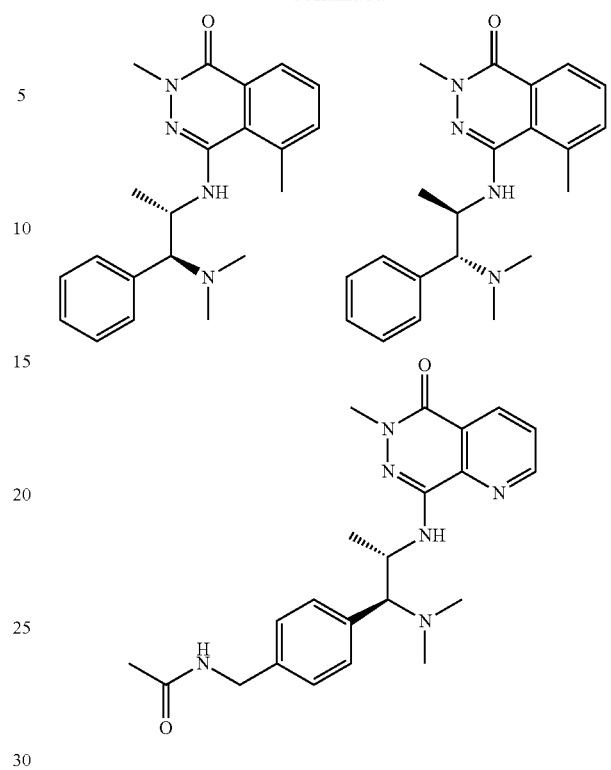
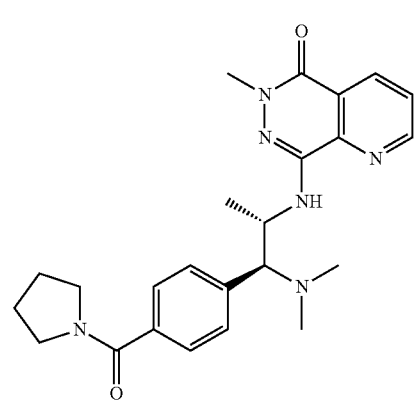
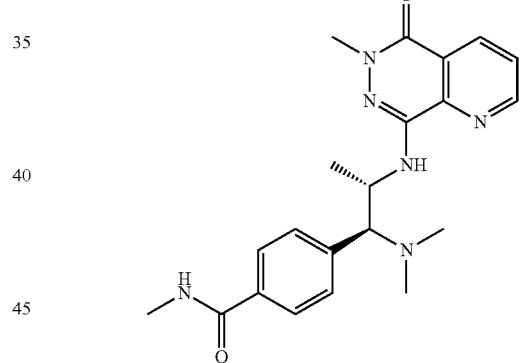
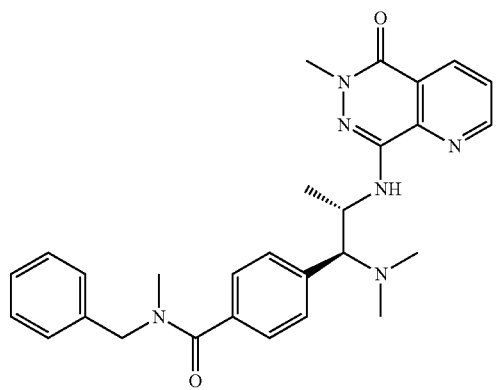
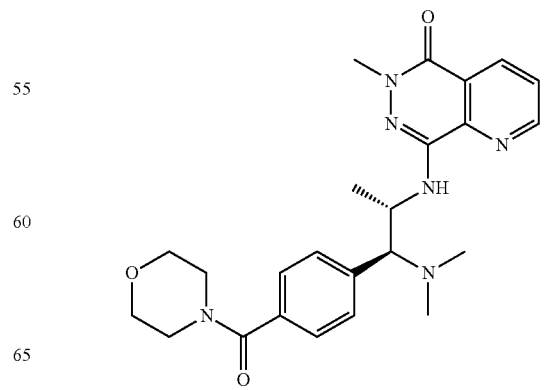

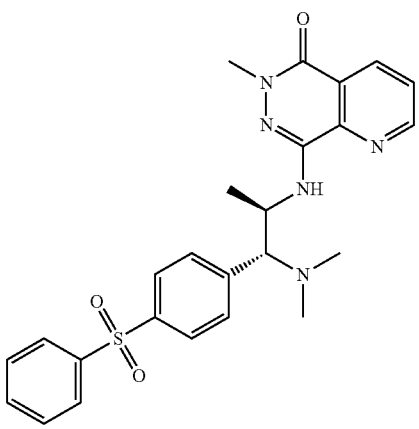

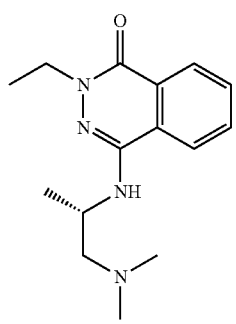

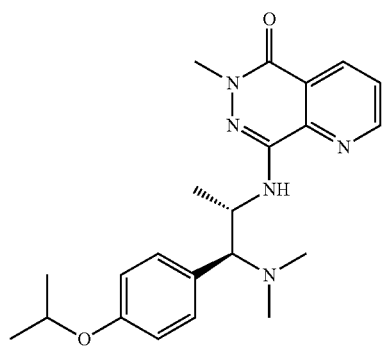

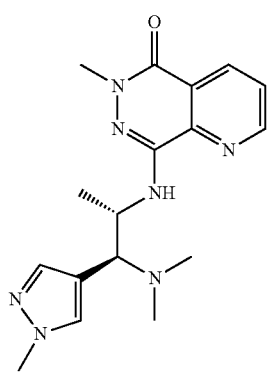

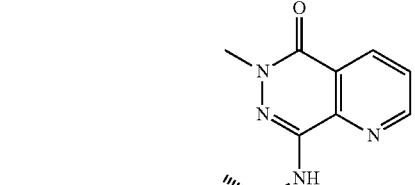

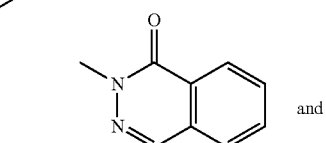

and

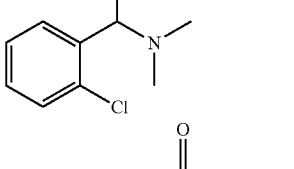

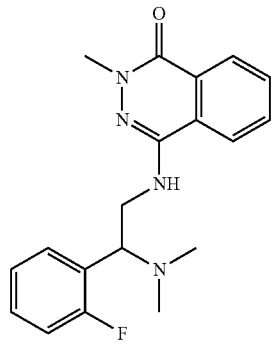 [SMILES: CN(C)C(CNc1nn(C)c(=O)c2ccccc12)c1ccccc1F]

and salts thereof.

In certain embodiments the compound of Formula (I) is a compound as described in the Examples herein, or a freebase or salt thereof.

Uses, Formulation and Administration

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain of PCAF. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof for the inhibition of a bromodomain of PCAF (in vitro or in vivo).

Another embodiment includes a method for treating a PCAFmediated disorder in an animal (e.g., a mammal such as a human) comprising administering a compound of formula (I), or a pharmaceutically acceptable salt thereof to the animal. PCAF mediated disorders include, but are not limited to those disorders described herein.

Another aspect includes the use of a compound of formula (I) or a salt thereof for the inhibition of a bromodomain of GCN5 (in vitro or in vivo).

Another embodiment includes a method for treating a GCN5 mediated disorder in an animal (e.g., a mammal such as a human) comprising administering a compound of formula (I), or a pharmaceutically acceptable salt thereof to the animal.

Another embodiment includes a method of increasing efficacy of a cancer treatment comprising a cytotoxic agent in an animal (e.g., a mammal such as a human) comprising administering to the animal an effective amount of a compound of formula (I) or a pharmaceutically acceptable salt thereof.

Another embodiment includes a method of delaying or preventing development of cancer resistance to a cytotoxic agent in an animal (e.g., a mammal such as a human), comprising administering to the animal a compound of formula (I) or a pharmaceutically acceptable salt thereof.

Another embodiment includes a method of extending the duration of response to a cancer therapy in an animal (e.g., a mammal such as a human), comprising administering to an animal undergoing the cancer therapy a compound of formula (I) or a pharmaceutically acceptable salt thereof, wherein the duration of response to the cancer therapy when the compound of formula (I) or the pharmaceutically acceptable salt thereof is administered is extended over the duration of response to the cancer therapy in the absence of the administration of the compound of formula (I) or the pharmaceutically acceptable salt thereof.

Another embodiment includes a method of treating cancer in an individual comprising administering to the individual (a) a compound of formula (I) or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

PCAF mediated Disorders

A "PCAF mediated disorder" is characterized by the participation of the PCAF in the inception, manifestation of one or more symptoms or disease markers, severity, or progression of a disorder.

PCAF mediated disorders include cancers, including, but not limited to acoustic neuroma, acute leukemia, acute lymphocytic leukemia, acute myelocytic leukemia, acute T-cell leukemia, androgen-responsive prostate cancer, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, drug resistant breast cancer, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric cancer, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pediatric acute lymphoblastic leukemia, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, wnt-dependent breast cancer, testicular tumors, uterine cancer, and Wilms' tumor.

In certain embodiments, the cancer is selected from the group consisting of gastric cancer, lung cancer, non-small cell lung cancer, pancreatic cancer, pediatric acute lymphoblastic leukemia, androgen-responsive prostate cancer, breast cancer, wnt-dependent breast cancer, drug-resistant breast cancer, estrogen-receptor positive breast cancer, leukemia, neuroblastoma, colon cancer, and cervical cancer. In certain embodiments, the cancer is lung cancer. In certain embodiments, the cancer is pancreatic cancer. In certain embodiments, the cancer is breast cancer. In certain embodiments, the cancer is leukemia. In certain embodiments, the cancer is colon cancer. In certain embodiments, the cancer is cervical cancer.

PCAF mediated disorders also include inflammatory diseases, inflammatory conditions, and autoimmune diseases, including, but not limited to: Addison's disease, acute gout, Alzheimer's disease (inflammatory-mediated neurotoxicity), ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, *Polyarteritis nodosa*, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In some embodiments, the disorder is an autoimmune disease. In some embodiments, the disorder is asthma.

PCAF mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; HIV infection; obesity; osteoporosis, dyslipidemia; hypercholesterolemia; Alzheimer's disease; metabolic syndrome; hepatic steatosis; type II diabetes; insulin resistance; diabetic retinopathy; osteoporosis; obesity, and parasitic infection (e.g., *Toxoplasma gondii*). In some embodiments, the disorder is osteoporosis. In some embodiments, the disorder is obesity. In some embodiments, the disorder is HIV infection. In some embodiments, the disorder is parasitic infection.

GCN5 Mediated Disorders

A "GCN5 mediated disorder" is characterized by the participation of the GCN5 in the inception, manifestation of one or more symptoms or disease markers, severity, or progression of a disorder.

GCN5 mediated disorders include cancers, including, but not limited to acoustic neuroma, acute leukemia, acute lymphocytic leukemia, acute myelocytic leukemia, acute T-cell leukemia, androgen-responsive prostate cancer, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, drug resistant breast cancer, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric cancer, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pediatric acute lymphoblastic leukemia, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, wnt-dependent breast cancer, testicular tumors, uterine cancer, and Wilms' tumor.

In certain embodiments, the cancer is selected from the group consisting of gastric cancer, lung cancer, non-small cell lung cancer, pancreatic cancer, pediatric acute lymphoblastic leukemia, androgen-responsive prostate cancer, breast cancer, wnt-dependent breast cancer, drug-resistant breast cancer, estrogen-receptor positive breast cancer, leukemia, neuroblastoma, colon cancer, and cervical cancer. In certain embodiments, the cancer is lung cancer. In certain embodiments, the cancer is pancreatic cancer. In certain embodiments, the cancer is breast cancer. In certain embodiments, the cancer is leukemia. In certain embodiments, the cancer is colon cancer. In certain embodiments, the cancer is cervical cancer.

GCN5 mediated disorders also include inflammatory diseases, inflammatory conditions, and autoimmune diseases, including, but not limited to: Addison's disease, acute gout, Alzheimer's disease (inflammatory-mediated neurotoxicity), ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, *Polyarteritis nodosa*, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In some embodiments, the disorder is an autoimmune disease. In some embodiments, the disorder is asthma.

GCN5 mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; HIV infection; obesity; osteoporosis, dyslipidemia; hypercholesterolemia; Alzheimer's disease; metabolic syndrome; hepatic steatosis; type II diabetes; insulin resistance; diabetic retinopathy; osteoporosis; obesity, and parasitic infection (e.g., *Toxoplasma gondii*). In some embodiments, the disorder is osteoporosis. In some embodiments, the disorder is obesity. In some embodiments, the disorder is HIV infection. In some embodiments, the disorder is parasitic infection.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{21}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/ Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multitargeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983

(Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-ILIS, BIRB-796, SCIO-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe Rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid(e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(Alfa Wassermann/J&J), interferon 1A-1F (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-10, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/ chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, an HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildaglliptin, sitaglliptin, saxagliptin, linagliptin, alogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynyl-phenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)

ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

The invention will now be illustrated by the following non-limiting Examples.

EXEMPLIFICATION

Experimental Procedure for Intermediate A

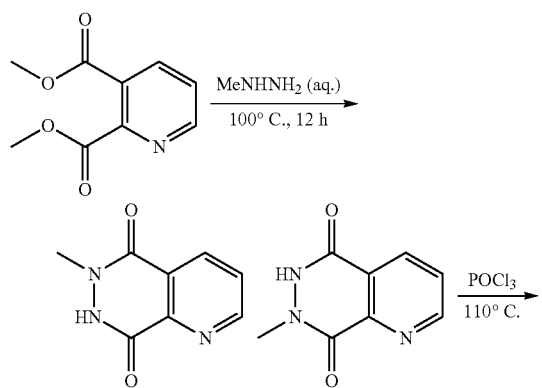

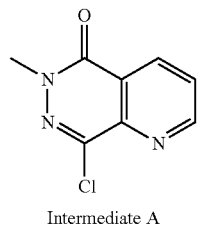

Intermediate A

Step 1:

6-methyl-6,7-dihydropyrido[2,3-d]pyridazine-5,8-dione

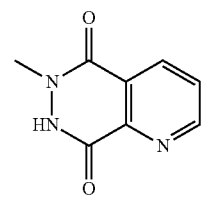

A mixture of dimethyl pyridine-2,3-dicarboxylate (100.0 g, 512.37 mmol) in methylhydrazine (40% aq., 1000 mL) was heated at reflux for 15 h, at which time LCMS indicated that the reaction had gone to completion. The mixture was concentrated under reduced pressure to give a mixture of the title compound and 7-methyl-6,7-dihydropyrido[2,3-d]pyridazine-5,8-dione (90.0 g, 99% yield) as a yellow solid. This crude material was used in the next step without further purification. LCMS M/Z (M+H) 178. (ratio of desired product:
by-product=4:3)

Step 2:

8-chloro-6-methylpyrido[2,3-d]pyridazin-5(6H)-one

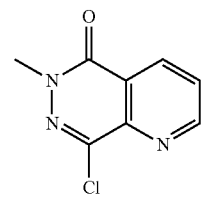

A mixture of 6-methyl-6,7-dihydropyrido[2,3-d]pyridazine-5,8-dione and 7-methyl-6,7-dihydropyrido[2,3-d]pyridazine-5,8-dione (90.0 g, 508.02 mmol) in POCl$_3$ (900 mL) was heated at reflux for 15 h, at which time LCMS indicated that the reaction had gone to completion. The mixture was concentrated under reduced pressure. The residue was slowly quenched by addition of a saturated aqueous solution of NaHCO$_3$ (1000 mL), and then extracted with ethyl acetate (3×1000 mL). The combined organic extracts were dried over Na$_2$SO$_4$ and concentrated under reduced pressure. The residue was purified by silica gel chromatography (petroleum ether:ethyl acetate=1:1) to give the title compound (12.5 g, 13% yield) as a light red solid. $^1$H NMR (400 MHz, DMSO-d6) δ 9.20 (d, J=3.6 Hz, 1H), 8.65 (d, J=7.2 Hz, 1H), 7.96 (dd, J=4.8, 6.4 Hz 1H), 3.72 (s, 3H). LCMS M/Z (M+H) 196.

Experimental Procedure for Intermediates B and C

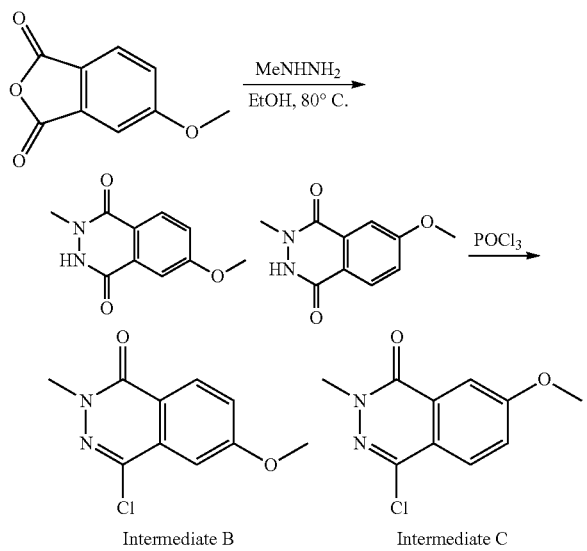

Intermediate B  Intermediate C

Step 1:

6-methoxy-2-methyl-2,3-dihydrophthalazine-1,4-dione and 7-methoxy-2-methyl-2,3-dihydrophthalazine-1,4-dione

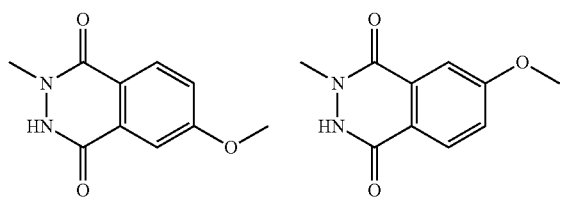

A mixture of 5-methoxyisobenzofuran-1,3-dione (4.0 g, 22.45 mmol) and methylhydrazine (40% aq., 7.76 g, 67.36 mmol) in ethanol (80 mL) was heated at reflux for 15 h, at which time LCMS indicated that the reaction had gone to completion. The mixture was concentrated under reduced pressure to give the title compound (3.60 g, 78% yield) (2:1 ratio of regioisomers) as a yellow solid. This crude material was used in the next step without further purification. LCMS M/Z (M+H) 207.

Step 2:

4-chloro-6-methoxy-2-methylphthalazin-1(2H)-one and 4-chloro-7-methoxy-2-methylphthalazin-1(2H)-one

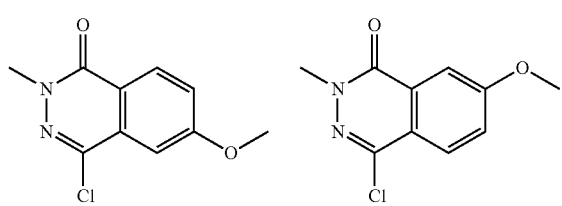

A mixture of 6- and 7-methoxy-2-methyl-2,3-dihydrophthalazine-1,4-dione (2.7 g, 13.09 mmol) in POCl₃ (50 mL) was heated at reflux for 15 h, at which time LCMS indicated that the reaction had gone to completion. The mixture was concentrated under reduced pressure, the residue was quenched by addition of a saturated aqueous solution of NaHCO₃ (100 mL), and then extracted with ethyl acetate (3×100 mL). The combined organic extracts were dried over Na₂SO₄ and concentrated under reduced pressure. The residue was purified by silica gel chromatography (petroleum ether:Ethyl acetate=5:1) to give the title compounds (1.1 g, 37% yield) (2:1 ratio of regioisomers) as a white solid. LCMS M/Z (M+H) 225.

Experimental Procedure for Intermediates D and E

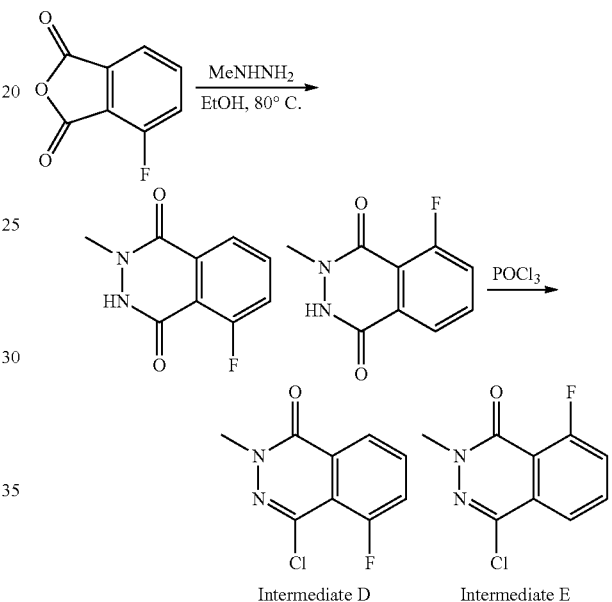

Intermediate D  Intermediate E

Step 1:

5-fluoro-2-methyl-2,3-dihydrophthalazine-1,4-dione and 8-fluoro-2-methyl-2,3-dihydrophthalazine-1,4-dione

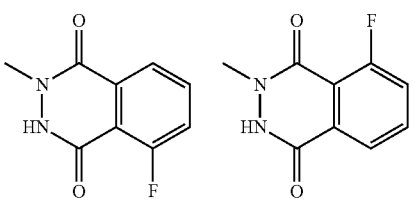

A mixture of 4-fluoroisobenzofuran-1,3-dione (5.0 g, 30.10 mmol) and methylhydrazine (40% aq., 3.5 g, 30.10 mmol) in ethanol (100 mL) was heated at reflux for 15 h, at which time LCMS indicated that the reaction had gone to completion. The mixture was concentrated under reduced pressure to give the mixture of title compounds (3.5 g, 60% yield) (2:1 ratio of regioisomers) as a yellow solid. This crude material was used in the next step without further purification. LCMS M/Z (M+H) 195.

Step 2:

4-chloro-5-fluoro-2-methylphthalazin-1(2H)-one and
4-chloro-8-fluoro-2-methylphthalazin-1(2H)-one

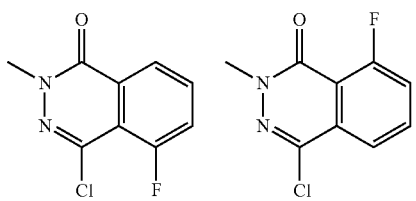

A mixture of 5 or 8-fluoro-2-methyl-2,3-dihydrophthalazine-1,4-dione (3.5 g, 18.03 mmol) in $POCl_3$ (50 mL) was heated at reflux for 15 h, at which time LCMS indicated that the reaction had gone to completion. The mixture was concentrated under reduced pressure, the residue was quenched by addition a saturated aqueous solution of $NaHCO_3$ (100 mL), and then extracted with ethyl acetate (3×100 mL). The combined organic extracts were dried over $Na_2SO_4$ and concentrated under reduced pressure. The residue was purified by silica gel chromatography (petroleum ether:Ethyl acetate=5:1) to give the title compounds (1.2 g, 31% yield) (2:1 ratio of regioisomers) as a white solid. LCMS M/Z (M+H) 213.

Experimental Procedure for Intermediate F

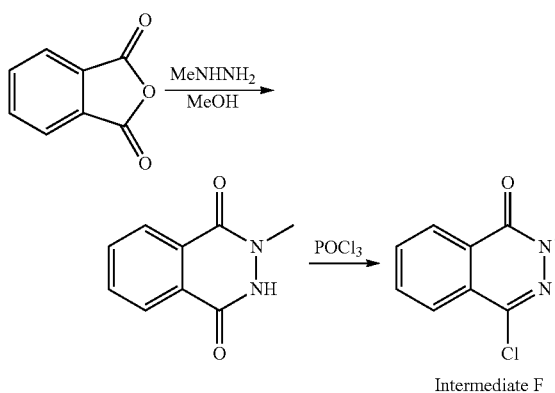

Intermediate F

Step 1:

2-methyl-2,3-dihydrophthalazine-1,4-dione

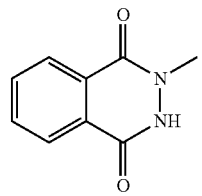

A mixture of isobenzofuran-1,3-dione (100 g, 675.15 mmol) and methylhydrazine (40% aq., 233.29 g, 2.03 mol) in methanol (1000 mL) was heated at reflux for 15 h, at which time LCMS indicated that the reaction had gone to completion. The mixture was concentrated under reduced pressure to give the crude title compound (103.1 g, 87% yield) as a yellow solid. This crude material was used in the next step without further purification. LCMS M/Z (M+H) 177.

Step 2:

4-chloro-2-methylphthalazin-1(2H)-one

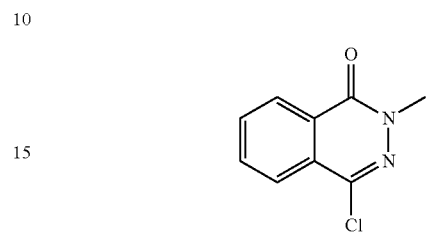

A mixture of 2-methyl-2,3-dihydrophthalazine-1,4-dione (100.0 g, 567.63 mmol) in $POCl_3$ (1000 mL) was heated to reflux for 15 h, at which time LCMS indicated that the reaction had gone to completion. The mixture was concentrated under reduced pressure. The residue was quenched by addition of a saturated aqueous solution of $NaHCO_3$ (300 mL), and then extracted with ethyl acetate (3×300 mL). The combined organic extracts were dried over $Na_2SO_4$ and concentrated under reduced pressure. The resulting residue was purified by silica gel chromatography (petroleum ether: ethyl acetate=5:1) to give the title compound (15.6 g, 14% yield) as a white solid. LCMS M/Z (M+H) 195.

Experimental Procedure for Intermediate G

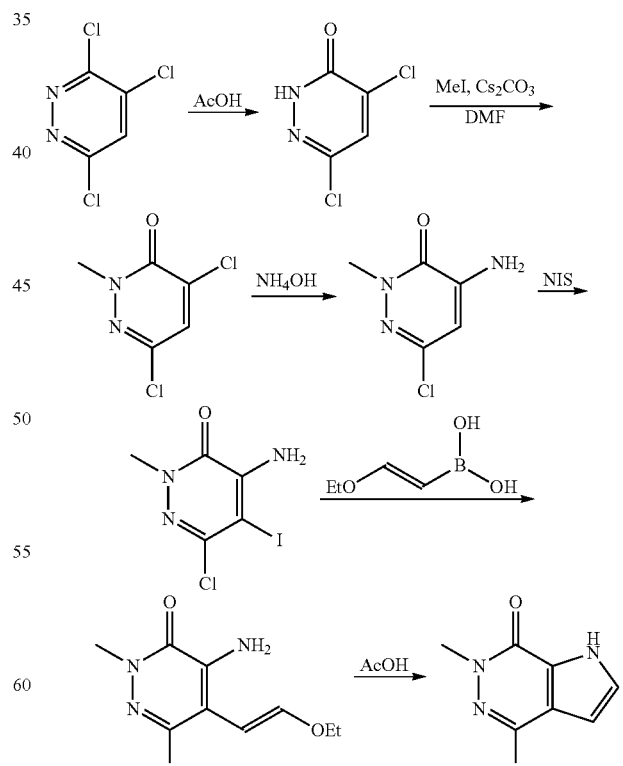

Intermediate G

Step 1:

4,6-dichloropyridazin-3(2H)-one and
5,6-dichloropyridazin-3(2H)-one

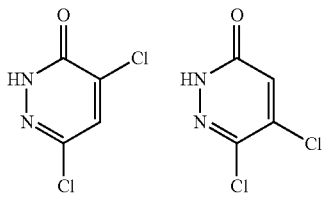 [SMILES: O=c1[nH]nc(Cl)cc1Cl ; O=c1cc(Cl)c(Cl)n[nH]1]

A solution of 3,4,6-trichloropyridazine (20.0 g, 109.04 mmol) in HOAc (100 mL) was heated at 100° C. for 12 h, at which time TLC indicated the reaction had gone to completion. The reaction mixture was concentrated under reduced pressure, and the resulting residue was purified by silica gel chromatography (petroleum ether:Ethyl acetate=1:1) to give the title compounds (11.2 g, 63% yield) (1:1 ratio of regioisomers) as a white solid. LCMS M/Z (M+H) 165.

Step 2:

4,6-dichloro-2-methylpyridazin-3(2H)-one and 5,6-dichloro-2-methylpyridazin-3(2H)-one

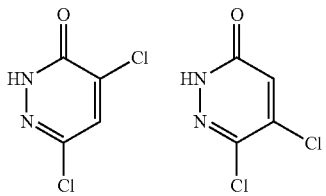 [SMILES: O=c1[nH]nc(Cl)cc1Cl ; O=c1cc(Cl)c(Cl)n[nH]1]

To a suspension of 4,6-dichloropyridazin-3(2H)-one and 5,6-dichloropyridazin-3(2H)-one (11.2 g, 67.89 mmol), and $Cs_2CO_3$ (33.2 g, 101.83 mmol) in DMF (100 mL) was added $CH_3I$ (10.6 g, 74.68 mmol). The resulting mixture was stirred at 25° C. for 15 h, at which time TLC indicated the reaction had gone to completion. The reaction mixture was quenched by addition of a saturated aqueous solution of ammonium chloride (100 mL), and then extracted with ethyl acetate (3×100 mL). The combined organic extracts were dried over $Na_2SO_4$ and concentrated under reduced pressure. The residue was purified by silica gel chromatography (petroleum ether:ethyl acetate=1:1) to give the title compounds (7.5 g, 62% yield) (1:1 ratio of regioisomers) as white solids. LCMS M/Z (M+H) 179.

Step 3:

4-amino-6-chloro-2-methylpyridazin-3(2H)-one

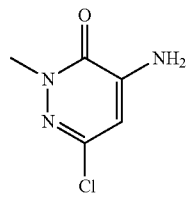

A mixture of 4,6-dichloro-2-methylpyridazin-3(2H)-one (7.5 g, 41.90 mmol, mixture with 5,6-dichloro-2-methylpyridazin-3(2H)-one) in ammonium hydroxide (48%, 50 mL) was heated at 120° C. for 15 h in a sealed tube, at which time LCMS indicated that the reaction had gone to completion. After cooled, the product was collected by filtration. The crude solid was washed with water and dried under reduced pressure to give a mixture of two regioisomers (3.8 g, 57%, 1:1 ratio) as white solids. LCMS M/Z (M+H) 160.

Step 4:

4-amino-6-chloro-5-iodo-2-methylpyridazin-3(2H)-one

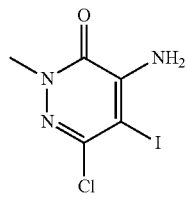

To a solution of 4-amino-6-chloro-2-methylpyridazin-3(2H)-one (3.8 g, 23.81 mmol, mixture with regio-isomers) in acetonitrile (60 mL) was added 1-iodopyrrolidine-2,5-dione (5.4 g, 23.81 mmol). The reaction mixture was heated to reflux for 3 h, at which time LCMS indicated that the reaction had gone to completion. After cooled, the reaction was quenched by addition of a saturated aqueous solution of ammonium chloride (20 mL), and then extracted with ethyl acetate (3×50 mL). The combined organic extracts were dried over $Na_2SO_4$ and concentrated under reduced pressure. The residue was purified by silica gel chromatography (petroleum ether:ethyl acetate=1:3) to give a mixture of regioisomers with a 1:1 ratio (2.5 g, 37% yield) as yellow solids. LCMS M/Z (M+H) 286.

Step 5:

(E)-4-amino-6-chloro-5-(2-ethoxyvinyl)-2-methylpyridazin-3(2H)-one

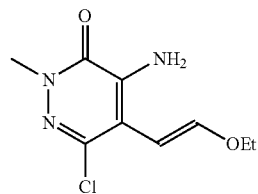

A mixture of 4-amino-6-chloro-5-iodo-2-methylpyridazin-3(2H)-one (2.50 g, 8.76 mmol, mixture of regioisomers), (E)-(2-ethoxyvinyl)boronic acid (1.22 g, 10.51 mmol), $Cs_2CO_3$ (5.71 g, 17.51 mmol) and Pd(dppf)$Cl_2$ (641 mg, 0.88 mmol) in dioxane/$H_2O$ (50 mL) was heated at 100° C. for 15 h under the $N_2$ atmosphere, at which time LCMS indicated that the reaction had gone to completion. The mixture was concentrated under reduced pressure and the residue was diluted with brine (60 mL). The solution was then extracted with ethyl acetate (3×50 mL). The combined organic extracts were dried over $Na_2SO_4$ and concentrated under reduced pressure. The residue was purified by silica gel chromatography (petroleum ether:ethyl acetate=1:1) to give the title compound (800 mg, 40% yield) as a light yellow solid. LCMS M/Z (M+H) 230. Only the desired regioisomer was isolated at this step.

Step 6:

4-chloro-6-methyl-1H-pyrrolo[2,3-d]pyridazin-7(6H)-one

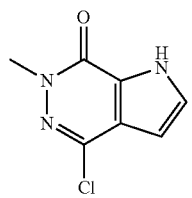

A solution of (E)-4-amino-6-chloro-5-(2-ethoxyvinyl)-2-methylpyridazin-3(2H)-one (800 mg, 3.48 mmol) in HOAc (30 mL) was heated at reflux for 15 h, at which time LCMS indicated that the reaction had gone to completion. The mixture was concentrated under reduced pressure and the residue was purified by silica gel chromatography (petroleum ether:ethyl acetate=3:1) to give the title compound (500 mg, 78% yield) as a white solid. LCMS M/Z (M+H) 184.

Experimental Procedure for Intermediates H & I

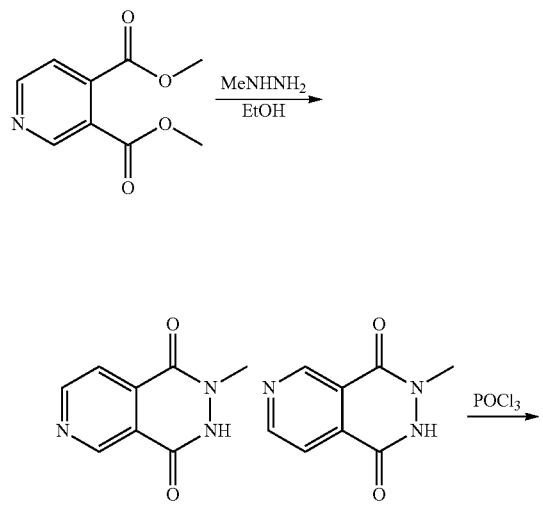

Intermediate H  Intermediate I

Step 1:

2-methyl-2,3-dihydropyrido[3,4-d]pyridazine-1,4-dione and 3-methyl-2,3-dihydropyrido[3,4-d]pyridazine-1,4-dione

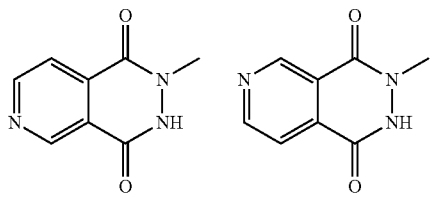

A mixture of dimethyl pyridine-3,4-dicarboxylate (5.0 g, 25.62 mmol) and methylhydrazine (40% aq., 8.85 g, 76.86 mmol) in ethanol (100 mL) was heated at reflux for 15 h, at which time LCMS indicated that the reaction had gone to completion. The mixture was concentrated under reduced pressure to give the title compounds (4.5 g, 99% yield) (ratio of the two isomers is 2:1) as yellow solids. This crude material was used in the next step without further purification. LCMS M/Z (M+H) 178.

Step 2:

4-chloro-2-methylpyrido[3,4-d]pyridazin-1(2H)-one and 1-chloro-3-methylpyrido[3,4-d]pyridazin-4(3H)-one

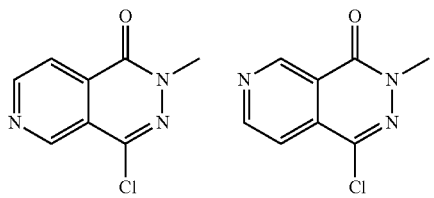

A mixture of 2 or 3-methyl-2,3-dihydropyrido[3,4-d]pyridazine-1,4-dione (4.5 g, 25.4 mmol) in POCl₃ (70 mL) was heated at reflux for 15 h, at which time LCMS indicated that the reaction had gone to completion. The mixture was concentrated under reduced pressure. The residue was quenched by addition of a saturated aqueous solution of NaHCO₃ (100 mL), and then extracted with ethyl acetate (3×120 mL). The combined organic extracts were dried over Na₂SO₄ and concentrated under reduced pressure. The resulting residue was purified by silica gel chromatography (petroleum ether:ethyl acetate=2:1) to give the title compounds (1.5 g, 30% yield) (2:1 ratio of regioisomers) as white solids. LCMS M/Z (M+H) 196.

Experimental Procedure for Intermediate J

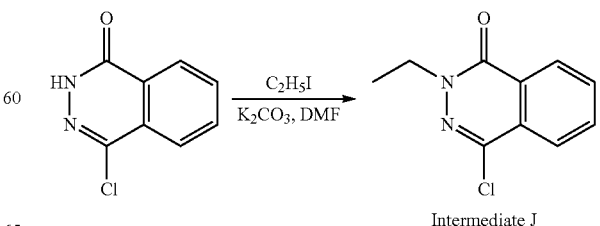

Intermediate J

Step 1:

4-chloro-2-ethylphthalazin-1(2H)-one

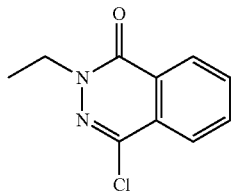

To a suspension of 4-chlorophthalazin-1(2H)-one (1.00 g, 5.54 mmol) and potassium carbonate (1.53 g, 11.1 mmol) in N,N-dimethylformamide (20 mL) was added iodoethane (1.04 g, 6.64 mmol). After addition, the reaction mixture was stirred at 80° C. for 15 h and then poured into water (20 mL). The resulting precipitate was collected by filtration, washed with water, and dried under reduced pressure to give the title compound (0.8 g, 69% yield) as a brown solid. This crude material was used in the next step without further treatment. LCMS M/Z (M+H) 209.

Experimental Procedure for Intermediates K and L

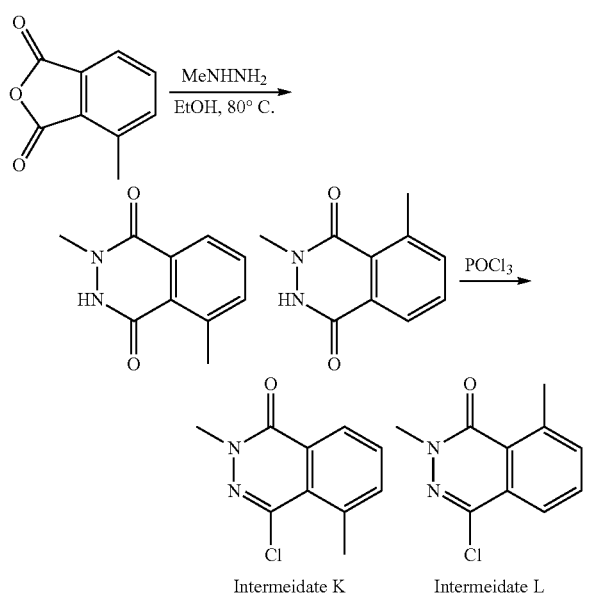

Step 1:

2,5-dimethyl-2,3-dihydrophthalazine-1,4-dione and 2,8-dimethyl-2,3-dihydrophthalazine-1,4-dione

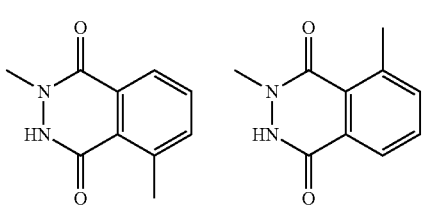

A mixture of 4-methylisobenzofuran-1,3-dione (5.0 g, 30.1 mmol) and 40% aqueous methylhydrazine (10.7 g, 92.5 mmol) in ethanol (100 mL) was heated at reflux for 15 h, at which time LCMS indicated that the reaction had gone to completion. The mixture was concentrated under reduced pressure to give the title compounds (4.3 g, 73% yield) (2:1 ratio of regioisomers) as yellow solids. This crude mixture was used in the next step without further purification. LCMS M/Z (M+H) 191.

Step 2:

4-chloro-2,5-dimethylphthalazin-1(2H)-one and 4-chloro-2,8-dimethylphthalazin-1(2H)-one

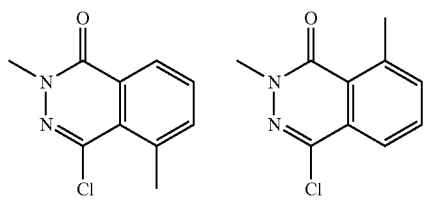

A mixture of 2,5 or 8-dimethyl-2,3-dihydrophthalazine-1,4-dione (4.3 g, 22.6 mmol) in POCl$_3$ (70 mL) was heated at reflux for 15 h, at which time LCMS indicated that the reaction had gone to completion. The mixture was concentrated under reduced pressure, the residue was quenched by addition of a saturated aqueous solution of NaHCO$_3$ (100 mL), and then extracted with ethyl acetate (3×100 mL). The combined organic extracts were dried over Na$_2$SO$_4$ and concentrated under reduced pressure. The residue was purified by silica gel chromatography (petroleum ether:ethyl acetate=5:1) to give the title compounds (1.5 g, 32% yield) (2:1 ratio of regioisomers) as white solids. LCMS M/Z (M+H) 209.

Experimental Procedure for Intermediate M

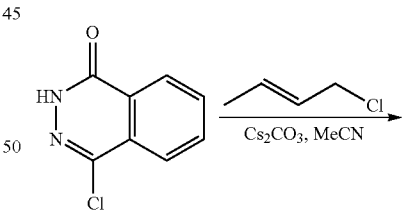

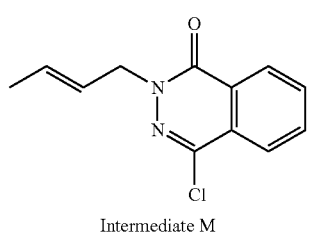

Intermediate M 2-(but-2-en-1-yl)-4-chlorophthalazin-1(2H)-one

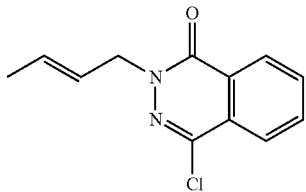 [SMILES: C/C=C/Cn1nc(Cl)c2ccccc2c1=O]

A round bottomed flask was charged with 4-chlorophthalazin-1-ol (0.75 g, 4.2 mmol), cesium carbonate (2.7 g, 8.3 mmol), and a stirbar. MeCN (20 mL) was added, followed by 1-chlorobut-2-ene (0.81 mL, 8.3 mmol), and the mixture was stirred at 50° C. 18 h. The reaction was diluted with ethyl acetate, filtered, celite was added, volatiles were evaporated in vacuo, and purified by silica gel flash chromatography (eluting with hexanes and ethyl acetate). Concentration in vacuo gave the title compound as a white crystalline solid. LCMS M/Z (M+H) 235.

Experimental Procedure for Intermediate N

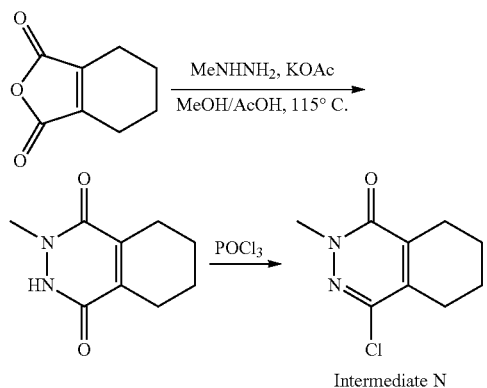

Intermediate N

Step 1:

2-methyl-2,3,5,6,7,8-hexahydrophthalazine-1,4-dione

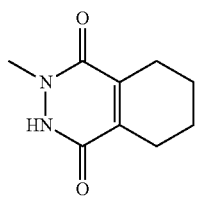

A pyrex vial was charged with 4,5,6,7-tetrahydroisobenzofuran-1,3-dione (1.0 g, 6.6 mmol), and potassium acetate (0.77 g, 7.9 mmol). To the solid was added a 1:1 mixture of $H_2O$:AcOH (10 mL) and methylhydrazine (40% aq., 0.91 g, 7.9 mmol). The vial was sealed and the reaction was heated at 115° C. overnight. After cooling to ambient temperature, the reaction was concentrated to dryness with toluene (3×). LCMS M/Z (M+H) 181.

Step 2:

4-chloro-2-methyl-5,6,7,8-tetrahydrophthalazin-1(2H)-one

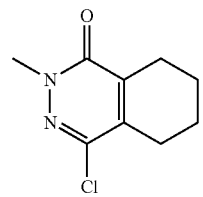

In a 100 mL round bottom flask crude 2-methyl-2,3,5,6,7,8-hexahydrophthalazine-1,4-dione (1.18 g, 6.55 mmol) was dissolved in $POCl_3$ (30 mL) and heated to 110° C. overnight. The reaction was cooled to ambient temperature then the excess $POCl_3$ removed by rotary evaporation. The residue was slowly poured into a saturated aqueous solution of $NaHCO_3$ and the pH adjusted to ~8. The aqueous phase was extracted with dichloromethane (3×), the combined organic phase was dried over $Na_2SO_4$, filtered concentrated and purified by silica gel chromatography using 10-30% gradient of ethyl acetate in hexane as eluent to provide the title compound (0.54 g, 41% yield) as a white solid. LCMS M/Z (M+H) 199.

Experimental Procedure for Intermediate O

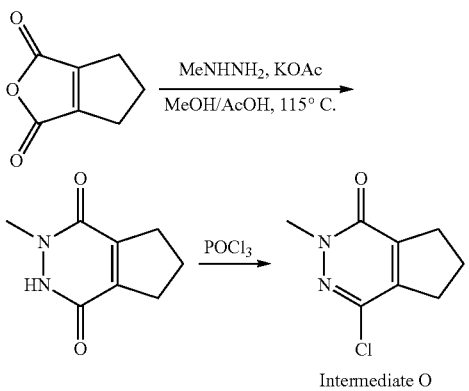

Intermediate O

Step 1:

2-methyl-2,3,6,7-tetrahydro-1H-cyclopenta[d]pyridazine-1,4(5H)-dione

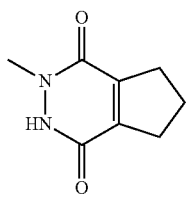

A pyrex vial was charged with 5,6-dihydro-1H-cyclopenta[c]furan-1,3(4H)-dione (1.0 g, 7.2 mmol), and potassium acetate (0.85 g, 8.7 mmol). To the solid was added a 1:1 mixture of $H_2O$:AcOH (10 mL) and methylhydrazine (0.46 mL, 8.7 mmol). The vial was sealed and the reaction was heated at 115° C. overnight. The reaction was cooled to ambient temperature and concentrated to dryness with toluene (3×). LCMS M/Z (M+H) 167.

Step 2:

4-chloro-2-methyl-2,5,6,7-tetrahydro-1H-cyclopenta[d]pyridazin-1-one

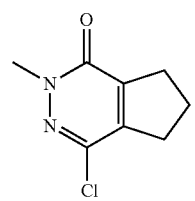

In a 100 mL round bottom flask crude 2-methyl-2,3,6,7-tetrahydro-1H-cyclopenta[d]pyridazine-1,4(5H)-dione (1.2 g, 7.1 mmol) was dissolved in POCl$_3$ (30 mL) and heated to 110° C. overnight. The reaction was cooled to ambient temperature then the excess POCl$_3$ was removed by rotary evaporation. The residue was slowly poured into a saturated aqueous solution of NaHCO$_3$ and the pH adjusted to ~8. The aqueous phase was extracted with dichloromethane (3×), the combined organic phase was dried over Na$_2$SO$_4$, filtered, concentrated and purified by silica gel chromatography using 10-30% gradient of ethyl acetate in hexane as eluent to provide the title compound (0.86 g, 66%) as a brown solid. LCMS M/Z (M+H) 199.

Experimental Procedure for Intermediate P

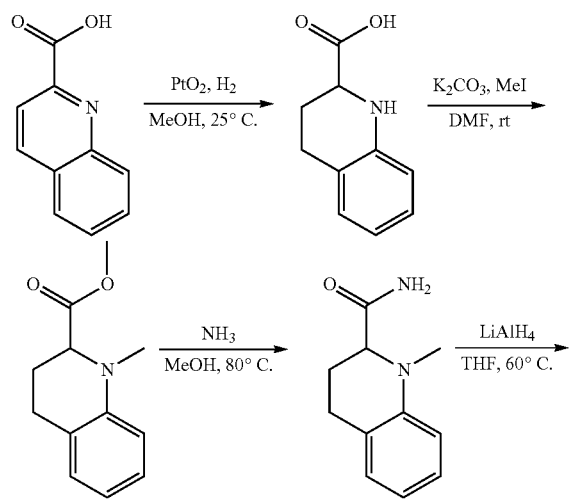

Step 1:

1,2,3,4-tetrahydroquinoline-2-carboxylic acid

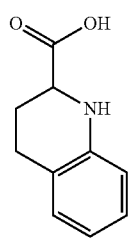 [SMILES: O=C(O)C1CCc2ccccc2N1]

A mixture of quinoline-2-carboxylic acid (2.5 g, 14 mmol) and PtO$_2$ (0.2 g) in methanol (50 mL) was stirred under hydrogen (15 psi) at 25° C. for 5 h, at which time TLC showed completion of the reaction. The solid was removed by filtration and the filtrate was concentrated under reduced pressure to give the crude title compound (1.5 g, 59% yield) as a yellow solid. LCMS M/Z (M+H) 178.

Step 2:

Methyl 1-methyl-1,2,3,4-tetrahydroquinoline-2-carboxylate

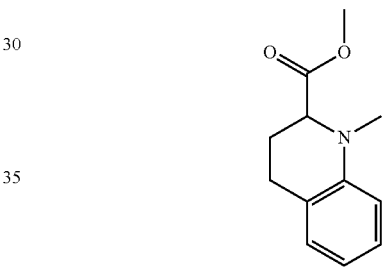

To a stirred and cooled suspension of 1,2,3,4-tetrahydroquinoline-2-carboxylic acid (1.5 g, 8.5 mmol) and potassium carbonate (2.92 g, 21.2 mmol) in DMF (30 mL) was added iodomethane (3.0 g, 21 mmol). After addition, the resulting mixture was stirred at ambient temperature for 2 h, at which time LCMS indicated the reaction had gone to completion. The reaction was poured into water (50 mL), and then extracted with ethyl acetate (3×30 mL). The combined organic extracts were dried over Na$_2$SO$_4$ and concentrated under reduced pressure to give the title compound (0.6 g, 35% yield) as a red solid. This crude material was used in the next step without further purification.

LCMS M/Z (M+H) 206.

Step 3:

1-methyl-1,2,3,4-tetrahydroquinoline-2-carboxamide

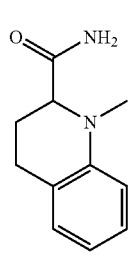

A mixture of methyl 1-methyl-1,2,3,4-tetrahydroquinoline-2-carboxylate (600 mg, 2.92 mmol) in 4M ammonia solution in methanol (20 mL) was heated 80° C. for 15 h, at which time LCMS indicated the reaction had gone to completion. The solvent was evaporated under reduced pressure to give the crude title compound (500 mg, 90% yield) as a yellow solid.

LCMS M/Z (M+H) 191.

Step 4:

(1-methyl-1,2,3,4-tetrahydroquinolin-2-yl)methanamine

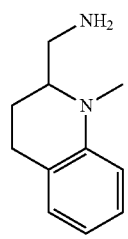

To a cooled (0° C.) solution of 1-methyl-1,2,3,4-tetrahydroquinoline-2-carboxamide (0.50 g, 2.63 mmol) in tetrahydrofuran (50 mL) was added LiAlH$_4$ (0.30 g, 7.9 mmol). After addition, the reaction mixture was heated at 60° C. for 15 h, at which time LCMS indicated the reaction had gone to completion. The mixture was quenched by addition of aqueous NaOH (10%, 0.3 mL) and water (1 mL), and filtrated. The filtrate was evaporated under reduced pressure to give the crude title compound (0.20 g, 43% yield) as a yellow oil. LCMS M/Z (M+H) 177. The compound was isolated as a racemic mixture.

Experimental Procedure for Intermediate Q

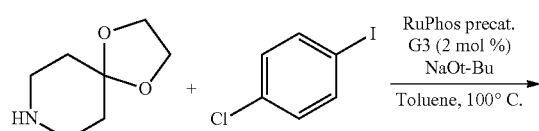

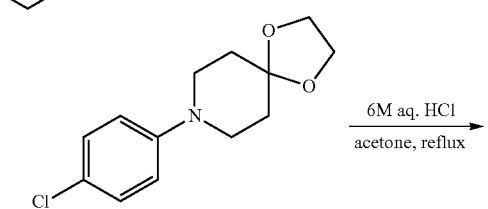

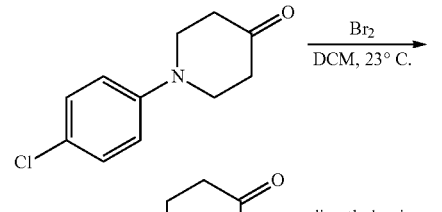

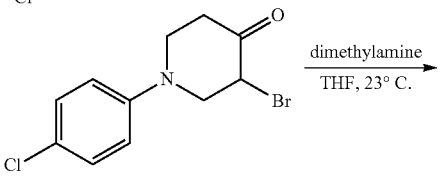

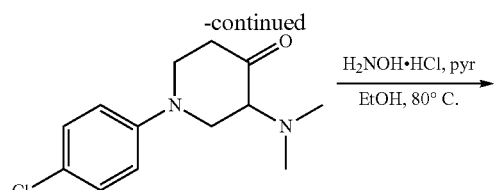

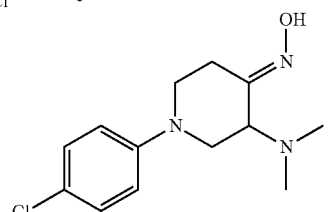

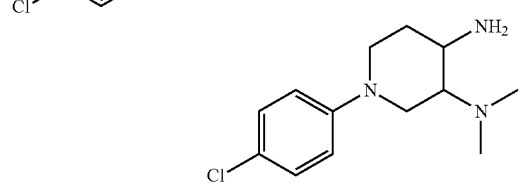

Intermediate Q

Step 1:

8-(4-chlorophenyl)-1,4-dioxa-8-azaspiro[4.5]decane

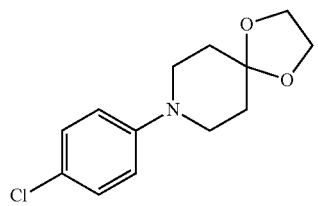 [SMILES: Clc1ccc(N2CCC3(CC2)OCCO3)cc1]

In a pyrex vial sodium 2-methylpropan-2-olate (2.24 g, 23.4 mmol), RuPhos 3$^{rd}$ generation precatalyst (0.26 g, 0.31 mmol) and 1-chloro-4-iodobenzene (5.57 g, 23.4 mmol) were added. The vial was evacuated and purged with N$_2$ (3×), then toluene (10 mL) and 1,4-dioxa-8-azaspiro[4.5]decane (2.0 mL, 166 mmol) were added. The vial was evacuated and purged with N$_2$ (3×) then heated at 100° C. overnight. The reaction was cooled to ambient temperature, concentrated to dryness and purified by silica gel chromatography (10% ethyl acetate in hexane) to provide 8-(4-chlorophenyl)-1,4-dioxa-8-azaspiro[4.5]decane (3.89 g, 98% yield). LCMS M/Z (M+H) 254.

Step 2:

1-(4-chlorophenyl)piperidin-4-one

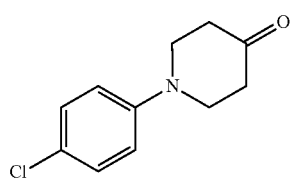 [SMILES: O=C1CCN(c2ccc(Cl)cc2)CC1]

In a 250 mL round bottom flask 8-(4-chlorophenyl)-1,4-dioxa-8-azaspiro[4.5]decane (3.89 g, 5.34 mmol) was diluted in acetone (100 mL) then 6M aqueous hydrochloric acid (50 mL) was added and the reaction was heated at reflux overnight. The reaction was cooled, then concentrated to remove acetone. The aqueous solution was neutralized with 6M NaOH (50 mL) then extracted with ethyl acetate (3×). The organic layers were combined, washed with brine, dried over Na₂SO₄, filtered and concentrated. The crude residue was purified by silica gel chromatography (10% ethyl acetate in hexane) to provide 1-(4-chlorophenyl)piperidin-4-one (2.96 g, 92% yield) as a yellow solid.

LCMS M/Z (M+H) 210.

Step 3:

3-bromo-1-(4-chlorophenyl)piperidin-4-one

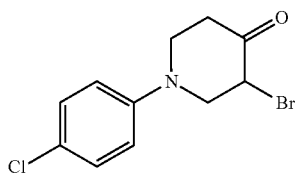 [SMILES: O=C1CCN(c2ccc(Cl)cc2)CC1Br]

In a 50 mL round bottom flask 1-(4-chlorophenyl)piperidin-4-one (0.500 g, 2.39 mmol) was diluted in dichloromethane (12 mL) and cooled to −10° C. (salt/ice bath) under an atm of N₂. Bromine (0.12 mL, 2.4 mmol) was added dropwise over 3 minutes maintaining an internal reaction temperature between −2 and −4° C. The reaction was then warmed to ambient temperature and mixed until clear. A saturated aqueous solution of NaHCO₃ was added and the reaction stirred for 0.5 h. The layers were separated and the aqueous layer was extracted with dichloromethane (1×). The combined organic layer was dried over Na₂SO₄, filtered, concentrated and used directly in the following reaction. LCMS M/Z (M+H) 288, 290.

Step 4:

1-(4-chlorophenyl)-3-(dimethylamino)piperidin-4-one

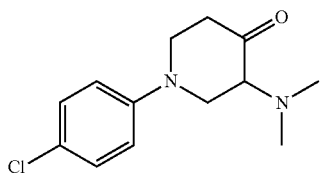 [SMILES: CN(C)C1CN(c2ccc(Cl)cc2)CCC1=O]

In a 100 mL round bottom flask crude 3-bromo-1-(4-chlorophenyl)piperidin-4-one (688 mg, 2.39 mmol) was dissolved in tetrahydrofuran (20 mL) and cooled to 0° C. Dimethylamine (2M in tetrahydrofuran, 4.78 mL, 9.56 mmol) was then added and the reaction was allowed to slowly warm to ambient temperature overnight. The crude reaction was concentrated and purified by silica gel chromatography to provide the title compound (212 mg, 35% yield) as an oil. LCMS M/Z (M+H) 253.

Step 5:

1-(4-chlorophenyl)-3-(dimethylamino)piperidin-4-one oxime

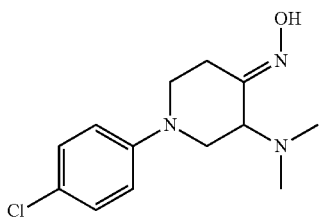 [SMILES: CN(C)C1CN(c2ccc(Cl)cc2)CC/C1=N\O]

In a 25 mL round bottom flask 1-(4-chlorophenyl)-3-(dimethylamino)piperidin-4-one (0.21 g, 0.84 mmol) and hydroxylamine hydrochloride (0.117 g, 1.68 mmol) were dissolved in ethanol (8 mL). Pyridine (0.22 mL, 2.72 mmol) was added and the reaction was heated at 80° C. overnight. The reaction was concentrated to dryness and purified by silica gel chromatography (0-100% gradient of 90:10:1 dichloromethane:methanol:NH₄OH mixing with dichloromethane) to provide the title compound (0.18 g, 80% yield) as a yellow oil. LCMS M/Z (M+H) 268.

Step 6:

1-(4-chlorophenyl)-N3,N3-dimethylpiperidine-3,4-diamine

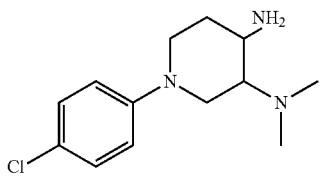 [SMILES: CN(C)C1CN(c2ccc(Cl)cc2)CCC1N]

In a 50 mL round bottom flask (E)-1-(4-chlorophenyl)-3-(dimethylamino)piperidin-4-one oxime (0.18 g, 0.68 mmol) was diluted with tetrahydrofuran (5 mL). The reaction flask was evacuated and purged with N₂ (3×). Borane (2M in tetrahydrofuran, 1.35 mL, 1.35 mmol) was then added and the reaction was heated at 70° C. overnight. The reaction was cooled to ambient temperature, quench by addition of methanol (6 mL), then heated at 70° C. for 1 h. The reaction was concentrated to dryness and purified by silica gel chromatography (50% dichloromethane and 50% 90:10:1 dichloromethane:methanol:NH₄OH) to provide the title compound (0.071 g, 42% yield) as an colorless oil. LCMS M/Z (M+H) 254. The compound was isolated as a racemic mixture of diastereoisomers.

Experimental Procedure for Intermediate R

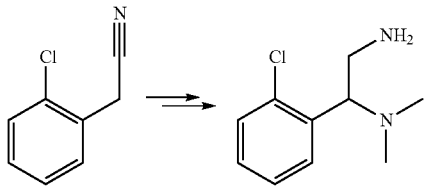

Intermediate R

1-(2-chlorophenyl)-N1,N1-dimethylethane-1,2-diamine

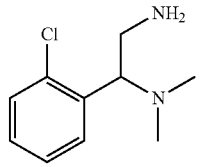

The title compound was prepared from 2-chlorophenylacetonitrile according to the procedure described in patent WO1984003278. LCMS M/Z (M+H) 199. The compound was isolated as a racemic mixture.

Experimental Procedure for Intermediates S and T

The following intermediates were prepared in a similar fashion to intermediate R, using the appropriate starting material instead of 2-chlorophenylacetonitrile.

| Intermediate | Compound Name | Structure | M/Z (M + H) |
|---|---|---|---|
| S | 1-(2-fluorophenyl)-N1,N1-dimethylethane-1,2-diamine (Racemic mixture) | 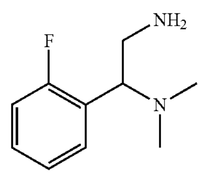 | 183 |
| T | 1-(4-chlorophenyl)-N1,N1-dimethylethane-1,2-diamine (Racemic mixture) | 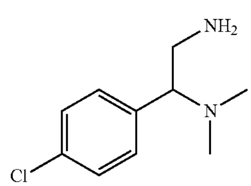 | 199 |

Experimental Procedure for Intermediate U

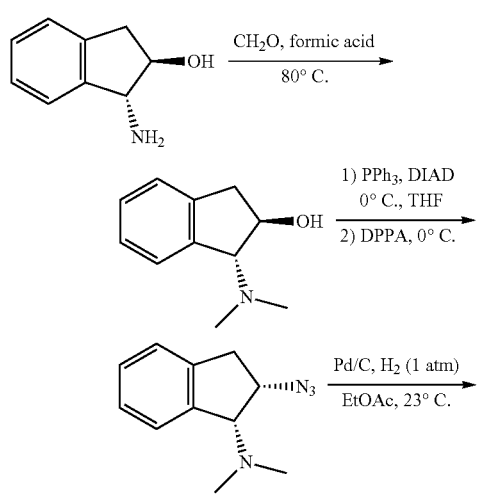

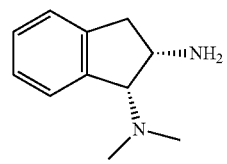

Intermediate U

(1R,2R)-1-Dimethylamino-2-indanol

Formic acid (90% purity, 1.2 mL) and 37% aqueous formaldehyde solution (9 mL) were added to (1R,2R)-1-amino-2-indanol (1.0 g, 6.7 mmol). After heating to 80° C. for 3 h, the solution was cooled to room temperature and treated with a saturated aqueous solution of $Na_2CO_3$ to make the solution alkaline. The mixture was extracted twice with ethyl acetate, and the combined organic layers were washed with brine, dried over $Na_2SO_4$, filtered and concentrated under reduced pressure. Purification: 40 g silica column, using 1:10:90 $NH_4OH$:methanol:dichloromethane in dichloromethane, 20% to 100% over 6 column volumes. Pure fractions were concentrated in vacuo to afford the title intermediate (0.96 g, 81% yield). LCMS M/Z (M+H) 178. The compound was isolated as a single enantiomer.

(1R,2S)-2-azido-N,N-dimethyl-2,3-dihydro-1H-inden-1-amine

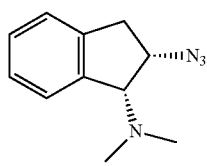

(1R,2R)-1-(dimethylamino)-2,3-dihydro-1H-inden-2-ol (574 mg, 3.22 mmol) dissolved in tetrahydrofuran (20 mL), Triphenylphosphine (1.1 g, 4.2 mmol) added and dissolved, cooled to 0° C. DIAD (970 µl, 4.83 mmol) added, stirred 15 minutes, then DPPA added (830 µl, 3.86 mmol). Stirred 3 hours, reaction complete. Crude reaction mixture impregnated on silica, purified by column chromatography (1:10:90 $NH_4OH$:methanol:dichloromethane, 0% to 100% in dichloromethane). Triphenylphosphine oxide co-elutes with product. The title intermediate was obtained after in vacuo concentration. LCMS M/Z (M+H) 203. The compound was isolated as a single enantiomer.

(1R,2S)—N1,N1-dimethyl-2,3-dihydro-1H-indene-1,2-diamine

SYNTHESIS OF EXAMPLE COMPOUNDS

Examples 1 A/B

Intermediate U

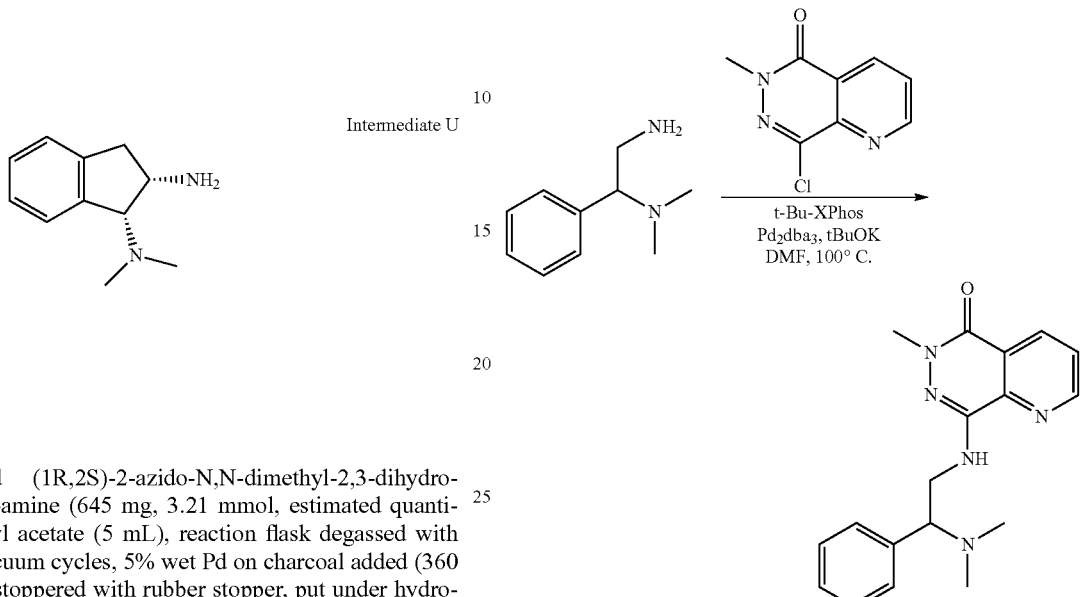

Dissolved (1R,2S)-2-azido-N,N-dimethyl-2,3-dihydro-1H-inden-1-amine (645 mg, 3.21 mmol, estimated quantities) in ethyl acetate (5 mL), reaction flask degassed with nitrogen/vacuum cycles, 5% wet Pd on charcoal added (360 mg). Flask stoppered with rubber stopper, put under hydrogen atmosphere using vacuum/$H_2$ gas cycles. Stirred 60 hours. Reaction complete. Filtered on celite, using ethyl acetate to wash palladium. Evaporation, high vac. Product used immediately in next step. (1R,2S)—N1,N1-dimethyl-2,3-dihydro-1H-indene-1,2-diamine (457 mg, 75% yield over 2 steps). LCMS M/Z (M+H) 177. The compound was isolated as a single enantiomer.

Example 1

8-((2-(dimethylamino)-2-phenylethyl)amino)-6-methylpyrido[2,3-d]pyridazin-5(6H)-one Experimental Procedure for Intermediate V Intermediate V

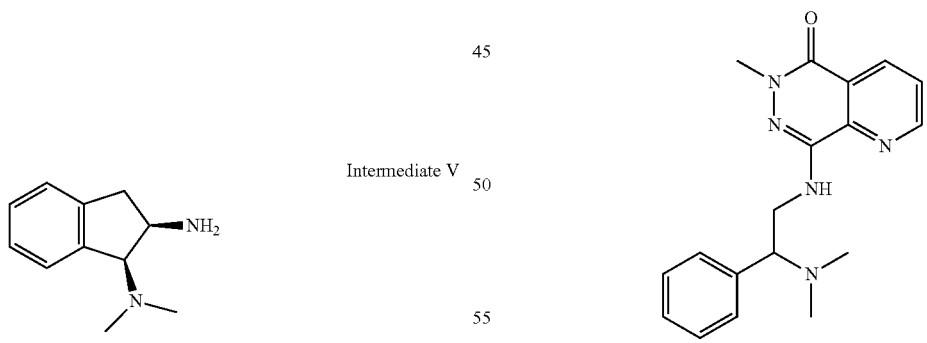

The title compound was prepared in a way similar to intermediate U, using (1S,2S)-1-Dimethylamino-2-indanol as a starting material instead of (1R,2R)-1-Dimethylamino-2-indanol. The compound was isolated as a single enantiomer.

A mixture of 8-chloro-6-methylpyrido[2,3-d]pyridazin-5 (6H)-one (Intermediate A, 100 mg, 0.510 mmol), $N^1,N^1$-dimethyl-1-phenylethane-1,2-diamine (100 mg, 0.610 mmol), t-Butyl-XPhos (44 mg, 0.10 mmol), t-BuOK (115 mg, 1.02 mmol) and Pd₂dba₃ (47 mg, 0.050 mmol) in DMF (5 mL) was heated at 100° C. under microwave conditions for 2 h under N₂, at which time LCMS indicated the reaction had gone to completion. The reaction mixture was poured into water (5 mL), and then extracted with ethyl acetate (3×10 mL). The combined organic extracts were dried over Na₂SO₄ and concentrated under reduced pressure. The residue was purified by reverse phase chromatography (acetonitrile 30-60%/0.1% NH₄OH in water) to give the title compound (24 mg, 14% yield) as a white solid. ¹H NMR (400 MHz, Methanol-d4) δ 8.99-8.97 (m, 1H), 8.63-8.61 (m, 1H), 7.72-7.79 (m, 1H), 7.37-7.32 (m, 5H), 4.01-3.97 (m, 1H), 3.88-3.71 (m, 5H), 2.29 (s, 6H). LCMS M/Z (M+H) 324.

(S)-8-((2-(dimethylamino)-2-phenylethyl)amino)-6-methylpyrido[2,3-d]pyridazin-5(6H)-one and (R)-8-((2-(dimethylamino)-2-phenylethyl)amino)-6-methylpyrido[2,3-d]pyridazin-5(6H)-one

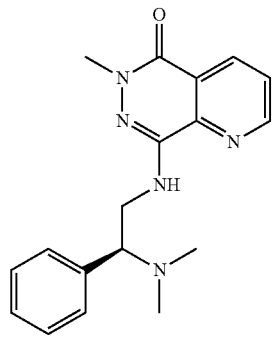

Example 1A

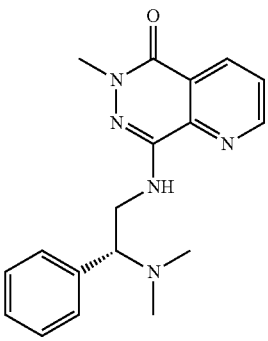

Example 1B

The enantiomers were separated by SFC using the conditions described in the following section. (Method C: Chiralpak ID column, 5 μM particle size, 2×10 cm dimensions, 75% CO₂/25% iPrOH with 0.1% NH₄OH eluent, 70 mL/min flow rate, 100 bar pressure, 40° C.).

Examples 2-18

The following compounds were prepared in a similar fashion to example 1, using either intermediate A (Examples 2, 7, 8, 11, 14-16 and 18), intermediate B (Example 3), intermediate C (Example 4), intermediate D (Example 5), intermediate E (Example 6), intermediate F (Example 9), intermediate G (Example 10), intermediate H (Example 12), intermediate I (Example 13) or intermediate J (Examples 17A/B). All examples in the following table were prepared using commercially available amines. The specific conditions for the separation of enantiomers are reported in the following section.

| Example | Compound | NMR | M/Z (M + H) |
|---|---|---|---|
| 2 | 8-((2-(dimethylamino)ethyl)amino)-6-methylpyrido[2,3-d]pyridazin-5(6H)-one | ¹H NMR (400 MHz, Methanol-d4) δ 9.03-9.01 (m, 1H), 8.63-8.60 (m, 1H), 7.82-7.78 (m, 1H), 3.69 (s, 3H), 3.56-3.53 (m, 2H), 2.68-2.65 (m, 2H), 2.32 (s, 6H). | 248 |
| 3 | | ¹H NMR (400 MHz, DMSO-d6) δ 8.15-8.13 (m, 1H), 7.54-7.53 (m, 1H), 7.38-7.36 (m, 1H), 6.65-6.62 (m, 1H), 3.93 (s, 3H), 3.54 (s, 3H), 3.39-3.35 (m, 4H), 2.21 (s, 6H). | 277 |

| Example | Compound | NMR | M/Z (M + H) |
|---|---|---|---|
| | 4-((2-(dimethylamino)ethyl)amino)-6-methoxy-2-methylphthalazin-1(2H)-one | | |
| 4 | 4-((2-(dimethylamino)ethyl)amino)-7-methoxy-2-methylphthalazin-1(2H)-one | ¹H NMR (400 MHz, DMSO-d6) δ 8.01-7.99 (m, 1H), 7.59-7.58 (m, 1H), 7.42-7.39 (m, 1H), 6.49-6.47 (m, 1H), 3.88 (s, 3H), 3.52 (s, 3H), 3.30-3.25 (m, 4H), 2.16 (s, 6H). | 277 |
| 5 | 4-((2-(dimethylamino)ethyl)amino)-5-fluoro-2-methylphthalazin-1(2H)-one | ¹H NMR (400 MHz, Methanol-d4) δ 8.18-8.15 (m, 1H), 7.81-7.78 (m, 1H), 7.63-7.60 (m, 1H), 3.68 (s, 3H), 3.52-3.49 (m, 2H), 2.70-2.66 (m, 2H), 2.35 (s, 6H). | 265 |
| 6 | 4-((2-(dimethylamino)ethyl)amino)-8-fluoro-2-methylphthalazin-1(2H)-one | ¹H NMR (400 MHz, CDCl₃) δ 7.71-7.67 (m, 1H), 7.50-7.48 (m, 1H), 7.38-7.33 (m, 1H), 5.30 (s, 1H), 3.68 (s, 3H), 3.38-3.34 (m, 2H), 2.62-2.60 (m, 2H), 2.28 (s, 6H). | 265 |

-continued

| Example | Compound | NMR | M/Z (M + H) |
|---|---|---|---|
| 7A | (S)-8-((2-(dimethylamino)propyl)amino)-6-methylpyrido[2,3-d]pyridazin-5(6H)-one | ¹H NMR (400 MHz, Methanol-d4) δ 9.05-9.04 (m, 1H), 8.65-8.63 (m, 1H), 7.85-7.82 (m, 1H), 3.72 (s, 3H), 3.52-3.47 (m, 1H), 3.40-3.33 (m, 1H), 3.03-3.02 (m, 1H), 2.36 (s, 6H), 1.11 (d, J = 6.4 Hz, 3H). (Single enantiomer; unknown absolute stereochemistry) | 262 |
| 7B | (R)-8-((2-(dimethylamino)propyl)amino)-6-methylpyrido[2,3-d]pyridazin-5(6H)-one | ¹H NMR (400 MHz, Methanol-d4) δ 9.03-9.02 (m, 1H), 8.63-8.61 (m, 1H), 7.82-7.79 (m, 1H), 3.69 (s, 3H), 3.52-3.47 (m, 1H), 3.40-3.35 (m, 1H), 3.08-3.07 (m, 1H), 2.38 (s, 6H), 1.11 (d, J = 6.8 Hz, 3H). (Single enantiomer; unknown absolute stereochemistry) | 262 |
| 8A | (S)-8-((1-(dimethylamino)propan-2-yl)amino)-6-methylpyrido[2,3-d]pyridazin-5(6H)-one | ¹H NMR (400 MHz, Methanol-d4) δ 9.02-9.01 (m, 1H), 8.63-8.60 (m, 1H), 7.81-7.78 (m, 1H), 4.20-4.11 (m, 1H), 3.69 (s, 3H), 2.69-2.63 (m, 1H), 2.38-2.33 (m, 1H), 2.29 (s, 6H), 1.29 (d, J = 6.8 Hz, 3H). (Single enantiomer; unknown absolute stereochemistry) | 262 |
| 8B | | ¹H NMR (400 MHz, Methanol-d4) δ 9.02-9.01 (m, 1H), 8.63-8.60 (m, 1H), 7.81-7.78 (m, 1H), 4.20-4.11 (m, 1H), 3.69 (s, 3H), 2.69-2.64 (m, 1H), 2.37-2.33 (m, 1H), 2.29 (s, 6H), 1.29 (d, J = 6.4 Hz, 3H). (Single enantiomer; unknown absolute stereochemistry) | 262 |

| Example | Compound | NMR | M/Z (M + H) |
|---|---|---|---|
| | (R)-8-((1-(dimethylamino)propan-2-yl)amino)-6-methylpyrido[2,3-d]pyridazin-5(6H)-one | | |
| 9 | 4-((2-(dimethylamino)ethyl)thio)-2-methylphthalazin-1(2H)-one | $^1$H NMR (400 MHz, Methanol-d4) δ 8.37-8.36 (m, 1H), 7.97-7.93 (m, 1H), 7.92-7.86 (m, 2H), 3.84 (s, 3H), 3.39-3.33 (m, 2H), 2.79-2.75 (m, 2H), 2.38 (s, 6H). | 264 |
| 10 | 4-((2-(dimethylamino)-2-phenylethyl)amino)-6-methyl-1H-pyrrolo[2,3-d]pyridazin-7(6H)-one | $^1$H NMR (400 MHz, Methanol-d4) δ 7.36-7.27 (m, 6H), 6.46 (d, J = 3.2 Hz, 1H), 3.99-3.96 (m, 1H), 3.82-3.78 (m, 1H), 3.71 (s, 3H), 3.68-3.64 (m, 1H), 2.29 (s, 6H). (Racemic mixture) | 312 |
| 11A | 8-(((1R,2R)-2-(dimethylamino)cyclohexyl)amino)-6-methylpyrido[2,3-d]pyridazin-5(6H)-one | $^1$H NMR (400 MHz, Methanol-d4) δ 9.05-9.04 (m, 1H), 8.66-8.63 (m, 1H), 7.85-7.82 (m, 1H), 3.89-3.86 (m, 1H), 3.71 (s, 3H), 2.89-2.86 (m, 1H), 2.45 (s, 7H), 2.05-2.02 (m, 1H), 1.90-1.87 (m, 1H), 1.79-1.76 (m, 1H), 1.41-1.39 (m, 4H). (Single enantiomer; unknown absolute stereochemistry; single diastereoisomer; and known relative stereochemistry) | 302 |

| Example | Compound | NMR | M/Z (M + H) |
|---|---|---|---|
| 11B | 8-(((1S,2S)-2-(dimethylamino)cyclohexyl)amino)-6-methylpyrido[2,3-d]pyridazin-5(6H)-one | ¹H NMR (400 MHz, Methanol-d4) δ 9.05-9.04 (m, 1H), 8.66-8.63 (m, 1H), 7.85-7.81 (m, 1H), 3.87-3.82 (m, 1H), 3.71 (s, 3H), 2.80-2.77 (m, 1H), 2.49-2.46 (m, 1H), 2.41 (s, 6H), 2.03-1.98 (m, 1H), 1.89-1.86 (m, 1H), 1.78-1.75 (m, 1H), 1.43-1.31 (m, 4H). (Single enantiomer; unknown absolute stereochemistry; single diastereoisomer; and known relative stereochemistry) | 302 |
| 12 | 4-((1-(dimethylamino)propan-2-yl)amino)-2-methylpyrido[3,4-d]pyridazin-1(2H)-one | ¹H NMR (400 MHz, Methanol-d4) δ 9.45 (s, 1H), 8.96 (s, 1H), 8.15 (s, 1H), 4.30-4.29 (s, 1H), 3.73 (s, 3H), 2.76-2.73 (m, 1H), 2.36 (s, 7H), 1.32 (d, J = 6.0 Hz, 3H). (Racemic mixture) | 262 |
| 13 | 1-((1-(dimethylamino)propan-2-yl)amino)-3-methylpyrido[3,4-d]pyridazin-4(3H)-one | ¹H NMR (400 MHz, Methanol-d4) δ 9.52 (s, 1H), 8.97-8.96 (m, 1H), 8.01-8.00 (m, 1H), 4.27-4.22 (m, 1H), 3.72 (s, 3H), 2.74-2.69 (m, 1H), 2.39-2.34 (m, 7H), 1.31 (d, J = 6.0 Hz, 3H). (Racemic mixture) | 262 |
| 14A | | ¹H NMR (400 MHz, Methanol-d4) δ 9.07-9.05 (m, 1H), 8.66-8.64 (m, 1H), 7.86-7.83 (m, 1H), 4.16-4.15 (m, 1H), 3.71 (s, 3H), 3.29-3.28 (m, 1H), 1.91-1.87 (m, 1H), 1.74-1.70 (m, 4H), 1.55-1.51 (m, 2H), 1.32-1.30 (m, 1H). (Single enantiomer; unknown absolute stereochemistry; single diastereoisomer; and known relative stereochemistry) | 274 |

| Example | Compound | NMR | M/Z (M + H) |
|---|---|---|---|
| | 8-(((1R,2S)-2-aminocyclohexyl)amino)-6-methylpyrido[2,3-d]pyridazin-5(6H)-one | | |
| 14B | 8-(((1S,2R)-2-aminocyclohexyl)amino)-6-methylpyrido[2,3-d]pyridazin-5(6H)-one | $^1$H NMR (400 MHz, Methanol-d4) δ 9.07-9.05 (m, 1H), 8.66-8.64 (m, 1H), 7.86-7.83 (m, 1H), 4.17-4.15 (m, 1H), 3.71 (s, 3H), 3.31-3.29 (m, 1H), 1.89-1.87 (m, 1H), 1.74-1.70 (m, 4H), 1.56-1.51 (m, 2H), 1.32-1.30 (m, 1H). (Single enantiomer; unknown absolute stereochemistry; single diastereoisomer; and known relative stereochemistry) | 274 |
| 15A | 8-(((1R,2S)-2-(dimethylamino)cyclohexyl)amino)-6-methylpyrido[2,3-d]pyridazin-5(6H)-one | $^1$H NMR (400 MHz, Methanol-d4) δ 9.09-9.07 (m, 1H), 8.68-8.66 (m, 1H), 7.87-7.84 (m, 1H), 4.49 (s, 1H), 3.72 (s, 3H), 2.36-2.32 (m, 7H), 2.31-2.28 (m, 1H), 2.15-2.13 (m, 1H), 1.94-1.91 (m, 1H), 1.54-1.52 (m, 2H), 1.49-1.43 (m, 2H), 1.31-1.30 (m, 1H). (Single enantiomer; unknown absolute stereochemistry; single diastereoisomer; and known relative stereochemistry) | 302 |
| 15B | 8-(((1S,2R)-2-(dimethylamino)cyclohexyl)amino)-6-methylpyrido[2,3-d]pyridazin-5(6H)-one | $^1$H NMR (400 MHz, Methanol-d4) δ 9.08-9.07 (m, 1H), 8.67-8.65 (m, 1H), 7.87-7.84 (m, 1H), 4.48 (s, 1H), 3.72 (s, 3H), 2.34-2.28 (m, 7H), 2.27-2.26 (m, 1H), 2.13-2.09 (m, 1H), 1.92-1.90 (m, 1H), 1.53-1.52 (m, 2H), 1.49-1.43 (m, 2H), 1.31-1.30 (m, 1H). (Single enantiomer; unknown absolute stereochemistry; single diastereoisomer; and known relative stereochemistry) | 302 |
| 16A | | $^1$H NMR (400 MHz, Methanol-d4) δ 9.08-9.07 (m, 1H), 8.68-8.66 (m, 1H), 8.54 (s, 1H), 7.88-7.85 (m, 1H), 4.57-4.52 (m, 1H), 3.74 (s, 3H), 3.66-3.62 (m, 1H), 2.85 (s, 6H), 2.30-2.23 (m, 2H), 1.92-1.87 (m, 4H). (Single enantiomer; unknown absolute stereochemistry; single diastereoisomer; and known relative stereochemistry) | 288 |

| Example | Compound | NMR | M/Z (M + H) |
|---|---|---|---|
| | 8-(((1R,2S)-2-(dimethylamino)cyclopentyl)amino)-6-methylpyrido[2,3-d]pyridazin-5(6H)-one (Formate salt) | | |
| 16B | 8-(((1S,2R)-2-(dimethylamino)cyclopentyl)amino)-6-methylpyrido[2,3-d]pyridazin-5(6H)-one | $^1$H NMR (400 MHz, Methanol-d4) δ 9.08-9.07 (m, 1H), 8.68-8.66 (m, 1H), 7.88-7.85 (m, 1H), 4.63-4.61 (m, 1H), 4.48-4.43 (m, 1H), 3.74 (s, 3H), 2.68 (s, 6H), 2.28-2.13 (m, 2H), 1.87-1.77 (m, 4H). (Single enantiomer; unknown absolute stereochemistry; single diastereoisomer; and known relative stereochemistry) | 288 |
| 17A | (R)-4-((1-(dimethylamino)propan-2-yl)amino)-2-ethylphthalazin-1(2H)-one | $^1$H NMR (400 MHz, Methanol-d4) δ 8.33-8.31 (m, 1H), 8.05-8.03 (m, 1H), 7.87-7.79 (m, 2H), 4.25-4.09 (m, 3H), 2.72-2.67 (m, 1H), 2.37-2.31 (m, 7H), 1.36 (t, J = 7.2 Hz, 3H), 1.29 (d, J = 6.4 Hz, 3H). (Single enantiomer; unknown absolute stereochemistry) | 275 |
| 17B | (S)-4-((1-(dimethylamino)propan-2-yl)amino)-2-ethylphthalazin-1(2H)-one | $^1$H NMR (400 MHz, Methanol-d4) δ 8.33-8.31 (m, 1H), 8.05-8.02 (m, 1H), 7.87-7.79 (m, 2H), 4.25-4.09 (m, 3H), 2.73-2.67 (m, 1H), 2.37-2.34 (m, 1H), 2.31 (s, 6H), 1.36 (t, J = 7.2 Hz, 3H), 1.29 (d, J = 6.4 Hz, 3H). (Single enantiomer; unknown absolute stereochemistry) | 275 |

| Example | Compound | NMR | M/Z (M + H) |
|---|---|---|---|
| 18 | 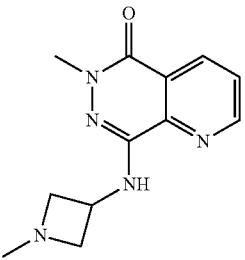 [SMILES: CN1CC(Nc2nn(C)c(=O)c3cccnc23)C1]<br>6-methyl-8-((1-methylazetidin-3-yl)amino)pyridol[2,3-d]pyridazin-5(6H)-one | $^1$H NMR (400 MHz, Methanol-d4) δ 9.04-9.03 (m, 1H), 8.63-8.61 (m, 1H), 7.83-7.80 (m, 1H), 4.52-4.45 (m, 1H), 3.85-3.81 (m, 2H), 3.67 (s, 3H), 3.24-3.20 (m, 2H), 2.43 (s, 3H). | 246 |

Example 19

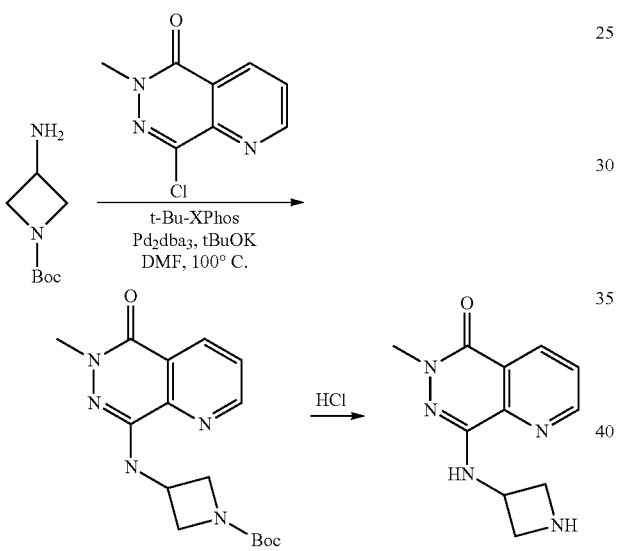

Step 1 tert-butyl 3-((6-methyl-5-oxo-5,6-dihydropyrido[2,3-d]pyridazin-8-yl)amino)azetidine-1-carboxylate

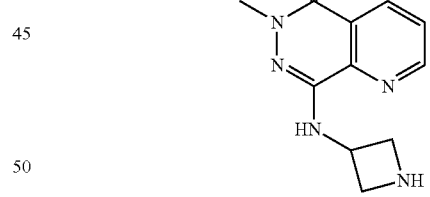

A mixture of 8-chloro-6-methylpyrido[2,3-d]pyridazin-5(6H)-one (Intermediate C, 300 mg, 1.53 mmol), tert-butyl 3-aminoazetidine-1-carboxylate (318 mg, 1.83 mmol), t-Butyl-XPhos (132 mg, 0.300 mmol), t-BuOK (345 mg, 3.06 mmol) and Pd$_2$dba$_3$ (141 mg, 0.150 mmol) in DMF (8 mL) was heated at 100° C. under microwave conditions for 2 h under N$_2$, at which time LCMS indicated the reaction had gone to completion. The reaction mixture was poured into water (10 mL) and then extracted with ethyl acetate (3×10 mL). The combined organic extracts were dried over Na$_2$SO$_4$ and concentrated under reduced pressure. The residue was purified by silica gel chromatography (petroleum ether/ethyl acetate=1:1) to give the title compound (220 mg, 43% yield) as a brown solid. LCMS M/Z (M+H) 332.

Step 2

8-(azetidin-3-ylamino)-6-methylpyrido[2,3-d]pyridazin-5(6H)-one

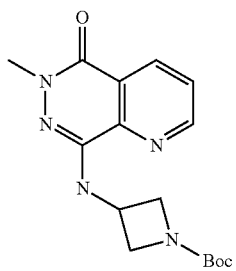 [SMILES: Cn1nc(NC2CN(C(=O)OC(C)(C)C)C2)c2ncccc2c1=O]

A solution of tert-butyl 3-((6-methyl-5-oxo-5,6-dihydropyrido[2,3-d]pyridazin-8-yl)amino) azetidine-1-carboxylate (100 mg, 0.300 mmol) in methanol (3 mL) was added 2M hydrogen chloride in methanol (3 mL). The resulting mixture was stirred at ambient temperature for 30 min and then concentrated in vacuo. The residue was purified by reverse phase chromatography (acetonitrile 28-58%/0.1% NH$_4$OH in water) to give the title compound (8.2 mg, 12% yield) as a white solid. $^1$H NMR (400 MHz, Methanol-d4) δ 9.06-9.04 (m, 1H), 8.64-8.62 (m, 1H), 7.84-7.81 (m, 1H), 4.79-4.77 (m, 1H), 4.08-4.03 (m, 2H), 3.95-3.91 (m, 2H), 3.68 (s, 3H). LCMS M/Z (M+H) 232.

Example 20

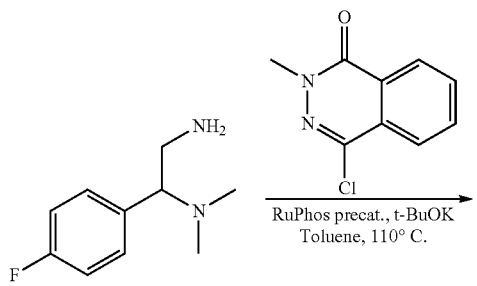

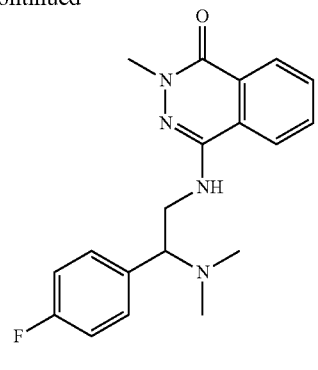

Example 20

4-((2-(dimethylamino)-2-(4-fluorophenyl)ethyl)amino)-2-methylphthalazin-1(2H)-one

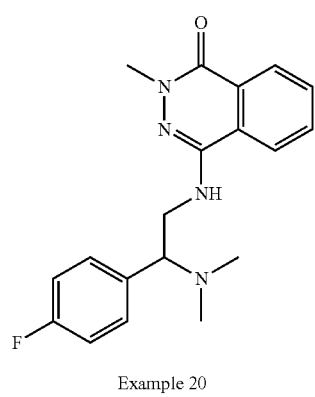

Example 20

A mixture of 4-chloro-2-methylphthalazin-1(2H)-one (Intermediate F, 100 mg, 0.515 mmol), 1-(4-fluorophenyl)-N1,N1-dimethylethane-1,2-diamine (180 mg, 1.04 mmol), sodium 2-methylpropan-2-oalate (100 mg, 1.04 mmol) and RuPhos $3^{rd}$ generation precatalyst (43 mg, 0.050 mmol) in toluene (5 mL) was degassed. The resulting mixture was heated at 110° C. for 2 h. The mixture was cooled and extracted with ethyl acetate and water. The organic phase was separated, dried over $Na_2SO_4$, filtered, concentrated in vacuo, and purified on a 10 g biotage silica gel column with ethyl acetate to 5% methanol in ethyl acetate to provide the title compound (70 mg, 40% yield). $^1$H NMR (400 MHz, Acetone-d6) δ 8.32-8.35 (m, 1H), 7.77-7.88 (m, 3H), 7.41-7.45 (m, 2H), 7.11 (t, J=8.79 Hz, 2H), 5.80-5.85 (m, 1H), 3.81-3.88 (m, 2H), 3.61 (s, 3H), 3.52-3.58 (m, 1H), 2.23 (s, 6H). LCMS M/Z (M+H) 341. The compound was isolated as a racemic mixture.

Examples 21-47

The following compounds were prepared in a similar fashion to example 20, using either intermediate F (Examples 21-30, 33-35, 38-45 and 47), intermediate M (Example 31), intermediate N (Example 36), intermediate O (Example 37) or intermediate A (Example 32 and 46). For examples 25-27, 32-34 and 46-47 the diamine starting material was prepared according to the procedures described before (Intermediates R, S, T, Q, U and V). For all the other examples, commercially available diamines were used. The specific conditions for the separation of enantiomers are reported in the following section.

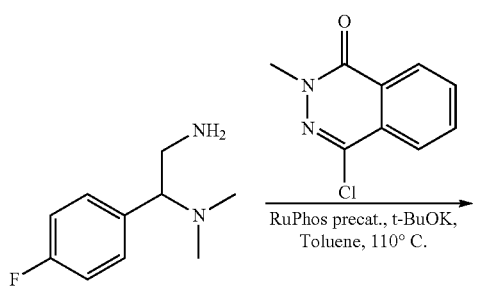

| Example | Compound Name | NMR | M/Z (M + H) |
|---|---|---|---|
| 21 | 4-((2-(dimethylamino)-2-(4-methoxyphenyl)ethyl)amino)-2-methylphthalazin-1(2H)-one | ¹H NMR (400 MHz, Acetone-d6) δ 8.33 (d, J = 6.96 Hz, 1H), 7.75-7.85 (m, 3H), 7.30 (d, J = 8.42 Hz, 2H), 6.92 (d, J = 8.61 Hz, 2H), 5.79 (br. s., 1H), 3.76-3.84 (m, 2H), 3.79 (s, 3H), 3.61 (s, 3H), 3.51-3.57 (m, 1H), 2.22 (s, 6H). (Racemic mixture) | 353 |
| 22 | 4-((2-(dimethylamino)-2-phenylethyl)amino)-2-methylphthalazin-1(2H)-one | ¹H NMR (400 MHz, Acetone-d6) δ 8.22 (d, J = 7.58 Hz, 1H), 8.00 (d, J = 8.03 Hz, 1H), 7.74-7.90 (m, 2H), 7.19-7.37 (m, 5H), 6.52 (br. s., 1H), 3.70-3.85 (m, 2H), 3.47-3.62 (m, 4H), 2.16 (s, 6H). (Racemic mixture) | 323 |
| 22A | (S)-4-((2-(dimethylamino)-2-phenylethyl)amino)-2-methylphthalazin-1(2H)-one | N/A (Single enantiomer; unknown absolute stereochemistry) | 323 |

-continued

| Example | Compound Name | NMR | M/Z (M + H) |
|---|---|---|---|
| 22B | 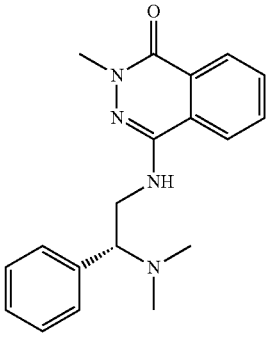 [SMILES: CN(C)[C@@H](CNc1nn(C)c(=O)c2ccccc12)c1ccccc1]<br>(R)-4-((2-(dimethylamino)-2-phenylethyl)amino)-2-methylphthalazin-1(2H)-one | N/A<br>(Single enantiomer; unknown absolute stereochemistry) | 323 |
| 23 | 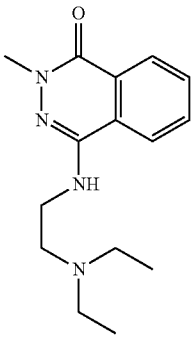 [SMILES: CCN(CC)CCNc1nn(C)c(=O)c2ccccc12]<br>4-((2-(diethylamino)ethyl)amino)-2-methylphthalazin-1(2H)-one | $^1$H NMR (400 MHz, Acetone-d6) δ 8.34 (d, J = 8.42 Hz, 1H), 7.63-7.97 (m, 3H), 5.77-6.08 (m, 1H), 3.62 (s, 3H), 3.39 (m, 2H), 2.79 (m, 2H), 2.60 (m, 4H), 1.05 (t, J = 7.05 Hz, 6H). | 275 |
| 24 | 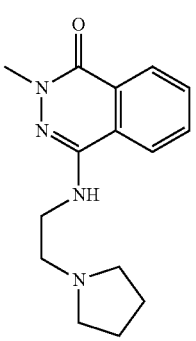 [SMILES: Cn1nc(NCCN2CCCC2)c2ccccc2c1=O]<br>2-methyl-4-((2-(pyrrolidin-1-yl)ethyl)amino)phthalazin-1(2H)-one | $^1$H NMR (400 MHz, Acetone-d6) δ 8.34 (d, J = 7.69 Hz, 1H), 7.95 (d, J = 7.69 Hz, 1H), 7.75-7.88 (m, 2H), 5.95 (br. s., 1H), 3.62 (s, 3H), 3.38-3.51 (m, 2H), 2.78-2.84 (m, 6H), 1.73-1.77 (m, 4H). | 273 |

-continued

| Example | Compound Name | NMR | M/Z (M + H) |
|---|---|---|---|
| 25 | 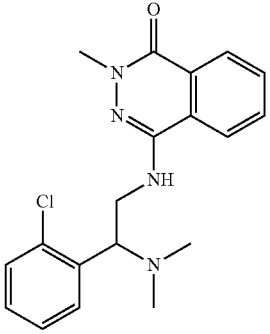<br>4-((2-(2-chlorophenyl)-2-(dimethylamino)ethyl)amino)-2-methylphthalazin-1(2H)-one | ¹H NMR (400 MHz, Acetone-d6) δ 8.30-8.36 (m, 1H), 7.86-7.92 (m, 1H), 7.76-7.84 (m, 2H), 7.64 (dd, J = 1.65, 7.69 Hz, 1H), 7.40 (dd, J = 1.28, 7.87 Hz, 1H), 7.30-7.36 (m, 1H), 7.24-7.28 (m,, 1H), 5.83 (br. s., 1H), 4.40 (t, J = 6.32 Hz, 1H), 3.88-3.94 (m, 1H), 3.56-3.62 (m, 1H), 3.60 (s, 3H), 2.30 (s, 6H). (Racemic mixture) | 357 |
| 26 | 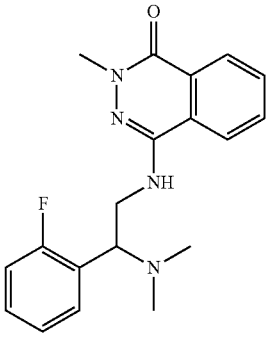 [SMILES: CN(C)C(CNc1nn(C)c(=O)c2ccccc12)c1ccccc1F]<br>4-((2-(dimethylamino)-2-(2-fluorophenyl)ethyl)amino)-2-methylphthalazin-1(2H)-one | ¹H NMR (400 MHz, Acetone-d6) δ 8.33 (dd, J = 1.37, 7.60 Hz, 1H), 7.87-7.94 (m, 1H), 7.73-7.86 (m, 2H), 7.51 (dt, J = 1.74, 7.37 Hz, 1H), 7.28-7.38 (m, 1H), 7.18-7.26 (m, 1H), 7.06-7.17 (m, 1H), 5.92 (br. s., 1H), 4.32 (dd, J = 6.13, 7.97 Hz, 1H), 3.90 (ddd, J = 3.75, 8.33, 12.63 Hz, 1H), 3.62-3.67 (m, 1H), 3.60 (s, 3H), 2.24 (s, 6H). (Racemic mixture) | 341 |
| 27 | 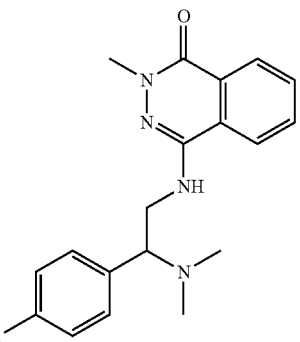<br>4-((2-(4-chlorophenyl)-2-(dimethylamino)ethyl)amino)-2-methylphthalazin-1(2H)-one | ¹H NMR (400 MHz, DMSO-d6) δ 8.23-8.27 (m, 1H), 7.95-7.97 (m, 1H), 7.75-7.86 (m, 2H), 7.30-7.40 (m, 4H), 6.53 (br. s., 1H), 3.70-3.80 (m, 2H), 3.55 (s, 3H), 3.40-3.45 (m, 1H), 2.10 (s, 6H). (Racemic mixture) | 357 |

| Example | Compound Name | NMR | M/Z (M + H) |
|---|---|---|---|
| 28 | 4-((1-(dimethylamino)propan-2-yl)amino)-2-methylphthalazin-1(2H)-one | ¹H NMR (400 MHz, DMSO-d6) δ 8.23 (dd, J = 1.09, 7.88 Hz, 1H), 8.14 (d, J = 7.88 Hz, 1H), 7.87 (dt, J = 1.42, 7.61 Hz, 1H), 7.77-7.83 (m, 1H), 6.30 (d, J = 7.01 Hz, 1H), 3.94-4.06 (m, 1H), 3.56 (s, 3H), 2.46 (dd, J = 6.46, 11.93 Hz, 1H), 2.21-2.26 (m, 1H), 2.19 (s, 6H), 1.21 (d, J = 6.35 Hz, 3H). (Racemic mixture) | 261 |
| 29 | 4-((2-(dimethylamino)ethyl)amino)-2-methylphthalazin-1(2H)-one | ¹H NMR (400 MHz, DMSO-d6) δ 8.22 (d, J = 7.66 Hz, 1H), 8.07 (d, J = 7.88 Hz, 1H), 7.72-7.93 (m, 2H), 6.59 (br. s., 1H), 3.55 (s, 3H), 3.34-3.39 (m, 2H), 2.49 (d, J = 5.04 Hz, 2H), 2.19 (s, 6H). | 247 |
| 30 | 2-methyl-4-(((1-methylpyrrolidin-2-yl)methyl)amino)phthalazin-1(2H)-one | ¹H NMR (400 MHz, DMSO-d6) δ 8.23 (dd, J = 1.09, 7.88 Hz, 1H), 8.10 (d, J = 7.66 Hz, 1H), 7.87 (dt, J = 1.53, 7.66 Hz, 1H), 7.77-7.84 (m, 1H), 6.62 (t, J = 5.47 Hz, 1H), 3.54-3.58 (m, 3H), 3.42-3.50 (m, 1H), 3.09 (ddd, J = 5.26, 7.44, 12.92 Hz, 1H), 2.93-3.00 (m, 1H), 2.52-2.57 (m, 1H), 2.34 (s, 3H), 2.09-2.18 (m, 1H), 1.85-1.96 (m, 1H), 1.54-1.71 (m, 3H). (Racemic mixture) | 273 |

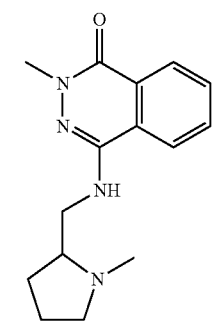 [SMILES: CN1CCCC1CNc1nn(C)c(=O)c2ccccc12]

| Example | Compound Name | NMR | M/Z (M + H) |
|---|---|---|---|
| 31 | (E)-2-(but-2-en-1-yl)-4-((1-(dimethylamino)propan-2-yl)amino)phthalazin-1(2H)-one (Trifluoroacetic acid salt) | ¹H NMR (400 MHz, DMSO-d6) δ 9.10 (br. s., 1H), 8.26 (d, J = 7.45 Hz, 1H), 8.12 (d, J = 8.10 Hz, 1H), 7.89-7.95 (m, 1H), 7.82-7.89 (m, 1H), 6.69 (d, J = 8.54 Hz, 1H), 5.55-5.72 (m, 2H), 4.50-4.57 (m, 2H), 4.39 (br. s., 1H), 3.29-3.40 (m, 1H), 3.16-3.27 (m, 1H), 2.80-2.87 (m, 6H), 1.65 (d, J = 4.82 Hz, 3H), 1.26 (d, J = 6.57 Hz, 3H). (Racemic mixture) | 301 |
| 32 | 8-((1-(4-chlorophenyl)-3-(dimethylamino)piperidin-4-yl)amino)-6-methylpyrido[2,3-d]pyridazin-5(6H)-one (Trifluoroacetic acid salt) | ¹H NMR (400 MHz, DMSO-d6) δ 9.44-9.36 (m, 1H), 9.12 (ddd, J = 1.6, 4.6, 9.5 Hz, 1H), 8.97-8.89 (m, 1H), 8.64 (ddd, J = 1.6, 6.5, 8.1 Hz, 1H), 7.93 (dt, J = 4.6, 8.2 Hz, 1H), 7.30 (dd, J = 2.2, 9.0 Hz, 2H), 7.16-7.06 (m, 2H), 4.75-4.66 (m, 1H), 4.45-4.33 (m, 1H), 4.10 (br. s., 1H), 3.94-3.86 (m, 1H), 3.73 (dd, J = 10.5, 18.8 Hz, 2H), 3.62 (s, 1H), 3.60-3.57 (m, 1H), 3.46 (d, J = 12.9 Hz, 1H), 3.38 (d, J = 12.7 Hz, 1H), 3.12 (t, J = 11.6 Hz, 2H), 3.01-2.82 (m, 5H), 2.16-2.01 (m, 1H), 1.98-1.84 (m, 1H). (Racemic mixture; and 60:40 diastereoisomeric mixture) | 413 |
| 32A | 8-((1-(4-chlorophenyl)-3-(dimethylamino)piperidin-4-yl)amino)-6-methylpyrido[2,3-d]pyridazin-5(6H)-one | N/A (Single unknown stereoisomer) | 413 |

-continued

| Example | Compound Name | NMR | M/Z (M + H) |
|---|---|---|---|
| 32B | 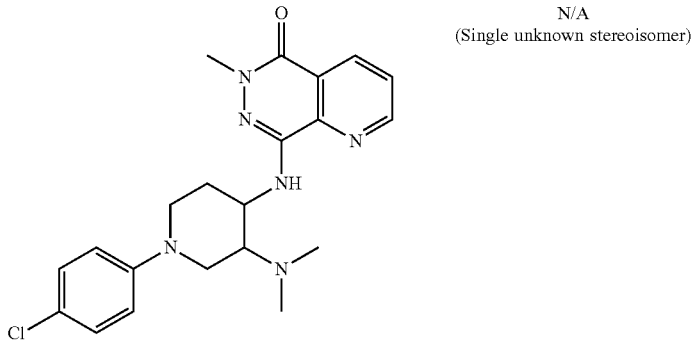

8-((1-(4-chlorophenyl)-3-(dimethylamino)piperidin-4-yl)amino)-6-methylpyrido[2,3-d]pyridazin-5(6H)-one | N/A (Single unknown stereoisomer) | 413 |
| 33 | 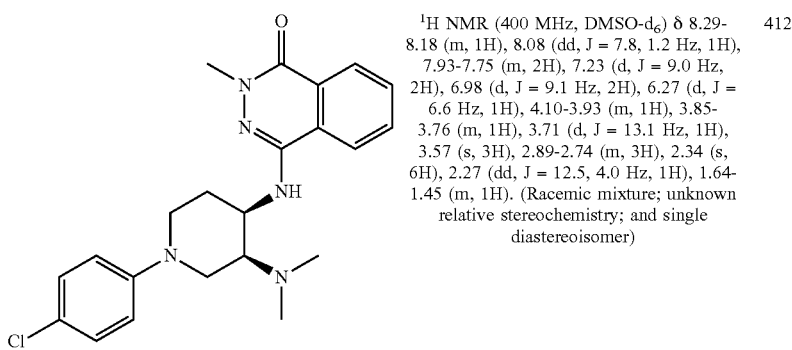

4-(((3S,4R)-1-(4-chlorophenyl)-3-(dimethylamino)piperidin-4-yl)amino)-2-methylphthalazin-1(2H)-one | $^1$H NMR (400 MHz, DMSO-$d_6$) δ 8.29-8.18 (m, 1H), 8.08 (dd, J = 7.8, 1.2 Hz, 1H), 7.93-7.75 (m, 2H), 7.23 (d, J = 9.0 Hz, 2H), 6.98 (d, J = 9.1 Hz, 2H), 6.27 (d, J = 6.6 Hz, 1H), 4.10-3.93 (m, 1H), 3.85-3.76 (m, 1H), 3.71 (d, J = 13.1 Hz, 1H), 3.57 (s, 3H), 2.89-2.74 (m, 3H), 2.34 (s, 6H), 2.27 (dd, J = 12.5, 4.0 Hz, 1H), 1.64-1.45 (m, 1H). (Racemic mixture; unknown relative stereochemistry; and single diastereoisomer) | 412 |
| 34 | 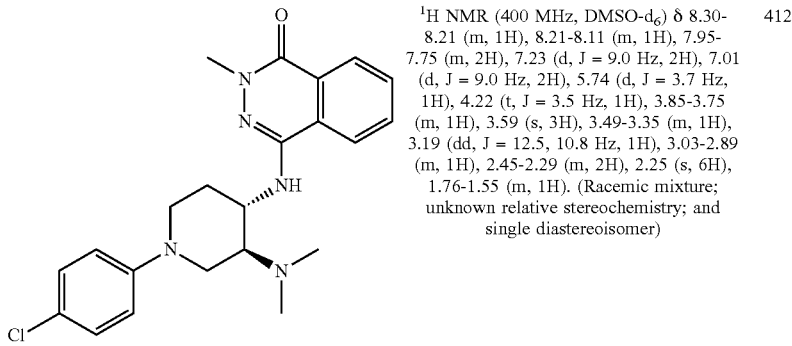

4-(((3S,4S)-1-(4-chlorophenyl)-3-(dimethylamino)piperidin-4-yl)amino)-2-methylphthalazin-1(2H)-one | $^1$H NMR (400 MHz, DMSO-$d_6$) δ 8.30-8.21 (m, 1H), 8.21-8.11 (m, 1H), 7.95-7.75 (m, 2H), 7.23 (d, J = 9.0 Hz, 2H), 7.01 (d, J = 9.0 Hz, 2H), 5.74 (d, J = 3.7 Hz, 1H), 4.22 (t, J = 3.5 Hz, 1H), 3.85-3.75 (m, 1H), 3.59 (s, 3H), 3.49-3.35 (m, 1H), 3.19 (dd, J = 12.5, 10.8 Hz, 1H), 3.03-2.89 (m, 1H), 2.45-2.29 (m, 2H), 2.25 (s, 6H), 1.76-1.55 (m, 1H). (Racemic mixture; unknown relative stereochemistry; and single diastereoisomer) | 412 |

| Example | Compound Name | NMR | M/Z (M + H) |
|---|---|---|---|
| 35 | 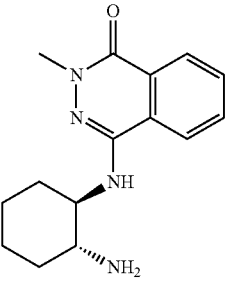 [SMILES: Cn1nc(N[C@@H]2CCCC[C@H]2N)c2ccccc2c1=O]<br>4-(((1R,2R)-2-aminocyclohexyl)amino)-2-methylphthalazin-1(2H)-one | ¹H NMR (400 MHz, DMSO-d6) δ 8.25-8.18 (m, 2H), 7.89-7.83 (m, 1H), 7.83-7.76 (m, 1H), 6.36 (d, J = 7.7 Hz, 1H), 3.58-3.52 (m, 3H), 3.49-3.38 (m, 1H), 3.32 (br. s., 2H), 2.69 (dt, J = 3.8, 10.2 Hz, 1H), 2.16 (d, J = 12.9 Hz, 1H), 1.89 (d, J = 12.9 Hz, 1H), 1.67 (d, J = 7.2 Hz, 2H), 1.33-1.05 (m, 4H). (Racemic mixture; single diastereoisomer; and known relative stereochemistry) | 273 |
| 36 | 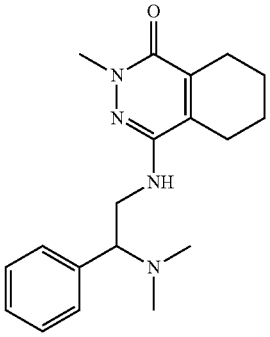 [SMILES: CN(C)C(CNc1nn(C)c(=O)c2c1CCCC2)c1ccccc1]<br>4-((2-(dimethylamino)-2-phenylethyl)amino)-2-methyl-5,6,7,8-tetrahydrophthalazin-1(2H)-one | ¹H NMR (400 MHz, DMSO-d6) δ 7.36-7.23 (m, 5H), 5.25 (t, J = 5.1 Hz, 1H), 3.68-3.63 (m, 1H), 3.61-3.52 (m, 1H), 3.45 (s, 3H), 3.37-3.32 (m, 1H), 2.34 (t, J = 5.6 Hz, 2H), 2.22-2.16 (m, 2H), 2.12 (s, 6H), 1.68-1.56 (m, 4H). (Racemic mixture) | 327 |
| 37 | 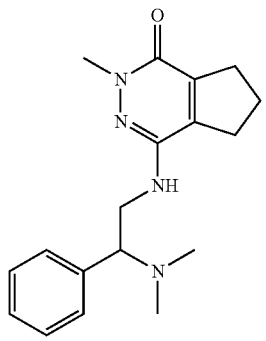 [SMILES: CN(C)C(CNc1nn(C)c(=O)c2c1CCC2)c1ccccc1]<br>4-((2-(dimethylamino)-2-phenylethyl)amino)-2-methyl-2,5,6,7-tetrahydro-1H-cyclopenta[d]pyridazin-1-one | ¹H NMR (400 MHz, DMSO-d6) δ 7.36-7.22 (m, 5H), 5.50 (t, J = 5.1 Hz, 1H), 3.68-3.55 (m, 2H), 3.46 (s, 3H), 3.39-3.33 (m, 1H), 2.69-2.58 (m, 4H), 2.11 (s, 6H), 1.99 (t, J = 7.4 Hz, 2H). (Racemic mixture) | 313 |

-continued

| Example | Compound Name | NMR | M/Z (M + H) |
|---|---|---|---|
| 38 | 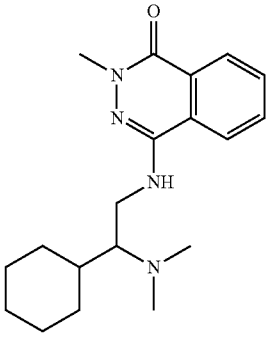 [SMILES: CN(C)C(CNc1nn(C)c(=O)c2ccccc12)C1CCCCC1]<br>4-((2-cyclohexyl-2-(dimethylamino)ethyl)amino)-2-methylphthalazin-1(2H)-one | $^1$H NMR (400 MHz, DMSO-d6) δ 8.23 (dd, J = 0.99, 7.99 Hz, 1H), 8.08 (d, J = 7.66 Hz, 1H), 7.88 (dt, J = 1.53, 7.66 Hz, 1H), 7.78-7.84 (m, 1H), 6.42 (t, J = 4.05 Hz, 1H), 3.57 (s, 3H), 2.56-2.69 (m, 1H), 2.32 (s, 6H), 1.41-1.90 (m, 7H), 0.93-1.30 (m, 6H). (Racemic mixture) | 329 |
| 39 | 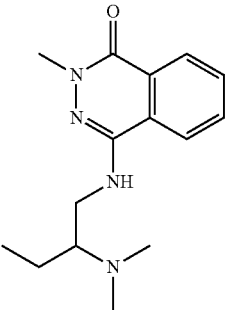 [SMILES: CCC(CNc1nn(C)c(=O)c2ccccc12)N(C)C]<br>4-((2-(dimethylamino)butyl)amino)-2-methylphthalazin-1(2H)-one | $^1$H NMR (400 MHz, DMSO-d6) δ 8.24 (dd, J = 1.09, 7.88 Hz, 1H), 8.09 (d, J = 7.88 Hz, 1H), 7.88 (dt, J = 1.42, 7.61 Hz, 1H), 7.81 (dt, J = 1.00, 7.60 Hz, 1H), 6.56 (br. s., 1H), 3.56 (s, 3H), 3.34-3.40 (m, 1H), 3.14-3.23 (m, 1H), 2.66-2.82 (m, 1H), 2.21-2.38 (m, 6H), 1.52 (qd, J = 6.90, 13.90 Hz, 1H), 1.39 (td, J = 7.06, 13.90 Hz, 1H), 0.92 (t, J = 7.44 Hz, 3H). (Racemic mixture) | 275 |
| 39A | 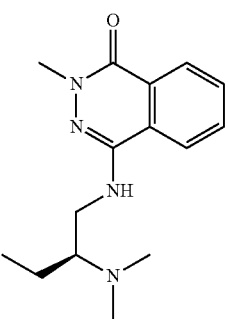 [SMILES: CC[C@@H](CNc1nn(C)c(=O)c2ccccc12)N(C)C]<br>(S)-4-((2-(dimethylamino)butyl)amino)-2-methylphthalazin-1(2H)-one | N/A<br>(Single enantiomer; unknown absolute stereochemistry) | 275 |

| Example | Compound Name | NMR | M/Z (M + H) |
|---|---|---|---|
| 39B | (R)-4-((2-(dimethylamino)butyl)amino)-2-methylphthalazin-1(2H)-one | N/A (Single enantiomer; unknown absolute stereochemistry) | 275 |
| 40 | 4-((2-(isopropylamino)ethyl)amino)-2-methylphthalazin-1(2H)-one | $^1$H NMR (400 MHz, DMSO-d6) δ 8.24 (dd, J = 1.20, 7.80 Hz, 2H), 7.86-7.93 (m, J = 1.40, 7.50, 7.50 Hz, 1H), 7.82 (t, J = 7.50 Hz, 1H), 7.14 (t, J = 5.15 Hz, 1H), 3.58 (s, 3H), 3.52-3.60 (m, 2H), 3.25 (spt, J = 6.50 Hz, 1H), 3.14 (t, J = 6.13 Hz, 2H), 1.22 (d, J = 6.57 Hz, 6H). | 261 |
| 41 | 2-methyl-4-((2-(piperidin-1-yl)ethyl)amino)phthalazin-1(2H)-one | $^1$H NMR (400 MHz, DMSO-d6) δ 8.23 (dd, J = 0.99, 7.77 Hz, 1H), 8.07 (d, J = 7.88 Hz, 1H), 7.87 (dt, J = 1.42, 7.61 Hz, 1H), 7.77-7.84 (m, 1H), 6.63 (t, J = 5.04 Hz, 1H), 3.56 (s, 3H), 3.37 (q, J = 6.40 Hz, 2H), 2.57 (t, J = 7.01 Hz, 2H), 2.35-2.48 (m, 4H), 1.45-1.55 (m, 4H), 1.32-1.43 (m, 2H). | 287 |

-continued

| Example | Compound Name | NMR | M/Z (M + H) |
|---|---|---|---|
| 42 | 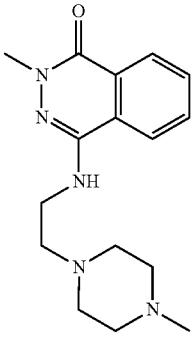<br>2-methyl-4-((2-(4-methylpiperazin-1-yl)ethyl)amino)phthalazin-1(2H)-one | $^1$H NMR (400 MHz, DMSO-d6) δ 8.23 (dd, J = 0.99, 7.77 Hz, 1H), 8.07 (d, J = 7.66 Hz, 1H), 7.87 (dt, J = 1.42, 7.61 Hz, 1H), 7.80 (dt, J = 1.20, 7.40 Hz, 1H), 6.62 (t, J = 5.36 Hz, 1H), 3.52-3.59 (m, 3H), 3.33-3.40 (m, 2H), 2.57 (t, J = 7.01 Hz, 2H), 2.39-2.53 (m, 4H), 2.20-2.38 (m, 4H), 2.14 (s, 3H). | 302 |
| 43 | 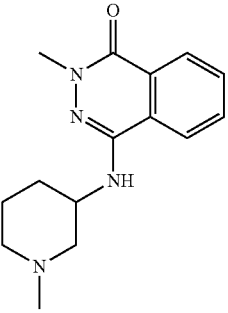 [SMILES: CN1CCCC(Nc2nn(C)c(=O)c3ccccc23)C1]<br>2-methyl-4-((1-methylpiperidin-3-yl)amino)phthalazin-1(2H)-one | $^1$H NMR (400 MHz, DMSO-d6) δ 8.23 (dd, J = 1.64, 7.77 Hz, 2H), 7.76-7.90 (m, 2H), 6.44 (br. s, 1H), 3.89-4.01 (m, 1H), 3.56 (s, 3H), 3.06 (d, J = 8.98 Hz, 1H), 2.72 (d, J = 10.51 Hz, 1H), 2.26 (br. s., 3H), 1.95-2.15 (m, 2H), 1.84-1.94 (m, 1H), 1.68-1.79 (m, 1H), 1.51-1.64 (m, 1H), 1.35-1.48 (m, 1H). (Racemic mixture) | 273 |
| 44 | 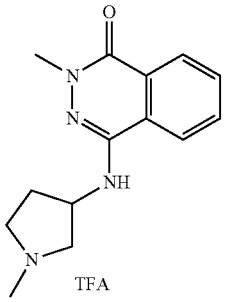 [SMILES: CN1CCC(Nc2nn(C)c(=O)c3ccccc23)C1]<br>2-methyl-4-((1-methylpyrrolidin-3-yl)amino)phthalazin-1(2H)-one (Trifluoroacetic acid salt) | N/A (Racemic mixture) | 259 |

-continued

| Example | Compound Name | NMR | M/Z (M + H) |
|---|---|---|---|
| 45 | 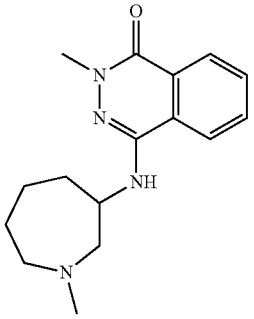 [SMILES: CN1CCCCC(Nc2nn(C)c(=O)c3ccccc23)C1]

2-methyl-4-((1-methylazepan-3-yl)amino)phthalazin-1(2H)-one | $^1$H NMR (400 MHz, DMSO-d6) δ 8.22 (dd, J = 0.9, 7.9 Hz, 1H), 8.16 (d, J = 7.9 Hz, 1H), 7.77-7.87 (m, 2H), 6.33 (d, J = 7.7 Hz, 1H), 3.95-4.01 (m, 1H), 3.55 (s, 3H), 2.80 (dd, J = 3.7, 12.9 Hz, 1H), 2.51-2.60 (m, 3H), 2.32 (s, 3H), 1.70-1.73 (m, 1H), 1.48-1.74 (m, 5H). (Racemic mixture) | 287 |
| 46A | 8-(((1R,2S)-1-(dimethylamino)-2,3-dihydro-1H-inden-2-yl)amino)-6-methylpyrido[2,3-d]pyridazin-5(6H)-one | $^1$H NMR (400 MHz, DMSO-d6) δ 9.06 (dd, J = 1.7, 4.5 Hz, 1H), 8.61 (dd, J = 1.6, 8.0 Hz, 1H), 7.89 (dd, J = 4.6, 7.9 Hz, 1H), 7.09-7.22 (m, 4H), 5.44-5.48 (m, 1H), 3.58 (s, 3H), 3.42-3.49 (m, 1H), 3.03-3.09 (m, 1H), 2.79-2.85 (m, 1H), 2.28 (s, 6H). (Single enantiomer; absolute stereochemistry assigned based on commercial starting material) | 336 |
| 46B | 8-(((1S,2R)-1-(dimethylamino)-2,3-dihydro-1H-inden-2-yl)amino)-6-methylpyrido[2,3-d]pyridazin-5(6H)-one | $^1$H NMR (400 MHz, DMSO-d$_6$) δ 9.06 (dd, J = 1.75, 4.60 Hz, 1H), 8.61 (dd, J = 1.75, 8.10 Hz, 1H), 7.81-7.93 (m, 1H), 6.92-7.33 (m, 4H), 5.47 (t, J = 11.50 Hz, 1H), 3.41-3.50 (m, 1H), 3.01-3.11 (m, 1H), 2.83 (m, 1H), 2.28 (br. s., 6H). (Single enantiomer; absolute stereochemistry assigned based on commercial starting material) | 336 |

| Example | Compound Name | NMR | M/Z (M + H) |
|---|---|---|---|
| 47A | 4-(((1R,2S)-1-(dimethylamino)-2,3-dihydro-1H-inden-2-yl)amino)-2-methylphthalazin-1(2H)-one | ¹H NMR (400 MHz, DMSO-d6) δ 8.24-8.29 (m, 2H), 7.83-7.88 (m, 2H), 7.12-7.22 (m, 4H), 5.56 (t, J = 8.5 Hz, 1H), 3.57 (s, 3H), 3.34-3.38 (m, 1H), 3.08 (dd, J = 7.8 Hz, 15.9 Hz, 1H), 2.83 (dd, J = 9.0 Hz, 15.6 Hz, 1H), 2.28 (s, 6H). (Single enantiomer; absolute stereochemistry assigned based on commercial starting material) | 335 |
| 47B | 4-(((1S,2R)-1-(dimethylamino)-2,3-dihydro-1H-inden-2-yl)amino)-2-methylphthalazin-1(2H)-one | ¹H NMR (400 MHz, DMSO-d6) δ 8.23-8.28 (m, 2H), 7.82-7.87 (m, 2H), 7.11-7.23 (m, 4H), 5.55 (t, J = 8.3 Hz, 1H), 3.56 (s, 3H), 3.32-3.36 (m, 1H), 3.04-3.10 (m, 1H), 2.81-2.85 (m, 1H), 2.27 (br. s, 6H). (Single enantiomer; absolute stereochemistry assigned based on commercial starting material) | 335 |

Example 48

The following compound was prepared in a similar fashion to example 20, using t-BuRockPhos 3$^{rd}$ generation precatalyst instead of RuPhos 3$^{rd}$ generation precatalyst.

| Example | Compound Name | NMR | M/Z (M + H) |
|---|---|---|---|
| 48 | 4-(2-(dimethylamino)ethoxy)-2-methylphthalazin-1(2H)-one (Trifluoroacetic acid salt) | ¹H NMR (400 MHz, DMSO-d6) δ 10.27-10.50 (m, 1H), 8.20-8.27 (m, 1H), 8.12-8.19 (m, 1H), 7.87-7.96 (m, 2H), 4.56-4.62 (m, 2H), 3.62 (m, 5H), 2.92 (s, 6H). | 248 |

Example 49

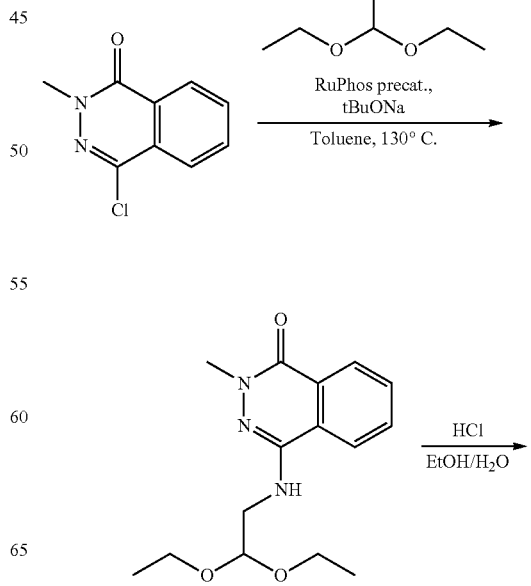

133
-continued

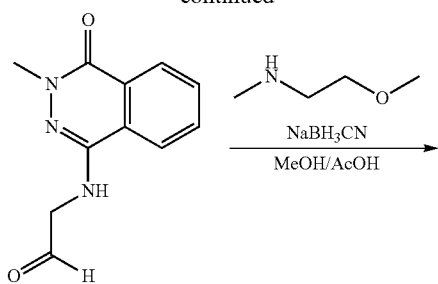

Step 1:

4-((2,2-diethoxyethyl)amino)-2-methylphthalazin-1(2H)-one

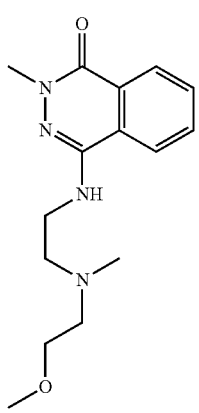

The title intermediate was prepared in a similar fashion to example 20, but was heated at 130° C. instead of 110° C. LCMS M/Z (M+H) 292.

134

Step 2:

2-((3-methyl-4-oxo-3,4-dihydrophthalazin-1-yl)amino)acetaldehyde

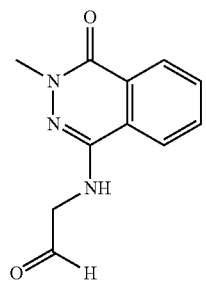 [SMILES: Cn1nc(NCC=O)c2ccccc2c1=O]

To a suspension of 4-((2,2-diethoxyethyl)amino)-2-methylphthalazin-1(2H)-one (75 mg, 0.26 mmol) in water (1 mL) was added 1.25M hydrogen chloride in ethanol (5.1 mL, 6.4 mmol) at room temperature. The reaction was heated at 40° C. for 45 min then concentrated in vacuo. The crude product was used immediately in the next step without purification. LCMS M/Z (M+H) 218.

Step 3:

4-((2-((2-methoxyethyl)(methyl)amino)ethyl)amino)-2-methylphthalazin-1(2H)-one

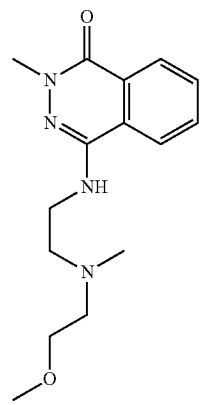 [SMILES: COCCN(C)CCNc1nn(C)c(=O)c2ccccc12]

To a solution of crude 2-((3-methyl-4-oxo-3,4-dihydrophthalazin-1-yl)amino)acetaldehyde in methanol (3 mL) was added 2-methoxy-N-methylethanamine (0.0688 g, 0.7722 mmol) and sodium cyanoborohydride (0.024 g, 0.39 mmol). The pH was then adjusted to 7 with acetic acid, and the reaction was stirred for about 30 minutes before it was quenched with an aqueous solution of sodium bicarbonate. The product was extracted with ethyl acetate (repeated 3 times), and the combined organic layers were dried with Na$_2$SO$_4$, filtered, and concentrated to dryness under reduced pressure. The crude product was purified by flash chromatography (hexane/ethyl acetate 9:1 to 0:10) to give the title compound (22 mg, 29% yield). $^1$H NMR (400 MHz, DMSO-d6) δ 8.24 (dd, J=1.53, 7.88 Hz, 1H), 8.07 (d, J=7.88 Hz, 1H), 7.88 (dt, J=1.42, 7.61 Hz, 1H), 7.81 (dt, J=1.00, 7.60 Hz, 1H), 6.69 (br. s, 1H), 3.54-3.59 (m, 3H), 3.46 (t, J=5.80 Hz, 2H), 3.35-3.41 (m, 2H), 3.22 (s, 3H), 2.60-2.80 (m, 2H), 2.35 (br. s., 2H), 1.90 (s, 3H). LCMS M/Z (M+H) 291.

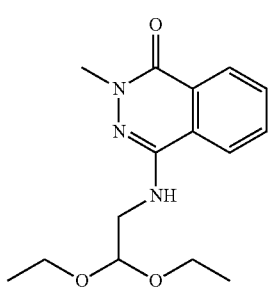

Example 49

Examples 50-51

The following compounds were prepared in a similar fashion to example 49. All examples in the following table were prepared using commercially available amines.

| Example | Compound Name | NMR | M/Z (M + H) |
|---|---|---|---|
| 50 | 4-((2-(azetidin-1-yl)ethyl)amino)-2-methylphthalazin-1(2H)-one | $^1$H NMR (400 MHz, DMSO-d6) δ 8.23 (dd, J = 1.53, 7.88 Hz, 1H), 8.09 (d, J = 8.32 Hz, 1H), 7.84-7.90 (m, 1H), 7.78-7.84 (m, 1H), 6.64 (t, J = 5.47 Hz, 1H), 3.54-3.58 (m, 3H), 3.19 (q, J = 6.50 Hz, 2H), 3.14 (t, J = 6.90 Hz, 4H), 2.61 (t, J = 6.79 Hz, 2H), 1.96 (quin, J = 6.95 Hz, 2H). | 259 |
| 51 | 2-methyl-4-((2-(methyl(oxetan-3-yl)amino)ethyl)amino)phthalazin-1(2H)-one | $^1$H NMR (400 MHz, DMSO-d6) δ 8.22-8.24 (m, 1H), 8.06-8.08 (m, 1H), 7.84-7.90 (m, 1H), 7.78-7.82 (m, 1H), 6.68-6.72 (m, 1H), 4.52 (br. s., 2H), 4.41 (br. s., 2H), 3.57-3.61 (m, 2H), 3.56 (s, 3H), 3.32-3.35 (m, 2H), 2.15 (br. s., 3H). | 289 |

Example 52

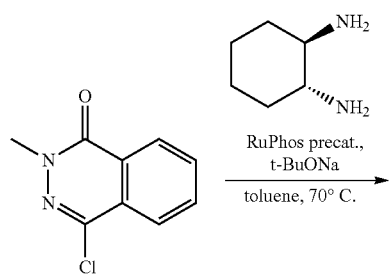

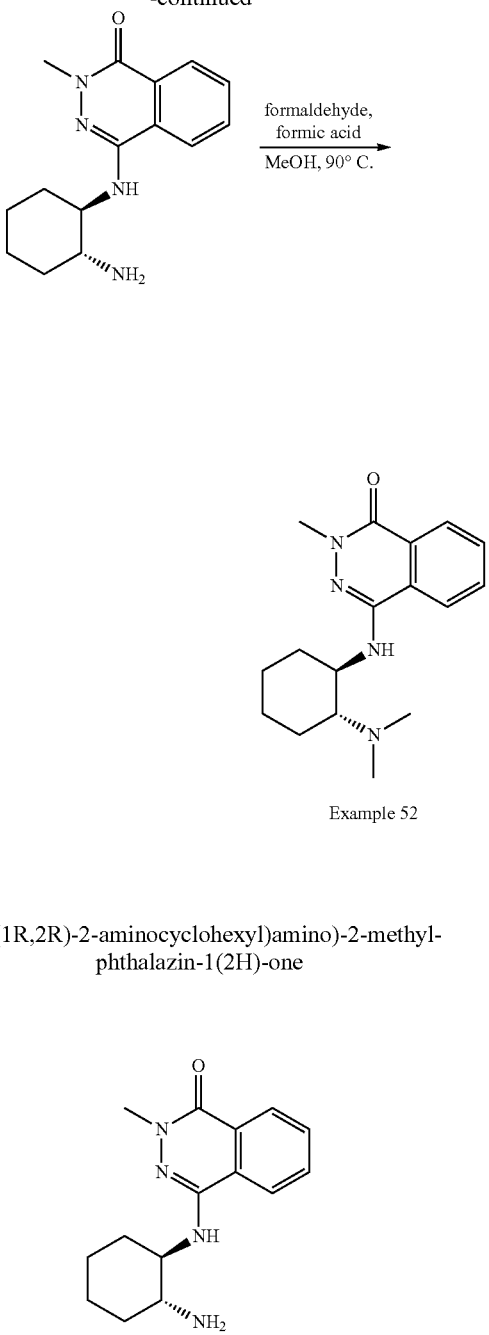

Example 52

Step 1:

4-(((1R,2R)-2-aminocyclohexyl)amino)-2-methyl-phthalazin-1(2H)-one

In a pyrex vial 4-chloro-2-methylphthalazin-1(2H)-one (300 mg, 1.54 mmol), RuPhos 3$^{rd}$ generation precatalyst (121 mg, 0.154 mmol), and sodium tert-butoxide (444 mg, 4.62 mmol) were added, the vial was sealed, and the atmosphere evacuated and purged with N$_2$ (3×). (+/−)-Transcyclohexanediamine (370 μL, 3.08 mmol) in toluene (6 mL) was then added, and the reaction was heated at 70° C. overnight. The crude reaction was concentrated in vacuo, deposited onto silica gel with aid of methanol, and purified by silica gel chromatography using 85% 90:10:1 dichloromethane:methanol:NH$_4$OH as eluent. The product fractions were concentrated and lyophilized to provide the title compound (191 mg, 45% yield).
LCMS M/Z (M+H) 273.

Step 2:

4-(((1R,2R)-2-(dimethylamino)cyclohexyl)amino)-2-methylphthalazin-1(2H)-one

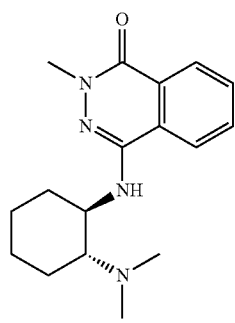

In a 25 mL round bottom flask, 4-(((1R,2R)-2-aminocyclohexyl)amino)-2-methylphthalazin-1(2H)-one (129 mg, 0.48 mmol) was dissolved in methanol (5 mL). Formaldehyde (37% in water, 2 mL) and formic acid (88%, 2 mL) were added, and the reaction was heated at 90° C. overnight. The reaction was cooled to ambient temperature, poured into a saturated aqueous solution of NaHCO$_3$, and extracted with dichloromethane. The extracts were washed with brine, dried over Na$_2$SO$_4$, filtered, concentrated in vacuo, and purified by silica gel chromatography (eluting with 75% 90:10:1 dichloromethane:methanol:NH$_4$OH mixing with dichloromethane) to provide 4-(((1R,2R)-2-(dimethylamino)cyclohexyl)amino)-2-methylphthalazin-1(2H)-one (96 mg, 69% yield) as a white solid. $^1$H NMR (400 MHz, DMSO-d6) δ 8.24 (dd, J=1.4, 7.8 Hz, 1H), 8.01 (d, J=7.9 Hz, 1H), 7.88 (dt, J=1.4, 7.6 Hz, 1H), 7.84-7.78 (m, 1H), 6.18 (d, J=4.8 Hz, 1H), 3.60 (t, J=4.4 Hz, 1H), 3.56 (s, 3H), 2.54 (d, J=3.3 Hz, 1H), 2.39 (d, J=12.5 Hz, 1H), 2.19 (s, 6H), 1.87-1.75 (m, 2H), 1.65 (br. S., 1H), 1.32-1.09 (m, 4H). LCMS M/Z (M+H) 301. (Racemic mixture; single diastereoisomer; and known relative stereochemistry)

Examples 53-54

The following compounds were prepared in a similar fashion to example 52. All examples in the following table were prepared using commercially available amines. The specific conditions for the separation of enantiomers are reported in the following section.

| Example | Compound Name | | NMR | M/Z (M + H) |
|---|---|---|---|---|
| 53 | | 4-(((1R,2R)-2-(dimethylamino)cyclopentyl)amino)-2-methylphthalazin-1(2H)-one | $^1$H NMR (400 MHz, DMSO-d6) δ 8.25-8.19 (m, 2H), 7.87 (dt, J = 1.3, 7.7 Hz, 1H), 7.83-7.78 (m, 1H), 6.52 (d, J = 7.7 Hz, 1H), 4.11 (t, J = 6.6 Hz, 1H), 3.56 (s, 3H), 2.83 (d, J = 6.8 Hz, 1H), 2.20 (s, 6H), 2.05 (dd, J = 7.3, 12.6 Hz, 1H), 1.81 (dd, J = 5.3, 12.0 Hz, 1H), 1.72-1.45 (m, 4H). (Racemic mixture; single diastereoisomer; and known relative stereochemistry) | 287 |
| 54 | | 4-(((1R,2S)-2-(dimethylamino)cyclohexyl)amino)-2-methylphthalazin-1(2H)-one | $^1$H NMR (400 MHz, DMSO-d6) δ 8.25 (dd, J = 1.3, 7.9 Hz, 1H), 8.11 (d, J = 7.9 Hz, 1H), 7.90 (dt, J = 1.5, 7.6 Hz, 1H), 7.86-7.80 (m, 1H), 5.50 (d, J = 3.5 Hz, 1H), 4.14 (br. s., 1H), 3.56 (s, 3H), 2.40-2.31 (m, 1H), 2.17 (s, 6H), 2.10-2.03 (m, 1H), 1.87 (d, J = 3.3 Hz, 1H), 1.73 (br. s., 1H), 1.64 (d, J = 12.5 Hz, 1H), 1.47-1.19 (m, 4H). (Racemic mixture; single diastereoisomer; and known relative stereochemistry) | 301 |
| 54A | | 4-(((1R,2S)-2-(dimethylamino)cyclohexyl)amino)-2-methylphthalazin-1(2H)-one | N/A (Single enantiomer; unknown absolute stereochemistry; single diastereoisomer; and known relative stereochemistry) | 301 |

| Example | Compound Name | NMR | M/Z (M+H) |
|---|---|---|---|
| 54B | 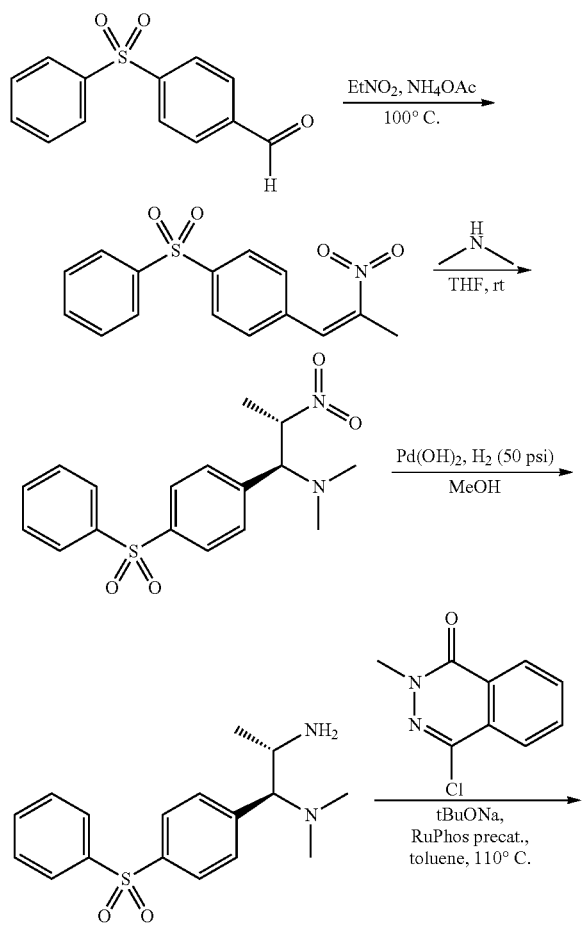

4-(((1S,2R)-2-(dimethylamino)cyclohexyl)amino)-2-methylphthalazin-1(2H)-one | N/A (Single enantiomer; unknown absolute stereochemistry; single diastereoisomer; and known relative stereochemistry) | 301 |

Example 55

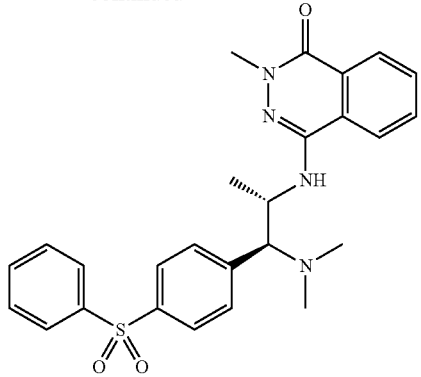

Example 55

Step 1:

1-(2-nitroprop-1-en-1-yl)-4-(phenylsulfonyl)benzene

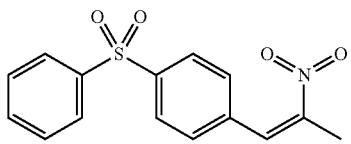 [SMILES: C/C(=C/c1ccc(S(=O)(=O)c2ccccc2)cc1)[N+](=O)[O-]]

A mixture of 4-(phenylsulfonyl)benzaldehyde (1.00 g, 4.06 mmol), nitroethane (3.05 g, 40.6 mmol), and ammonium acetate (0.08 g, 1 mmol) was heated at 120° C. for 2 h. The resulting mixture was cooled, concentrated in vacuo, and purified on a 40 g biotage silica gel column with hexane to 30% ethyl acetate in hexane to provide the title compound (360 mg, 30% yield). LCMS M/Z (M+Na) 326. The E/Z sterereochemistry was not determined.

Step 2:

(1S,2S)—N,N-dimethyl-2-nitro-1-(4-(phenylsulfonyl)phenyl)propan-1-amine

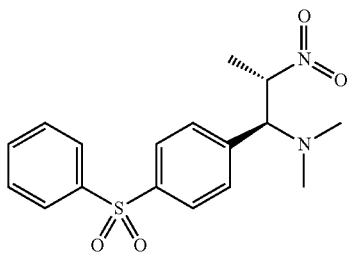 [SMILES: C[C@@H]([C@H](c1ccc(S(=O)(=O)c2ccccc2)cc1)N(C)C)[N+](=O)[O-]]

To 1-(2-nitroprop-1-en-1-yl)-4-(phenylsulfonyl)benzene (0.360 g, 1.19 mmol) was added a 2M dimethylamine solution in tetrahydrofuran (0.72 mL, 1.4 mmol). After completion of the reaction the reaction mixture was concentrated in vacuo and co-evaporated with methanol to provide the title compound (360 mg, 87% yield) as a white solid. Since the compound is unstable, it was immediately used in the next step. LCMS M/Z (M+H) 349. The compound was isolated as a racemic mixture with unknown relative stereochemistry: the assignment was based on the most probable according to the literature.

Step 3:

(1S,2S)—N1,N1-dimethyl-1-(4-(phenylsulfonyl)phenyl)propane-1,2-diamine

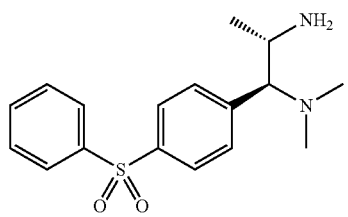 [SMILES: C[C@H](N)[C@H](c1ccc(S(=O)(=O)c2ccccc2)cc1)N(C)C]

To (1S,2S)—N,N-dimethyl-2-nitro-1-(4-(phenylsulfonyl)phenyl)propan-1-amine (0.360 g, 1.03 mmol) in methanol (10 mL) was added palladium hydroxide (0.140 g, 1.03 mmol).

The resulting mixture was stirred under 1 atmosphere of hydrogen for 18 h. The mixture was filtered over celite and the filtrate was concentrated in vacuo to dryness. The residue was used as such in the next step. LCMS M/Z (M+H) 319. The compound was isolated as a racemic mixture with unknown relative stereochemistry: the assignment was based on the previous step.

Step 4:

4-(((1S,2S)-1-(dimethylamino)-1-(4-(phenylsulfonyl)phenyl)propan-2-yl)amino)-2-methylphthalazin-1(2H)-one

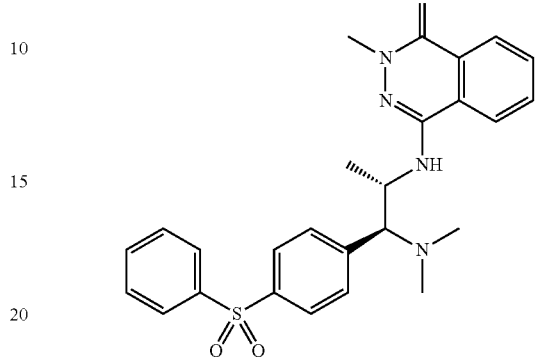

The title compound was prepared in a similar fashion to example 20. $^1$H NMR (400 MHz, Acetone-d6) δ 8.35 (dd, J=2.47, 6.68 Hz, 1H), 8.01 (dd, J=7.78, 10.71 Hz, 3H), 7.86-7.93 (m, 2H), 7.81-7.85 (m, 2H), 7.61-7.73 (m, 3H), 7.56 (d, J=8.24 Hz, 2H), 5.97 (d, J=2.93 Hz, 1H), 4.28-4.58 (m, 1H), 3.72-3.82 (m, 1H), 3.63 (s, 3H), 2.17 (s, 6H), 1.08 (d, J=6.23 Hz, 3H). LCMS M/Z (M+H) 477. The compound was isolated as a racemic mixture with unknown relative stereochemistry: the assignment was based on the most probable according to the literature.

Examples 56-67

The following compounds were prepared in a similar fashion to example 55, using either intermediate F (Examples 56-57 and 59-63), or intermediate A (Examples 58 and 64-67). The specific conditions for the separation of enantiomers are reported in the following section.

| Example | Compound Name | NMR | M/Z (M + H) |
|---|---|---|---|
| 56 | 4-(((1S,2S)-1-(dimethylamino)-1-phenylbutan-2-yl)amino)-2-methylphthalazin-1(2H)-one | $^1$H NMR (500 MHz, DMSO-d6) δ 8.26 (d, J = 7.63 Hz, 1H), 8.13 (d, J = 7.48 Hz, 1H), 7.80-7.90 (m, 2H), 7.18-7.37 (m, 5H), 6.11-6.12 (m, 1H), 4.39 (br. s., 1H), 3.63-3.65 (m, 1H), 3.59 (br.s., 3H), 2.07 (s, 6H), 1.07-1.20 (m, 2H), 0.51-0.87 (m, 3H). (Racemic mixture; unknown relative stereochemistry; and single diastereoisomer) | 351 |

| Example | Compound Name | NMR | M/Z (M + H) |
|---|---|---|---|
| 57 | 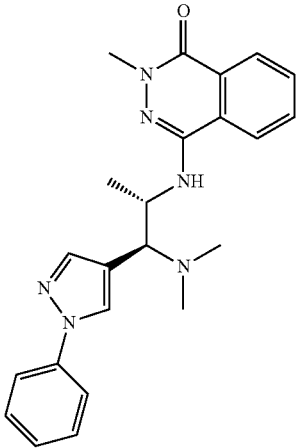<br>4-(((1S,2S)-1-(dimethylamino)-1-(1-phenyl-1H-pyrazol-4-yl)propan-2-yl)amino)-2-methylphthalazin-1(2H)-one | $^1$H NMR (400 MHz, Acetone-d6) δ 8.40 (s, 1H), 8.36 (d, J = 7.51 Hz, 1H), 7.88-7.95 (m, 4H), 7.79-7.87 (m, 1H), 7.72 (s, 1H), 7.51 (t, J = 7.97 Hz, 2H), 7.26-7.35 (m, 1H), 6.47 (br. s., 1H), 4.13 (dd, J = 5.86, 10.25 Hz, 1H), 3.78 (d, J = 10.25 Hz, 1H), 3.66 (s, 3H), 2.18 (s, 6H), 1.24 (d, J = 6.04 Hz, 3H). (Racemic mixture; unknown relative stereochemistry; and single diastereoisomer) | 403 |
| 58 | 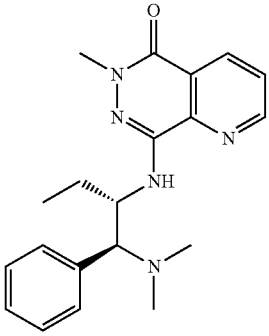 [SMILES: CC[C@H](Nc1nn(C)c(=O)c2cccnc12)[C@H](c1ccccc1)N(C)C]<br>8-(((1S,2S)-1-(dimethylamino)-1-phenylbutan-2-yl)amino)-6-methylpyrido[2,3-d]pyridazin-5(6H)-one | $^1$H NMR (400 MHz, Acetone-d6) δ 9.03 (dd, J = 1.83, 4.58 Hz, 1H), 8.64 (dd, J = 1.65, 8.06 Hz, 1H), 7.85 (dd, J = 4.58, 8.06 Hz, 1H), 7.36-7.42 (m, 2H), 7.28-7.35 (m, 3H), 6.35-6.59 (m, 1H), 4.39 (td, J = 3.71, 5.77 Hz, 1H), 3.72 (d, J = 9.34 Hz, 1H), 3.63 (s, 3H), 2.13 (s, 6H), 1.17 (m, 2H), 0.83 (t, J = 7.51 Hz, 3H). (Racemic mixture; unknown relative stereochemistry; and single diastereoisomer) | 352 |
| 59 | 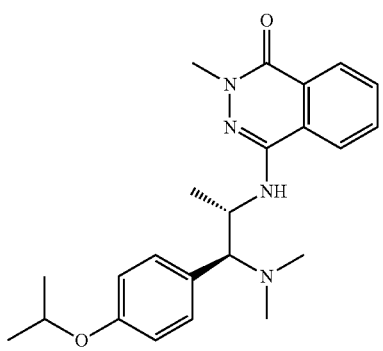 [SMILES: CC(C)Oc1ccc([C@@H]([C@H](C)Nc2nn(C)c(=O)c3ccccc23)N(C)C)cc1]<br>4-(((1S,2S)-1-(dimethylamino)-1-(4-isopropoxyphenyl)propan-2-yl)amino)-2-methylphthalazin-1(2H)-one | $^1$H NMR (400 MHz, Acetone-d6) δ 8.36 (d, J = 7.69 Hz, 1H), 7.88 (d, J = 4.03 Hz, 2H), 7.77-7.85 (m, 1H), 7.22 (d, J = 8.61 Hz, 2H), 6.95 (d, J = 8.61 Hz, 2H), 6.25 (br. s., 1H), 4.53-4.76 (m, 1H), 4.25 (tdd, J = 2.01, 3.91, 7.99 Hz, 1H), 3.66 (s, 3H), 3.59 (d, J = 10.07 Hz, 1H), 2.13 (s, 6H), 1.29-1.35 (m, 6H), 1.12 (d, J = 6.04 Hz, 3H). (Racemic mixture; unknown relative stereochemistry; and single diastereoisomer) | 395 |

| Example | Compound Name | NMR | M/Z (M + H) |
|---|---|---|---|
| 60 | 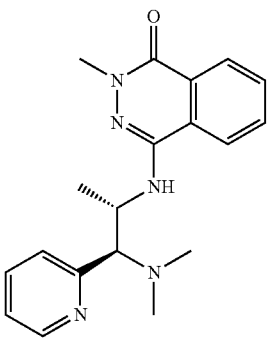 [SMILES: C[C@H](Nc1nn(C)c(=O)c2ccccc12)[C@H](c1ccccn1)N(C)C]<br>4-(((1R,2S)-1-(dimethylamino)-1-(pyridin-2-yl)propan-2-yl)amino)-2-methylphthalazin-1(2H)-one | ¹H NMR (400 MHz, DMSO-d6) δ 8.61-8.66 (m, 1H), 8.27 (dd, J = 0.77, 7.77 Hz, 1H), 8.05 (d, J = 7.88 Hz, 1H), 7.92 (dt, J = 1.42, 7.61 Hz, 1H), 7.78-7.88 (m, 2H), 7.29-7.36 (m, 2H), 6.36 (d, J = 4.82 Hz, 1H), 4.53-4.64 (m, 1H), 3.78 (d, J = 10.29 Hz, 1H), 3.61 (s, 3H), 2.12 (s, 6H), 0.97 (d, J = 6.13 Hz, 3H).<br>(Racemic mixture; unknown relative stereochemistry; and single diastereoisomer) | 338 |
| 61 | 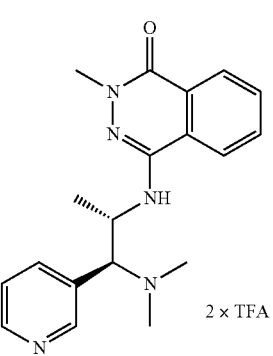 [SMILES: C[C@H](Nc1nn(C)c(=O)c2ccccc12)[C@H](c1cccnc1)N(C)C]<br>4-(((1S,2S)-1-(dimethylamino)-1-(pyridin-3-yl)propan-2-yl)amino)-2-methylphthalazin-1(2H)-one (bis(trifluoroacetic acid) salt) | N/A<br>(Racemic mixture; unknown relative stereochemistry; and single diastereoisomer) | 338 |
| 62 | 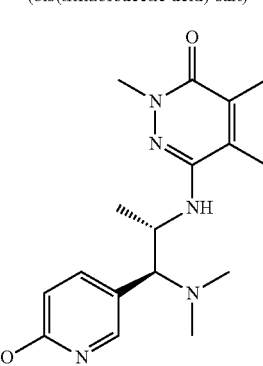<br>4-(((1S,2S)-1-(dimethylamino)-1-(6-methoxypyridin-3-yl)propan-2-yl)amino)-2-methylphthalazin-1(2H)-one | N/A<br>(Racemic mixture; unknown relative stereochemistry; and single diastereoisomer) | 368 |

| Example | Compound Name | NMR | M/Z (M + H) |
|---|---|---|---|
| 63 | 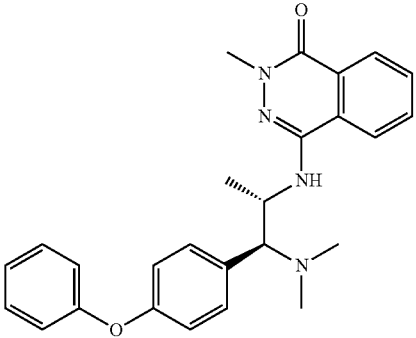 [SMILES: C[C@H](Nc1nn(C)c(=O)c2ccccc12)[C@H](c1ccc(Oc2ccccc2)cc1)N(C)C]<br>4-(((1S,2S)-1-(dimethylamino)-1-(4-phenoxyphenyl)propan-2-yl)amino)-2-methylphthalazin-1(2H)-one | $^1$H NMR (400 MHz, DMSO-d6) δ 8.27 (dd, J = 1.20, 7.99 Hz, 1H), 8.03 (d, J = 7.66 Hz, 1H), 7.90 (dt, J = 1.09, 7.55 Hz, 1H), 7.80-7.87 (m, 1H), 7.36-7.45 (m, 2H), 7.19-7.32 (m, 2H), 7.15 (t, J = 7.40 Hz, 1H), 7.02 (s, 4H), 6.21-6.34 (m, 1H), 4.28-4.44 (m, 1H), 3.54-3.68 (m, 4H), 2.10 (s, 6H), 1.05 (d, J = 6.35 Hz, 3H). (Racemic mixture; unknown relative stereochemistry; and single diastereoisomer) | 430 |
| 64 | 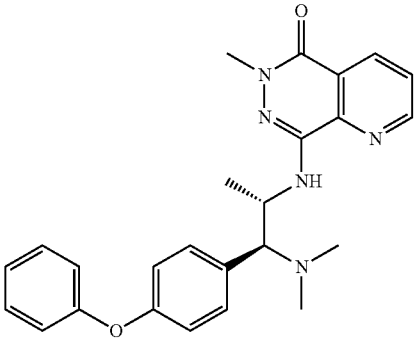 [SMILES: C[C@H](Nc1nn(C)c(=O)c2cccnc12)[C@H](c1ccc(Oc2ccccc2)cc1)N(C)C]<br>8-(((1S,2S)-1-(dimethylamino)-1-(4-phenoxyphenyl)propan-2-yl)amino)-6-methylpyrido[2,3-d]pyridazin-5(6H)-one | N/A<br>(Racemic mixture; unknown relative stereochemistry; and single diastereoisomer) | 431 |
| 65A | 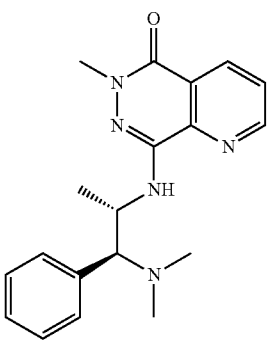 [SMILES: C[C@H](Nc1nn(C)c(=O)c2cccnc12)[C@H](c1ccccc1)N(C)C]<br>8-(((1S,2S)-1-(dimethylamino)-1-phenylpropan-2-yl)amino)-6-methylpyrido[2,3-d]pyridazin-5(6H)-one | $^1$H NMR (400 MHz, DMSO-d6) δ 9.09 (dd, J = 4.6, 1.7 Hz, 1H), 8.61 (dd, J = 8.1, 1.7 Hz, 1H), 7.89 (dd, J = 8.1, 4.6 Hz, 1H), 7.43-7.37 (m, 2H), 7.35 (d, J = 7.2 Hz, 1H), 7.30-7.26 (m, 2H), 6.89 (d, J = 3.9 Hz, 1H). 4.23 (s, 1H), 3.65 (d, J = 10.0 Hz, 1H), 3.62 (s, 3H), 2.07 (s, 6H), 1.08 (d, J = 6.1 Hz, 3H). (Single enantiomer; single diastereoisomer; unknown absolute and relative stereochemistry) | 338 |

| Example | Compound Name | NMR | M/Z (M + H) |
|---|---|---|---|
| 65B | 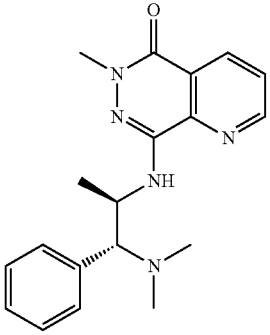 [SMILES: C[C@@H](Nc1nn(C)c(=O)c2cccnc12)[C@@H](c1ccccc1)N(C)C]<br>8-(((1R,2R)-1-(dimethylamino)-1-phenylpropan-2-yl)amino)-6-methylpyrido[2,3-d]pyridazin-5(6H)-one | ¹H NMR (400 MHz, DMSO-d6) δ 9.09 (dd, J = 4.6, 1.7 Hz, 1H), 8.61 (dd, J = 8.0, 1.7 Hz, 1H), 7.89 (dd, J = 8.1, 4.6 Hz, 1H), 7.43-7.36 (m, 2H), 7.36-7.31 (m, 1H), 7.30-7.26 (m, 2H), 6.89 (d, J = 3.9 Hz, 1H), 4.23 (ddd, J = 10.1, 6.1, 4.0 Hz, 1H), 3.65 (d, J = 10.0 Hz, 1H), 3.62 (s, 3H), 2.07 (s, 6H), 1.08 (d, J = 6.1 Hz, 3H). (Single enantiomer; single diastereoisomer; unknown absolute and relative stereochemistry) | 338 |
| 66 | 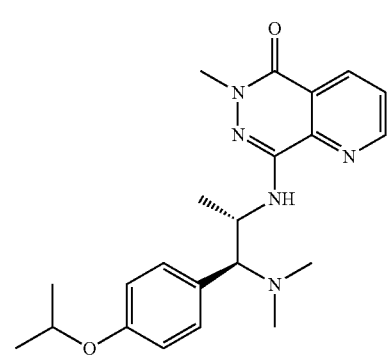 [SMILES: CC(C)Oc1ccc([C@@H]([C@H](C)Nc2nn(C)c(=O)c3cccnc23)N(C)C)cc1]<br>8-(((1S,2S)-1-(dimethylamino)-1-(4-isopropoxyphenyl)propan-2-yl)amino)-6-methylpyrido[2,3-d]pyridazin-5(6H)-one | ¹H NMR (400 MHz, Acetone-d6) δ 9.03 (br. s., 1H), 8.64 (d, J = 6.41 Hz, 1H), 7.73-7.96 (m, 1H), 7.22 (d, J = 8.24 Hz, 2H), 6.94 (d, J = 8.24 Hz, 2H), 4.54-4.79 (m, 1H), 4.26 (br. s., 1H), 3.65 (s, 3H), 3.58 (d, J = 9.89 Hz, 1H), 2.13 (s, 6H), 1.32 (d, J = 5.86 Hz, 6H), 1.15 (d, J = 5.86 Hz, 3H). (Racemic mixture; unknown relative stereochemistry; and single diastereoisomer) | 395 |
| 67 | 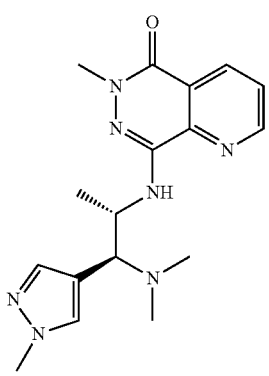<br>8-(((1S,2S)-1-(dimethylamino)-1-(1-methyl-1H-pyrazol-4-yl)propan-2-yl)amino)-6-methylpyrido[2,3-d]pyridazin-5(6H)-one | ¹H NMR (400 MHz, DMSO-d6) δ 8.95-9.21 (m, 1H), 8.48-8.68 (m, 1H), 8.08 (s, 1H), 7.78-7.94 (m, 1H), 6.99-7.18 (m, ,1H), 4.10-4.22 (m, 1H), 4.06 (s, 3H), 3.82-3.91 (m, 1H), 3.60 (s, 3H), 2.02(s, 6H), 1.09 (d, J = 6.13 Hz, 3H). (Racemic mixture; unknown relative stereochemistry; and single diastereoisomer) | 343 |

Example 68

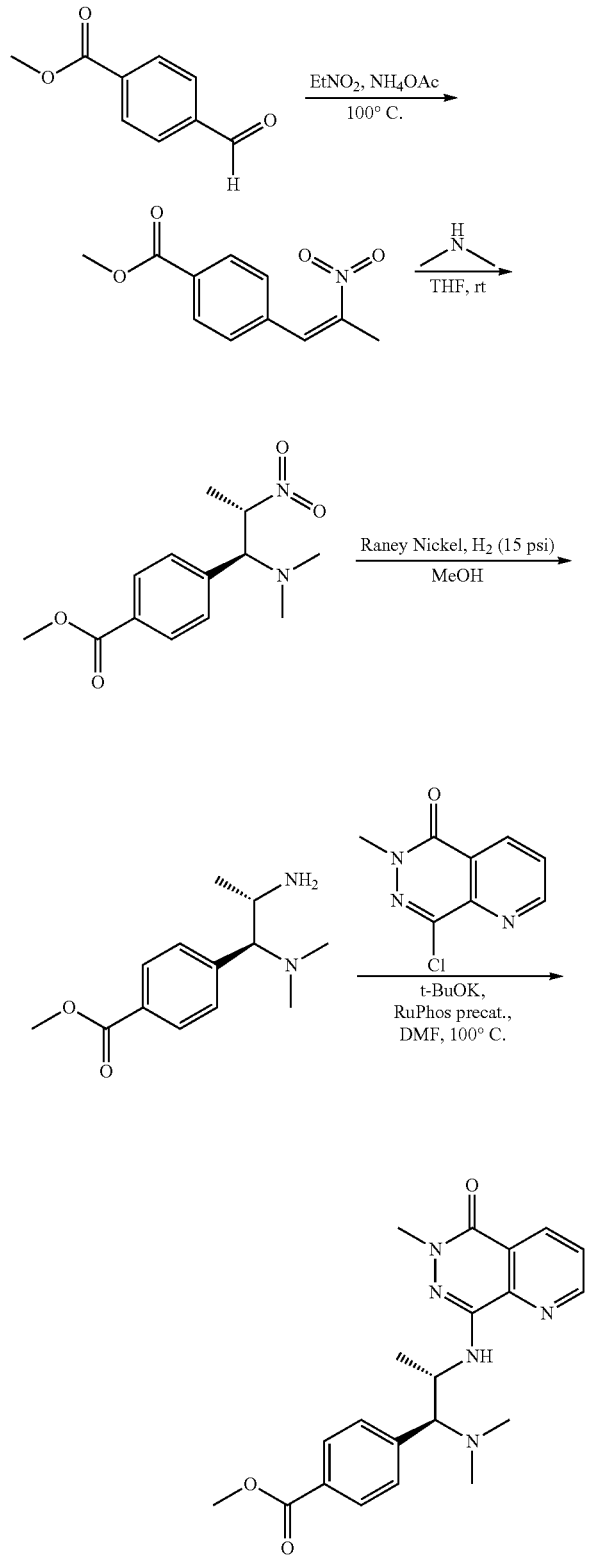

Example 68

Step 1:

Methyl 4-(2-nitroprop-1-en-1-yl)benzoate

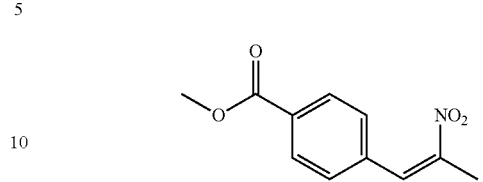

A mixture of methyl 4-formylbenzoate (10.0 g, 60.92 mmol) and ammonium acetate (0.90 g, 12 mmol) in nitroethane (100 mL) was heated at 100° C. for 15 h, at which time LCMS indicated the reaction had gone to completion. The solvent was concentrated in vacuo. The residue was dissolved in ethyl acetate (150 mL) and washed with water (2×100 mL). The separated organic layer was dried over $Na_2SO_4$ and concentrated under reduced pressure to give the title compound (10.5 g, 78% yield) as a yellow solid. This crude material was used in the next step without further purification. The E/Z stereochemistry was not determined.

Step 2:

Methyl 4-((1S,2S)-1-(dimethylamino)-2-nitropropyl)benzoate

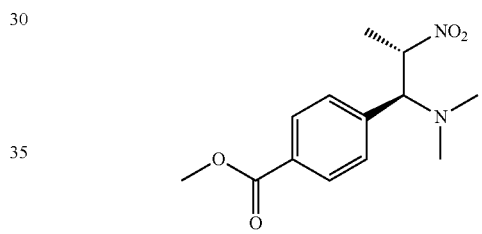

A mixture of (Z)-methyl 4-(2-nitroprop-1-en-1-yl)benzoate (10.5 g, 47.5 mmol) in tetrahydrofuran (15 mL) was added a 2M dimethylamine solution in tetrahydrofuran (118.7 mL, 237.3 mmol). After addition, the mixture was stirred at 25° C. for 15 h, at which time LCMS indicated the reaction had gone to completion. The solvent was evaporated under reduced pressure to give the crude title compound (10.6 g, 84% yield) as a yellow solid. LCMS M/Z (M+H) 267. The compound was isolated as a racemic mixture with unknown relative stereochemistry: the assignment was based on the most probable according to the literature.

Step 3:

Methyl 4-((1S,2S)-2-amino-1-(dimethylamino)propyl)benzoate

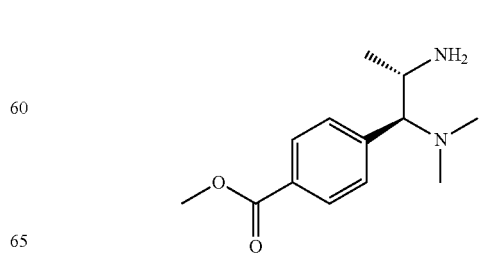

A mixture of methyl 4-((1S,2S)-1-(dimethylamino)-2-nitropropyl)benzoate (10.0 g, 37.5 mmol) and Raney Ni (5.0 g) in methanol (50 mL) was stirred under hydrogen (15 psi) at 25° C. for 5 h, at which time LCMS indicated the reaction had gone to completion. The solid was removed by filtration, and the filtrate was concentrated under reduced pressure. The crude product was purified by silica gel chromatography (petroleum ether:ethyl acetate=1:1) to give the title compound (8.6 g, 97% yield) as a colorless oil. LCMS M/Z (M+H) 237. The compound was isolated as a racemic mixture with unknown relative stereochemistry: the assignment was based on the previous step.

Step 4:

Methyl 4-((1S,2S)-1-(dimethylamino)-2-((6-methyl-5-oxo-5,6-dihydropyrido[2,3-d]pyridazin-8-yl)amino)propyl)benzoate

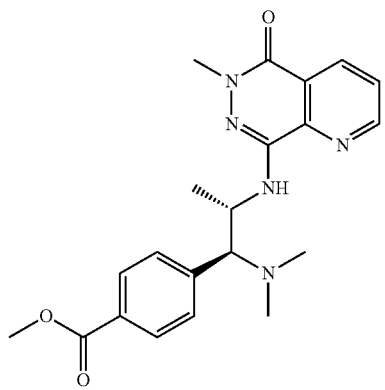 [SMILES: COC(=O)c1ccc([C@@H]([C@H](C)Nc2nn(C)c(=O)c3cccnc23)N(C)C)cc1]

In twenty parallel batches, a mixture of 8-chloro-6-methylpyrido[2,3-d]pyridazin-5(6H)-one (Intermediate A, 300 mg, 1.53 mmol), methyl 4-((1S,2S)-2-amino-1-(dimethylamino)propyl)benzoate (543 mg, 2.30 mmol), t-BuOK (344 mg, 3.07 mmol), and RuPhos $3^{rd}$ generation precatalyst (30 mg, 0.04 mmol) in DMF (8 mL) was heated at 100° C. under microwave conditions for 2 h under $N_2$, at which time LCMS indicated the reaction had gone to completion. The reaction mixture was poured into water (5 mL) and then extracted with ethyl acetate (3×10 mL). The combined organic extracts were dried over $Na_2SO_4$ and concentrated in vacuo. The combined residue was purified by reverse phase chromatography (acetonitrile 50-80%/0.1% $NH_4OH$ in water) to give the title compound (750 mg was obtained after the twenty batches were combined, 6% yield) as a white solid. $^1H$ NMR (400 MHz, Methanol-d4) δ 9.02-9.00 (m, 1H), 8.61-8.59 (m, 1H), 8.02 (d, J=8.4 Hz, 2H), 7.86-7.89 (m, 1H), 7.39 (d, J=8.0 Hz, 2H), 4.51-4.48 (m, 1H), 3.91 (s, 3H), 3.73 (s, 3H), 3.72-3.70 (m, 1H), 2.18 (s, 6H), 1.13 (d, J=6.0 Hz, 3H). LCMS M/Z (M+H) 396. The compound was isolated as a racemic mixture with unknown relative stereochemistry: the assignment was based on the most probable according to the literature.

Examples 69-75

The following compounds were prepared in a similar fashion to example 68, using either intermediate L (Example 69), intermediate K (Example 70), intermediate G (Example 71), intermediate F (Example 73), or intermediate A (Examples 72 and 74-75). For examples 69-71 and 73-74 the diamine starting material can also be prepared according to the procedures described before in example 55 step 1-3. The specific conditions for the separation of enantiomers are reported in the following section.

| Example | Compound Name | NMR | M/Z (M + H) |
|---|---|---|---|
| 69A | 4-(((1S,2S)-1-(dimethylamino)-1-phenylpropan-2-yl)amino)-2,8-dimethylphthalazin-1(2H)-one | $^1H$ NMR (400 MHz, Methanol-d4) δ 7.75-7.70 (m, 2H), 7.60-7.59 (m, 1H), 7.38-7.25 (m, 5H), 4.48-4.41 (m, 1H), 3.69-3.63 (m, 4H), 2.91 (s, 3H), 2.17 (s, 6H), 1.08 (d, J = 6.0 Hz, 3H). (Single enantiomer; single diastereoisomer; unknown absolute and relative stereochemistry) | 351 |

| Example | Compound Name | NMR | M/Z (M + H) |
|---|---|---|---|
| 69B | 4-(((1R,2R)-1-(dimethylamino)-1-phenylpropan-2-yl)amino)-2,8-dimethylphthalazin-1(2H)-one | $^1$H NMR (400 MHz, Methanol-d4) δ 7.76-7.70 (m, 2H), 7.60-7.58 (m, 1H), 7.39-7.27 (m, 5H), 4.51-4.44 (m, 1H), 3.70-3.68 (m, 4H), 2.91 (s, 3H), 2.20 (s, 6H), 1.08 (d, J = 6.4 Hz, 3H). (Single enantiomer; single diastereoisomer; unknown absolute and relative stereochemistry) | 351 |
| 70A | 4-(((1S,2S)-1-(dimethylamino)-1-phenylpropan-2-yl)amino)-2,5-dimethylphthalazin-1(2H)-one | $^1$H NMR (400 MHz, Methanol-d4) δ 8.31-8.29 (m, 1H), 7.72-7.70 (m, 2H), 7.45-7.31 (m, 5H), 4.31-4.24 (m, 1H), 3.75 (s, 3H), 3.66 (d, J = 9.6 Hz, 1H), 2.91 (s, 3H), 2.17 (s, 6H), 1.17 (d, J = 6.0 Hz, 3H). (Single enantiomer; single diastereoisomer; unknown absolute and relative stereochemistry) | 351 |
| 70B | 4-(((1R,2R)-1-(dimethylamino)-1-phenylpropan-2-yl)amino)-2,5-dimethylphthalazin-1(2H)-one | $^1$H NMR (400 MHz, Methanol-d4) δ 8.31-8.28 (m, 1H), 7.12-7.70 (m, 2H), 7.45-7.30 (m, 5H), 4.31-4.24 (m, 1H), 3.75 (s, 3H), 3.65 (d, J = 6.4 Hz, 1H), 2.91 (s, 3H), 2.17 (s, 6H), 1.17 (d, J = 6.0 Hz, 3H). (Single enantiomer; single diastereoisomer; unknown absolute and relative stereochemistry) | 351 |

| Example | Compound Name | NMR | M/Z (M + H) |
|---|---|---|---|
| 71A | 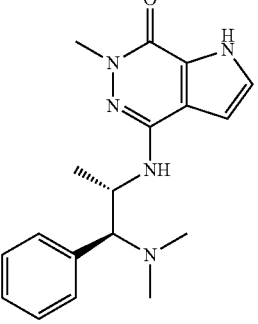<br>4-(((1S,2S)-1-(dimethylamino)-1-phenylpropan-2-yl)amino)-6-methyl-1H-pyrrolo[2,3-d]pyridazin-7(6H)-one | $^1$H NMR (400 MHz, DMSO-d6) δ 12.24-11.14 (m, 1H), 7.36-7.28 (m, 4H), 7.22-7.19 (m, 2H), 6.56-6.55 (m, 1H), 5.82-5.80 (m, 1H), 4.36-4.33 (m, 1H), 3.58 (s, 3H), 3.55-3.52 (m, 1 H), 2.08 (s, 6H), 0.98 (d, J = 6.0 Hz, 3H). (Single enantiomer; single diastereoisomer; unknown absolute and relative stereochemistry) | 326 |
| 71B | 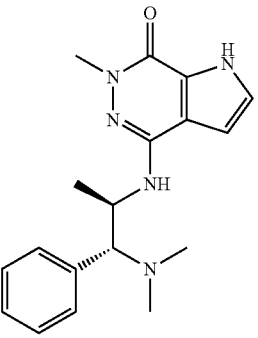 [SMILES: C[C@@H](Nc1nn(C)c(=O)c2[nH]ccc12)[C@@H](c1ccccc1)N(C)C]<br>4-(((1R,2R)-1-(dimethylamino)-1-phenylpropan-2-yl)amino)-6-methyl-1H-pyrrolo[2,3-d]pyridazin-7(6H)-one | $^1$H NMR (400 MHz, DMSO-d6) δ 12.45 (br. s., 1H), 7.38-7.20 (m, 6H), 6.56 (d, J = 3.2 Hz, 1H), 5.81 (d, J = 5.2 Hz, 1H), 4.36-4.34 (m, 1H), 3.58-3.52 (m, 4H), 2.08 (s, 6H), 0.98 (d, J = 6.8 Hz, 3H). (Single enantiomer; single diastereoisomer; unknown absolute and relative stereochemistry) | 326 |
| 72 | 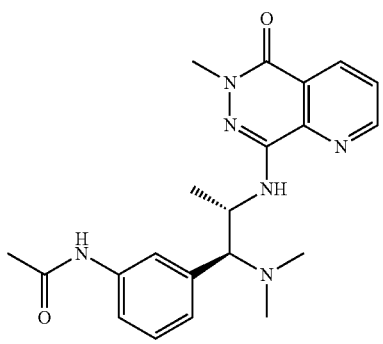 [SMILES: CC(=O)Nc1cccc([C@@H]([C@H](C)Nc2nn(C)c(=O)c3cccnc23)N(C)C)c1]<br>N-(3-((1S,2S)-1-(dimethylamino)-2-((6-methyl-5-oxo-5,6-dihydropyrido[2,3-d]pyridazin-8-yl)amino)propyl)phenyl)acetamide | $^1$H NMR (400 MHz, Methanol-d4) δ 9.05-9.04 (m, 1H), 8.69-8.66 (m, 1H), 7.86-7.83 (m, 1H), 7.58-7.56 (m, 1H), 7.50 (s, 1H), 7.37-7.33 (m, 1H), 7.06-7.04 (m, 1H), 4.51-4.44 (m, 1H), 3.77 (s, 3H), 3.62 (d, J = 9.6 Hz, 1H), 2.22 (s, 6H), 2.04 (s, 3H), 1.18 (d, J = 6.0 Hz, 3H). (Racemic mixture; unknown relative stereochemistry; and single diastereoisomer) | 395 |

| Example | Compound Name | NMR | M/Z (M + H) |
|---|---|---|---|
| 73A | 4-(((1S,2S)-1-(dimethylamino)-1-phenylpropan-2-yl)amino)-2-methylphthalazin-1(2H)-one | $^1$H NMR (400 MHz, Methanol-d4) δ 8.39-8.37 (m, 1H), 7.99-7.86 (m, 3H), 7.41-7.29 (m, 5H), 4.55-4.51 (m, 1H), 3.78 (s, 3H), 3.70-3.68 (m, 1H), 2.21 (s, 6H), 1.13 (d, J = 6.4 Hz, 3H). (Single enantiomer; single diastereoisomer; unknown absolute and relative stereochemistry) | 337 |
| 73B | 4-(((1R,2R)-1-(dimethylamino)-1-phenylpropan-2-yl)amino)-2-methylphthalazin-1(2H)-one | $^1$H NMR (400 MHz, Methanol-d4) δ 8.39-8.37 (m, 1H), 7.99-7.86 (m, 3H), 7.41-7.29 (m, 5H), 4.55-4.51 (m, 1H), 3.78 (s, 3H), 3.70-3.68 (m, 1H), 2.21 (s, 6H), 1.13 (d, J = 6.4 Hz, 3H). (Single enantiomer; single diastereoisomer; unknown absolute and relative stereochemistry) | 337 |
| 74 | 8-((1-(dimethylamino)-1-(4-(phenylsulfonyl)phenyl)propan-2-yl)amino)-6-methylpyrido[2,3-d]pyridazin-5(6H)-one | $^1$H NMR (400 MHz, DMSO-d6) δ 9.06 (dd, J = 1.7, 4.6 Hz, 1H), 8.59 (dd, J = 1.7, 8.1 Hz, 1H), 7.95-7.99 (m, 3H), 7.88 (dd, J = 4.6, 8.1 Hz, 1H), 7.62-7.72 (m, 3H), 7.52 (dd, J = 8.3 Hz, 2H), 6.77 (d, J = 4.2 Hz, 1H), 4.24-4.27 (m, 1H), 3.77 (d, J = 9.4 Hz, 1H), 3.66 (s, 3H), 2.03 (s, 6H), 1.01 (d, J = 6.1 Hz, 3H). (Racemic mixture; unknown relative stereochemistry; and single diastereoisomer) | 478 |

| Example | Compound Name | NMR | M/Z (M + H) |
|---|---|---|---|
| 74A | 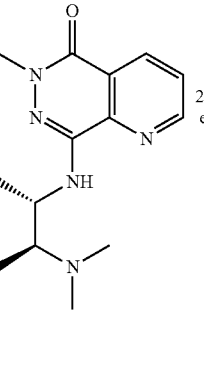<br>8-(((1S,2S)-1-(dimethylamino)-1-(4-(phenylsulfonyl)phenyl)propan-2-yl)amino)-6-methylpyrido[2,3-d]pyridazin-5(6H)-one | $^1$H NMR (400 MHz, Methanol-d4) δ 8.96-8.98 (m, 1H), 8.61-8.63 (m, 1H), 7.94-7.98 (m, 4H), 7.80-7.81 (m, 1H), 7.47-7.60 (m, 5H), 4.46-4.50 (m, 1H), 3.71-3.73 (m, 4H), 2.15 (s, 6H), 1.08 (d, J = 6.4 Hz, 3H). (Single enantiomer; single diastereoisomer; unknown absolute and relative stereochemistry) | 478 |
| 74B | 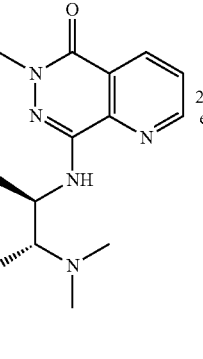<br>8-(((1R,2R)-1-(dimethylamino)-1-(4-(phenylsulfonyl)phenyl)propan-2-yl)amino)-6-methylpyrido[2,3-d]pyridazin-5(6H)-one | $^1$H NMR (400 MHz, Methanol-d4) δ 8.97-8.98 (m, 1H), 8.61-8.63 (m, 1H), 7.94-7.98 (m, 4H), 7.80-7.81 (m, 1H), 7.47-7.60 (m, 5H), 4.46-4.50 (m, 1H), 3.71-3.74 (m, 4H), 2.15 (s, 6H), 1.08 (d, J = 6.4 Hz, 3H). (Single enantiomer; single diastereoisomer; unknown absolute and relative stereochemistry) | 478 |
| 75 | 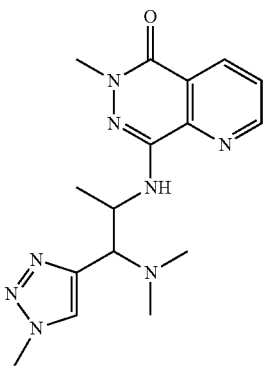 [SMILES: CC(Nc1nn(C)c(=O)c2cccnc12)C(c1cn(C)nn1)N(C)C]<br>8-((1-(dimethylamino)-1-(1-methyl-1H-1,2,3-triazol-4-yl)propan-2-yl)amino)-6-methylpyrido[2,3-d]pyridazin-5(6H)-one | $^1$H NMR (400 MHz, DMSO-d6) δ 9.01-9.21 (m, 1H), 8.46-8.68 (m, 1H), 8.08 (s, 1H), 7.78-7.93 (m, 1H), 6.96-7.16 (m, 1H), 4.12-4.22 (m, 1H), 4.06 (s, 3H), 3.83-3.91 (m, 1H), 3.60 (s, 3H), 2.02 (s, 6H), 1.10 (d, J = 5.9 Hz, 3H). (Racemic mixture; unknown relative stereochemistry; and single diastereoisomer) | 343 |

Example 76

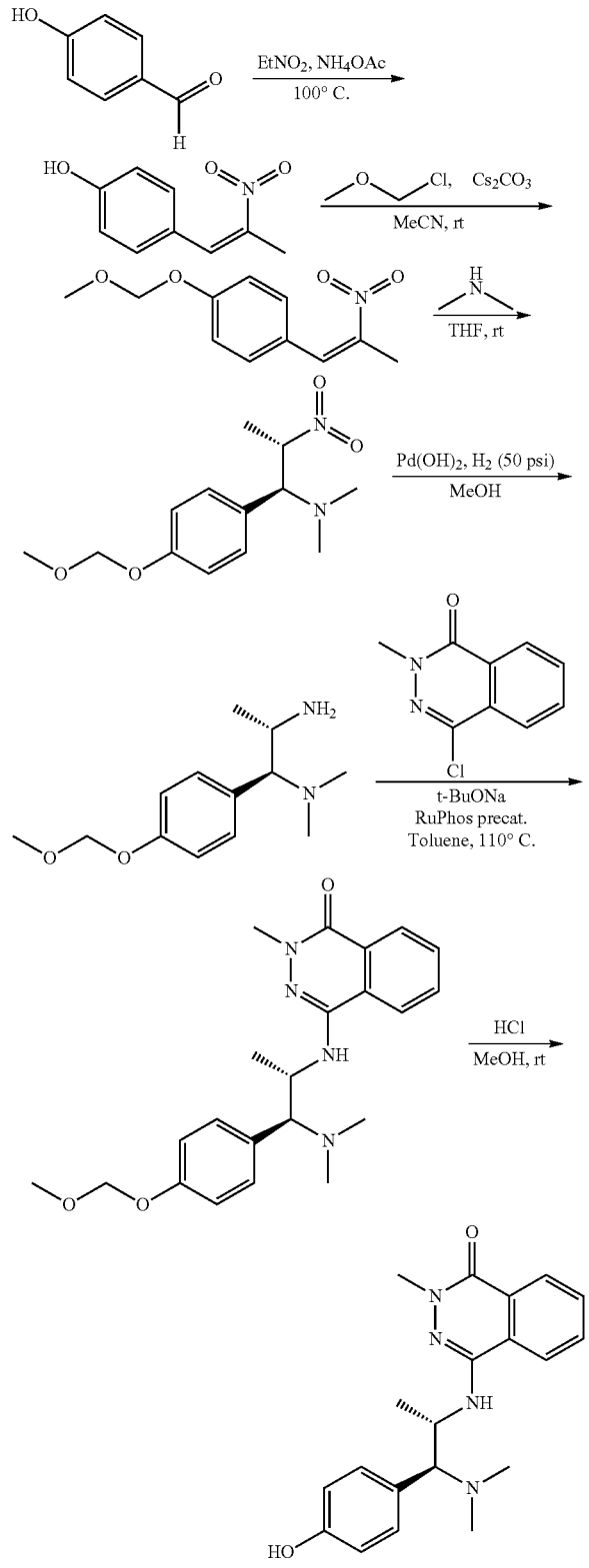

Example 76

Step 1

4-(2-nitroprop-1-en-1-yl)phenol

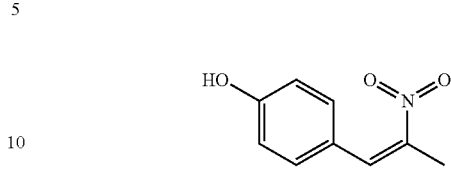

The title intermediate was prepared in a similar fashion to step 1 of example 55, using 4-hydroxybenzaldehyde instead of 4-(phenylsulfonyl)benzaldehyde. LCMS M/Z (M+H) 180. The E/Z sterereochemistry was not determined.

Step 2

1-(methoxymethoxy)-4-(2-nitroprop-1-en-1-yl)benzene

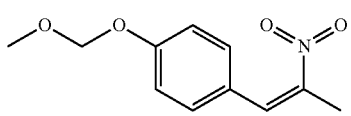 [SMILES: COCOc1ccc(/C=C(/C)[N+](=O)[O-])cc1]

To a solution of 4-(2-nitrovinyl)phenol (13.5 g, 81.8 mmol) in acetonitrile (160 mL) and maintained at room temperature using a water bath was added chloro(methoxy)methane (6.83 mL, 89.9 mmol) followed by the addition of cesium carbonate (29.3 g, 89.9 mmol) in portions (caution: exothermic reaction). After 1 h at room temperature, extra chloro(methoxy)methane (0.62 mL, 8.2 mmol) was added and the reaction was stirred for an additional 2 h. When TLC showed complete consumption of the starting material, the reaction is diluted with tert-butyl methyl ether (200 mL) and filtered through celite. The filtrate is concentrated to dryness under reduced pressure to give an orange-brown oil that was used without purification in the next step. LCMS M/Z (M+H) 223.

Step 3

(1S,2S)-1-(4-(methoxymethoxy)phenyl)-N,N-dimethyl-2-nitropropan-1-amine

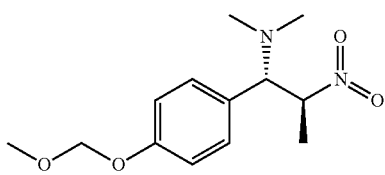 [SMILES: COCOc1ccc([C@@H]([C@H](C)[N+](=O)[O-])N(C)C)cc1]

To crude 1-(methoxymethoxy)-4-(2-nitroprop-1-en-1-yl)benzene (8.0 g, 36 mmol) was added 2M dimethylamine in tetrahydrofuran (89.6 mL, 179.2 mmol). After addition, the mixture was stirred at room temperature overnight, then the solvent was evaporated in vacuo to give the crude title compound. LCMS M/Z (M+H) 269.

Step 4

(1S,2S)-1-(4-(methoxymethoxy)phenyl)-N1,N1-dimethylpropane-1,2-diamine

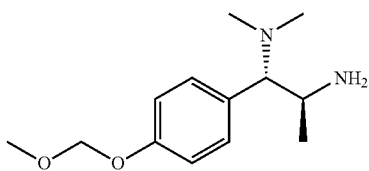 [SMILES: COCOc1ccc([C@@H]([C@H](C)N)N(C)C)cc1]

The title intermediate was prepared in a similar fashion to step 3 from example 55. LCMS M/Z (M+H) 239.

Step 5

4-(((1S,2S)-1-(dimethylamino)-1-(4-(methoxymethoxy)phenyl)propan-2-yl)amino)-2-methylphthalazin-1(2H)-one

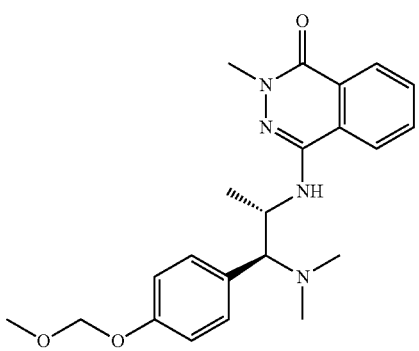 [SMILES: COCOc1ccc([C@@H]([C@H](C)Nc2nn(C)c(=O)c3ccccc23)N(C)C)cc1]

The title intermediate was prepared in a similar fashion to example 20. LCMS M/Z (M+H) 397.

Step 6

4-(((1S,2S)-1-(dimethylamino)-1-(4-hydroxyphenyl)propan-2-yl)amino)-2-methylphthalazin-1(2H)-one

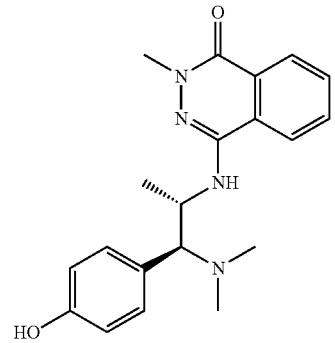 [SMILES: C[C@H](Nc1nn(C)c(=O)c2ccccc12)[C@H](c1ccc(O)cc1)N(C)C]

To a solution of 4-(((1S,2S)-1-(dimethylamino)-1-(4-(methoxymethoxy)phenyl)propan-2-yl)amino)-2-methylphthalazin-1(2H)-one (1.5 g, 3.8 mmol) (low purity) in methanol (100 mL) was added a 2M aqueous hydrochloric acid (50 mL) at room temperature. The mixture was heated to 45° C. for 5 h, then concentrated under reduced pressure. The pH of the aqueous solution was adjusted to 8 and the product was extracted with ethyl acetate (repeated 2 times). The combined organic layers were dried with Na$_2$SO$_4$, filtered and concentrated to dryness under reduced pressure. The crude product was purified by flash chromatography (dichloromethane/methanol 97:3 to 60:40) to give the title compound (650 mg, 48% yield). $^1$H NMR (400 MHz, DMSO-d6) δ 9.35 (s, 1H), 8.27 (dd, J=1.31, 7.88 Hz, 1H), 7.99 (d, J=8.00 Hz, 1H), 7.90 (dt, J=1.42, 7.61 Hz, 1H), 7.81-7.86 (m, 1H), 7.03 (d, J=8.54 Hz, 2H), 6.76 (d, J=8.54 Hz, 2H), 6.31 (d, J=4.16 Hz, 1H), 4.19-4.31 (m, 1H), 3.61 (s, 3H), 3.51 (d, J=9.63 Hz, 1H), 2.05 (s, 6H), 1.02 (d, J=6.13 Hz, 3H). LCMS M/Z (M+H) 353. The compound was isolated as a racemic mixture with unknown relative stereochemistry: the assignment was based on the most probable according to the literature.

Example 77

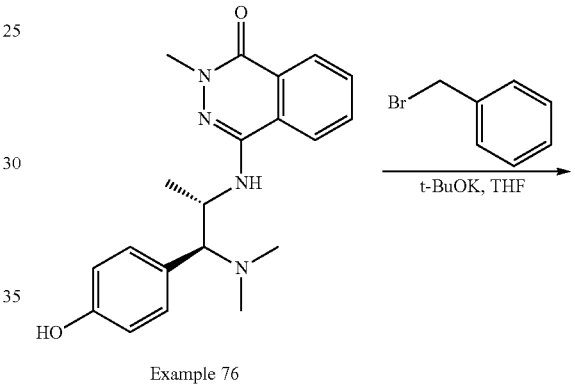

Example 76

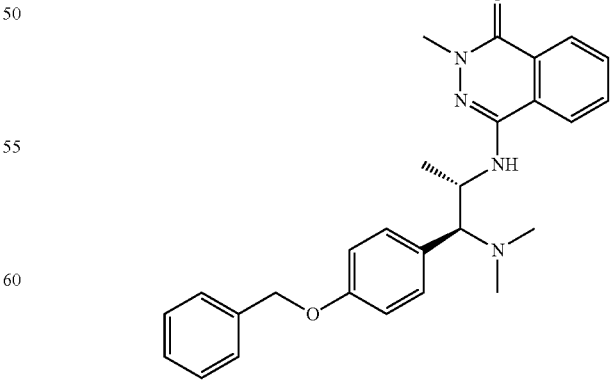

Example 77

4-((1-(4-(benzyloxy)phenyl)-1-(dimethylamino)propan-2-yl)amino)-2-methylphthalazin-1(2H)-one

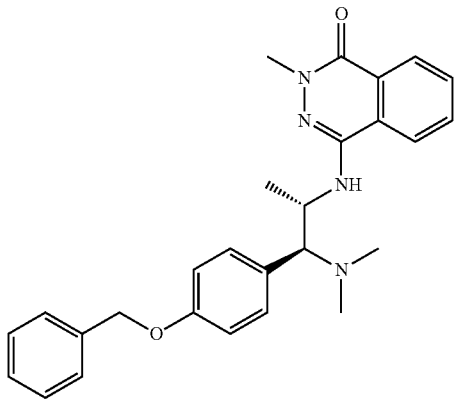 [SMILES: C[C@H](Nc1nn(C)c(=O)c2ccccc12)[C@H](c1ccc(OCc2ccccc2)cc1)N(C)C]

To a solution of 1-(dimethylamino)-1-(4-hydroxyphenyl) propan-2-yl)amino)-2-methylphthalazin-1(2 h)-one (20 mg, 0.06 mmol) in tetrahydrofuran (1 mL) were added sodium 2-methylpropan-2-olate (6.5 mg, 0.07 mmol) and benzyl bromide (8 µL, 0.06 mmol) at room temperature. Additional sodium 2-methylpropan-2-olate (26 mg, 0.28 mmol) and benzyl bromide (32 µL, 0.24 mmol) were added over a period of a few hours. After a period of 18 h the resulting mixture was extracted with ethyl acetate and saturated solution of ammonium chloride. The organic phase was separated and concentrated in vacuo, and the residue was purified by flash chromatography with ethyl acetate to 20% methanol in ethyl acetate to provide the title compound (10 mg, 40% yield). $^1$H NMR (400 MHz, Acetone-d6) δ 8.36 (d, J=7.32 Hz, 1H), 7.77-7.98 (m, 3H), 7.52 (d, J=7.32 Hz, 2H), 7.42 (t, J=7.32 Hz, 2H), 7.36 (d, J=7.32 Hz, 1H), 7.28 (d, J=8.42 Hz, 2H), 7.08 (d, J=8.61 Hz, 2H), 6.25-6.35 (m, 1H), 5.14 (s, 2H), 4.30 (br. s., 1H), 3.54-3.75 (m, 3H), 2.17 (s, 6H), 1.12 (d, J=6.04 Hz, 3H). LCMS M/Z (M+H) 443. The compound was isolated as a racemic mixture with unknown relative stereochemistry: the assignment was based on the most probable according to the literature.

Examples 78-80

The following compounds were prepared in a similar fashion to example 77, using alkyl halides or fluoropyridine instead of benzyl bromide.

| Example | Compound Name | NMR | M/Z (M + H) |
|---|---|---|---|
| 78 | 4-(((1S,2S)-1-(4-(cyclopropylmethoxy)phenyl)-1-(dimethylamino)propan-2-yl)amino)-2-methylphthalazin-1(2H)-one | $^1$H NMR (400 MHz, Acetone-6) δ 8.36 (d, J = 7.32 Hz, 1H), 7.74-7.93 (m, 3H), 7.23 (d, J = 8.42 Hz, 2H), 6.96 (d, J = 8.61 Hz, 2H), 6.26 (br. s., 1H), 4.27 (br. s., 1H), 3.86 (d, J = 6.96 Hz, 2H), 3.66 (s, 3H), 2.14 (s, 6H), 1.20-1.33 (m, 1H), 1.12 (d, J = 6.04 Hz, 3H), 0.53-0.68 (m, 2H), 0.32-0.43 (m, 2H). (Racemic mixture; unknown relative stereochemistry; and single diastereoisomer) | 407 |
| 79 | 4-(((1S,2S)-1-(dimethylamino)-1-(4-methoxyphenyl)propan-2-yl)amino)-2-methylphthalazin-1(2H)-one | $^1$H NMR (400 MHz, Acetone-d6) δ 8.34-8.37 (m, 1H), 8.15-8.20 (m, 1H), 7.80-7.88 (m, 3H), 7.35-7.40 (m, 1H), 7.03 (d, J = 8.42 Hz, 2H), 6.41-6.45 (m, 1H), 4.55-4.70 (m, 1H), 3.85 (s, 3H), 3.76-3.77 (m, 1H), 3.66 (s, 3H), 2.40 (br. s., 6H), 1.16 (d, J = 6.04 Hz, 3H). (Racemic mixture; unknown relative stereochemistry; and single diastereoisomer) | 367 |

| Example | Compound Name | NMR | M/Z (M + H) |
|---|---|---|---|
| 80 | 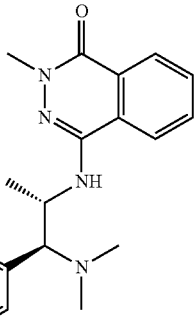<br>4-(((1S,2S)-1-(dimethylamino)-1-(4-(pyridin-2-yloxy)phenyl)propan-2-yl)amino)-2-methylphthalazin-1(2H)-one | ¹H NMR (400 MHz, Acetone-d6) δ 8.39-8.51 (m, 1H), 8.35 (dd, J = 1.37, 7.60 Hz, 1H), 8.19 (dd, J = 1.46, 4.94 Hz, 1H), 7.76-7.95 (m, 4H), 7.58 (d, J = 6.96 Hz, 2H), 7.26 (d, J = 8.24 Hz, 2H), 7.15 (dd, J = 5.04, 6.68 Hz, 1H), 7.05 (d, J = 8.24 Hz, 1H), 4.53-4.76 (m, 1H), 4.13-4.35 (m, 1H), 3.66 (s, 3H), 2.48 (s, 6H), 1.13-1.24 (d, J = 8 Hz, 3H). (Racemic mixture; unknown relative stereochemistry; and single diastereoisomer) | 430 |

Example 81

4-((1S,2S)-1-(dimethylamino)-2-((6-methyl-5-oxo-5,6-dihydropyrido[2,3-d]pyridazin-8-yl)amino)propyl)benzoic acid

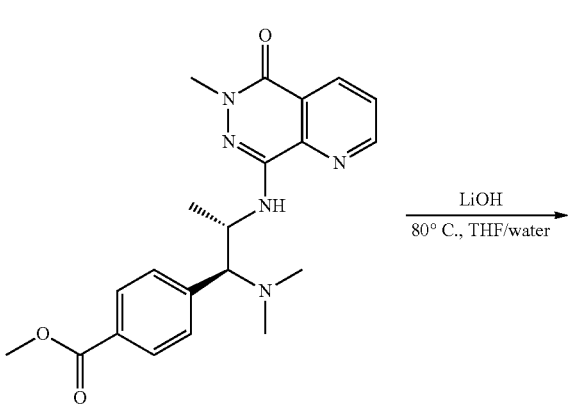

Example 68

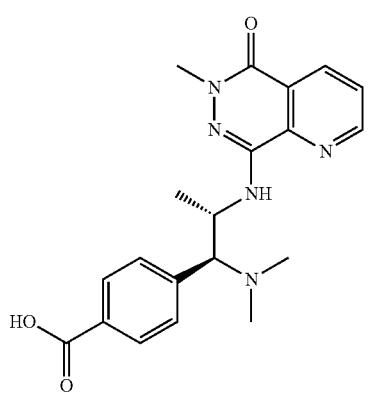

Example 81

To a stirred solution of methyl 4-((1S,2S)-1-(dimethylamino)-2-((6-methyl-5-oxo-5,6-dihydropyrido[2,3-d]pyridazin-8-yl)amino)propyl)benzoate (700 mg, 0.77 mmol) in tetrahydrofuran (10 mL)/water (5 mL) was added lithium hydroxide (212 mg, 8.55 mmol) in portions. After addition, the mixture was stirred at 80° C. for 2 h, at which time LCMS indicated the reaction had gone to completion. After cooled, the mixture was concentrated under reduced pressure. The residue was dissolved in water (5 mL) and acidified to pH 3-4 with 5M aqueous hydrochloric acid. The resulting precipitate was collected by filtration, washed with water, and dried under reduced pressure to give the title compound (400 mg, 59% yield) as a white solid. ¹H NMR (400 MHz, Methanol-d4) δ 9.11-9.10 (m, 1H), 8.72-8.69 (m, 1H), 8.11 (d, J=7.6 Hz, 2H), 7.91-7.89 (m, 1H), 7.58 (d, J=8.0 Hz, 2H), 4.61-4.58 (m, 1H), 4.40-4.37 (m, 1H), 3.81 (s, 3H), 2.63 (s, 6H), 1.18 (d, J=6.0 Hz, 3H). LCMS M/Z (M+H) 382. The compound was isolated as a racemic mixture with unknown relative stereochemistry: the assignment was based on example 68.

Example 82

8-(((1S,2S)-1-(dimethylamino)-1-(4-(morpholine-4-carbonyl)phenyl)propan-2-yl)amino)-6-methylpyrido[2,3-d]pyridazin-5(6H)-one

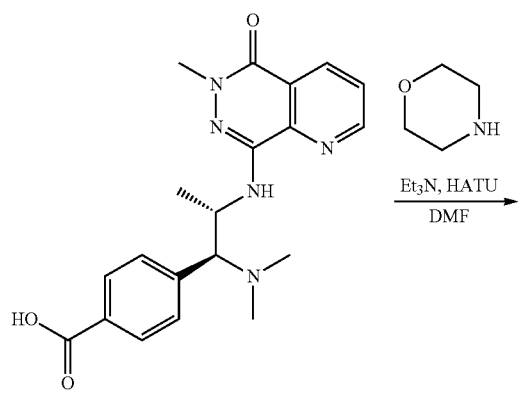

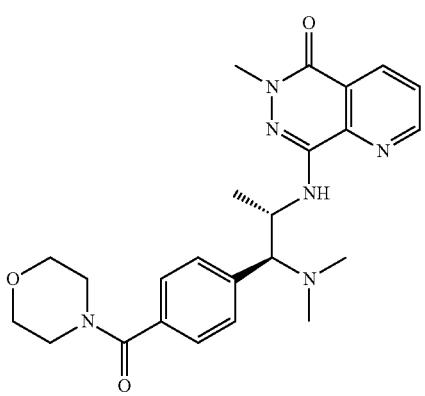 [SMILES: C[C@H](Nc1nn(C)c(=O)c2cccnc12)[C@H](c1ccc(C(=O)N2CCOCC2)cc1)N(C)C]

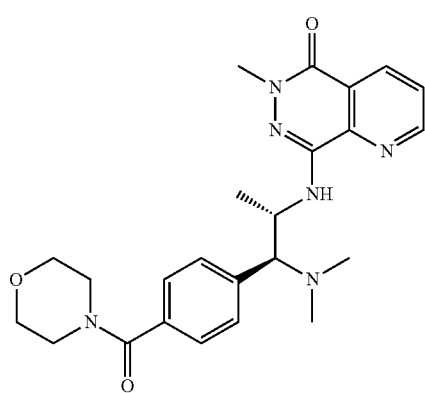

Example 82

A mixture of 4-((1S,2S)-1-(dimethylamino)-2-((6-methyl-5-oxo-5,6-dihydropyrido[2,3-d]pyridazin-8-yl)amino)propyl)benzoic acid (35 mg, 0.09 mmol), morpholine (9 mg, 0.10 mmol), HATU (42 mg, 0.11 mmol) and TEA (11 mg, 0.11 mmol) in DMF (8 mL) was stirred at room temperature for 10 h, at which time LCMS indicated the reaction had gone to completion. The reaction was concentrated under reduced pressure and the residue was then partitioned between dichloromethane (10 mL) and water (8 mL). The separated organic phase was concentrated under reduced pressure. The crude product was purified by reverse phase chromatography (acetonitrile 4-34%/0.1% NH$_4$OH in water) to give the title compound (31.8 mg, 77% yield) as a white solid. $^1$H NMR (400 MHz, Methanol-d4) δ 9.05-9.03 (m, 1H), 8.70-8.68 (m, 1H), 7.88-7.86 (m, 1H), 7.49 (d, J=8.0 Hz, 2H), 7.42 (d, J=8.0 Hz, 2H), 4.51-4.49 (m, 1H), 3.77-3.51 (m, 12H), 2.22 (s, 6H), 1.18 (d, J=6.0 Hz, 3H). LCMS M/Z (M+H) 451. The compound was isolated as a racemic mixture with unknown relative stereochemistry: the assignment was based on example 81.

Examples 83-85

The following compounds were prepared in a similar fashion to example 82. All examples in the following table were prepared using commercially available amines.

| Example | Compound Name | NMR | M/Z (M + H) |
|---|---|---|---|
| 83 | 8-(((1S,2S)-1-(dimethylamino)-1-(4-(pyrrolidine-1-carbonyl)phenyl)propan-2-yl)amino)-6-methylpyrido[2,3-d]pyridazin-5(6H)-one | $^1$H NMR (400 MHz, Methanol-d4) δ 9.05-9.03 (m, 1H), 8.69-8.66 (m, 1H), 7.87-7.83 (m, 1H), 7.58 (d, J = 8.0 Hz, 2H), 7.41 (d, J = 8.0 Hz, 2H), 4.55-4.51 (m, 1H), 3.77-3.71 (m, 4H), 3.63-3.51 (m, 2H), 3.54-3.51 (m, 2H), 2.22 (s, 6H), 2.05-1.93 (m, 4H), 1.18 (d, J = 6.4 Hz, 3H). (Racemic mixture; unknown relative stereochemistry; and single diastereoisomer) | 435 |
| 84 | N-benzyl-4-((1S,2S)-1-(dimethylamino)-2-((6-methyl-5-oxo-5,6-dihydropyrido[2,3-d]pyridazin-8-yl)amino)propyl)-N-methylbenzamide | $^1$H NMR (400 MHz, Methanol-d4) δ 9.01-8.93 (m, 1H), 8.65-8.63 (m, 1H), 7.82-7.80 (m, 1H), 7.51-7.29 (m, 9H), 4.78-4.76 (m, 1H), 4.57-4.49 (m, 2H), 3.73-3.68 (m, 4H), 3.04 (s, 3H), 2.1-2.17 (m, 6H), 1.16-1.13 (m, 3H). (Racemic mixture; unknown relative stereochemistry; and single diastereoisomer) | 485 |

| Example | Compound Name | NMR | M/Z (M + H) |
|---|---|---|---|
| 85 | 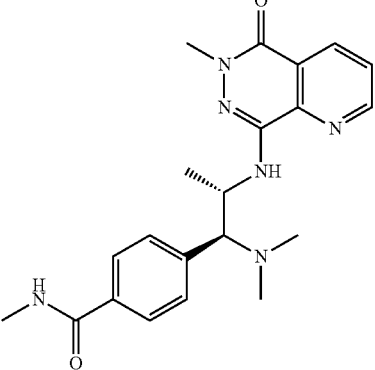  4-((1S,2S)-1-(dimethylamino)-2-((6-methyl-5-oxo-5,6-dihydropyrido[2,3-d]pyridazin-8-yl)amino)propyl)-N-methylbenzamide | $^1$H NMR (400 MHz, Methanol-d4) δ 9.08-9.07 (m, 1H), 8.70-8.68 (m, 1H), 7.86-7.85 (m, 3H), 7.47-7.46 (m, 2H), 4.54-4.50 (m, 1H), 3.80-3.72 (m, 4H), 2.96 (s, 3H), 2.22 (s, 6H), 1.17 (d, J = 6.4 Hz, 3H). (Racemic mixture; unknown relative stereochemistry; and single diastereoisomer) | 395 |

Example 86

Isopropyl 4-((1S,2S)-1-(dimethylamino)-2-((6-methyl-5-oxo-5,6-dihydropyrido[2,3-d]pyridazin-8-yl)amino)propyl)benzoate

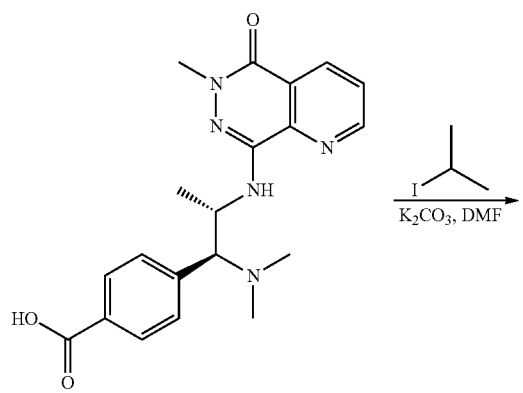

Example 81

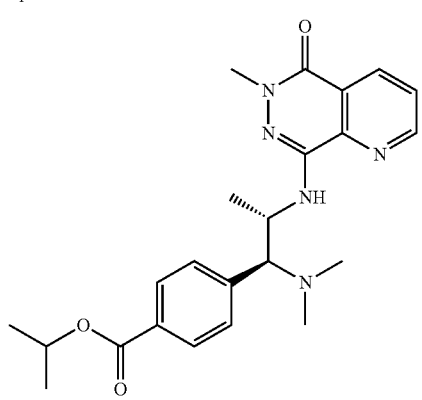

Example 86

To a solution of 4-((1S,2S)-1-(dimethylamino)-2-((6-methyl-5-oxo-5,6-dihydropyrido[2,3-d]pyridazin-8-yl)amino)propyl)benzoic acid (35 mg, 0.09 mmol) and potassium carbonate (25 mg, 0.15 mmol) in DMF (3 mL) was added 2-iodopropane (31 mg, 0.18 mmol). The reaction mixture was stirred at ambient temperature for 4 h, at which time LCMS indicated that the reaction had gone to completion. The mixture was concentrated under reduced pressure. The residue was diluted with ethyl acetate (15 mL), washed with water (2×10 mL) and concentrated under reduced pressure. The residue was purified by reverse phase chromatography (acetonitrile 15-45%/0.1% NH$_4$OH in water) to give the title compound (23 mg, 59% yield) as a white solid. $^1$H NMR (400 MHz, Methanol-d4) δ 9.05-9.04 (m, 1H), 8.69-8.66 (m, 1H), 8.03 (d, J=8.4 Hz, 2H), 7.87-7.84 (m, 1H), 7.42 (d, J=8.4 Hz, 2H), 5.26-5.24 (m, 1H), 4.54-4.51 (m, 1H), 3.77-3.73 (m, 4H), 2.22 (s, 6H), 1.40 (d, J=6.4 Hz, 6H), 1.17 (d, J=6.4 Hz, 3H). LCMS M/Z (M+H) 424. The compound was isolated as a racemic mixture with unknown relative stereochemistry: the assignment was based on example 81.

Example 87

The following compound was prepared in a similar fashion to example 86, using benzyl bromide instead of 2-iodopropane.

| Example | Compound Name | NMR | M/Z (M + H) |
|---|---|---|---|
| 87 | 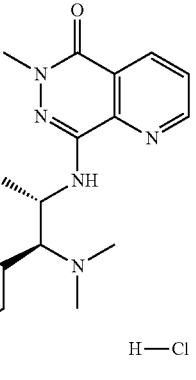<br>benzyl 4-((1S,2S)-1-(dimethylamino)-2-((6-methyl-5-oxo-5,6-dihydropyrido[2,3-d]pyridazin-8-yl)amino)propyl)benzoate hydrochloride | 1H NMR (400 MHz, Methanol-d4) δ 9.15-9.13 (m, 1H), 8.74-8.71 (m, 1H), 8.28-8.26 (m, 2H), 7.92-7.81 (m, 3H), 7.52-7.39 (m, 5H), 5.44 (s, 2H), 5.13-5.08 (m, 1H), 4.77 (d, J = 11.2 Hz, 1H), 3.82 (s, 3H), 2.89 (s, 3H), 2.78 (s, 3H), 1.17 (d, J = 6.8 Hz, 3H). (Racemic mixture; unknown relative stereochemistry; and single diastereoisomer) | 472 |

Example 88

4-(((1S,2S)-1-(dimethylamino)-1-(6-oxo-1,6-dihydropyridin-3-yl)propan-2-yl)amino)-2-methylphthalazin-1(2H)-one

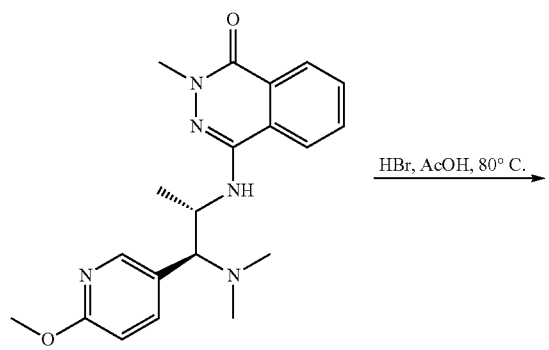

Example 62

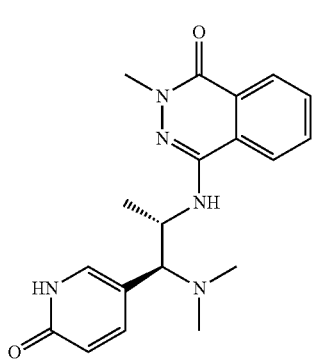

Example 88

To a solution of 4-(((1S,2S)-1-(dimethylamino)-1-(6-methoxypyridin-3-yl)propan-2-yl)amino)-2-methylphthalazin-1(2H)-one (50 mg, 0.14 mol) in acetic acid (2 mL) was added 48 wt. % aqueous HBr (0.2 mL). The reaction was heated to 80° C. for 3 h, then quenched in iced water. The pH was adjusted to 10 with potassium carbonate and the product was extracted with ethyl acetate (repeated three times). The combined organic layers were dried with $Na_2SO_4$, filtered and concentrated to dryness under reduced pressure. The crude product was purified by flash chromatography (dichloromethane/methanol 95:5 to 70:30) to give the title compound (33 mg, 69% yield). $^1$H NMR (400 MHz, DMSO-d6) δ 11.50 (br. s, 1H), 8.26 (dd, J=1.42, 7.77 Hz, 1H), 8.05 (d, J=8.10 Hz, 1H), 7.89 (dt, J=1.53, 7.66 Hz, 1H), 7.80-7.86 (m, 1H), 7.39 (dd, J=2.63, 9.42 Hz, 1H), 7.10 (d, J=2.41 Hz, 1H), 6.32 (d, J=9.42 Hz, 1H), 6.26 (d, J=4.82 Hz, 1H), 4.24-4.35 (m, 1H), 3.60 (s, 3H), 3.32-3.36 (m, 1H), 2.12 (s, 6H), 1.06 (d, J=6.35 Hz, 3H). LCMS M/Z (M+H) 354. The compound was isolated as a racemic mixture with unknown relative stereochemistry: the assignment was based on example 62.

Examples 89 and 90
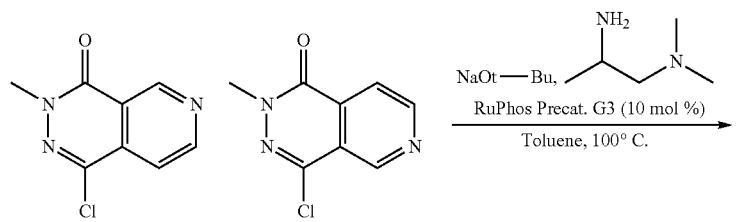
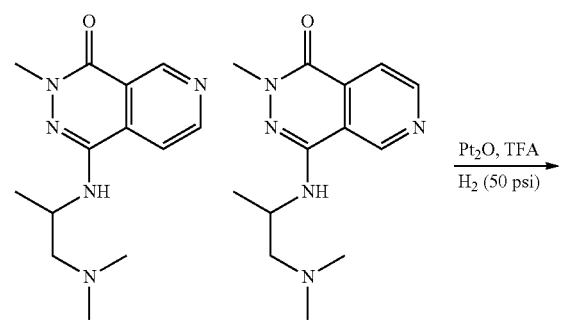
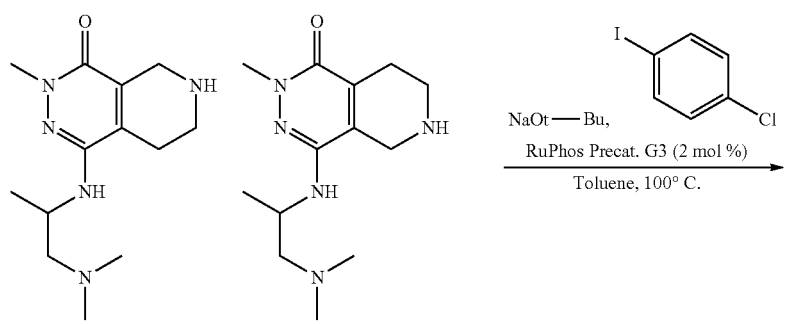
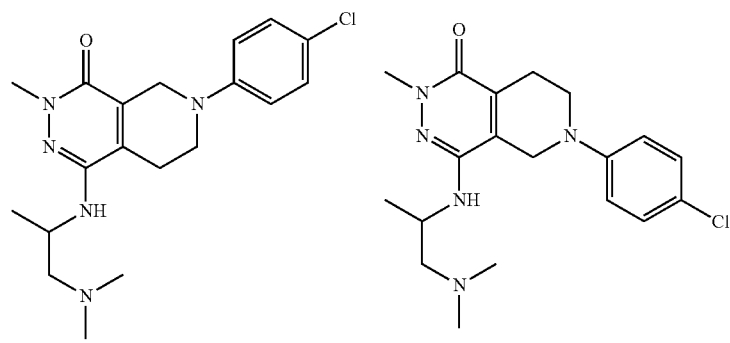
Example 89                Example 90

Step 1:

1-((1-(dimethylamino)propan-2-yl)amino)-3-methyl-pyrido[3,4-d]pyridazin-4(3H)-one and 4-((1-(dimethylamino)propan-2-yl)amino)-2-methylpyrido[3,4-d]pyridazin-1(2H)-one

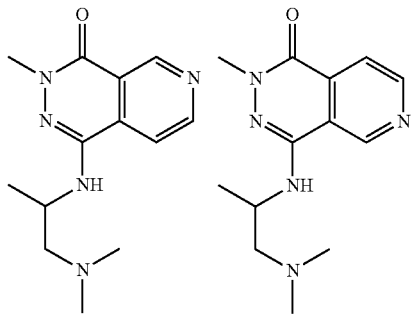

In a pyrex vial a 1:1 mixture of 4-chloro-2-methylpyrido[3,4-d]pyridazin-1(2H)-one and 1-chloro-3-methylpyrido[3,4-d]pyridazin-4(3H)-one (Intermediates H and I, 300 mg, 1.53 mmol), RuPhos $3^{rd}$ generation precatalyst (121 mg, 0.153 mmol), and sodium tert-butoxide (442 mg, 4.6 mmol) were added, the vial was sealed and the atmosphere evacuated and purged with $N_2$ (3×). To this solution N1,N1-dimethylpropane-1,2-diamine (395 μL, 3.07 mmol), and toluene (5 mL) were added. The reaction was heated at 100° C. for 3 h. The crude reaction was concentrated in vacuo, deposited onto silica gel with aid of methanol, and purified by silica gel flash chromatography using a 40-100% gradient of 90:10:1 dichloromethane:methanol:$NH_4OH$ and dichloromethane as eluent. The product fractions were concentrated in vacuo to provide a mixture of the title compounds (335 mg, 84% yield) as a dark orange oil.

LCMS M/Z (M+H) 262.

Step 2:

1-((1-(dimethylamino)propan-2-yl)amino)-3-methyl-5,6,7,8-tetrahydropyrido[3,4-d]pyridazin-4(3H)-one and 4-((1-(dimethylamino)propan-2-yl)amino)-2-methyl-5,6,7,8-tetrahydropyrido[3,4-d]pyridazin-1(2H)-one

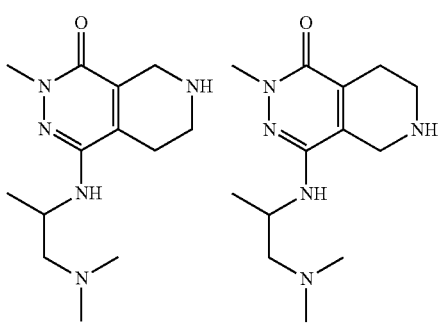

A pressure vessel was charged with 4-((1-(dimethylamino)propan-2-yl)amino)-2-methylpyrido[3,4-d]pyridazin-1(2H)-one and 1-((1-(dimethylamino)propan-2-yl)amino)-3-methyl-5,6,7,8-tetrahydropyrido[3,4-d]pyridazin-4(3H)-one (335 mg, 1.28 mmol), TFA (15 mL) and platinum(IV) oxide (60 mg, 0.26 mmol). The vessel was sealed, evacuated and purged with $N_2$ (3×), evacuated and purged with $H_2$ (3×), pressurized to 50 psi with $H_2$ and mixed at ambient temperature overnight. The reaction was complete after 15 h, and no trifluoroacetamide was observed. The reaction was filtered through a pad of celite washing with dichloromethane then concentrated and used directly in the following reaction.

LCMS M/Z (M+H) 266.

Step 3:

6-(4-chlorophenyl)-1-((1-(dimethylamino)propan-2-yl)amino)-3-methyl-5,6,7,8-tetrahydropyrido[3,4-d]pyridazin-4(3H)-one and 6-(4-chlorophenyl)-4-((1-(dimethylamino)propan-2-yl)amino)-2-methyl-5,6,7,8-tetrahydropyrido[3,4-d]pyridazin-1(2H)-one

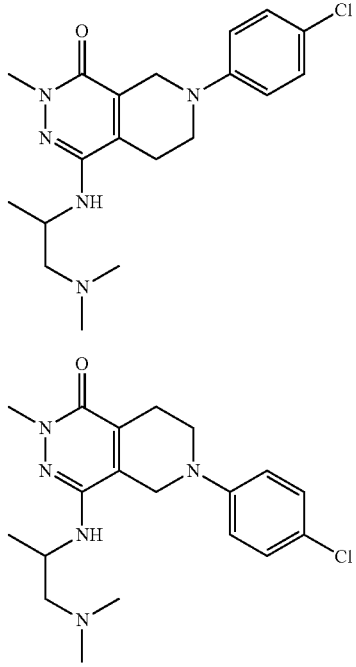

Example 89

Example 90

In a pyrex flask RuPhos $3^{rd}$ generation precatalyst (30 mg, 0.03 mmol) and 1-((1-(dimethylamino)propan-2-yl)amino)-3-methyl-5,6,7,8-tetrahydropyrido[3,4-d]pyridazin-4(3H)-one and 4-((1-(dimethylamino)propan-2-yl)amino)-2-methyl-5,6,7,8-tetrahydropyrido[3,4-d]pyridazin-1(2H)-one (340 mg, 1.28 mmol), sodium tert-butoxide (390 mg, 4.1 mmol) and 1-chloro-4-iodobenzene (460 mg, 1.92 mmol) were added. The vial was evacuated and purged with $N_2$ (3×) then toluene (5 mL) was added. The vial was evacuated and purged with $N_2$ (3×) then heated at 100° C. overnight. The reaction was concentrated in vacuo to dryness and purified by silica gel flash chromatography using 90:10:1 dichloromethane: methanol:$NH_4OH$ as eluent. The regioisomeric products could not be separated by normal phase chromatography. Reverse phase HPLC was used to separate the regioisomers. A 10 min 10-55% gradient of water/MeCN (0.1% TFA) method was used. Example 89 (more polar) and example 90 were independently treated with a saturated aqueous solution of $NaHCO_3$, extracted with dichloromethane, dried over $Na_2SO_4$, filtered, concentrated and lyophilized to provide both title compounds as a yellow solid. Example 89 (58 mg, 12% yield): Racemic mixture $^1$H NMR (400 MHz, DMSO-d6) δ 7.29-7.24 (m, 2H), 7.05-6.99 (m, 2H), 5.38 (d, J=6.5 Hz, 1H), 4.01 (s, 2H), 3.84-3.75 (m, 1H), 3.52-3.45 (m, 6H), 2.42-2.34 (m, 1H), 2.23-2.13 (m, 8H), 1.14 (d, J=6.3 Hz, 3H). LCMS M/Z (M+H) 376. Example 90 (120 mg, 25% yield): Racemic mixture $^1$H NMR (400 MHz, DMSO-d6) δ 7.31-7.26 (m, 2H), 7.15-7.10 (m, 2H), 5.53 (d, J=7.4 Hz, 1H), 3.93 (d, J=17.1 Hz, 4H), 3.49 (s, 3H), 3.44 (d, J=4.6 Hz, 2H), 2.61-2.55 (m, 2H), 2.43-2.35 (m, 1H), 2.19 (s, 6H), 1.18 (d, J=6.5 Hz, 3H). LCMS M/Z (M+H) 376.

Separation of Enantiomers for the Final Compounds

The enantiomers of some final compounds were separated by supercritical fluid chromatography, using a PIC-100 SFC instrument (100 bar pressure; 40° C. column temperature; 70 mL/min flow rate; 220 nm UV detection) under the specific condition described below.

| Method | Example | Column type & Particule size | Column dimensions | Mobile Phase A | Mobile Phase B |
|---|---|---|---|---|---|
| A | 39B 39A | Chiralpak AD 5 μm | 2 × 10 cm | 85% $CO_2$ | Isocratic 15% Methanol w/0.1% $NH_4OH$ |
| B | 22A 22B | Chiralpak AD 5 μm | 2 × 10 cm | 80% $CO_2$ | Isocratic 20% Methanol w/0.1% $NH_4OH$ |
| C | 1B 1A | Chiralpak ID 5 μm | 2 × 10 cm | 75% $CO_2$ | Isocratic 25% IPA w/ 0.1% $NH_4OH$ |
| D | 65A 65B | Cellulose-4 5 μm | 2 × 10 cm | 75% $CO_2$ | Isocratic 25% Methanol w/0.1% $NH_4OH$ |
| E | 54B 54A 73B 73A | Chiralpak ID 5 μm | 2 × 10 cm | 80% $CO_2$ | Isocratic 20% Methanol w/0.1% $NH_4OH$ |
| F | 32B 32A | Chiralpak ID 5 μm | 2 × 10 cm | 60% $CO_2$ | Isocratic 40% Methanol w/0.1% $NH_4OH$ |

The enantiomers of some final compounds were separated by supercritical fluid chromatography (SFC), using a Waters Thar SFC-80 instrument (145 bar pressure; 38° C. column temperature; 220 nm UV detection)) under the specific condition described below.

| Method | Example | Column type & Particule size | Column dimensions | Mobile Phase A | Mobile Phase B | Flow rate (mL/min) |
|---|---|---|---|---|---|---|
| G | 7A 7B | Chiralpak AD 5 μm | 3 × 25 cm | 75% $CO_2$ | Isocratic 25% IPA w/0.1% $NH_4OH$ | 60 |
| H | 8A 8B | Chiralpak AD 10 μm | 3 × 25 cm | 70% $CO_2$ | Isocratic 30% Methanol w/ 0.1% $NH_4OH$ | 80 |
| I | 11A 11B | Chiralpak IC 5 μm | 3 × 25 cm | 60% $CO_2$ | Isocratic 40% Ethanol w/ 0.1% $NH_4OH$ | 60 |
| J | 14A 14B | Chiralpak AD 10 μm | 3 × 25 cm | 60% $CO_2$ | Isocratic 40% Methanol w/ 0.1% $NH_4OH$ | 70 |
| K | 15A 15B | Chiralpak AD 5 μm | 3 × 25 cm | 70% $CO_2$ | Isocratic 30% Methanol w/ 0.1% $NH_4OH$ | 60 |
| L | 16A 16B | Chiralpak AD 5 μm | 3 × 25 cm | 75% $CO_2$ | Isocratic 25% IPA w/0.1% $NH_4OH$ | 60 |
| M | 17A 17B | Chiralpak AD 5 μm | 3 × 25 cm | 70% $CO_2$ | Isocratic 30% Ethanol w/ 0.1% $NH_4OH$ | 80 |
| N | 69A 69B | Chiralpak AD 10 μm | 3 × 25 cm | 70% $CO_2$ | Isocratic 30% Ethanol w/ 0.1% $NH_4OH$ | 80 |
| O | 70A 70B | Chiralpak AD 10 μm | 3 × 25 cm | 70% $CO_2$ | Isocratic 30% Ethanol w/ 0.1% $NH_4OH$ | 70 |
| P | 71A 71B | Chiralpak C-2 10 μm | 3 × 25 cm | 65% $CO_2$ | Isocratic 35% Methanol w/ 0.1% $NH_4OH$ | 70 |
| Q | 74A 74B | Chiralpak OD 10 μm | 5 × 30 cm | 80% $CO_2$ | Isocratic 20% Ethanol w/ 0.1% $NH_4OH$ | 200 |

Biological Data

IC$_{50}$ Measurements for Inhibitors Using PCAF AlphaLisa Binding Assay

His/Flag epitope tagged PCAF$_{719-832}$ bromodomain was cloned, expressed and purified to homogeneity in-house. PCAF bromodomain binding and inhibition of the compounds disclosed herein was assessed by monitoring the engagement of biotinylated small molecule ligand (known to bind to the PCAF bromodomain) with the target using the AlphaLisa technology (Perkin-Elmer). Specifically, in a 384 well ProxiPlate PCAF bromodomain (225 nM final) was combined with the biotinylated small molecule ligand (6 nM final) in 50 mM HEPES (pH 7.5), 75 mM NaCl, 1 mM TCEP, 0.01% (w/v) BSA, and 0.008% (w/v) Brij-35 either in the presence of DMSO (final 0.2% DMSO) or compound dilution series in DMSO. After 15 minute incubation at room temperature AlphaLisa streptavidin acceptor beads and AlphaLisa anti-histidine donor beads were added to a final concentration of 12.5 µg/mL each. After 90 minutes of equilibration plates were read on an Envision instrument and IC$_{50}$s calculated using a four parameter non-linear curve fit.

PCAF IC$_{50}$ values for the Examples 1-90 were determined using the general procedure described above.

| Example | Structure | PCAF IC$_{50}$ (µM) |
|---|---|---|
| 1 | | 0.086 |
| 1A | | 0.045 |
| 1B | 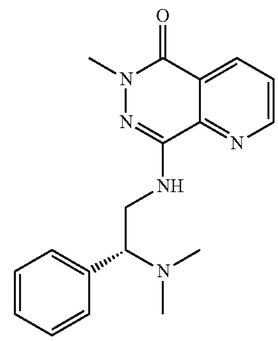 | 2.2 |
| 2 | 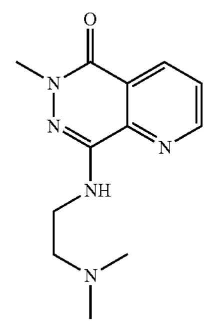 [SMILES: CN(C)CCNc1nn(C)c(=O)c2cccnc12] | 0.14 |
| 3 | 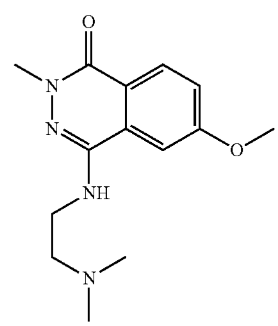 | 0.41 |
| 4 | 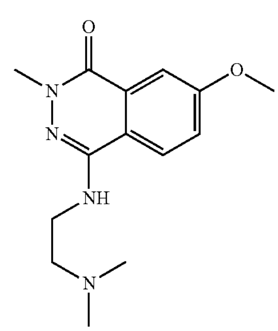 | 0.47 |

-continued

| Example | Structure | PCAF IC$_{50}$ (μM) |
|---|---|---|
| 5 | (2-methyl-1-oxo-5-fluoro-phthalazin-4-yl)-NH-CH$_2$CH$_2$-N(CH$_3$)$_2$ | 0.13 |
| 6 | (2-methyl-1-oxo-8-fluoro-phthalazin-4-yl)-NH-CH$_2$CH$_2$-N(CH$_3$)$_2$ | 0.087 |
| 7A | 3-methyl-4-oxo-pyrido[2,3-d]pyridazin-8-yl-NH-CH$_2$-CH(CH$_3$)-N(CH$_3$)$_2$ | 0.86 |
| 7B | 3-methyl-4-oxo-pyrido[2,3-d]pyridazin-8-yl-NH-CH$_2$-(R)-CH(CH$_3$)-N(CH$_3$)$_2$ | 0.072 |

-continued

| Example | Structure | PCAF IC$_{50}$ (μM) |
|---|---|---|
| 8A | 3-methyl-4-oxo-pyrido[2,3-d]pyridazin-8-yl-NH-(R)-CH(CH$_3$)-CH$_2$-N(CH$_3$)$_2$ | 0.042 |
| 8B | 3-methyl-4-oxo-pyrido[2,3-d]pyridazin-8-yl-NH-(S)-CH(CH$_3$)-CH$_2$-N(CH$_3$)$_2$ | >5 |
| 9 | (2-methyl-1-oxo-phthalazin-4-yl)-S-CH$_2$CH$_2$-N(CH$_3$)$_2$ | 0.89 |
| 10 | 6-methyl-7-oxo-1H-pyrrolo[2,3-d]pyridazin-4-yl-NH-CH$_2$-CH(Ph)-N(CH$_3$)$_2$ | 0.24 |

| Example | Structure | PCAF IC$_{50}$ (μM) |
|---|---|---|
| 11A | 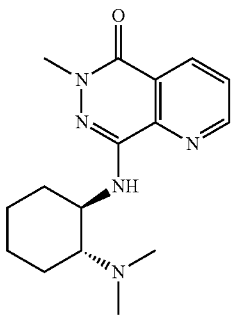 | 0.18 |
| 11B | 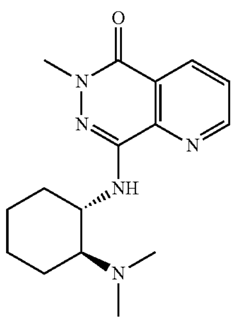 [SMILES: CN(C)[C@H]1CCCC[C@@H]1Nc1nn(C)c(=O)c2cccnc12] | >5 |
| 12 | 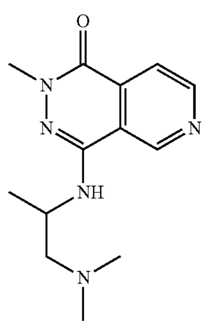 [SMILES: CC(CN(C)C)Nc1nn(C)c(=O)c2ccncc12] | 0.22 |
| 13 | 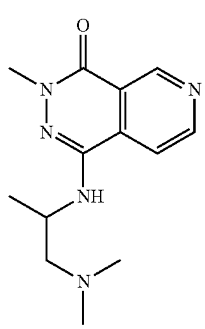 [SMILES: CC(CN(C)C)Nc1nn(C)c(=O)c2cnccc12] | 0.15 |
| 14A | 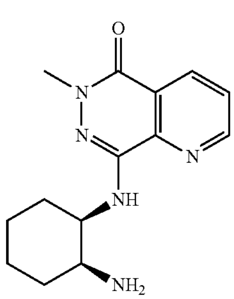 [SMILES: Cn1nc(N[C@@H]2CCCC[C@@H]2N)c2ncccc2c1=O] | >5 |
| 14B | | 1.5 |
| 15A | | 0.078 |
| 15B | | 1.5 |
| 16A | | 0.057 |

-continued

| Example | Structure | PCAF IC$_{50}$ (μM) |
|---|---|---|
| 16B | 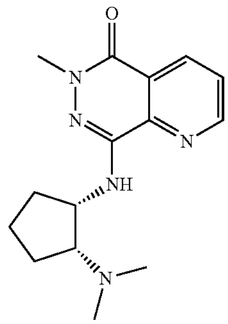 [SMILES: CN(C)[C@@H]1CCC[C@@H]1Nc1nn(C)c(=O)c2cccnc12] | 0.86 |
| 17A | 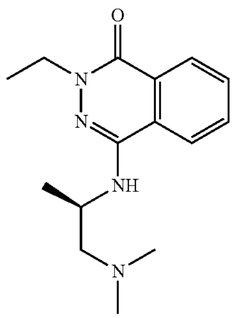 | >5 |
| 17B | 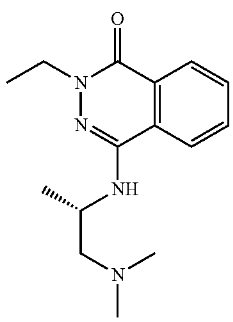 [SMILES: CCn1nc(N[C@@H](C)CN(C)C)c2ccccc2c1=O] | 0.28 |
| 18 | 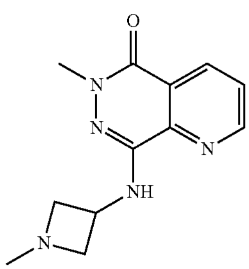 [SMILES: CN1CC(Nc2nn(C)c(=O)c3cccnc23)C1] | 1.5 |
| 19 | 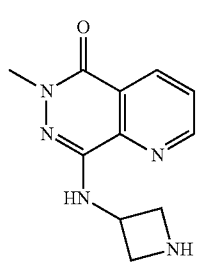 [SMILES: Cn1nc(NC2CNC2)c2ncccc2c1=O] | 3.4 |

-continued

| Example | Structure | PCAF IC$_{50}$ (μM) |
|---|---|---|
| 20 | 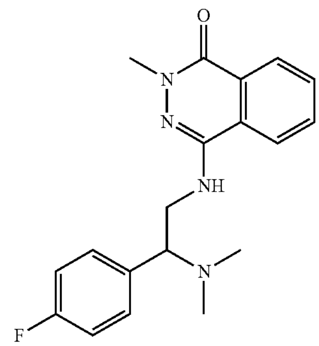 [SMILES: CN(C)C(CNc1nn(C)c(=O)c2ccccc12)c1ccc(F)cc1] | 0.11 |
| 21 | 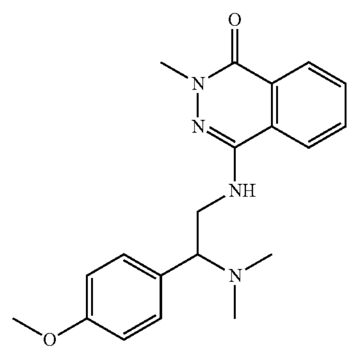 [SMILES: COc1ccc(C(CNc2nn(C)c(=O)c3ccccc23)N(C)C)cc1] | 0.064 |
| 22 | 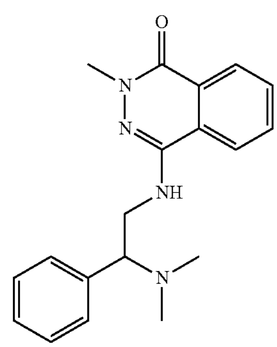 | 0.14 |
| 22A | 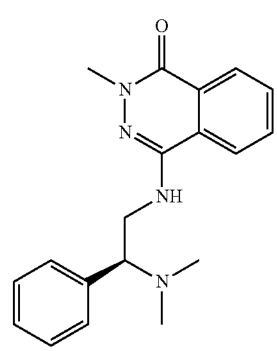 [SMILES: CN(C)[C@H](CNc1nn(C)c(=O)c2ccccc12)c1ccccc1] | 0.047 |

-continued
| Example | Structure | PCAF IC$_{50}$ (μM) |
|---|---|---|
| 22B | 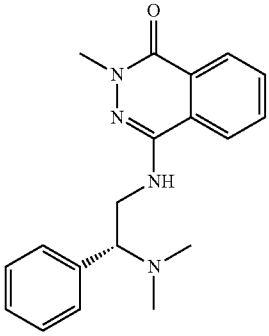 | 0.55 |
| 23 | 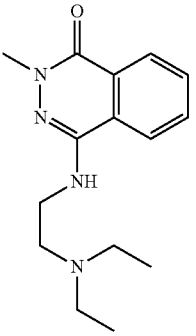 [SMILES: CCN(CC)CCNc1nn(C)c(=O)c2ccccc12] | 2.4 |
| 24 | 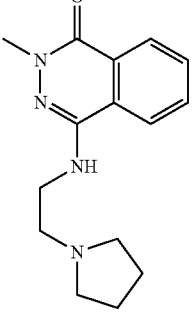 | 0.92 |
| 25 | 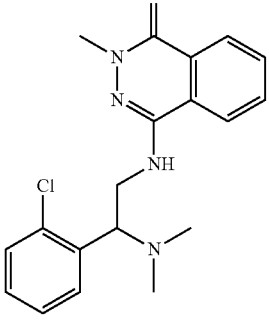 | 0.11 |
| 26 | 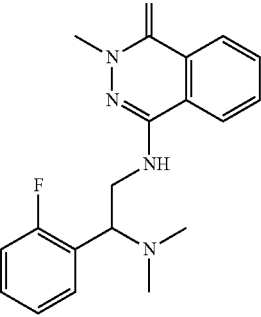 | 0.11 |
| 27 | 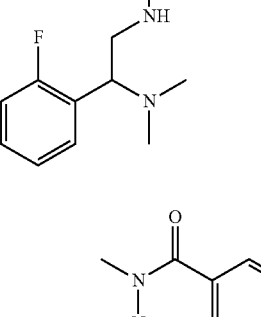 | 0.12 |
| 28 | 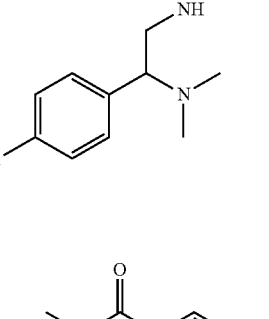 | 0.066 |
| 29 | 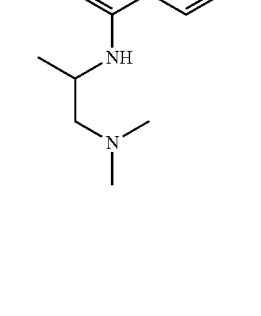 | 0.15 |

| Example | Structure | PCAF IC$_{50}$ (μM) |
|---|---|---|
| 30 | 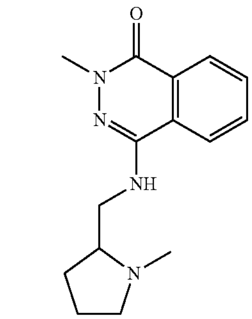 [SMILES: CN1CCCC1CNc1nn(C)c(=O)c2ccccc12] | 1.7 |
| 31 | (TFA) | 8.1 |
| 32 | (TFA) | 0.14 |
| 32A | 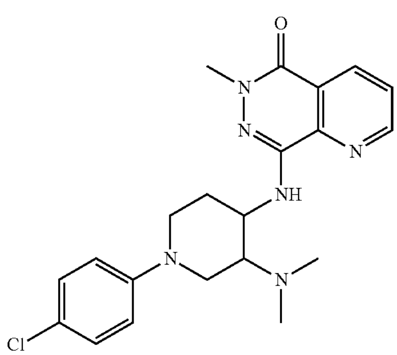 [SMILES: CN(C)C1CN(c2ccc(Cl)cc2)CCC1Nc1nn(C)c(=O)c2cccnc12] | 0.15 |
| 32B | 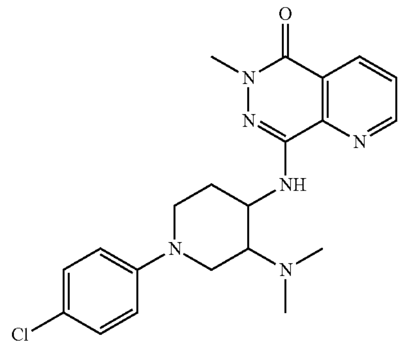 [SMILES: CN(C)C1CN(c2ccc(Cl)cc2)CCC1Nc1nn(C)c(=O)c2cccnc12] | 0.069 |
| 33 | 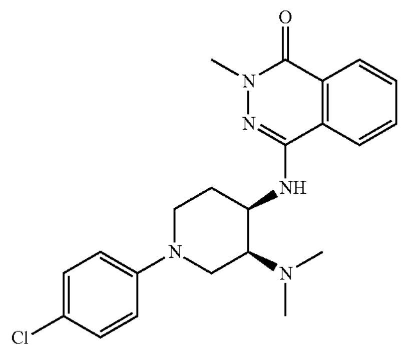 [SMILES: CN(C)[C@H]1CN(c2ccc(Cl)cc2)CC[C@H]1Nc1nn(C)c(=O)c2ccccc12] | 0.17 |
| 34 | 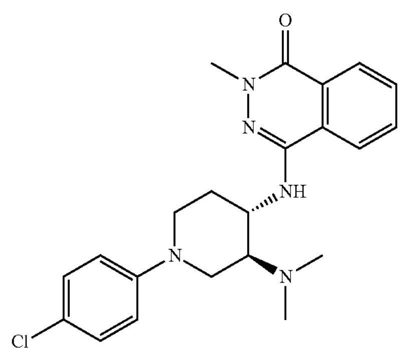 [SMILES: CN(C)[C@H]1CN(c2ccc(Cl)cc2)CC[C@@H]1Nc1nn(C)c(=O)c2ccccc12] | 0.040 |
| 35 | 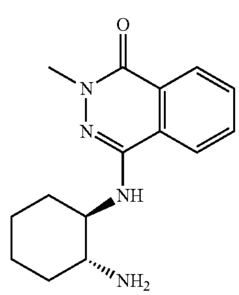 [SMILES: Cn1nc(N[C@@H]2CCCC[C@H]2N)c2ccccc2c1=O] | 12 |

-continued

| Example | Structure | PCAF IC$_{50}$ (μM) |
|---|---|---|
| 36 | (2-methyl-1-oxo-5,6,7,8-tetrahydrophthalazin-4-yl) linked to NH-CH$_2$-CH(phenyl)-N(CH$_3$)$_2$ | 0.82 |
| 37 | (2-methyl-1-oxo-2,5,6,7-tetrahydrocyclopenta[d]pyridazin-4-yl) linked to NH-CH$_2$-CH(phenyl)-N(CH$_3$)$_2$ | 0.13 |
| 38 | (2-methyl-1-oxo-phthalazin-4-yl)-NH-CH$_2$-CH(cyclohexyl)-N(CH$_3$)$_2$ | 0.70 |
| 39 | (2-methyl-1-oxo-phthalazin-4-yl)-NH-CH$_2$-CH(Et)-N(CH$_3$)$_2$ | 0.18 |

-continued

| Example | Structure | PCAF IC$_{50}$ (μM) |
|---|---|---|
| 39A | (2-methyl-1-oxo-phthalazin-4-yl)-NH-CH$_2$-CH(Et)-N(CH$_3$)$_2$ (S) | 0.55 |
| 39B | (2-methyl-1-oxo-phthalazin-4-yl)-NH-CH$_2$-CH(Et)-N(CH$_3$)$_2$ (R) | 0.089 |
| 40 | (2-methyl-1-oxo-phthalazin-4-yl)-NH-CH$_2$-CH$_2$-NH-iPr | 9.4 |
| 41 | (2-methyl-1-oxo-phthalazin-4-yl)-NH-CH$_2$-CH$_2$-piperidinyl | 2.2 |

-continued

| Example | Structure | PCAF IC$_{50}$ (μM) |
|---|---|---|
| 42 | 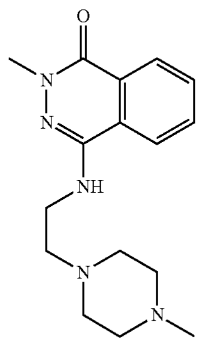 | 9.6 |
| 43 | 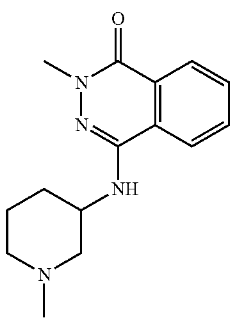 [SMILES: CN1CCCC(Nc2nn(C)c(=O)c3ccccc23)C1] | 0.79 |
| 44 | TFA | 0.26 |
| 45 | 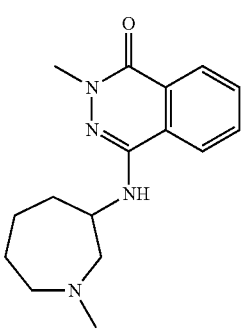 [SMILES: CN1CCCCC(Nc2nn(C)c(=O)c3ccccc23)C1] | 1.2 |

-continued

| Example | Structure | PCAF IC$_{50}$ (μM) |
|---|---|---|
| 46A | 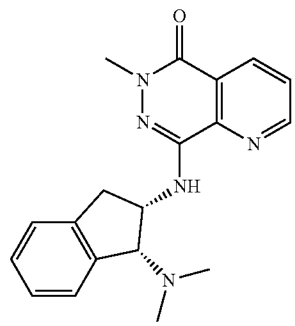 [SMILES: CN(C)[C@@H]1c2ccccc2C[C@@H]1Nc1nn(C)c(=O)c2cccnc12] | 4.8 |
| 46B | 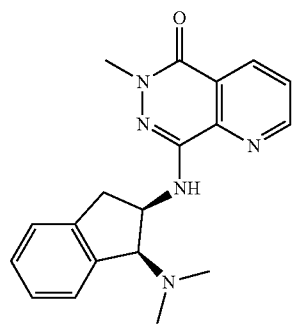 [SMILES: CN(C)[C@H]1c2ccccc2C[C@H]1Nc1nn(C)c(=O)c2cccnc12] | >5 |
| 47A | 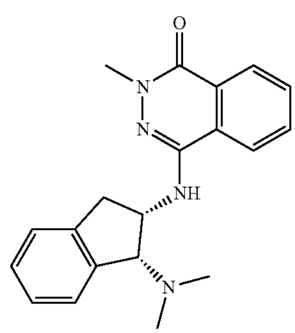 [SMILES: CN(C)[C@@H]1c2ccccc2C[C@@H]1Nc1nn(C)c(=O)c2ccccc12] | 2.7 |
| 47B | 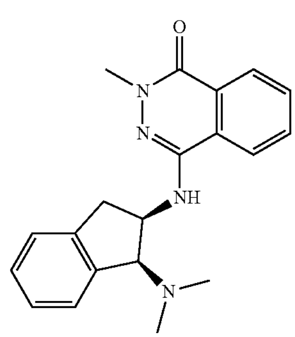 [SMILES: CN(C)[C@H]1c2ccccc2C[C@H]1Nc1nn(C)c(=O)c2ccccc12] | >5 |

-continued
| Example | Structure | PCAF IC$_{50}$ (μM) |
|---|---|---|
| 48 | 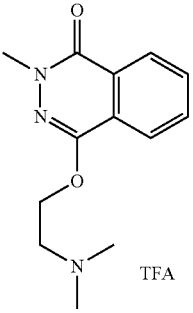 TFA | 0.45 |
| 49 | 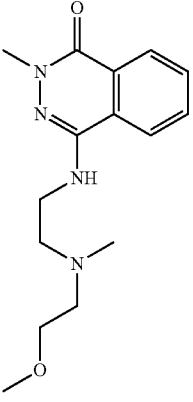 | 3.5 |
| 50 | 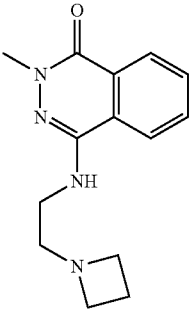 | 0.99 |
| 51 | 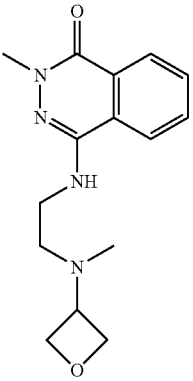 | 0.80 |
-continued
| Example | Structure | PCAF IC$_{50}$ (μM) |
|---|---|---|
| 52 | 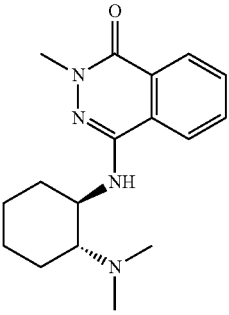 [SMILES: CN(C)[C@@H]1CCCC[C@H]1Nc1nn(C)c(=O)c2ccccc12] | 0.82 |
| 53 | 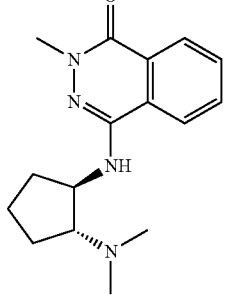 | 2.1 |
| 54 | 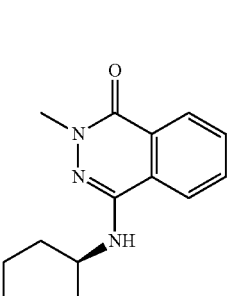 | 0.11 |
| 54A | 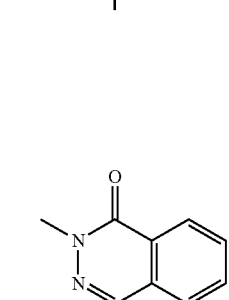 | 0.045 |

-continued

| Example | Structure | PCAF IC50 (μM) |
|---|---|---|
| 54B | 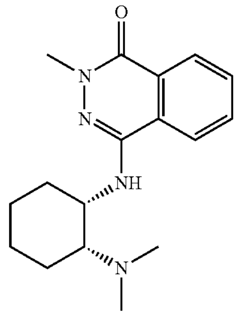 [SMILES: CN(C)[C@@H]1CCCC[C@@H]1Nc1nn(C)c(=O)c2ccccc12] | 11 |
| 55 | 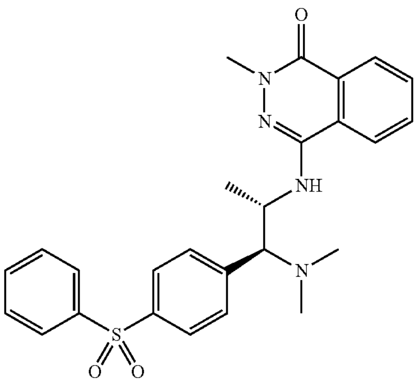 [SMILES: C[C@H](Nc1nn(C)c(=O)c2ccccc12)[C@H](c1ccc(S(=O)(=O)c2ccccc2)cc1)N(C)C] | 0.061 |
| 56 | 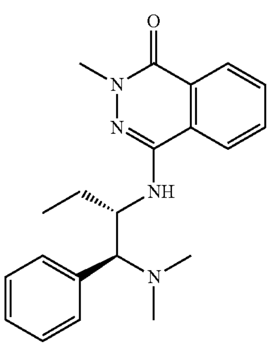 [SMILES: CC[C@H](Nc1nn(C)c(=O)c2ccccc12)[C@H](c1ccccc1)N(C)C] | 0.041 |
| 57 | 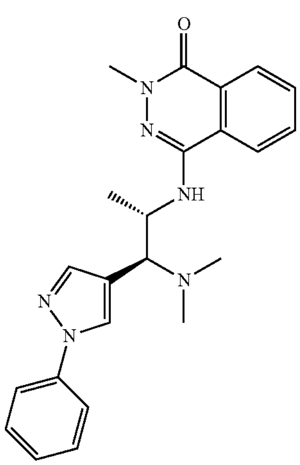 [SMILES: C[C@H](Nc1nn(C)c(=O)c2ccccc12)[C@H](c1cnn(-c2ccccc2)c1)N(C)C] | 0.075 |
| 58 | | 0.04 |
| 59 | | 0.033 |
| 60 | | 0.021 |
| 61 | | 0.086 (2 × TFA) |

| Example | Structure | PCAF IC$_{50}$ (μM) |
|---|---|---|
| 62 | 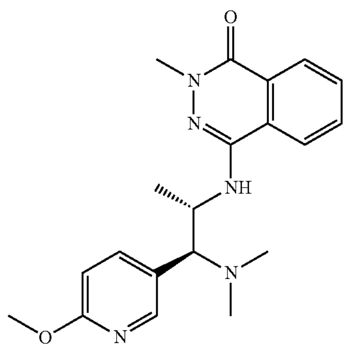 [SMILES: COc1ccc([C@@H]([C@H](C)Nc2nn(C)c(=O)c3ccccc23)N(C)C)cn1] | 0.063 |
| 63 | 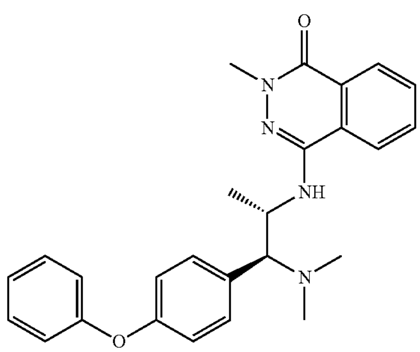 [SMILES: C[C@H](Nc1nn(C)c(=O)c2ccccc12)[C@H](c1ccc(Oc2ccccc2)cc1)N(C)C] | 0.025 |
| 64 | 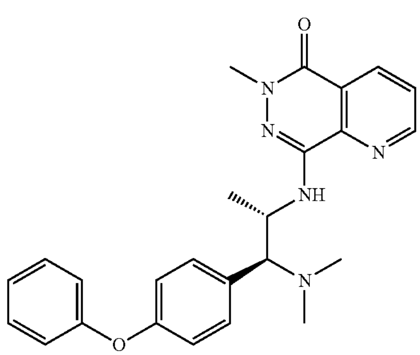 [SMILES: C[C@H](Nc1nn(C)c(=O)c2cccnc12)[C@H](c1ccc(Oc2ccccc2)cc1)N(C)C] | 0.29 |
| 65A | 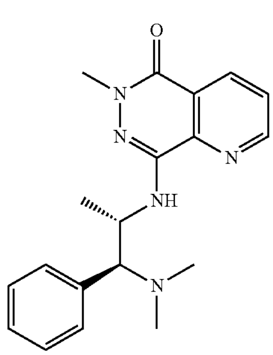 [SMILES: C[C@H](Nc1nn(C)c(=O)c2cccnc12)[C@H](c1ccccc1)N(C)C] | 1.9 |
| 65B | | 0.019 |
| 66 | | N/A |
| 67 | | N/A |
| 68 | | 0.16 |

| Example | Structure | PCAF IC$_{50}$ (μM) |
|---|---|---|
| 69A | 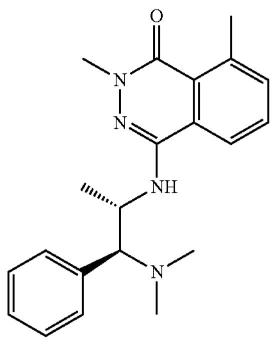 [SMILES: Cc1cccc2c(N[C@@H](C)[C@H](c3ccccc3)N(C)C)nn(C)c(=O)c12] | >5 |
| 69B | 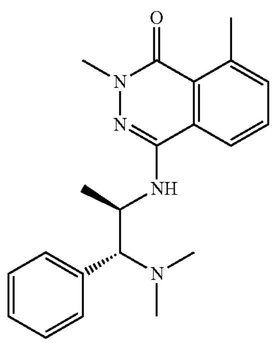 [SMILES: Cc1cccc2c(N[C@H](C)[C@@H](c3ccccc3)N(C)C)nn(C)c(=O)c12] | 0.17 |
| 70A | 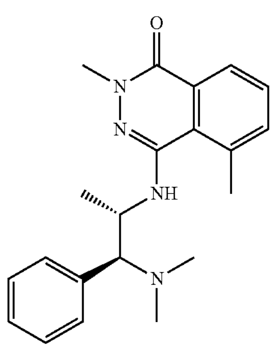 [SMILES: Cc1cccc2c(=O)n(C)nc(N[C@@H](C)[C@H](c3ccccc3)N(C)C)c12] | 0.036 |
| 70B | 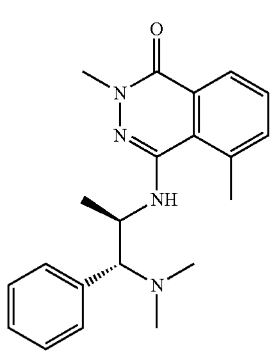 [SMILES: Cc1cccc2c(=O)n(C)nc(N[C@H](C)[C@@H](c3ccccc3)N(C)C)c12] | 1.8 |
| 71A | | >5 |
| 71B | | 0.083 |
| 72 | | 0.099 |
| 73A | | 0.023 |

-continued

| Example | Structure | PCAF IC$_{50}$ (μM) |
|---|---|---|
| 73B | 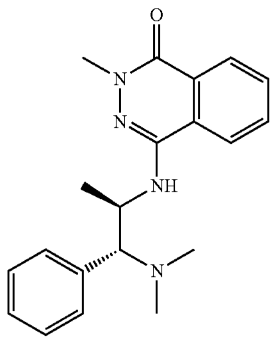 [SMILES: C[C@@H](Nc1nn(C)c(=O)c2ccccc12)[C@@H](c1ccccc1)N(C)C] | 0.68 |
| 74 | 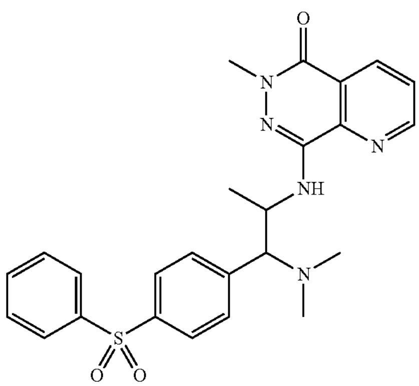 [SMILES: CC(Nc1nn(C)c(=O)c2cccnc12)C(c1ccc(S(=O)(=O)c2ccccc2)cc1)N(C)C] | 0.040 |
| 74A | 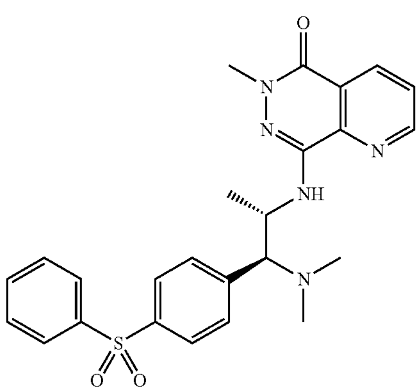 [SMILES: C[C@H](Nc1nn(C)c(=O)c2cccnc12)[C@H](c1ccc(S(=O)(=O)c2ccccc2)cc1)N(C)C] | 0.020 |
| 74B | 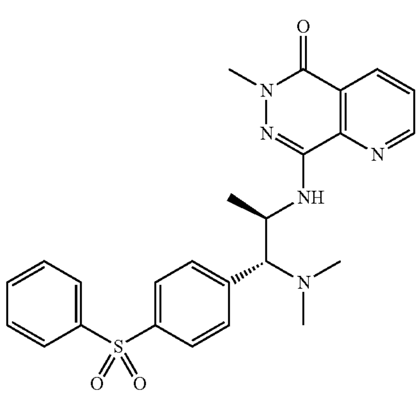 [SMILES: C[C@@H](Nc1nn(C)c(=O)c2cccnc12)[C@@H](c1ccc(S(=O)(=O)c2ccccc2)cc1)N(C)C] | 2.3 |

-continued

| Example | Structure | PCAF IC$_{50}$ (μM) |
|---|---|---|
| 75 | | 0.13 |
| 76 | | 0.042 |
| 77 | | 0.036 |
| 78 | | 0.044 |

-continued

| Example | Structure | PCAF IC$_{50}$ (μM) |
|---|---|---|
| 79 | 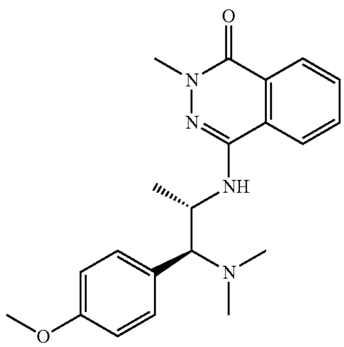 [SMILES: COc1ccc([C@@H]([C@H](C)Nc2nn(C)c(=O)c3ccccc23)N(C)C)cc1] | 0.073 |
| 80 | 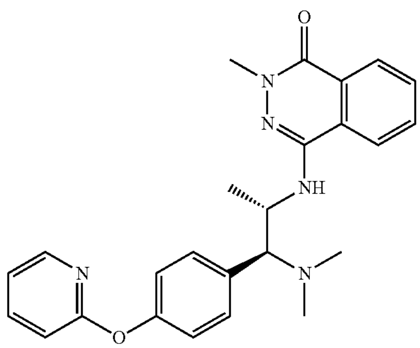 [SMILES: C[C@H](Nc1nn(C)c(=O)c2ccccc12)[C@H](c1ccc(Oc2ccccn2)cc1)N(C)C] | 0.046 |
| 81 | 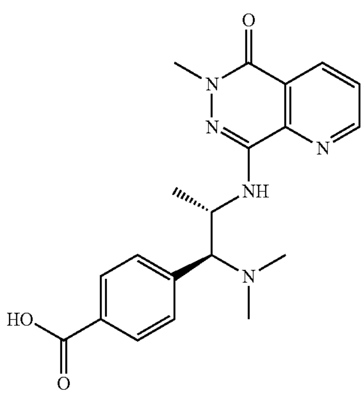 [SMILES: C[C@H](Nc1nn(C)c(=O)c2cccnc12)[C@H](c1ccc(C(=O)O)cc1)N(C)C] | 0.098 |
| 82 | 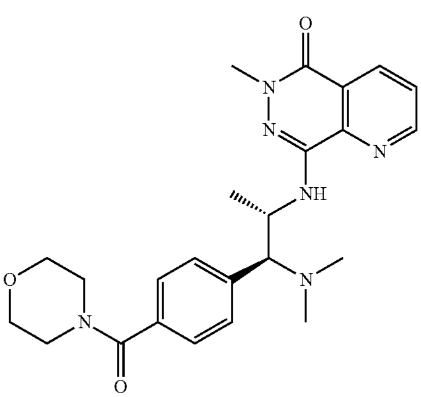 [SMILES: C[C@H](Nc1nn(C)c(=O)c2cccnc12)[C@H](c1ccc(C(=O)N2CCOCC2)cc1)N(C)C] | 0.059 |

-continued

| Example | Structure | PCAF IC$_{50}$ (μM) |
|---|---|---|
| 83 | 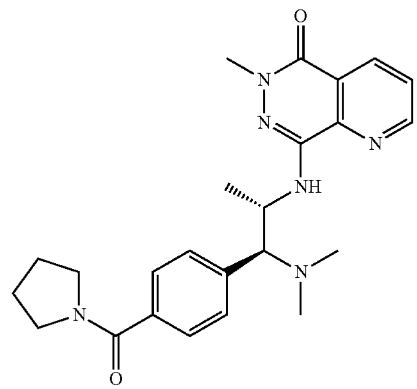 [SMILES: C[C@H](Nc1nn(C)c(=O)c2cccnc12)[C@H](c1ccc(C(=O)N2CCCC2)cc1)N(C)C] | 0.071 |
| 84 | 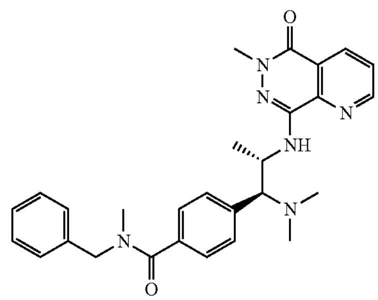 [SMILES: C[C@H](Nc1nn(C)c(=O)c2cccnc12)[C@H](c1ccc(C(=O)N(C)Cc2ccccc2)cc1)N(C)C] | 0.056 |
| 85 | 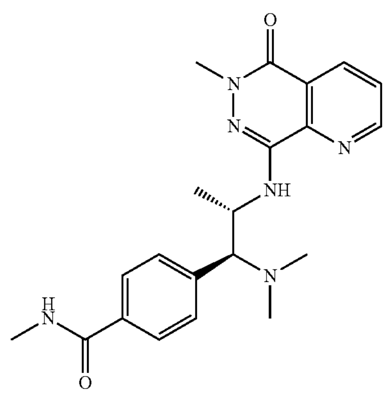 [SMILES: CNC(=O)c1ccc([C@@H]([C@H](C)Nc2nn(C)c(=O)c3cccnc23)N(C)C)cc1] | 0.050 |
| 86 | 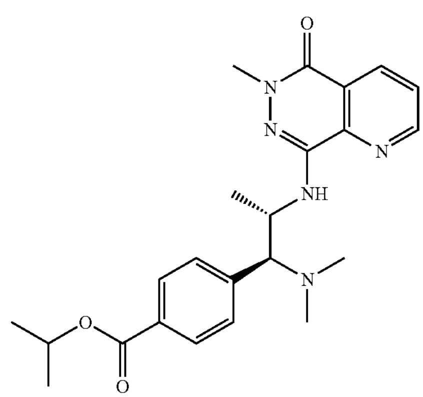 [SMILES: CC(C)OC(=O)c1ccc([C@@H]([C@H](C)Nc2nn(C)c(=O)c3cccnc23)N(C)C)cc1] | 0.030 |

-continued

| Example | Structure | PCAF IC$_{50}$ (μM) |
|---|---|---|
| 87 | 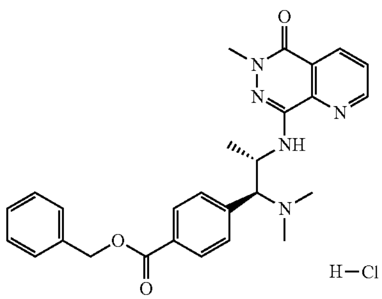 [SMILES: C[C@H](Nc1nn(C)c(=O)c2cccnc12)[C@H](c1ccc(C(=O)OCc2ccccc2)cc1)N(C)C ; Cl] | 0.029 |
| 88 | 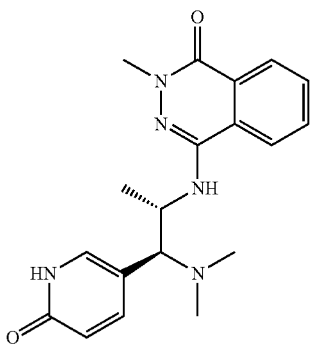 [SMILES: C[C@H](Nc1nn(C)c(=O)c2ccccc12)[C@H](c1ccc(=O)[nH]c1)N(C)C] | 0.080 |
| 89 | 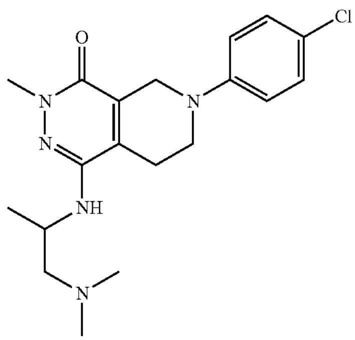 [SMILES: CC(CN(C)C)Nc1nn(C)c(=O)c2c1CCN(c1ccc(Cl)cc1)C2] | 1.2 |
| 90 | 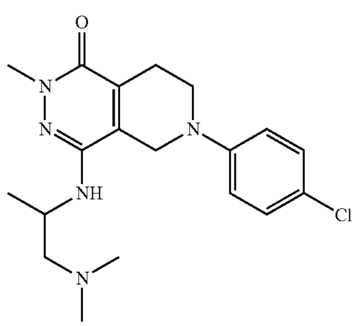 [SMILES: CC(CN(C)C)Nc1nn(C)c(=O)c2c1CN(c1ccc(Cl)cc1)CC2] | 0.82 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:
1. A compound of formula (I):

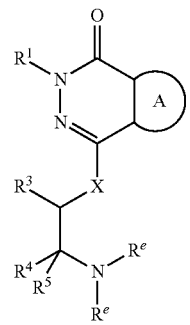

or a salt thereof, wherein:
$R^1$ is selected from the group consisting of, $C_{1-6}$ alkyl, $C_{2-6}$ alkenyl, $C_{2-6}$ alkynyl, and 3-12 membered heterocyclyl that includes 1 to 4 heteroatoms selected from nitrogen, oxygen and sulfur, wherein each $C_{1-6}$ alkyl, $C_{2-6}$ alkenyl, $C_{2-6}$ alkynyl, and 3-12 membered heterocyclyl is optionally substituted with one or more groups independently selected from the group consisting of oxo, halo, amino, hydroxy, and $C_{1-6}$alkoxy;

X is $N(R^a)$, or S;

each $R^a$ is independently selected from the group consisting of hydrogen, $C_{1-6}$ alkyl, $C_{2-6}$ alkenyl, $C_{2-6}$ alkynyl, $C_{1-6}$ alkoxy, and $C_3$-$C_{10}$carbocyclyl, wherein each $C_{1-6}$ alkyl, $C_{2-6}$alkenyl, $C_{2-6}$ alkynyl, $C_{1-6}$ alkoxy, and $C_3$-$C_{10}$carbocyclyl is optionally substituted with one or more groups independently selected from the group consisting of oxo, halo, amino, hydroxy, $C_{1-6}$alkoxy, and $C_1$-$C_6$ alkyl that is optionally substituted with one or more groups independently selected from the group consisting of oxo and halo;

$R^3$ and $R^4$ are each independently selected from the group consisting of hydrogen, $C_{1-6}$ alkyl, $C_{2-6}$ alkenyl, $C_{2-6}$ alkynyl, $C_{1-6}$ alkoxy, $C_3$-$C_{10}$carbocyclyl, and 3-12 membered heterocyclyl that includes 1 to 4 heteroatoms selected from nitrogen, oxygen and sulfur, wherein each $C_{1-6}$alkyl, $C_{2-6}$ alkenyl, $C_{2-6}$alkynyl, $C_{1-6}$ alkoxy, $C_3$-$C_{10}$carbocyclyl, and 3-12 membered heterocyclyl is optionally substituted with one or more groups $R^b$; or $R^3$ and $R^4$ taken together with the atoms to which they are attached form a $C_3$-$C_{10}$carbocyclyl or 3-12 membered heterocyclyl that includes 1 to 4 heteroatoms selected from nitrogen, oxygen and sulfur, which $C_3$-$C_{10}$carbocyclyl and 3-12 membered heterocyclyl is optionally substituted with one or more groups $R^b$;

$R^5$ is hydrogen or $C_{1-6}$alkyl, or $R^4$ and $R^5$ taken together with the atoms to which they are attached form a $C_3$-$C_{10}$carbocyclyl or 3-12 membered heterocyclyl that includes 1 to 4 heteroatoms selected from nitrogen, oxygen and sulfur, which $C_3$-$C_{10}$carbocyclyl and 3-12 membered heterocyclyl is optionally substituted with one or more groups independently selected from the group consisting of $C_{1-6}$alkyl, $C_{2-6}$alkenyl, $C_{2-6}$alkynyl, $C_{1-6}$alkoxy, $C_{3-6}$carbocyclyl, oxo, halo, hydroxy, and —$NO_2$, wherein any $C_{1-6}$alkyl, $C_{2-6}$ alkenyl, $C_{2-6}$alkynyl, $C_{1-6}$alkoxy, and $C_{3-6}$ carbocyclyl, is optionally substituted with one or more groups independently selected from the group consisting of halo, hydroxy, and $C_{1-6}$ alkoxy;

each $R^b$ is independently selected from the group consisting of $C_{1-6}$alkyl, $C_{2-6}$ alkenyl, $C_{2-6}$ alkynyl, $C_3$-$C_{10}$carbocyclyl, 3-12 membered heterocyclyl that includes 1 to 4 heteroatoms selected from nitrogen, oxygen and sulfur, oxo, halo, —$NO_2$, —$N(R^c)_2$, —CN, —C(O)—$N(R^c)_2$, —S(O)—$N(R^c)_2$, —$S(O)_2$—$N(R^c)_2$, —O—$R^c$, —S—$R^c$, —O—C(O)—$R^c$, —C(O)—$R^c$, —C(O)—$OR^c$, —S(O)—$R^c$, —$S(O)_2$—$R^c$, —C(O)—$N(R^c)_2$, —$N(R^c)$—C(O)—$R^c$, —$N(R^c)$—S(O)—$R^c$, and —$N(R^c)$—$S(O)_2$—$R^c$, wherein any $C_{1-6}$alkyl, $C_{2-6}$ alkenyl, $C_{2-6}$alkynyl, $C_3$-$C_{10}$carbocyclyl, and 3-12 membered heterocyclyl is optionally substituted with one or more groups independently selected from the group consisting of oxo, halo, —$NO_2$, —$N(R^c)_2$, —CN, —C(O)—$N(R^c)_2$, —S(O)—$N(R^c)_2$, —$S(O)_2$—$N(R^c)_2$, —O—$R^c$, —S—$R^c$, —O—C(O)—$R^c$, —C(O)—$R^c$, —C(O)—O—$R^c$, —S(O)—$R^c$, —$S(O)_2$—$R^c$, —C(O)—$N(R^c)_2$, —$N(R^c)$—C(O)—$R^c$, —$N(R^c)$—S(O)—$R^c$, and —$N(R^c)$—$S(O)_2$—$R^c$;

each $R^c$ is independently selected from the group consisting of hydrogen, $C_{1-6}$alkyl, $C_{2-6}$ alkenyl, $C_{2-6}$ alkynyl, $C_{1-6}$ alkoxy, $C_3$-$C_{10}$carbocyclyl, and 3-12 membered heterocyclyl that includes 1 to 4 heteroatoms selected from nitrogen, oxygen and sulfur, wherein each $C_{1-6}$ alkyl, $C_{2-6}$ alkenyl, $C_{2-6}$alkynyl, $C_{1-6}$ alkoxy, $C_3$-$C_{10}$carbocyclyl, and 3-12 membered heterocyclyl is optionally substituted with one or more groups independently selected from the group consisting of oxo, halo, amino, hydroxy, $C_{1-6}$ alkoxy, $C_3$-$C_{10}$carbocyclyl, 3-12 membered heterocyclyl that includes 1 to 4 heteroatoms selected from nitrogen, oxygen and sulfur, and $C_1$-$C_6$ alkyl that is optionally substituted with one or more groups independently selected from the group consisting of oxo and halo; or two $R^c$ are taken together with the nitrogen to which they are attached to form a 3-12 membered heterocyclyl that includes 1 to 4 heteroatoms selected from nitrogen, oxygen and sulfur that is optionally substituted with one or more groups independently selected from the group consisting of oxo, halo and $C_{1-3}$ alkyl that is optionally substituted with one or more groups independently selected from the group consisting of oxo and halo;

ring A is a 5- or 6-membered heterocyclyl or a 5- or 6-membered carbocyclyl, which 5- or 6-membered heterocyclyl and 5- or 6-membered carbocyclyl is optionally substituted with one or more groups independently selected from the group consisting of $C_{1-6}$ alkyl, $C_{2-6}$ alkenyl, $C_{2-6}$ alkynyl, $C_3$-$C_{10}$carbocyclyl, 3-12 membered heterocyclyl that includes 1 to 4 heteroatoms selected from nitrogen, oxygen and sulfur, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—O—$R^d$, —S(O)—$R^d$, —$S(O)_2$—$R^d$, —C(O)—$N(R^d)_2$, —$N(R^d)$—C(O)—$R^d$, —$N(R^d)$—S(O)—$R^d$, —O—C(O)—$N(R^d)_2$, —$N(R^d)$—C(O)—O—$R^d$, —$N(R^d)$—C(O)—$N(R^d)_2$, and —$N(R^d)$—$S(O)_2$—$R^d$, wherein any $C_{1-6}$ alkyl, $C_{2-6}$ alkenyl, $C_{2-6}$alkynyl, $C_3$-$C_{10}$carbocyclyl, and 3-12 membered heterocyclyl is optionally substituted with one or more groups independently selected from the group consisting of oxo halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—O—$R^d$, —S(O)—$R^d$, —$S(O)_2$—$R^d$, —C(O)—$N(R^d)_2$, —$N(R^d)$—C(O)—$R^d$, —$N(R^d)$—S(O)—$R^d$, —O—C(O)—$N(R^d)_2$, —$N(R^d)$—C(O)—O—$R^d$, —$N(R^d)$—C(O)—$N(R^d)_2$, and —$N(R^d)$—$S(O)_2$—$R^d$;

each $R^d$ is independently selected from the group consisting of hydrogen, $C_{1-6}$ alkyl, $C_{2-6}$ alkenyl, $C_{2-6}$ alkynyl, $C_{1-6}$ alkoxy, $C_3$-$C_{10}$carbocyclyl, and 3-12 membered heterocyclyl that includes 1 to 4 heteroatoms selected from nitrogen, oxygen and sulfur, wherein each $C_{1-6}$ alkyl, $C_{2-6}$ alkenyl, $C_{2-6}$alkynyl, $C_{1-6}$ alkoxy, $C_3$-$C_{10}$carbocyclyl, and 3-12 membered heterocyclyl is optionally substituted with one or more groups $R^f$; or two $R^d$ are taken together with the nitrogen to which they are attached to form a 3-12 membered heterocyclyl that includes 1 to 4 heteroatoms selected from nitrogen, oxygen and sulfur that is optionally substituted with one or more groups $R^f$;

each $R^e$ is independently selected from the group consisting of hydrogen, $C_{1-6}$alkyl, $C_{2-6}$ alkenyl, $C_{2-6}$ alkynyl, $C_{1-6}$ alkoxy, $C_3$-$C_{10}$carbocyclyl, and 3-12 membered heterocyclyl that includes 1 to 4 heteroatoms selected from nitrogen, oxygen and sulfur, wherein each $C_{1-6}$ alkyl, $C_{2-6}$ alkenyl, $C_{2-6}$alkynyl, $C_{1-6}$ alkoxy, $C_3$-$C_{10}$carbocyclyl, and 3-12 membered heterocyclyl is optionally substituted with one or more groups independently selected from the group consisting of oxo, halo, amino, hydroxy, $C_{1-6}$ alkoxy, $C_3$-$C_{10}$carbocyclyl, 3-12 membered heterocyclyl that includes 1 to 4 heteroatoms selected from nitrogen, oxygen and sulfur, and $C_1$-$C_6$ alkyl that is optionally substituted with one or more groups independently selected from the group consisting of oxo and halo; or two $R^e$ are taken together with the nitrogen to which they are attached to form a 3-12 membered heterocyclyl that includes 1 to 4 heteroatoms selected from nitrogen, oxygen and sulfur that is optionally substituted with one or more groups independently selected from the group consisting of oxo, halo and $C_{1-3}$ alkyl that is optionally substituted with one or more groups independently selected from the group consisting of oxo and halo; or one $R^e$ taken together with $R^3$ and the atoms to which they are attached form a 3-12 membered heterocyclyl that includes 1 to 4 heteroatoms selected from nitrogen, oxygen and sulfur that is optionally substituted with one or more groups independently selected from the group consisting of $C_{1-6}$alkyl, $C_{2-6}$alkenyl, $C_{2-6}$ alkynyl, and $C_{1-6}$ alkoxy, wherein each $C_{1-6}$ alkyl, $C_{2-6}$ alkenyl, $C_{2-6}$ alkynyl, and $C_{1-6}$ alkoxy is optionally substituted with one or more groups independently selected from the group consisting of oxo, halo, amino, hydroxy, $C_{1-6}$ alkoxy and $C_3$-$C_{10}$carbocyclyl; or one $R^e$ taken together with $R^4$ and the atoms to which they are attached form a 3-12 membered heterocyclyl that includes 1 to 4 heteroatoms selected from nitrogen, oxygen and sulfur that is optionally substituted with one or more groups independently selected from the group consisting of $C_{1-6}$ alkyl, $C_{2-6}$ alkenyl, $C_{2-6}$ alkynyl, and $C_{1-6}$ alkoxy, wherein each $C_{1-6}$alkyl, $C_{2-6}$alkenyl, $C_{2-6}$alkynyl, and $C_{1-6}$ alkoxy is optionally substituted with one or more groups independently selected from oxo, halo, amino, hydroxy, $C_{1-6}$ alkoxy and $C_3$-$C_{10}$carbocyclyl;

each $R^f$ is independently selected from the group consisting of $C_{1-6}$alkyl, $C_{2-6}$ alkenyl, $C_{2-6}$ alkynyl, $C_3$-$C_{10}$carbocyclyl, 3-12 membered heterocyclyl that includes 1 to 4 heteroatoms selected from nitrogen, oxygen and sulfur, oxo, halo, —$NO_2$, —$N(R^g)_2$, —CN, —C(O)—$N(R^g)_2$, —S(O)—$N(R^g)_2$, —$S(O)_2$—$N(R^g)_2$, —O—$R^g$, —S—$R^g$, —O—C(O)—$R^g$, —C(O)—$R^g$, —C(O)—OR$^g$, —S(O)—R$^g$, —S(O)$_2$—R$^g$, —N(R$^g$)—C(O)—R$^g$, —N(R$^g$)—S(O)—R$^g$, —N(R$^g$)—C(O)—N(R$^g$)$_2$, and —N(R$^g$)—S(O)$_2$—R$^g$, wherein any C$_{1-6}$alkyl, C$_{2-6}$ alkenyl, C$_{2-6}$alkynyl, C$_3$-C$_{10}$carbocyclyl, and 3-12 membered heterocyclyl is optionally substituted with one or more groups independently selected from the group consisting of oxo, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —N(R$^g$)—C(O)—R$^g$, —N(R$^g$)—S(O)—R$^g$, —N(R$^g$)—C(O)—N(R$^g$)$_2$, and —N(R$^g$)—S(O)$_2$—R$^g$; and each R$^g$ is independently selected from the group consisting of hydrogen, C$_{1-6}$ alkyl, C$_{2-6}$ alkenyl, C$_{2-6}$ alkynyl, C$_{1-6}$ alkoxy, C$_3$-C$_{10}$carbocyclyl, and 3-12 membered heterocyclyl that includes 1 to 4 heteroatoms selected from nitrogen, oxygen and sulfur, wherein each C$_{1-6}$ alkyl, C$_{2-6}$ alkenyl, C$_{2-6}$alkynyl, C$_{1-6}$ alkoxy, C$_3$-C$_{10}$carbocyclyl, and 3-12 membered heterocyclyl is optionally substituted with one or more groups independently selected from the group consisting of oxo, halo, amino, hydroxy, C$_{1-6}$ alkoxy, C$_3$-C$_{10}$carbocyclyl, 3-12 membered heterocyclyl that includes 1 to 4 heteroatoms selected from nitrogen, oxygen and sulfur, and C$_1$-C$_6$ alkyl that is optionally substituted with one or more groups independently selected from the group consisting of oxo and halo; or two R$^g$ are taken together with the nitrogen to which they are attached to form a 3-12 membered heterocyclyl that includes 1 to 4 heteroatoms selected from nitrogen, oxygen and sulfur that is optionally substituted with one or more groups independently selected from the group consisting of oxo, halo and C$_{1-3}$ alkyl that is optionally substituted with one or more groups independently selected from the group consisting of oxo and halo.

2. The compound of claim 1 which has a formula selected from formulae I(a-j):

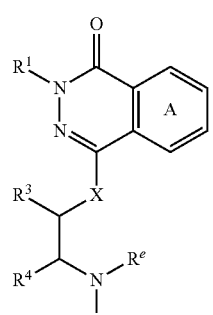
(Ia)

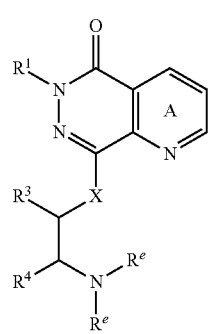
(Ib)

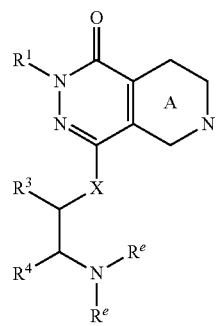
(Ic)

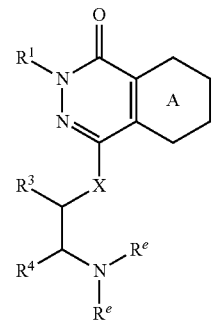
(Id)

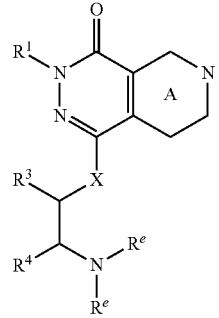
(Ie)

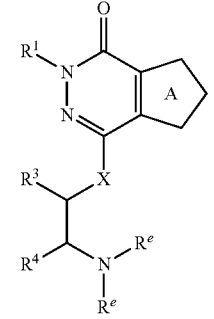
(If)

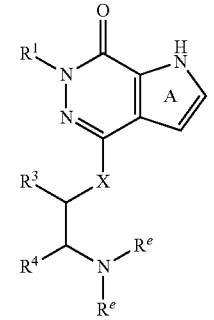
(Ig)

-continued

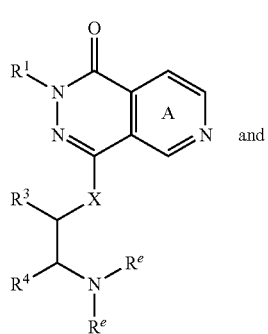

(Ih)

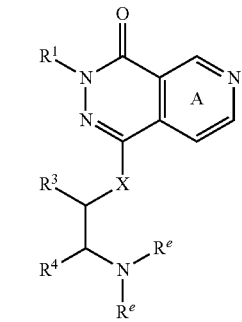

(Ij)

wherein ring A is optionally substituted with one or more groups independently selected from the group consisting of C$_{1-6}$ alkyl, C$_{2-6}$ alkenyl, C$_{2-6}$ alkynyl, C$_3$-C$_{10}$carbocyclyl, 3-12 membered heterocyclyl that includes 1 to 4 heteroatoms selected from nitrogen, oxygen and sulfur, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, and —N(R$^d$)—S(O)$_2$—R$^d$, wherein any C$_{1-6}$alkyl, C$_{2-6}$alkenyl, C$_{2-6}$alkynyl, C$_3$-C$_{10}$carbocyclyl, and 3-12 membered heterocyclyl is optionally substituted with one or more groups independently selected from the group consisting of oxo, halo, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —C(O)—R$^d$, —C(O)—O—R$^d$, —S(O)—R$^d$, —S(O)$_2$—R$^d$, —C(O)—N(R$^d$)$_2$, —N(R$^d$)—C(O)—R$^d$, —N(R$^d$)—S(O)—R$^d$, —N(R$^d$)—S(O)$_2$—R$^d$; and salts thereof.

3. The compound of claim wherein ring A is optionally substituted with one or more groups independently selected from the group consisting of C$_{1-6}$ alkyl, phenyl, halo, and —O—R$^d$, wherein any C$_{1-6}$alkyl and phenyl is optionally substituted with one or more groups independently selected from halo.

4. The compound of claim 1 wherein ring A is optionally substituted with one or more groups independently selected from the group consisting of methoxy, 4-chlorophenyl, fluoro, and methyl.

5. The compound of claim 1 wherein R$^1$ is C$_{1-6}$ alkyl, optionally substituted with one or more groups independently selected from the group consisting of oxo, halo, amino, hydroxy, and C$_{1-6}$ alkoxy.

6. The compound of claim 1 wherein R$^1$ is methyl or ethyl.

7. The compound of claim 1 wherein X is S.

8. The compound of claim 1 wherein X is N(H).

9. The compound of claim 1 wherein R$^3$ is hydrogen or C$_{1-6}$ alkyl.

10. The compound of claim 1 wherein R$^3$ is hydrogen, methyl, or ethyl.

11. The compound of claim 1 wherein R$^4$ is hydrogen, C$_{1-6}$ alkyl, C$_3$-C$_{10}$carbocyclyl, or 3-12 membered heterocyclyl that includes 1 to 4 heteroatoms selected from nitrogen, oxygen and sulfur, wherein each C$_{1-6}$ alkyl, C$_3$-C$_{10}$carbocyclyl, and 3-12 membered heterocyclyl is optionally substituted with one or more groups R$^b$.

12. The compound of claim 1 wherein R$^4$ is selected from the group consisting of H, phenyl, methyl, ethyl, cyclohexyl, 4-fluorophenyl, 4-methoxyphenyl, 4-chlorophenyl, 1-methyltriazol-4-yl, 1-phenylpyrazol-4-yl, 1-methylpyrazol-4-yl, pyrid-3-yl, 4-(phenyl sulfonyl)phenyl, 4-hydroxyphenyl, 4-(methoxycarbonyl)phenyl, 2-chlorophenyl, 2-fluorophenyl, 4-carboxyphenyl,

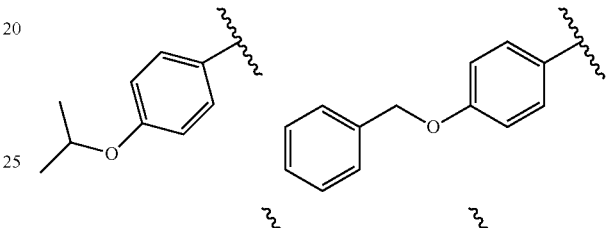

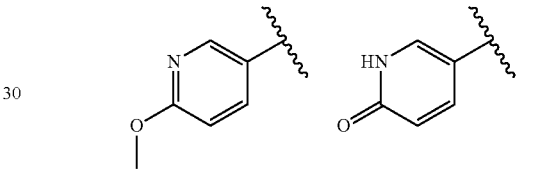

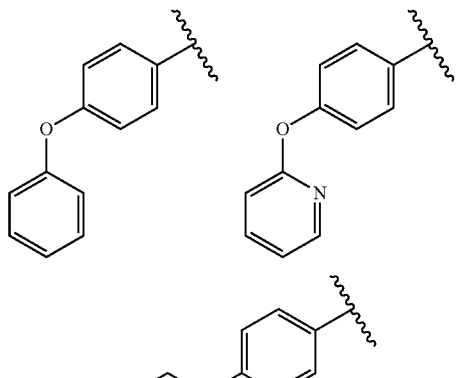

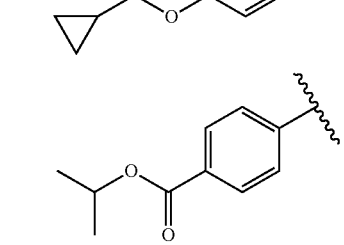

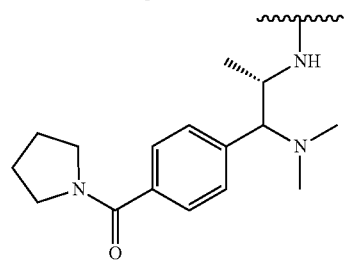

-continued

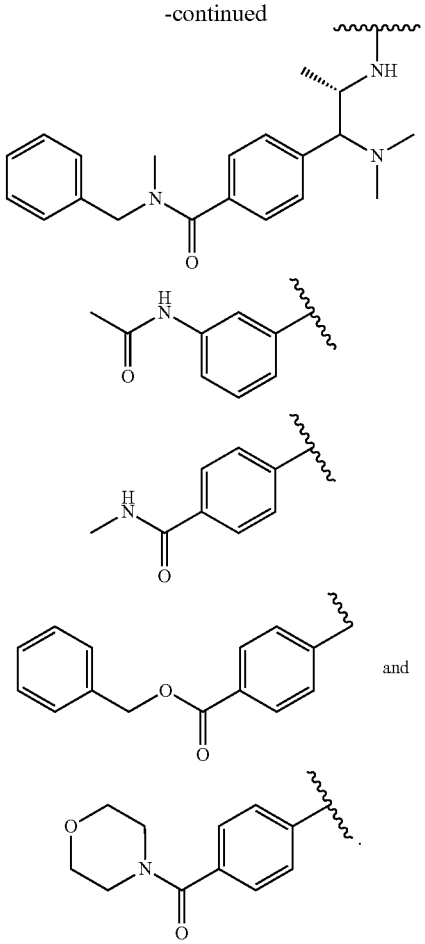

and

13. The compound of claim 1 wherein $R^3$ and $R^4$ taken together with the atoms to which they are attached form a $C_3$-$C_{10}$carbocyclyl or 3-12 membered heterocyclyl that includes 1 to 4 heteroatoms selected from nitrogen, oxygen and sulfur, which $C_3$-$C_{10}$carbocyclyl and 3-12 membered heterocyclyl is optionally substituted with one or more groups $R^b$.

14. The compound of claim 1 wherein $R^3$ and $R^4$ taken together with the atoms to which they are attached form a $C_3$-$C_{10}$carbocyclyl or 3-12 membered heterocyclyl that includes 1 to 4 heteroatoms selected from nitrogen, oxygen and sulfur selected from the group consisting of: cyclohexane, cyclopentane, piperidine, and indane, which $C_3$-$C_{10}$carbocyclyl and 3-12 membered heterocyclyl is optionally substituted with one or more groups $R^b$.

15. The compound of claim 1 wherein one $R^e$ taken together with $R^3$ and the atoms to which they are attached form a 3-12 membered heterocyclyl that includes 1 to 4 heteroatoms selected from nitrogen, oxygen and sulfur that is optionally substituted with one or more groups independently selected from the group consisting of $C_{1-6}$ alkyl, $C_{2-6}$ alkenyl, $C_{2-6}$ alkynyl, and $C_{1-6}$ alkoxy, wherein each $C_{1-6}$alkyl, $C_{2-6}$ alkenyl, $C_{2-6}$alkynyl, and $C_{1-6}$ alkoxy is optionally substituted with one or more groups independently selected from oxo, halo, amino, hydroxy, $C_{1-6}$ alkoxy and $C_3$-$C_{10}$carbocyclyl.

16. The compound of claim 1 wherein one $R^e$ taken together with $R^3$ and the atoms to which they are attached form an azetidine ring, which ring is optionally substituted with one or more groups independently selected from the group consisting of $C_{1-6}$alkyl, $C_{2-6}$alkenyl, $C_{2-6}$ alkynyl, and $C_{1-6}$ alkoxy, wherein each $C_{1-6}$ alkyl, $C_{2-6}$ alkenyl, $C_{2-6}$ alkynyl, and $C_{1-6}$ alkoxy is optionally substituted with one or more groups independently selected from oxo, halo, amino, hydroxy, $C_{1-6}$ alkoxy and $C_3$-$C_{10}$carbocyclyl.

17. The compound of claim 1 wherein one $R^e$ taken together with $R^4$ and the atoms to which they are attached form a 3-12 membered heterocyclyl that includes 1 to 4 heteroatoms selected from nitrogen, oxygen and sulfur that is optionally substituted with one or more groups independently selected from the group consisting of $C_{1-6}$ alkyl, $C_{2-6}$ alkenyl, $C_{2-6}$alkynyl, and $C_{1-6}$ alkoxy, wherein each $C_{1-6}$ alkyl, $C_{2-6}$ alkenyl, $C_{2-6}$ alkynyl, and $C_{1-6}$ alkoxy is optionally substituted with one or more groups independently selected from oxo, halo, amino, hydroxy, $C_{1-6}$ alkoxy and $C_3$-$C_{10}$carbocyclyl.

18. The compound of claim 1 wherein one $R^e$ taken together with $R^4$ and the atoms to which they are attached form a 3-12 membered heterocyclyl that includes 1 to 4 heteroatoms selected from nitrogen, oxygen and sulfur that is selected from the group consisting of pyrrolidine, piperidine, and azepane, which 3-12 membered heterocyclyl is optionally substituted with one or more groups independently selected from the group consisting of $C_{1-6}$alkyl, $C_{2-6}$ alkenyl, $C_{2-6}$alkynyl, and $C_{1-6}$ alkoxy, wherein each $C_{1-6}$ alkyl, $C_{2-6}$ alkenyl, $C_{2-6}$ alkynyl, and $C_{1-6}$ alkoxy is optionally substituted with one or more groups independently selected from oxo, halo, amino, hydroxy, $C_{1-6}$ alkoxy and $C_3$-$C_{10}$carbocyclyl.

19. The compound of claim 1 wherein the group:

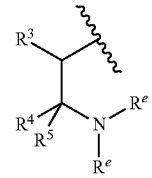

is selected from the group consisting of:

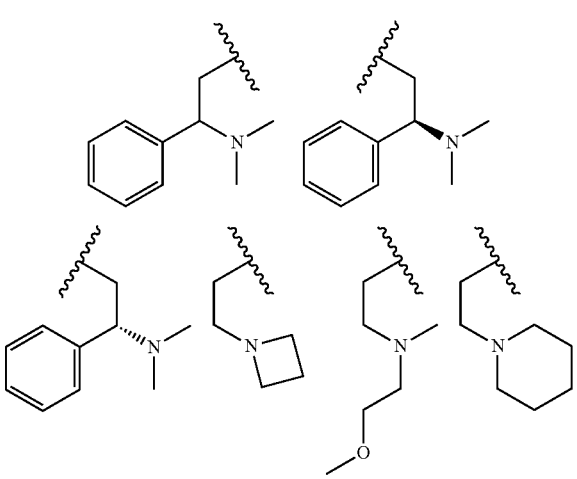

223
-continued
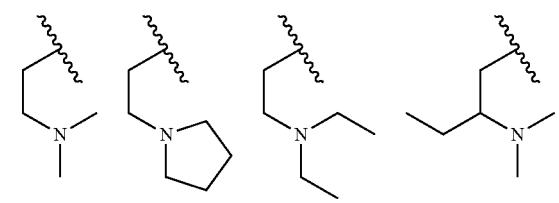
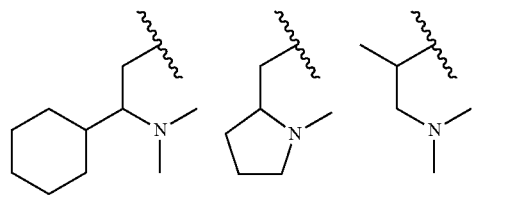
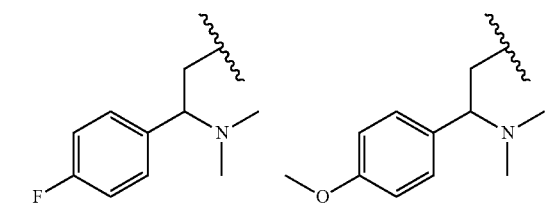
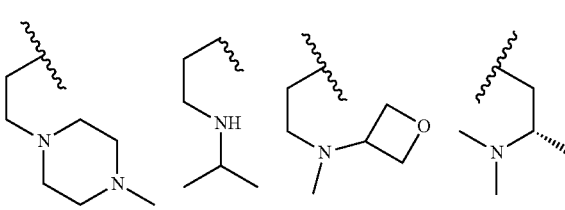
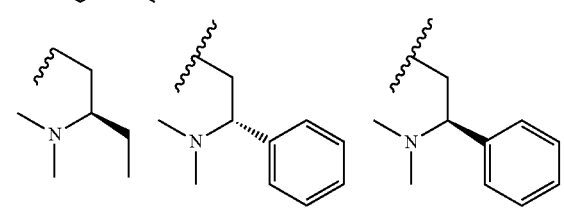
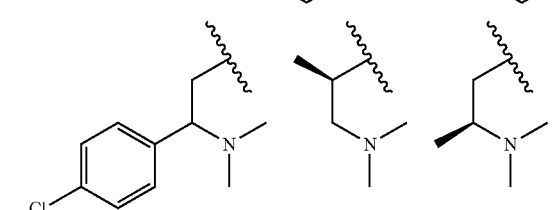
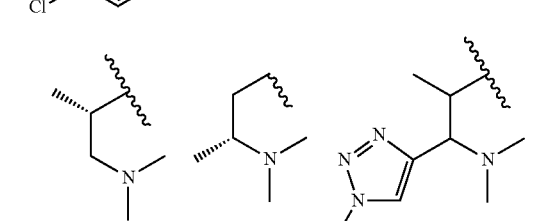
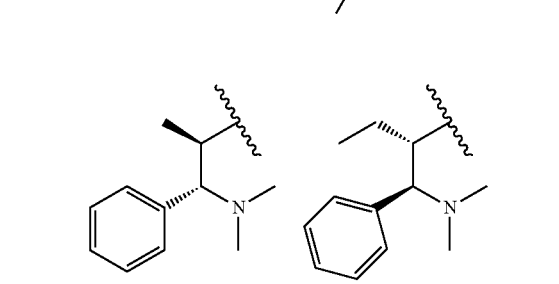
224
-continued
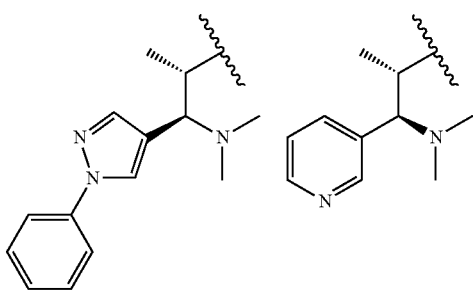
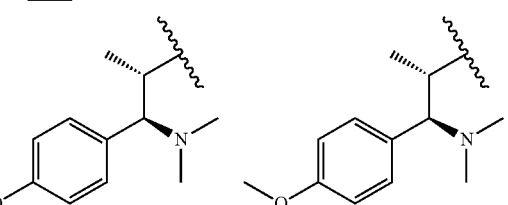
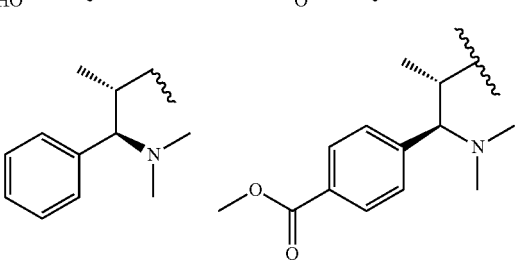
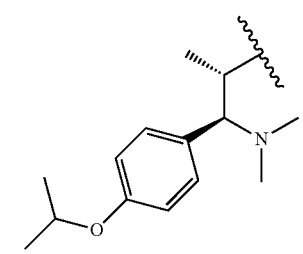
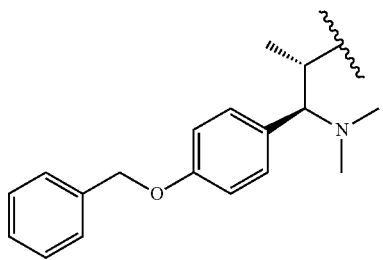
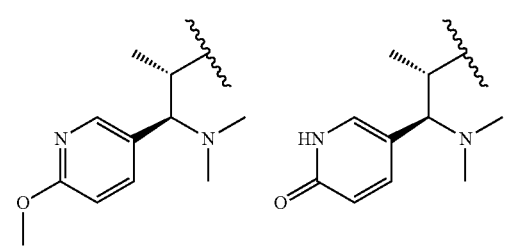

225
-continued
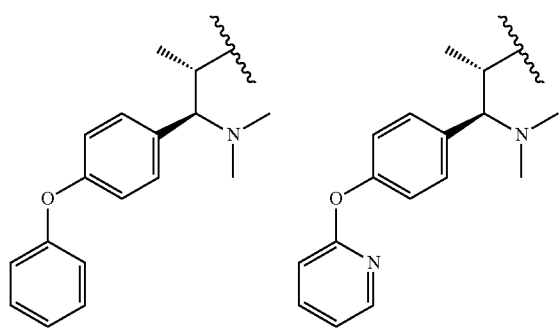
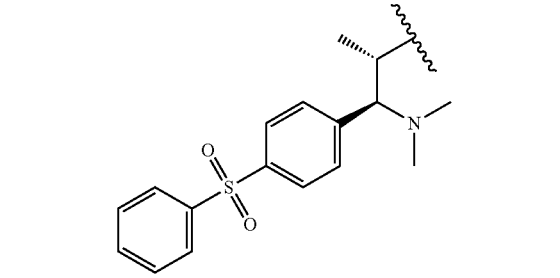
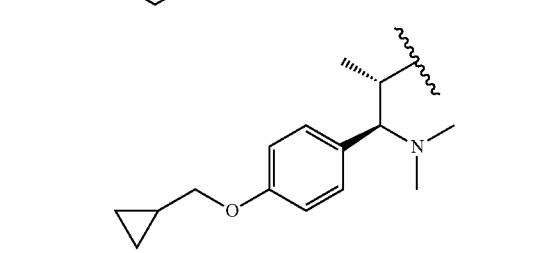
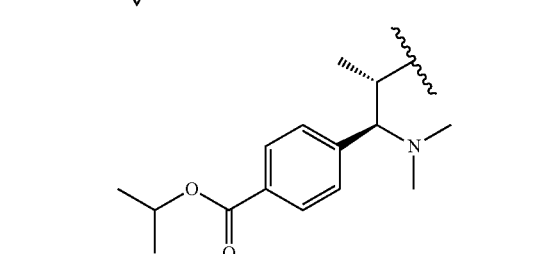
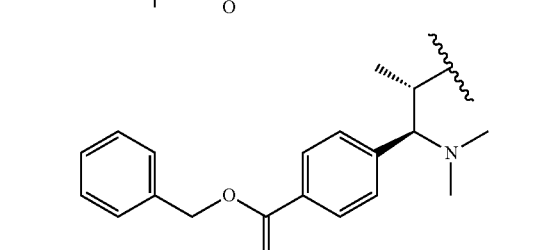
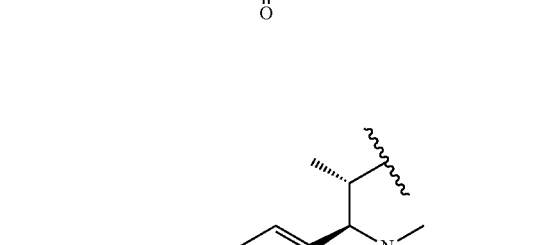
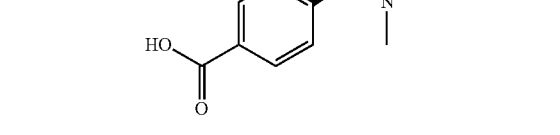
226
-continued
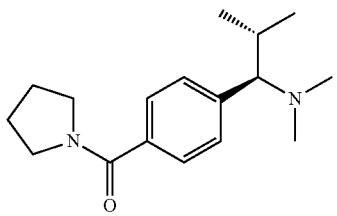
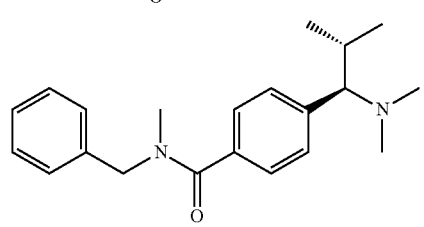
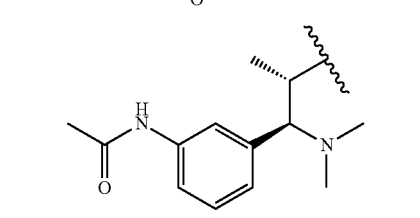
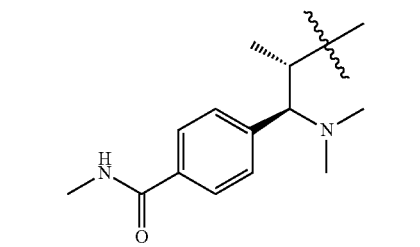
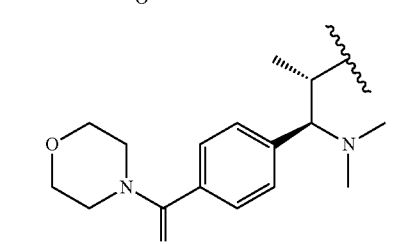
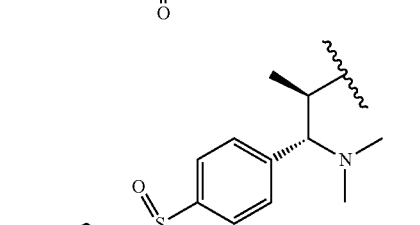
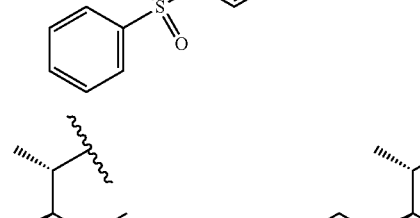
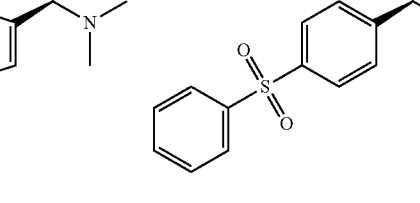

-continued
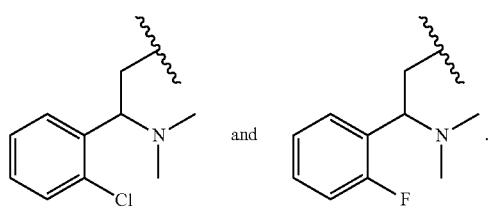
and
20. The compound of claim 1 wherein the group:
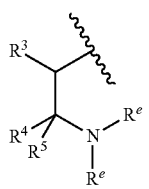
is selected from the group consisting of:
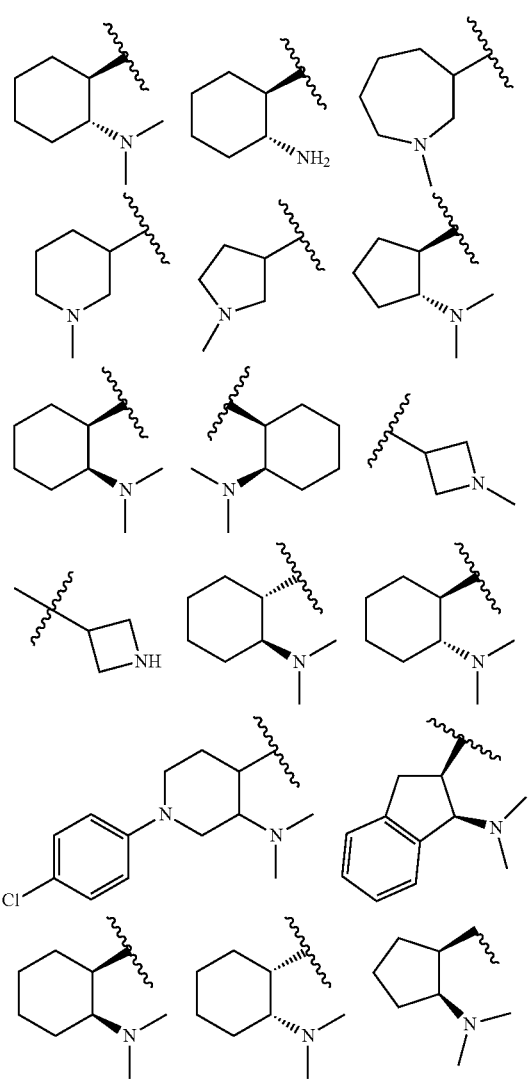
-continued
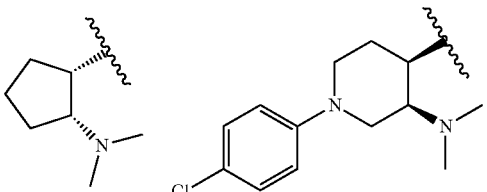
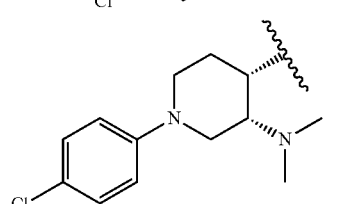
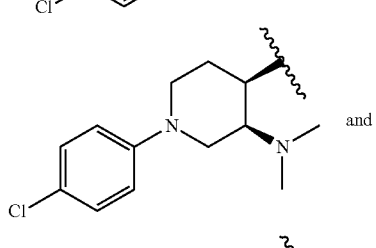
and
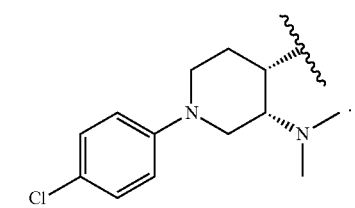 [SMILES: *[C@H]1CCN(c2ccc(Cl)cc2)C[C@H]1N(C)C]
21. The compound of claim 1 wherein the group:
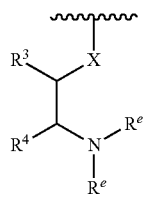
is selected from the group consisting of:
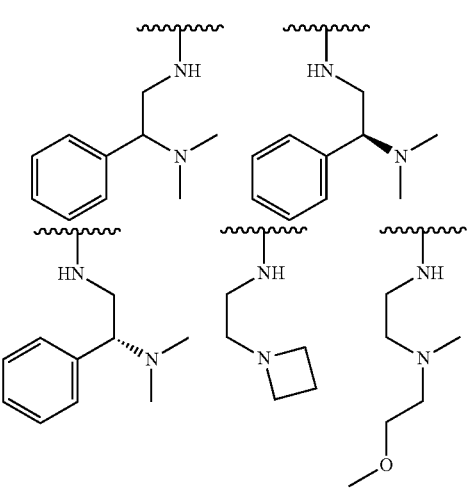

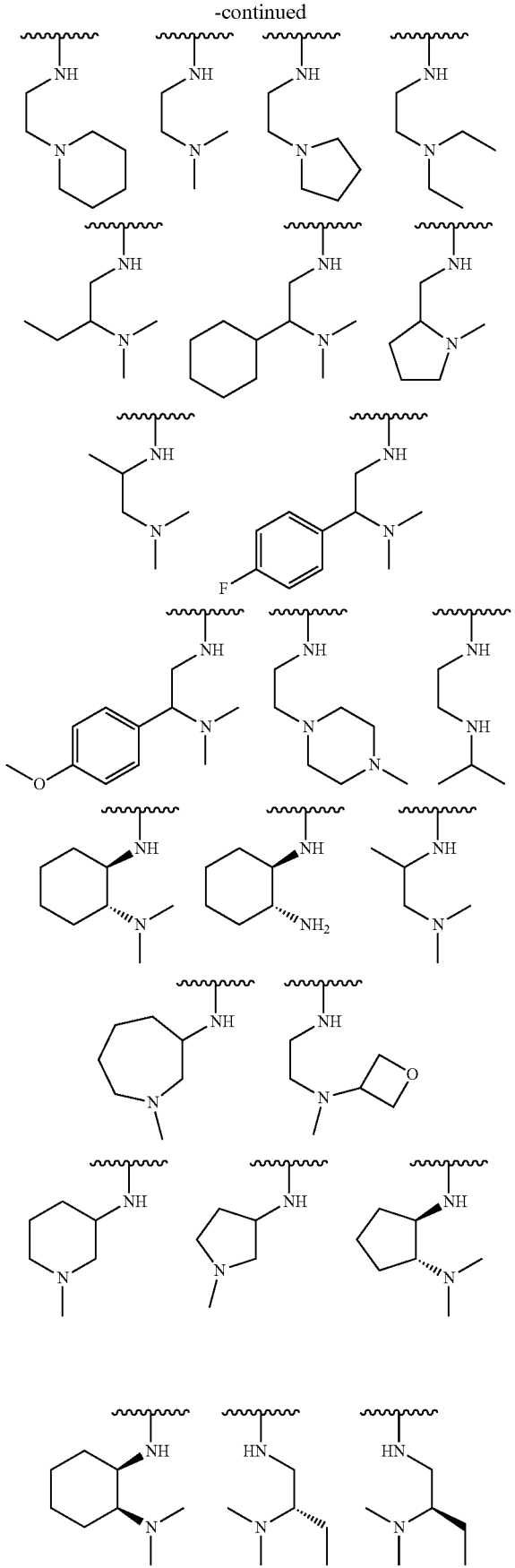
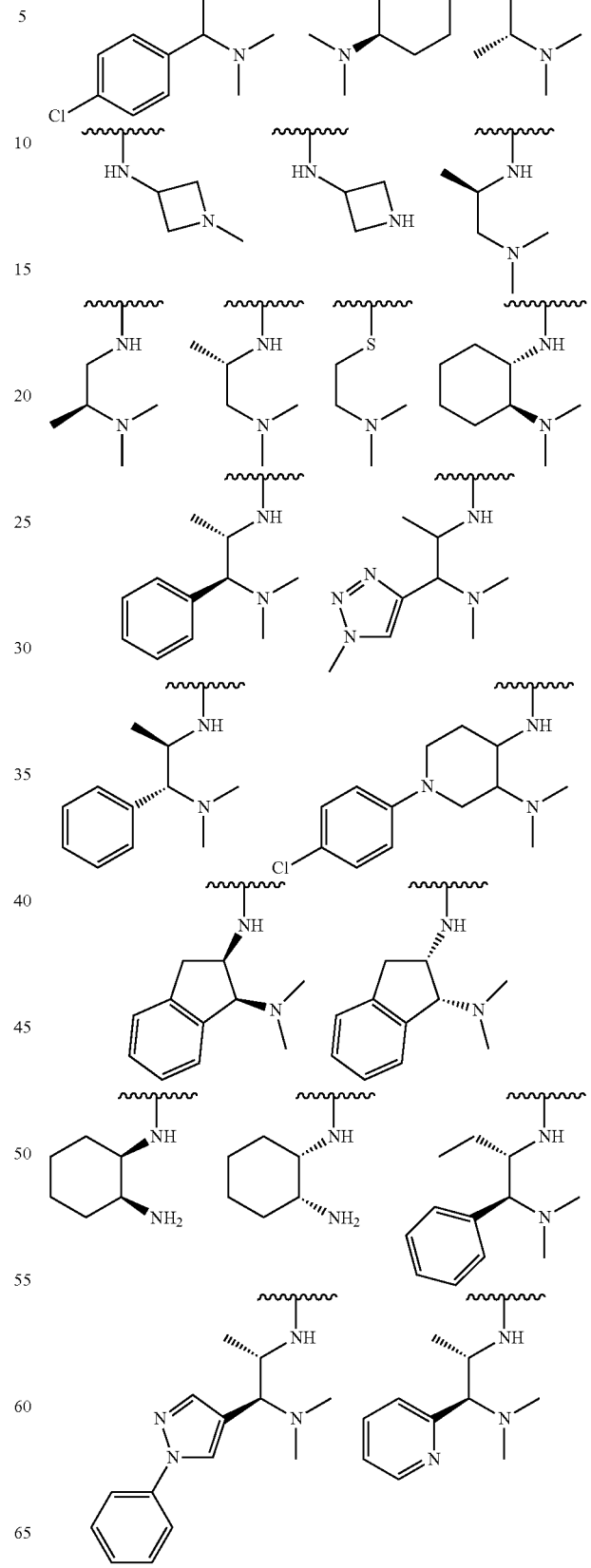

231
-continued
232
-continued
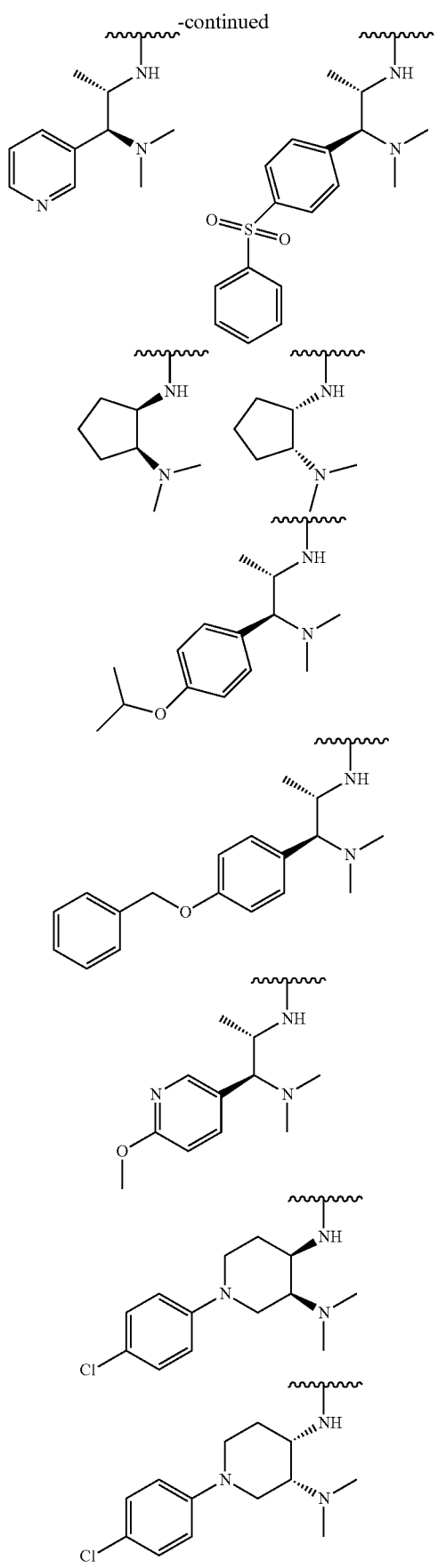
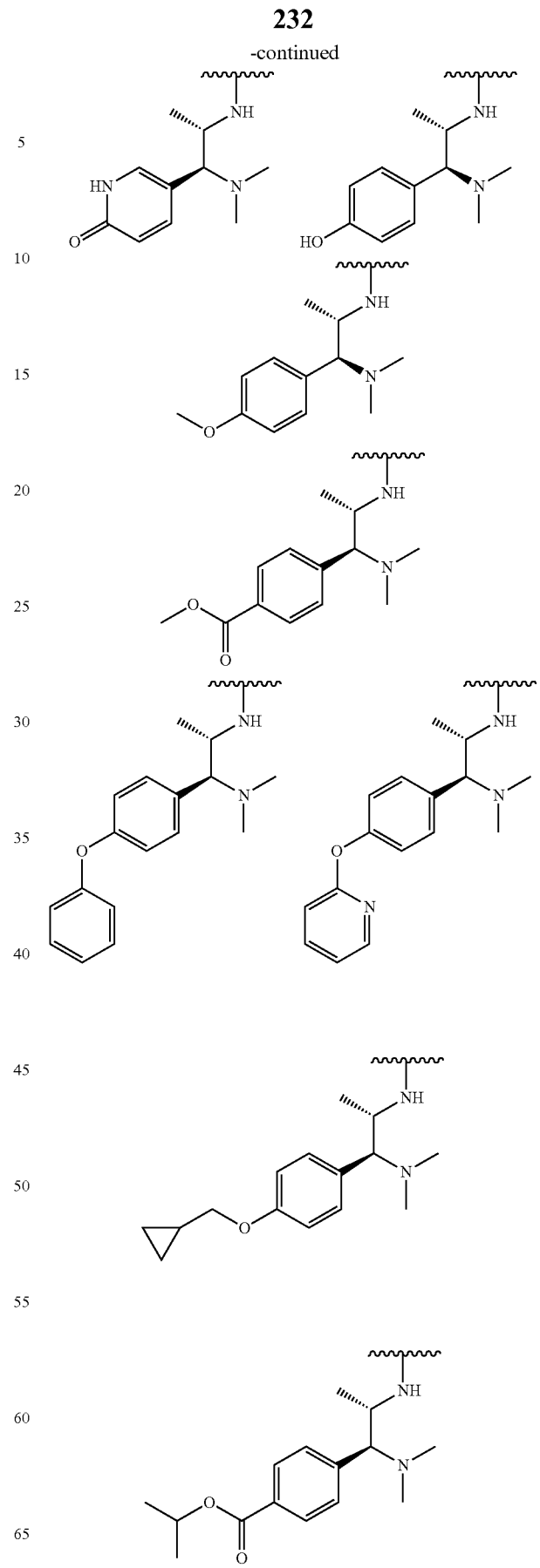

233
-continued
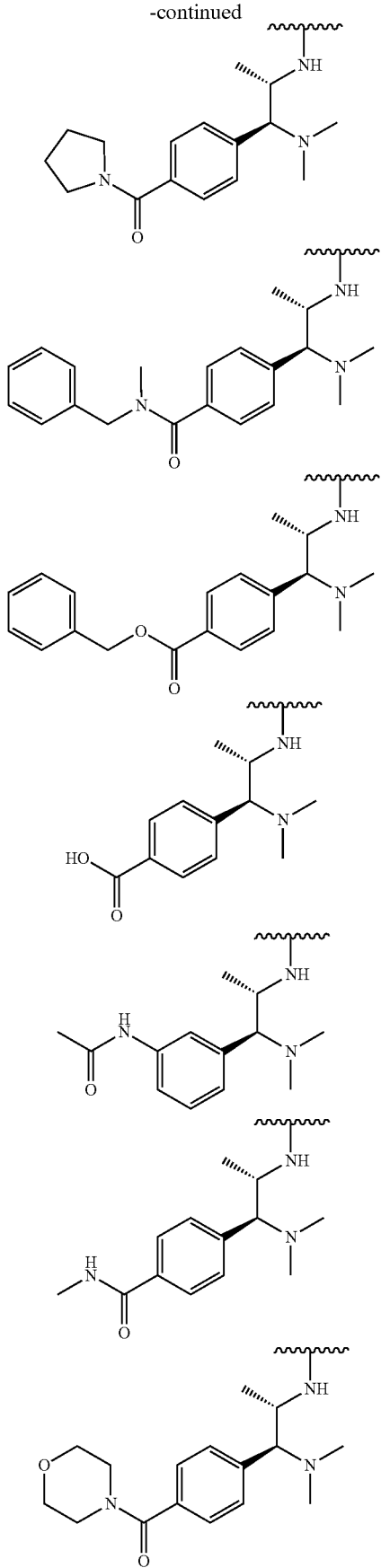
234
-continued
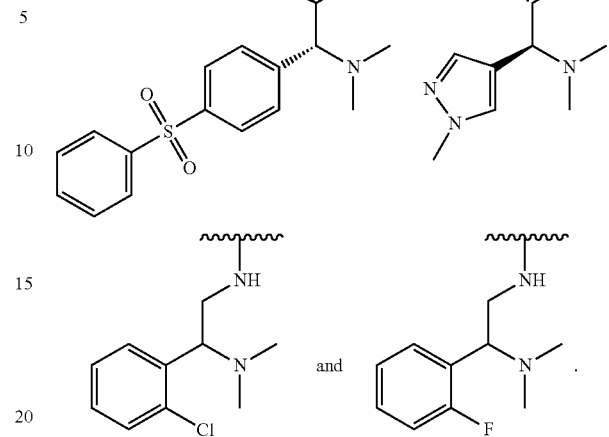
22. A compound selected from the group consisting of:
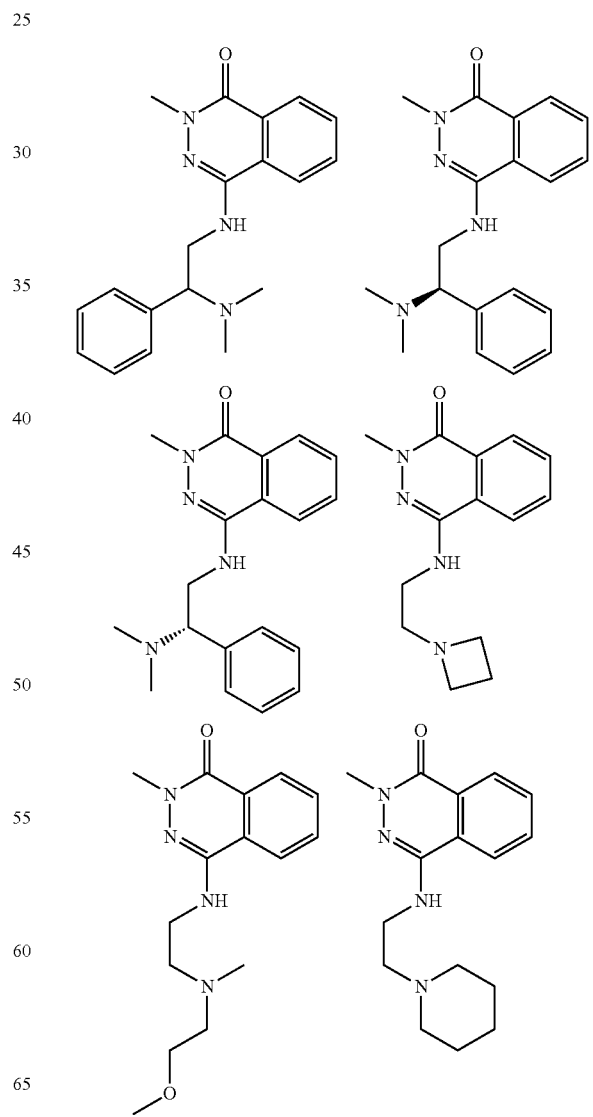

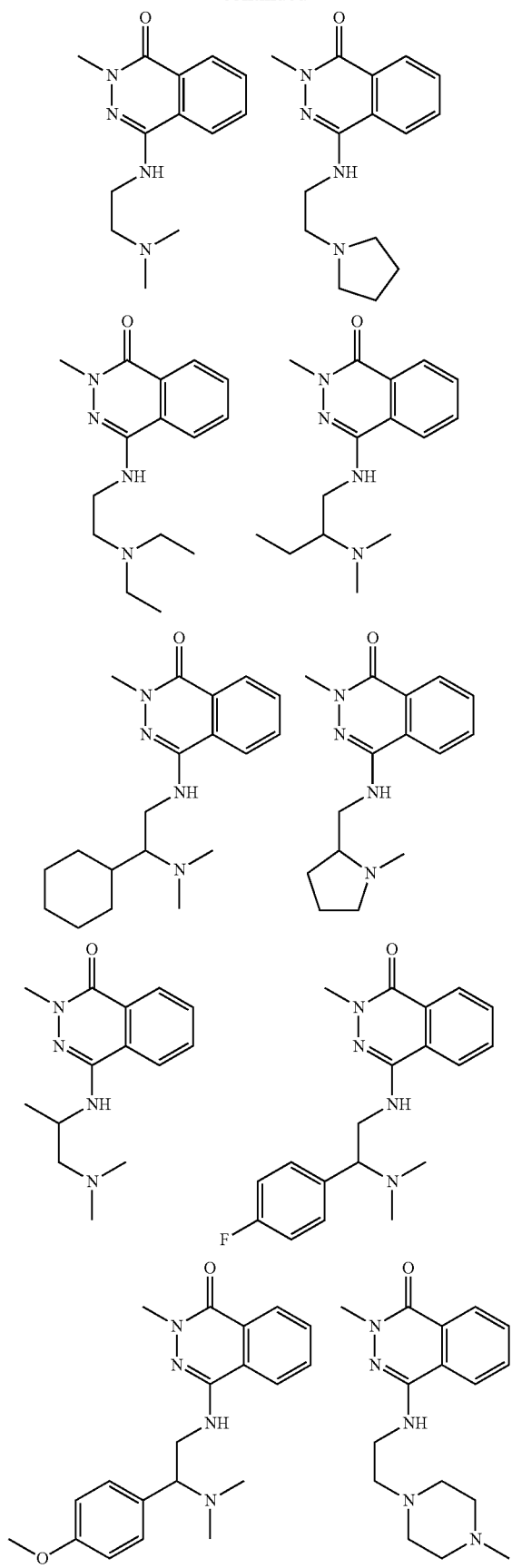
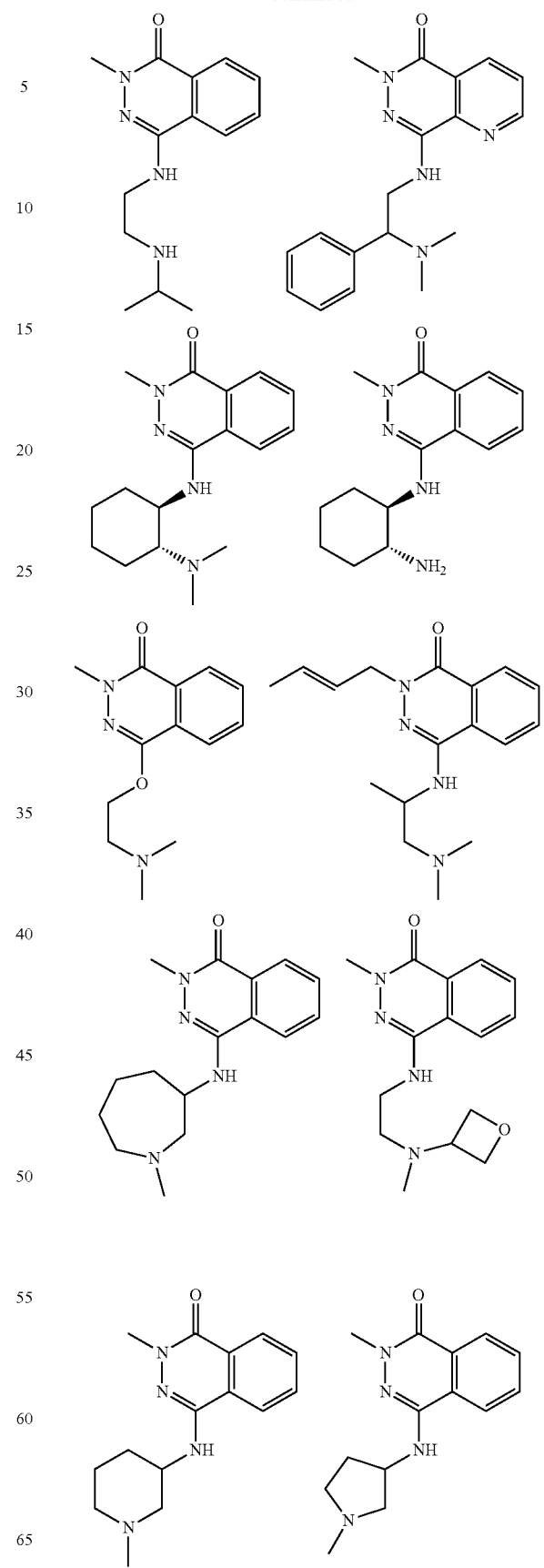

237
-continued
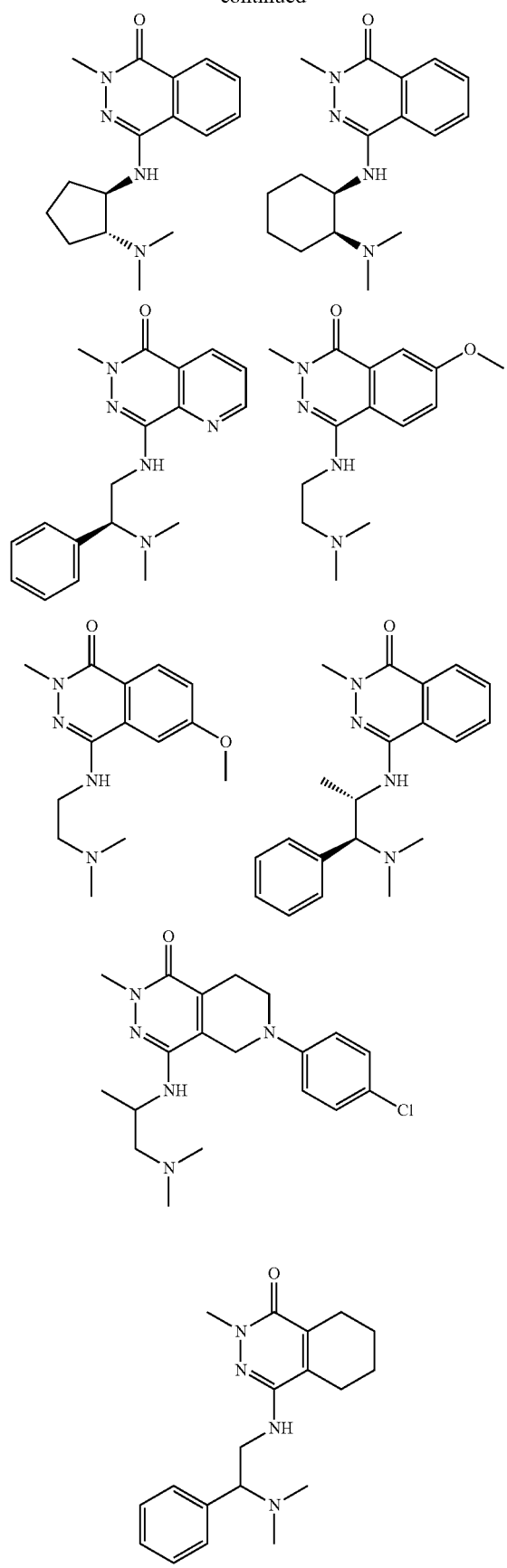
238
-continued
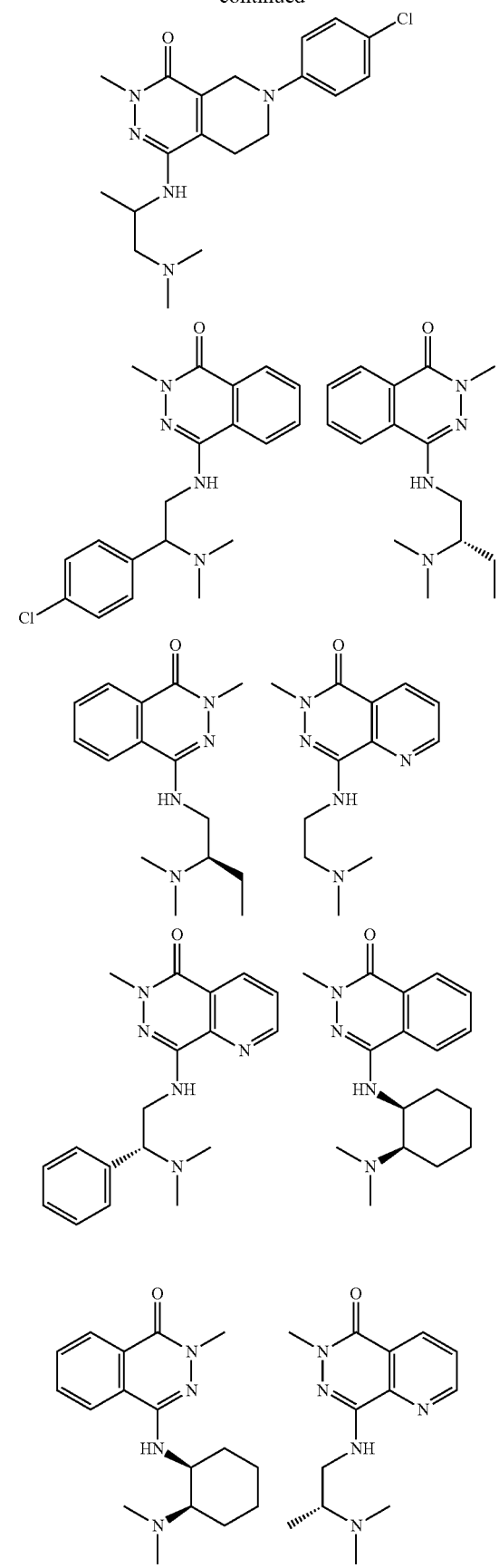

239
-continued
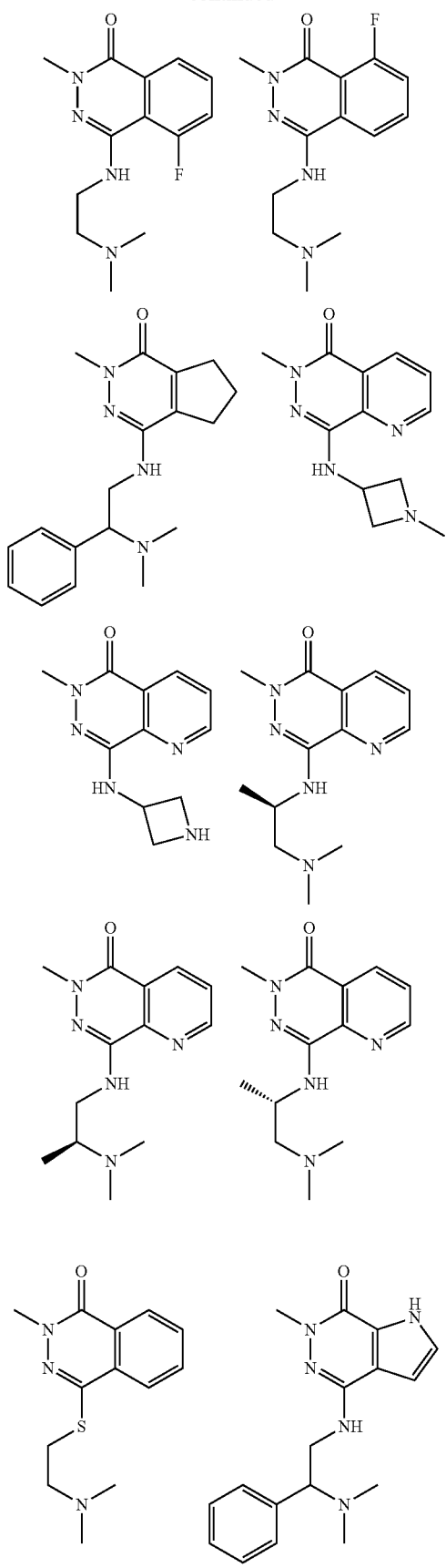
240
-continued
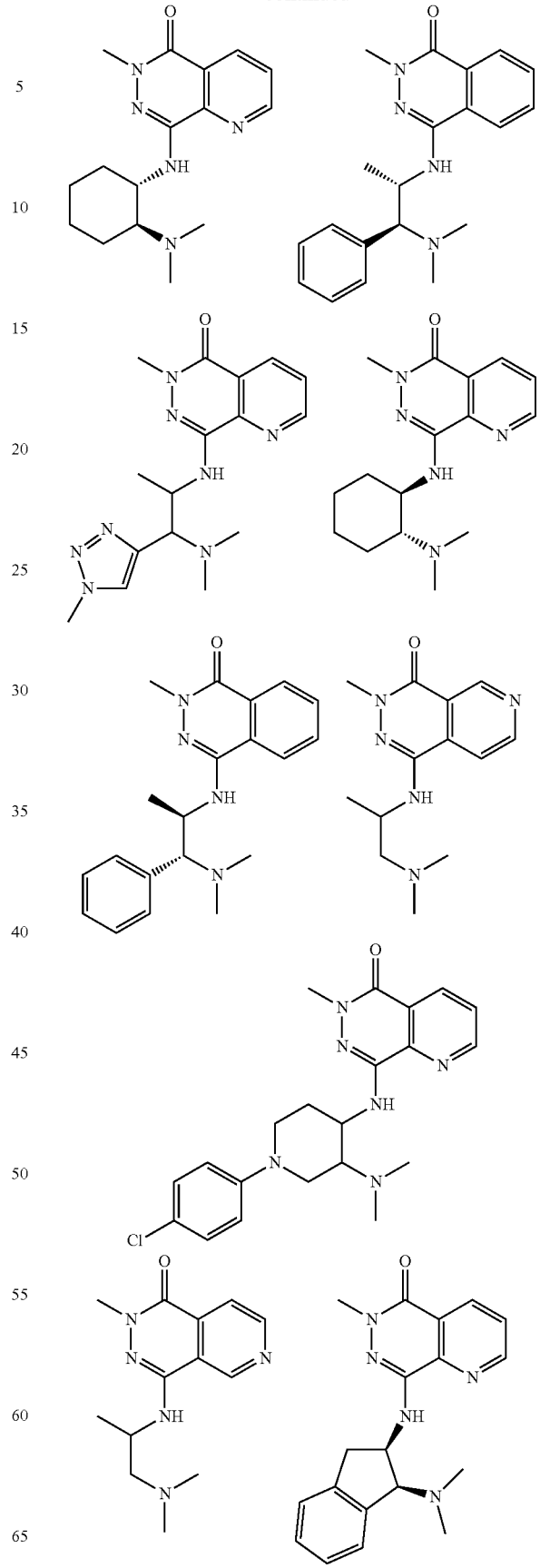

-continued
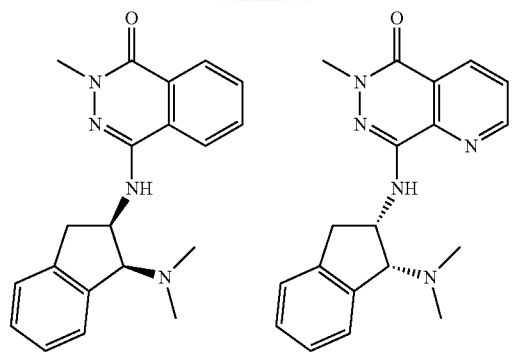
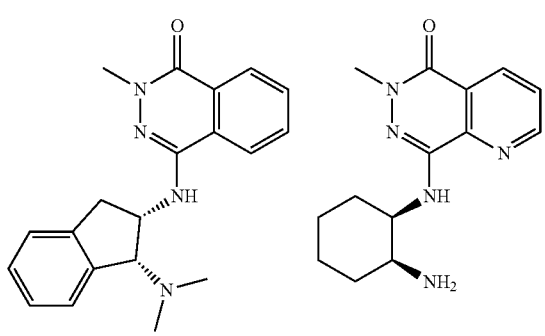
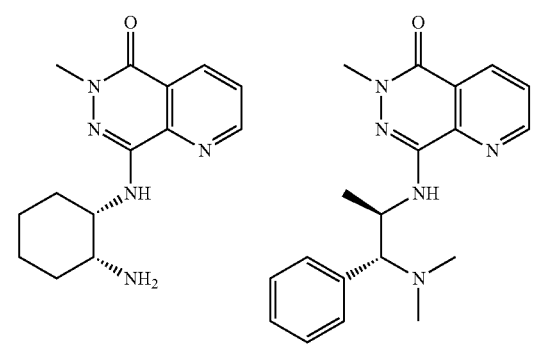
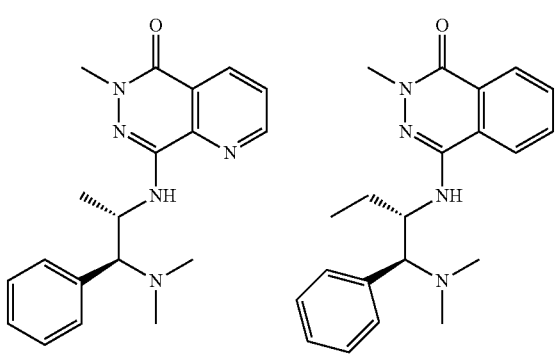
-continued
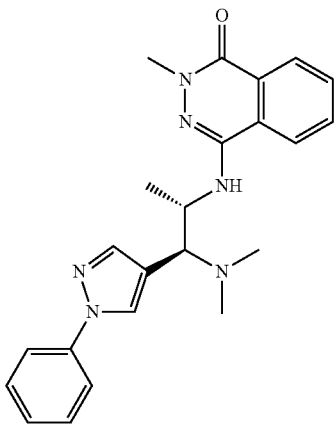
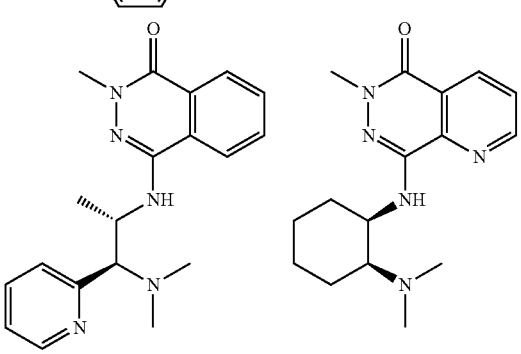
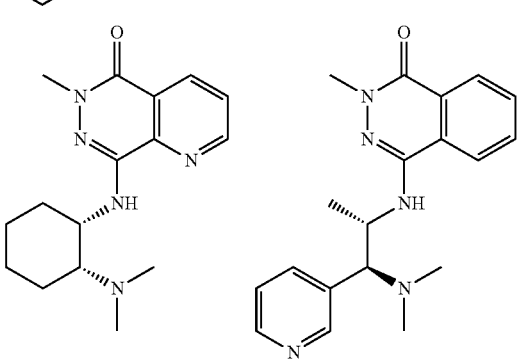
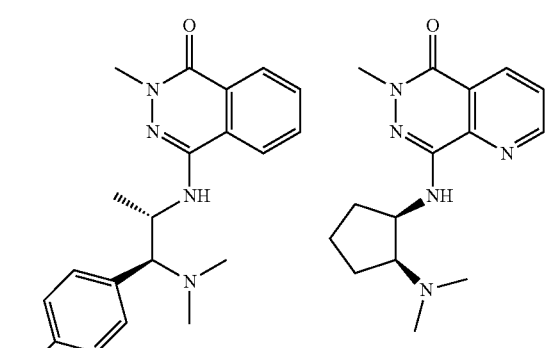

243
-continued
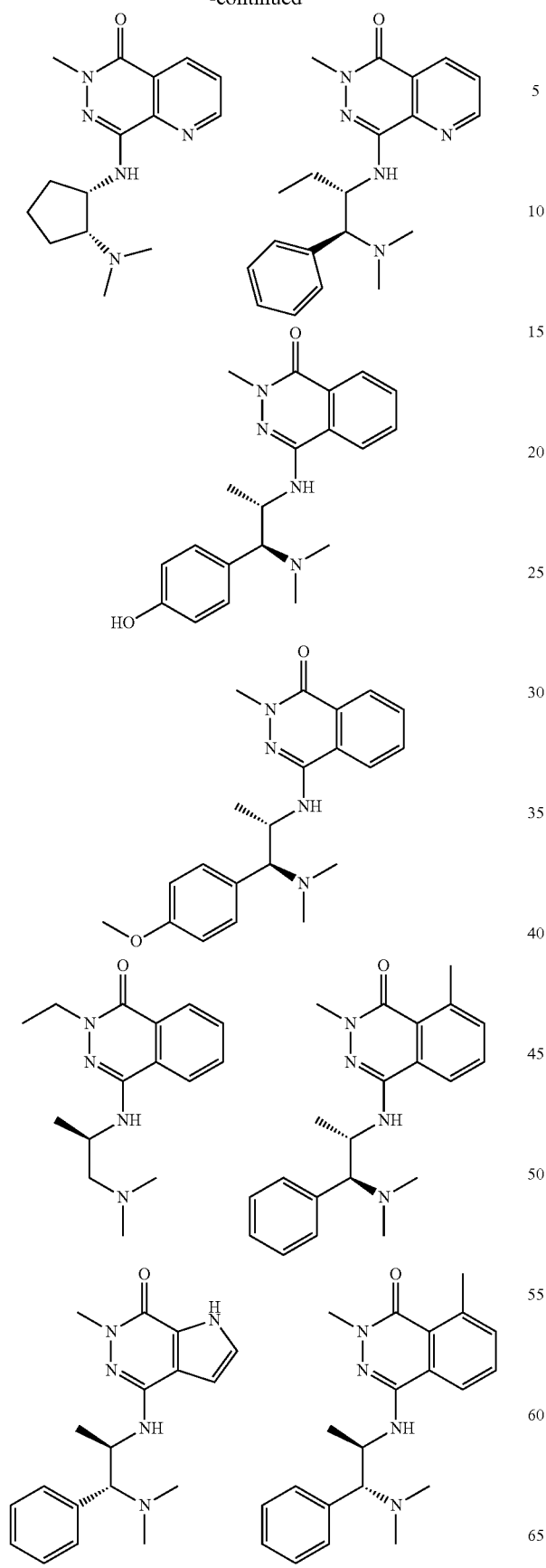
244
-continued
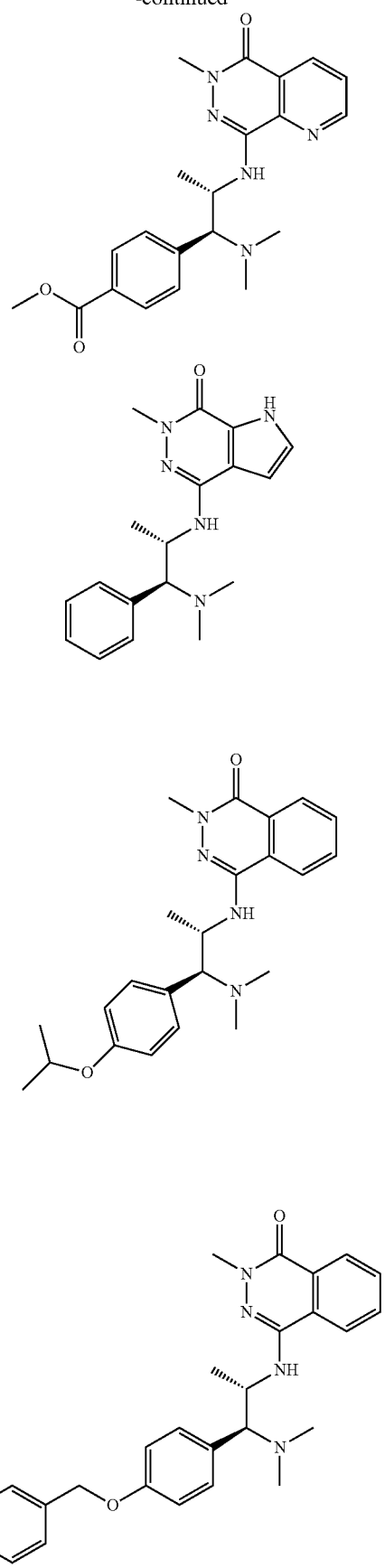

-continued
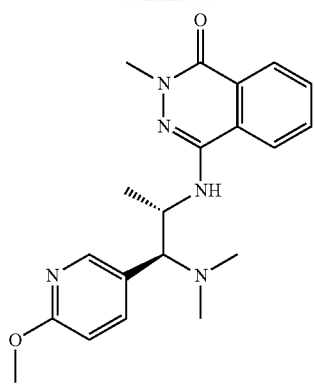
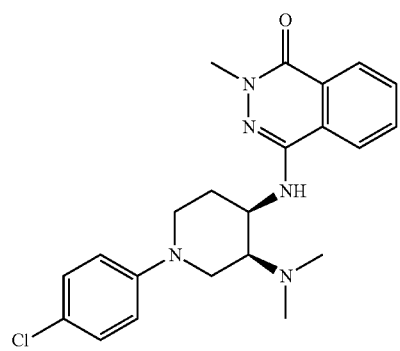
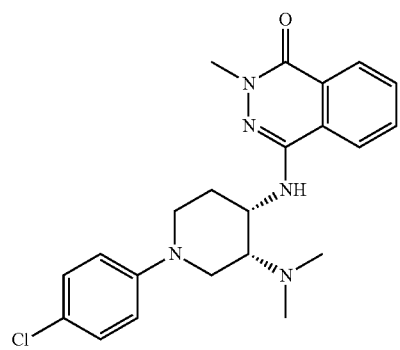
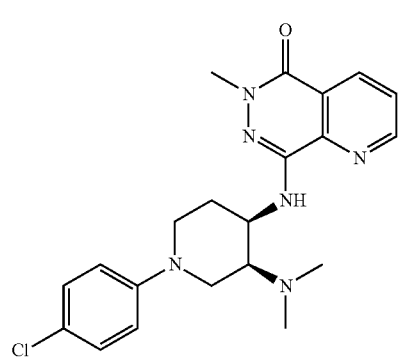
-continued
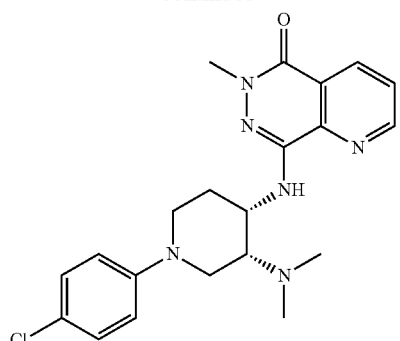
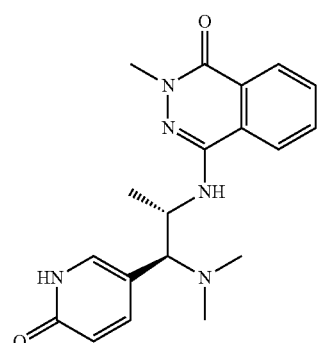
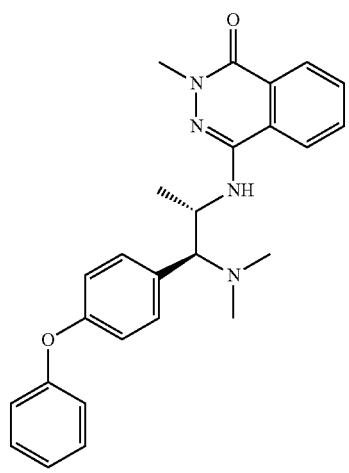
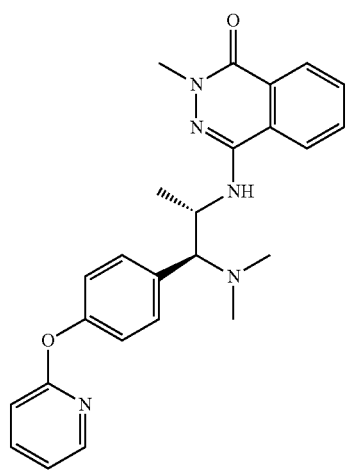

247
-continued
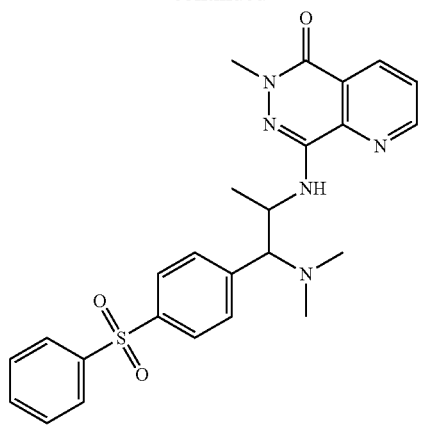
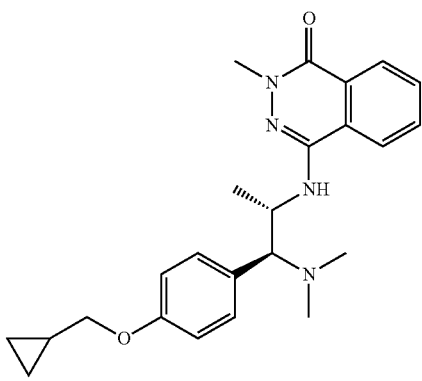
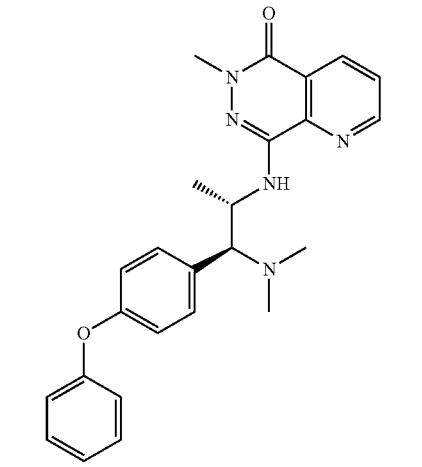
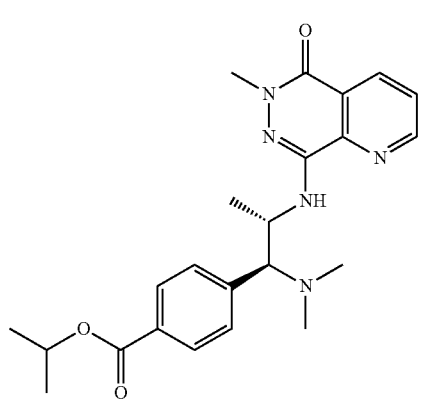
248
-continued
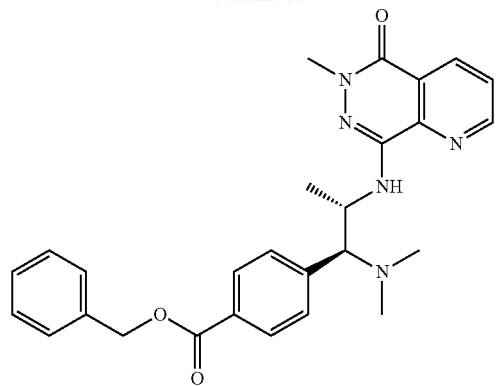
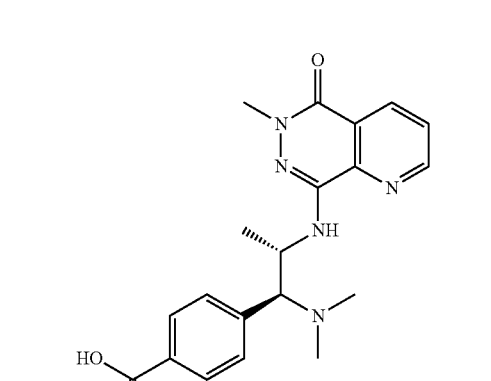
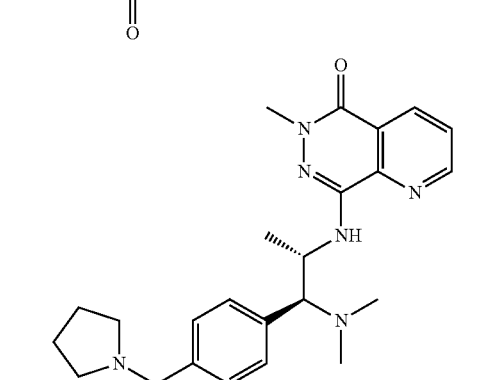
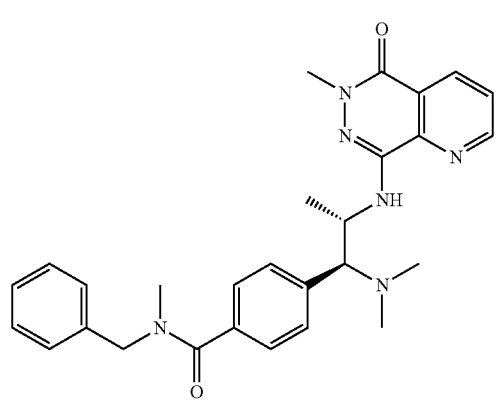

249
-continued
250
-continued
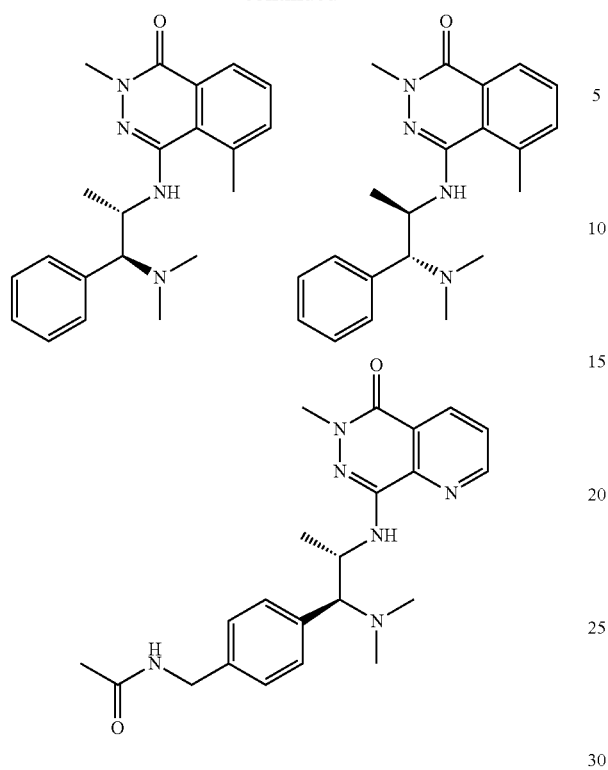
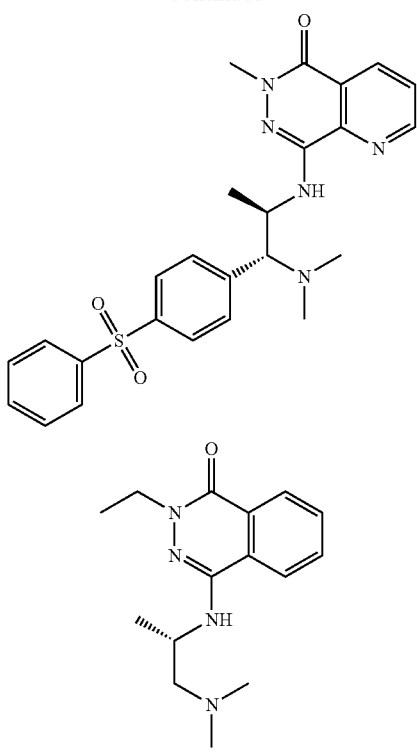
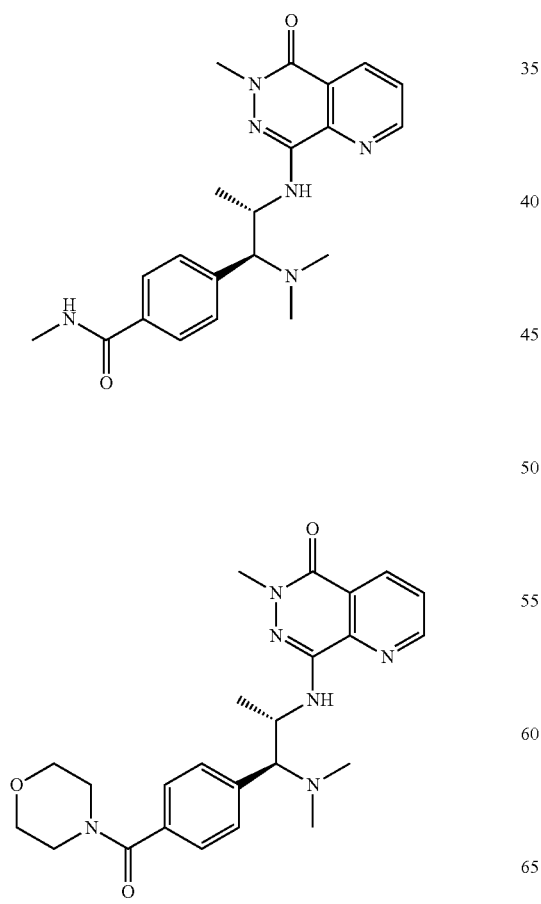

251
-continued
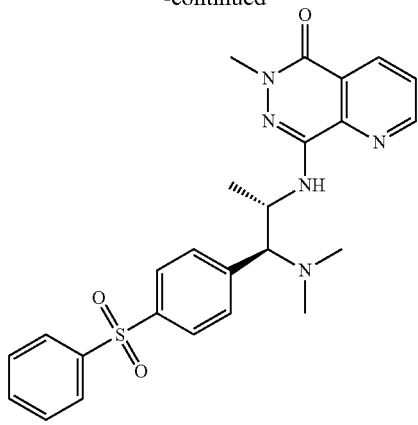
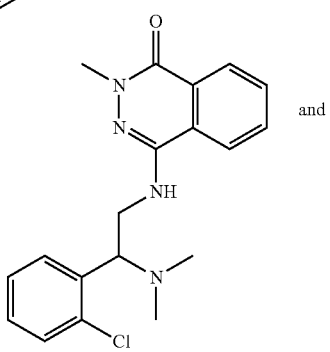
and
252
-continued
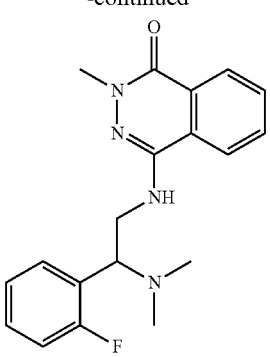
or a salt thereof.
23. A composition comprising a compound of formula (I) as described in claim 1 or a pharmaceutically acceptable salt thereof, and a pharmaceutically acceptable adjuvant, carrier, or vehicle.
* * * * *

UNITED STATES PATENT AND TRADEMARK OFFICE
CERTIFICATE OF CORRECTION

| | | |
|---|---|---|
| PATENT NO. | : 10,155,764 B2 | Page 1 of 4 |
| APPLICATION NO. | : 15/449692 | |
| DATED | : December 18, 2018 | |
| INVENTOR(S) | : Brian K. Albrecht et al. | |

It is certified that error appears in the above-identified patent and that said Letters Patent is hereby corrected as shown below:

On the Title Page

Item (72), Inventors, please delete "Anthony F. Romero" and insert -- F. Anthony Romero --;

In the Claims

Column 214, Lines 20-21, Claim 1, please delete "$C_{1-6}$ alkyl, $C_{2-6}$ alkenyl, $C_{2-6}$ alkynyl," and insert -- $C_{1-6}$alkyl, $C_{2-6}$alkenyl, $C_{2-6}$alkynyl, --;

Column 214, Lines 23-24, Claim 1, please delete "each $C_{1-6}$ alkyl, $C_{2-6}$ alkenyl, $C_{2-6}$ alkynyl," and insert -- each $C_{1-6}$alkyl, $C_{2-6}$alkenyl, $C_{2-6}$alkynyl, --;

Column 214, Lines 30-31, Claim 1, please delete "$C_{1-6}$ alkyl, $C_{2-6}$ alkenyl, $C_{2-6}$ alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 214, Lines 31-32, Claim 1, please delete "each $C_{1-6}$ alkyl, $C_{2-6}$alkenyl, $C_{2-6}$ alkynyl, $C_{1-6}$ alkoxy" and insert -- each $C_{1-6}$alkyl, $C_{2-6}$alkenyl, $C_{2-6}$alkynyl, $C_{1-6}$alkoxy --;

Column 214, Lines 40-41, Claim 1, please delete "$C_{1-6}$ alkyl, $C_{2-6}$ alkenyl, $C_{2-6}$ alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 214, Line 44, Claim 1, please delete "each $C_{1-6}$alkyl, $C_{2-6}$ alkenyl" and insert -- each $C_{1-6}$alkyl, $C_{2-6}$alkenyl --;

Column 214, Line 63, Claim 1, please delete "$C_{2-6}$ alkenyl" and insert -- $C_{2-6}$alkenyl --;

Column 214, Line 64, Claim 1, please delete "$C_{3-6}$ carbocycyl" and insert -- $C_{3-6}$carbocycyl --;

Column 214, Line 67, Claim 1, please delete "and $C_{1-6}$ alkoxy;" and insert -- and $C_{1-6}$alkoxy; --;

Signed and Sealed this
Fifth Day of November, 2019

Andrei Iancu
*Director of the United States Patent and Trademark Office*

CERTIFICATE OF CORRECTION (continued)
U.S. Pat. No. 10,155,764 B2

Column 215, Line 2, Claim 1, please delete "$C_{2-6}$ alkenyl, $C_{2-6}$ alkynyl" and insert -- $C_{2-6}$alkenyl, $C_{2-6}$alkynyl, --;

Column 215, Lines 22-23, Claim 1, please delete "$C_{2-6}$ alkenyl, $C_{2-6}$ alkynyl, $C_{1-6}$ alkoxy" and insert -- $C_{2-6}$alkenyl, $C_{2-6}$alkynyl, $C_{1-6}$alkoxy --;

Column 215, Lines 25-26, Claim 1, please delete "each $C_{1-6}$ alkyl, $C_{2-6}$ alkenyl, $C_{2-6}$alkynyl, $C_{1-6}$ alkoxy," and insert -- each $C_{1-6}$alkyl, $C_{2-6}$alkenyl, $C_{2-6}$alkynyl, $C_{1-6}$alkoxy, --;

Column 215, Line 30, Claim 1, please delete "hydroxy, $C_{1-6}$ alkoxy" and insert -- hydroxy, $C_{1-6}$alkoxy --;

Column 215, Line 33, Claim 1, please delete "and $C_1$-$C_6$ alkyl" and insert -- and $C_{1-6}$alkyl --;

Column 215, Line 41, Claim 1, please delete "and $C_{1-3}$ alkyl" and insert -- and $C_{1-3}$alkyl --;

Column 215, Lines 48-49, Claim 1, please delete "of $C_{1-6}$ alkyl, $C_{2-6}$ alkenyl, $C_{2-6}$ alkynyl," and insert -- of $C_{1-6}$alkyl, $C_{2-6}$alkenyl, $C_{2-6}$alkynyl, --;

Column 215, Line 59, Claim 1, please delete "$C_{1-6}$ alkyl, $C_{2-6}$ alkenyl, $C_{2-6}$ alkynyl," and insert -- $C_{1-6}$alkyl, $C_{2-6}$alkenyl, $C_{2-6}$alkynyl, --;

Column 216, Lines 4-5, Claim 1, please delete "$C_{1-6}$ alkyl, $C_{2-6}$ alkenyl, $C_{2-6}$ alkynyl, $C_{1-6}$ alkoxy," and insert -- $C_{1-6}$alkyl, $C_{2-6}$alkenyl, $C_{2-6}$alkynyl, $C_{1-6}$alkoxy, --;

Column 216, Lines 7-8, Claim 1, please delete "each $C_{1-6}$ alkyl, $C_{2-6}$ alkenyl, $C_{2-6}$alkynyl, $C_{1-6}$ alkoxy," and insert -- each $C_{1-6}$alkyl, $C_{2-6}$alkenyl, $C_{2-6}$alkynyl, $C_{1-6}$alkoxy, --;

Column 216, Lines 17-18, Claim 1, please delete "$C_{2-6}$ alkenyl, $C_{2-6}$ alkynyl, $C_{1-6}$ alkoxy," and insert -- $C_{2-6}$alkenyl, $C_{2-6}$alkynyl, $C_{1-6}$alkoxy, --;

Column 216, Lines 20-21, Claim 1, please delete "$C_{1-6}$ alkyl, $C_{2-6}$ alkenyl, $C_{2-6}$alkynyl, $C_{1-6}$ alkoxy," and insert -- $C_{1-6}$alkyl, $C_{2-6}$alkenyl, $C_{2-6}$alkynyl, $C_{1-6}$alkoxy, --;

Column 216, Line 25, Claim 1, please delete "hydroxy, $C_{1-6}$ alkoxy" and insert -- hydroxy, $C_{1-6}$alkoxy --;

Column 216, Line 28, Claim 1, please delete "and $C_1$-$C_6$ alkyl" and insert -- and $C_{1-6}$alkyl --;

Column 216, Line 36, Claim 1, please delete "and $C_{1-3}$ alkyl" and insert -- and $C_{1-3}$alkyl --;

Column 216, Lines 44-45, Claim 1, please delete "$C_{2-6}$ alkynyl, and $C_{1-6}$ alkoxy," and insert -- $C_{2-6}$alkynyl, and $C_{1-6}$alkoxy, --;

Column 216, Lines 45-46, Claim 1, please delete "each $C_{1-6}$ alkyl, $C_{2-6}$ alkenyl, $C_{2-6}$ alkynyl, and $C_{1-6}$ alkoxy," and insert -- each $C_{1-6}$alkyl, $C_{2-6}$alkenyl, $C_{2-6}$alkynyl, and $C_{1-6}$alkoxy, --;

CERTIFICATE OF CORRECTION (continued)
U.S. Pat. No. 10,155,764 B2

Column 216, Line 49, Claim 1, please delete "hydroxy, $C_{1-6}$ alkoxy" and insert -- hydroxy, $C_{1-6}$alkoxy --;

Column 216, Lines 55-56, Claim 1, please delete "of $C_{1-6}$ alkyl, $C_{2-6}$ alkenyl, $C_{2-6}$ alkynyl, and $C_{1-6}$ alkoxy," and insert -- of $C_{1-6}$alkyl, $C_{2-6}$alkenyl, $C_{2-6}$alkynyl, and $C_{1-6}$alkoxy, --;

Column 216, Line 57, Claim 1, please delete "and $C_{1-6}$ alkoxy is" and insert -- and $C_{1-6}$alkoxy is --;

Column 216, Line 59, Claim 1, please delete "hydroxy, $C_{1-6}$ alkoxy" and insert -- hydroxy, $C_{1-6}$alkoxy --;

Column 216, Line 62, Claim 1, please delete "of $C_{1-6}$alkyl, $C_{2-6}$ alkenyl, $C_{2-6}$ alkynyl," and insert -- of $C_{1-6}$alkyl, $C_{2-6}$alkenyl, $C_{2-6}$alkynyl, --;

Column 217, Line 4, Claim 1, please delete "$C_{1-6}$alkyl, $C_{2-6}$ alkenyl," and insert -- $C_{1-6}$alkyl, $C_{2-6}$alkenyl, --;

Column 217, Lines 15-16, Claim 1, please delete "$C_{1-6}$ alkyl, $C_{2-6}$ alkenyl, $C_{2-6}$ alkynyl, $C_{1-6}$ alkoxy," and insert -- $C_{1-6}$alkyl, $C_{2-6}$alkenyl, $C_{2-6}$alkynyl, $C_{1-6}$alkoxy, --;

Column 217, Lines 18-19, Claim 1, please delete "each $C_{1-6}$ alkyl, $C_{2-6}$ alkenyl, $C_{2-6}$alkynyl, $C_{1-6}$ alkoxy," and insert -- each $C_{1-6}$alkyl, $C_{2-6}$alkenyl, $C_{2-6}$alkynyl, $C_{1-6}$alkoxy, --;

Column 217, Line 23, Claim 1, please delete "hydroxy, $C_{1-6}$ alkoxy" and insert -- hydroxy, $C_{1-6}$alkoxy --;

Column 217, Line 26, Claim 1, please delete "and $C_1$-$C_6$ alkyl" and insert -- and $C_{1-6}$alkyl --;

Column 217, Line 34, Claim 1, please delete "and $C_{1-3}$ alkyl" and insert -- and $C_{1-3}$alkyl --;

Column 219, Line 31, Claim 2, please delete "$C_{1-6}$ alkyl, $C_{2-6}$ alkenyl, $C_{2-6}$ alkynyl," and insert -- $C_{1-6}$alkyl, $C_{2-6}$alkenyl, $C_{2-6}$alkynyl, --;

Column 219, Line 48, Claim 3, please delete "The compound of claim wherein" and insert -- The compound of claim 1 wherein --;

Column 219, Line 50, Claim 3, please delete "of $C_{1-6}$ alkyl, phenyl" and insert -- of $C_{1-6}$alkyl, phenyl --;

Column 219, Line 58, Claim 5, please delete "$R^1$ is $C_{1-6}$ alkyl," and insert -- $R^1$ is $C_{1-6}$alkyl, --;

Column 219, Line 61, Claim 5, please delete "hydroxy, and $C_{1-6}$ alkoxy." and insert -- hydroxy, and $C_{1-6}$alkoxy. --;

Column 219, Line 67, Claim 9, please delete "hydrogen or $C_{1-6}$ alkyl." and insert -- hydrogen or $C_{1-6}$alkyl. --;

CERTIFICATE OF CORRECTION (continued)
U.S. Pat. No. 10,155,764 B2

Column 220, Line 4, Claim 11, please delete "$C_{1-6}$ alkyl, $C_3$-$C_{10}$Carbocyclyl," and insert -- $C_{1-6}$alkyl, $C_3$-$C_{10}$Carbocyclyl, --;

Column 220, Line 6, Claim 11, please delete "each $C_{1-6}$ alkyl." and insert -- each $C_{1-6}$alkyl. --;

Column 220, Line 14, Claim 12, please delete "4-(phenyl sulfonyl)phenyl," and insert -- 4-(phenylsulfonyl)phenyl, --;

Column 221, Lines 59-60, Claim 15, please delete "of $C_{1-6}$ alkyl, $C_{2-6}$ alkenyl, $C_{2-6}$ alkynyl, and $C_{1-6}$ alkoxy," and insert -- of $C_{1-6}$alkyl, $C_{2-6}$alkenyl, $C_{2-6}$alkynyl, and $C_{1-6}$alkoxy, --;

Column 221, Line 61, Claim 15, please delete "$C_{2-6}$ alkenyl, $C_{2-6}$alkynyl, and $C_{1-6}$ alkoxy is" and insert -- $C_{2-6}$alkenyl, $C_{2-6}$alkynyl, and $C_{1-6}$alkoxy is --;

Column 221, Line 63, Claim 15, please delete "hydroxy, $C_{1-6}$ alkoxy" and insert -- hydroxy, $C_{1-6}$alkoxy --;

Column 222, Line 3, Claim 16, please delete "$C_{1-6}$ alkoxy wherein each" and insert -- $C_{1-6}$alkoxy wherein each --;

Column 222, Lines 3-4, Claim 16, please delete "each $C_{1-6}$ alkyl, $C_{2-6}$ alkenyl, $C_{2-6}$ alkynyl, and $C_{1-6}$ alkoxy is" and insert -- each $C_{1-6}$alkyl, $C_{2-6}$alkenyl, $C_{2-6}$alkynyl, and $C_{1-6}$alkoxy is --;

Column 222, Line 6, Claim 16, please delete "hydroxy, $C_{1-6}$ alkoxy and" and insert -- hydroxy, $C_{1-6}$alkoxy and --;

Column 222, Lines 13-14, Claim 17, please delete "of $C_{1-6}$ alkyl, $C_{2-6}$ alkenyl, $C_{2-6}$alkynyl, and $C_{1-6}$ alkoxy," and insert -- of $C_{1-6}$alkyl, $C_{2-6}$alkenyl, $C_{2-6}$alkynyl, and $C_{1-6}$alkoxy, --;

Column 222, Lines 14-15, Claim 17, please delete "each $C_{1-6}$ alkyl, $C_{2-6}$ alkenyl, $C_{2-6}$ alkynyl, and $C_{1-6}$ alkoxy is" and insert -- each $C_{1-6}$alkyl, $C_{2-6}$alkenyl, $C_{2-6}$alkynyl, and $C_{1-6}$alkoxy is --;

Column 222, Line 17, Claim 17, please delete "hydroxy, $C_{1-6}$ alkoxy and" and insert -- hydroxy, $C_{1-6}$alkoxy and --;

Column 222, Lines 27-28, Claim 18, please delete "of $C_{1-6}$alkyl, $C_{2-6}$ alkenyl, $C_{2-6}$alkynyl, and $C_{1-6}$ alkoxy," and insert -- of $C_{1-6}$alkyl, $C_{2-6}$alkenyl, $C_{2-6}$alkynyl, and $C_{1-6}$alkoxy, --;

Column 222, Lines 28-29, Claim 18, please delete "each $C_{1-6}$ alkyl, $C_{2-6}$ alkenyl, $C_{2-6}$ alkynyl, and $C_{1-6}$ alkoxy is" and insert -- each $C_{1-6}$alkyl, $C_{2-6}$alkenyl, $C_{2-6}$alkynyl, and $C_{1-6}$alkoxy is --;

Column 222, Line 31, Claim 18, please delete "hydroxy, $C_{1-6}$ alkoxy and" and insert -- hydroxy, $C_{1-6}$alkoxy and -- therefor.